USOO6114371A

United States Patent [19]
Tang et al.

[11] Patent Number: 6,114,371
[45] Date of Patent: Sep. 5, 2000

[54] 3-(CYCLOHEXANOHETEROARYLIDENYL)-2-INDOLINONE PROTEIN TYROSINE KINASE INHIBITORS

[75] Inventors: Peng Cho Tang, Moraga; Li Sun, Foster City; Gerald McMahon, Kenwood; Robert A. Blake, Foster City, all of Calif.

[73] Assignee: Sugen, Inc., So. San Francisco, Calif.

[21] Appl. No.: 09/190,970

[22] Filed: Nov. 12, 1998

Related U.S. Application Data

[63] Continuation-in-part of application No. 09/099,842, Jun. 19, 1998.
[60] Provisional application No. 60/050,977, Jun. 20, 1997, and provisional application No. 60/059,384, Sep. 19, 1997.
[51] Int. Cl.$^7$ .................. A01N 43/38; A61K 31/535; C07D 413/04; C07D 401/04; C07D 405/04
[52] U.S. Cl. .................. 514/414; 514/235.2; 514/323; 544/143; 544/144; 546/201; 548/454
[58] Field of Search .................. 514/235.2, 323, 514/414; 544/143, 144; 546/201; 548/454

[56] References Cited

U.S. PATENT DOCUMENTS

| Re. 36,256 | 7/1999 | Spada et al. | 514/249 |
|---|---|---|---|
| 4,966,849 | 10/1990 | Vallee et al. | 435/199 |
| 5,217,999 | 6/1993 | Levitzki et al. | 514/613 |
| 5,302,606 | 4/1994 | Spada et al. | 514/357 |
| 5,330,992 | 7/1994 | Eissenstat et al. | 514/312 |
| 5,786,488 | 7/1998 | Tang et al. | 548/455 |
| 5,834,504 | 11/1998 | Tang et al. | 514/418 |
| 5,880,141 | 3/1999 | Tang et al. | 514/339 |
| 5,883,113 | 3/1999 | Tang et al. | 514/418 |
| 5,883,116 | 3/1999 | Tang et al. | 514/418 |
| 5,886,020 | 3/1999 | Tang et al. | 514/418 |

FOREIGN PATENT DOCUMENTS

| 0 566 226 A1 | 10/1993 | European Pat. Off. . |
|---|---|---|
| 91/15495 | 10/1991 | WIPO . |
| 92/20642 | 11/1992 | WIPO . |
| 92/21660 | 12/1992 | WIPO . |
| 94/03427 | 2/1994 | WIPO . |
| 94/10202 | 5/1994 | WIPO . |
| 94/14808 | 7/1994 | WIPO . |
| WO 98/50356 | 11/1998 | WIPO . |
| WO 99/10325 | 3/1999 | WIPO . |

OTHER PUBLICATIONS

Akbasak and Sunar–Akbasak et al., "Oncogenes: cause or consequence in the development of glial tumors," *J. Neurol. Sci.* 111:119–133 (1992).
Andreani et al., "Synthesis and potential coanthracyclinic activity of substituted 3–(5–imidazo[2,1–b]thiazolylmethylene)–2–indolinones," *Eur. J. Med. Chem.* 32:919–924 (1997).
Arteaga et al., "Blockade of the Type I Somatomedin Receptor Inhibits Growth of Human Breast Cancer Cells in Athymic Mice," *J. Clin. Invest.* 84:1418–1423 (1989).

Baserga, "The Insulin–like Growth Factor I Receptor: A Key to Tumor Growth?" *Cancer Research* 55:249–252 (1995).
Bolen et al., "The Src family of tyronsine protein kinases in hemopoietic signal transduction," *FASEB J.* 6:3403–3409 (1992).
Bolen, "Nonreceptor tyrosine protein kinases," *Oncogene* 8:2025–2031 (1993).
Bonner et al., "Structure and Biological Activity of Human Homologs of the raf/mil Oncogene," *Molecular and Cellular Biology* 5:1400–1407 (1985).
Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994).
Decker and Lohmann–Matthes, "A quick and simple method for the quantitation of lactate dehydrogenase release in measurements of cellular cytotoxicity and tumor necrosis factor (TNF) activity," *J. Immunol. Methods* 15:61–69 (1988).
Dickson et al., "Tyrosine kinase receptor—nuclear protooncogene interactions in breast cancer," *Cancer Treatment Res.* 61:249–273 (1992).
Fantl et al., "Distinct Phosphotyrosines on a Growth Factor Receptor Bind to Specific Molecules That Mediate Different Signaling Pathways," *Cell* 69:413–423 (1992).
Fendly et al., "Characterization of Murine Monoclonal Antibodies Reactive to Either the Human Epidermal Growth Factor Receptor of HER2/neu Gene Product," *Cancer Research* 50:1550–1558 (1990).
Floege et al., "Factors involved in the regulation of mesangial cell proliferation in vitro and in vivo," *Kidney International* 43:S47–S54 (1993).
Goldring and Goldring, "Cytokines and Cell Growth Control," *Critical Reviews in Eukaryotic Gene Expression* 1:301–326 (1991).
Honegger et al., "Point Mutation at the ATP Binding Site of EGF Receptor Abolishes Protein–Tyrosine Kinase Activity and Alters Cellular Routing," *Cell* 51:199–209 (1987).
Jellinek et al., "Inhibition of Receptor Binding by High–Affinity RNA Ligands to Vascular Endothelial Growth Factor," *Biochemistry* 33:10450–10456 (1994).
Kendall and Thomas, "Inhibition of vascular endothelial cell growth factor activity by an endogenously encoded soluble receptor," *Proc. Natl. Acad. Sci. USA* 90:10705–10709 (1993).
Kim et al., "Inhibition of vascular endothelial growth factor–induced angiogenesis suppresses tumour growth in vivo," *Nature* 362:841–844 (1993).

(List continued on next page.)

*Primary Examiner*—Johann Richter
*Assistant Examiner*—Dominic Keating

[57] ABSTRACT

The present invention relates to novel 3-(cyclohexanoheteroarylidenyl)-2-indolinone compounds and physiologically acceptable salts and prodrugs thereof which are expected to modulate the activity of protein tyrosine kinases and therefore to be useful in the prevention and treatment of protein tyrosine kinase related cellular disorders such as cancer.

25 Claims, No Drawings

OTHER PUBLICATIONS

Kinsella et al., "Protein Kinase C Regulates Endothelial Cell Tube Formation on Basement Membrane Matrix, Matrigel," *Exp. Cell Research* 199:56–62 (1992).

Koch et al., "SH2 and SH3 Domains: Elements That Control Interactions of Cytoplasmic Signaling Proteins," *Science* 252:668–674 (1991).

Komada et al., "The cell dissociation and motility triggered by scatter factor/hepatocyte growth factor are mediated through the cytoplasmic domain of the c–Met receptor," *Oncogene* 8:2381–2390 (1993).

Korc et al., "Overexpression of the Epidermal Growth Factor Receptor in Human Pancreatic Cancer is Associated with Concomitant Increases in the Levels of Epidermal Growth Factor and Transforming Growth Factor Alpha," *J. Clin. Invest.* 90:1352–1360 (1992).

Korzeniewski and Callewaert, "An Enzyme–Release Assay for Natural Cytotoxicity[1]," *J. Immunol. Methods* 64:313–320 (1983).

Kumabe et al., "Amplification of α–platelet–derived growth factor receptor gene lacking an exon coding for a portion of the extracellular region in a primary brain tumor of glial origin," *Oncogene* 7:627–633 (1992).

Lee and Donoghue, "Intracellular retention of membrane–anchored v–sis protein abrogates autocrine signal transduction," *Journal of Cell Biology* 118:1057–1070 (1992).

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," Experimental Therapeutics—Proceedings of the American Association for Cancer Research 35:381 at abstract No. 2268 (Mar. 1994).

Morrison et al., "Signal Transduction From Membrane to Cytoplasm: Growth Factors and Membrane–Bound Oncogene Products Increase Raf–1 Phosphorylation and Associated Protein Kinase Activity," *Proc. Natl. Acad. Sci. USA* 85:8855–8859 (1988).

Mosmann, "Rapid Colorimetric Assay for Cellular Growth and Survival: Application to Proliferation and Cytotoxicity Assays," *J. Immunol. Methods* 65:55–63 (1983).

Plowman et al., "Receptor Tyrosine Kinases as Targets for Drug Intervention," *DN&P* 7(6):334–339 (1994).

Rygaard and Povlsen, "Heterotransplantation of a Human Malignant Tumour to 'Nude' Mice," *Acta path. microbiol. scand.* 77:758–760 (1969).

Sandberg–Nordqvist et al., "Characterization of Insulin–Like Growth Factor 1 in Human Primary Brain Tumors," *Cancer Research* 53:2475–2478 (1993).

Schlessinger and Ullrich, "Growth Factor Signalling by Receptor Tyrosine Kinases," *Neuron* 9:383–391 (1992).

Slamon et al., "Studies of the HER–2/neu Proto–oncogene in Human Breast and Ovarian Cancer," *Science* 244:707–712 (1989).

Songyang et al., "SH2 Domains Recognize Specific Phosphopeptide Sequences," *Cell* 72:767–778 (1993).

Songyang et al., "Specific Motifs Recognized by the SH2 Domains of Csk, 3BP2, fps/fes, GRB–2, HCP, SHC, Syk and Vav," *Molecular and Cellular Biology* 14:2777–2785 (1994).

Superti–Furga et al., "A functional screen in yeast for regulators and antagonizers of heterologous protein tyrosine kinases," *Nature Biotech* 14:600–605 (1996).

Superti–Furga et al., "Csk inhibition of c–Src activity requires both the SH2 and SH3 domains of Src," *EMBO J.* 12:2625–2634 (1993).

Takano et al., "Inhibition of angiogenesis by a novel diaminoanthraquinone that inhibits protein kinase C," *Mol. Bio. Cell* 4:358A at abstract No. 2076 (1993).

Torp et al., "Expression of the Epidermal Growth Factor Receptor Gene in Human Brain Metastases," *AMPIS* 100:713–719 (1992).

Tuzi et al., "Expression of growth factor receptors in human brain tumours," *Br. J. Cancer* 63:227–233 (1991).

Voller et al., "Ch 45—Enzyme–Linked Immunosorbent Assay," in *Manual of Clinical Immunology*, $2^{nd}$ edition, Rose and Friedman editors, American Society of Microbiology, Washington, D.C., pp. 359–371 (1980).

Wright et al., "Inhibition of Angiogenesis in Vitro and In Ovo With an Inhibitor of Cellular Protein Kinases, MDL 27032," *J. Cellular Physiology* 152:448–457 (1992).

Andreani et al., "In Vivo Cardiotonic Activity of Pyridylmethylene–2–indolinones," *Arzneimittel–Forschung Drug Research* 48(II):727–729 (1998).

Carpenedo et al., "Identification and Measurement of Oxindole (2–Indolinone) in the Mammalian Brain and Other Rate Organs," *Analytical Biochemistry* 244:74–79 (1997).

Chen et al., "Effects of 3,3–Dipyridylmethyl–1–Phenyl–2–Indolinone on γ–Aminobutyric Acid Elicited Chloride Current of Snail Central Neuron," *Chinese Journal of Physiology* 40(3):149–156 (1997).

Damiani et al., "Inhibition of Copper–Mediated Low Density Lipoprotein Peroxidation by Quinoline and Indolinone Nitroxide Radicals," *Biochemical Pharmacology* 48(6):1155–1161 (1994).

Davis et al, "Synthesis and Microbiological Properties of 3–Amino–1–Hydroxy–2–Indolinone and Related Compounds," *Journal of Medicinal Chemistry* 16(9):1043–1045 (1973).

Graziani et al., "Hepatocyte Growth Factor/Scatter Factor Stimulates the Ras–Guanine Nucleotide Exchanger*," *The Journal of Biological Chemistry* 268(13):9165–9168 (1993).

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993).

Maass et al., "Viral Resistance to the Thiazolo–Iso–Indolinones, a New Class of Nonnucleoside Inhibitors of Human Immunodeficiency Virus Type 1 Reverse Transcriptase," *Antimicrobial Agents and Chemotherapy* 37(12):2612–2617 (1993).

Moreto et al., "3,3–Bis–(4–Hydroxyphenyl)–7–Methyl–2–Indolinone (BHMI), the Active Metabolite of the Laxative Sulisatin," *Arzneimittel–Forschung Drug Research* 29(II):1561–1564 (1979).

Moreto et al., "Study of the Laxative Properties of the Disodium Salt of the Sulfuric Diester of 3,3 Bis–(4–Hydroxyphenyl)–7–Methyl–2–Indolinone (Dan–603) in the Rat," *European Journal of Pharmacology* 36:221–226 (1976).

Singh et al., "Indolinone Derivatives as Potential Antimicrobial Agents," *Zantralbl. Mikrobiol.* 144:105–109 (1989).

Singh et al., "Synthesis and Anticonvulsant Activity of New 1–Substituted 1'–Methyl–3–Chloro–2–Oxosprio (Azetidin–3', 4–Indol–2' Ones)," *Bolletino Chimico Farmaceutico* 133:76–79 (1994).

Soldi et al., "Platelet–Activating Factor (PAF) Induces the Early Tyrosine Phosphorylation of Focal Adhesion Kinase ($p125^{FAK}$) in Human Endothelial Cells," *Oncogene* 13(3):515–525 (1996).

Tsai et al., "The Effect of 3,3–Di–Pyridyl–Methyl–1–Phenyl–2–Indolinone on the Nerve Terminal Currents of Mouse Skeletal Muscles," *Neuorpharmacology* 31(9):943–947 (1992).

Zaman et al., "Tyrosine Kinase Activity of Purified Recombinant Cytoplasmic Domain of Platelet–Derived Growth Factor β–Receptor (β–PDGFR) and Discovery of a Novel Inhibitor of Receptor Tyrosine Kinases," *Biochemical Pharmacology* 57(1):57–64 (1999).

Zhang et al., "Microtubule Effects of Welwistatin, a Cyanobacterial Indolinone that Circumvents Multiple Drug Resistance," *Molecular Pharmacology* 49:228–294 (1996).

3-(CYCLOHEXANOHETEROARYLIDENYL)-2-INDOLINONE PROTEIN TYROSINE KINASE INHIBITORS

RELATED APPLICATIONS

This application is a continuation-in-part of U.S. patent application Ser. No. 09/099,842, entitled "3-(CYCLOHEXANOHETEROARYLIDENYL)-2-INDOLINONE PROTEIN TYROSINE KINASE INHIBITORS", filed Jun. 19, 1998 by Tang et al, which claims priority to U.S. provisional patent application Serial No. 60/050,977, filed Jun. 20, 1997, and U.S. provisional patent application Serial No. 60/059,384, filed Sep. 19, 1997, all of which are hereby incorporated by reference in their entirety, including any drawings, as if they were fully set forth herein.

INTRODUCTION

The present invention relates generally to organic chemistry, biochemistry, pharmacology and medicine. More particularly, it relates to novel heterocyclic compounds, and their physiologically acceptable salts and prodrugs (all of which modulate the activity of protein tyrosine kinases ("PTKs") and, therefore, are expected to exhibit a salutary effect against disorders related to abnormal PTK activity), as well as related methods and products.

BACKGROUND OF THE INVENTION

The following is only offered as background information to aid the reader in understanding the invention and is not admitted to be or describe prior art to the present invention.

Protein kinases ("PKs") are enzymes that catalyze the phosphorylation of hydroxy groups on tyrosine, serine and threonine residues of proteins. The consequences of this seemingly simple activity are staggering; cell growth, differentiation and proliferation; i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can conveniently be broken down into two classes, the protein tyrosine kinases (PTKs) and the serine-threonine kinases (STKs).

One of the prime aspects of PTK activity is its involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, affect numerous cellular responses such as cell division (proliferation), cell differentiation, cell growth, expression of metabolic effects to the extracellular microenvironment, etc. For a more complete discussion, see Schlessinger and Ullrich, *Neuron*, 9:303–391 (1992) which is incorporated by reference, including any drawings, as if fully set forth herein.

Growth factor receptors with PK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and the insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of a glycosylated extracellular domain composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed in the later group, is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

One further member of the tyrosine kinase growth factor receptor family is the fibroblast growth factor ("FGF") receptor group. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the PTK sequence is interrupted by regions of unrelated amino acid sequences.

A more complete listing of the known RTK subfamilies is described in Plowman et al., *DN&P*, 7(6):334–339 (1994) which is incorporated by reference, including any drawings, as if fully set forth herein.

In addition to the RTKs, there also exists a family of entirely intracellular PTKs called "non-receptor tyrosine kinases" or "cellular tyrosine kinases". This latter designation, abbreviated "CTK", will be used herein. CTKs do not contain extracellular and transmembrane domains. At present, over 24 CTKs in 11 subfamilies (Src, Frk, Btk, Csk, Abl, Zap070, Fes/Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025–2031 (1993), which is incorporated by reference, including any drawings, as if fully set forth herein.

The serine-threonine kinases or STKs, like the CTKs, are predominantly intracellular although there are a few receptor kinases of the STK type. STKs are the most common of the cytosolic kinases; i.e., kinases which perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, large number of diverse cancers. Others pathogenic conditions which have been associated with PTKs include, without limitation, psoriasis, hepatic cirrhosis, diabetes, atherosclerosis, angiogenesis, restinosis, ocular diseases, rheumatoid arthritis and other inflammatory disorders, autoimmune disease and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and a number of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. App. No. 4,966,849); soluble receptors and antibodies (App. No. WO 94/10202, Kendall and Thomas, *Proc. Nat'l Acad. Sci.,* 90:10705–09 (1994), Kim, et al., *Nature,* 362:841–844 (1993)); RNA ligands (Jelinek, et al., *Biochemistry,* 33:10450–56); Takano, et al., *Mol. Bio. Cell* 4:358A (1993); Kinsella, et al., *Exp. Cell Res.* 199:56–62 (1992); Wright, et al., *J. Cellular Phys.,* 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.,* 35:2268 (1994)).

More recently, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as PTK inhibitors. Styryl compounds (U.S. Pat. No. 5,217,999), styryl-substituted pyridyl compounds (U.S. Pat. No. 5,302,606), quinazoline derivatives (EP App. No. 0 566 266 Al), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

The present invention is based in part on the identification of small organic molecules which modulate PTK activity and which, therefore, are expected to be useful in the treatment and prevention of disorders driven by abnormal PTK activity, and the discovery of a family of novel heterocyclic compounds which are expected to exhibit PTK modulating activity.

Thus, the present invention relates generally to novel 3-(cyclohexanoheteroarylidenyl)-2-indolinones which modulate the activity of both receptor (RTK) and non-receptor (CTK) protein tyrosine kinases (PTKs). In another aspect, this invention relates to 3-(cyclohexanoheteroarylidenyl)-2-indolinones which are particularly active toward PDGFR RTKs and Src/Lck CTKs. In addition, the present invention relates to the preparation and use of pharmacological compositions of the disclosed compounds and their physiologically acceptable salts and prodrugs in the treatment or prevention of PTK driven disorders such as, by way of example and not limitation, cancer, diabetes, hepatic cirrhosis, atherosclerosis, angiogenesis and renal disease.

A "3-cyclohexanoheteroarylidenyl-2-indolinone" refers to a chemical compound having the general structure shown in Formula 1.

The terms "2-indolinone", 2-oxindole or oxindolin-2-one all refer to that portion of the molecule depicted in Formula 1 consisting of the aryl six-member ring fused to the five-member pyrrolidone ring.

As used herein, a "pyrrolidone" refers to a five-member ring having the chemical structure:

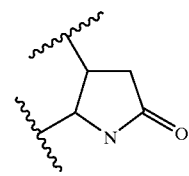

The term "cyclohexanoheteroaryl", refers to the bicyclic six-member ring/five member ring (containing A and B) portion of the molecule shown in Formula 1.

The term "cyclohexanoheteroarylidenyl" group refers that portion of the molecule depicted in Formula 1 consisting of the double bond which is adjacent to the "=X" on the pyrrolidone ring and the $R^2$ and the cyclohexanoheteraryl group attached to the double bond.

A "pharmacological composition" refers to a mixture of one or more of the compounds described herein, or physiologically acceptable salts or prodrugs thereof, with other chemical components, such as physiologically acceptable carriers and excipients. The purpose of a pharmacological composition is to facilitate administration of a compound to an organism.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxyic acid once inside the cell where water solubility is beneficial.

As used herein, an "ester" is a carboxy group, as defined herein, wherein "R" is any of the listed groups other than hydrogen.

As used herein, a "physiologically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples, without limitation, of excipients include calcium carbonate, calcium phosphate, various sugars and types of starch, cellulose derivatives, gelatin, vegetable oils and polyethylene glycols.

1. THE COMPOUNDS

A. General Structural Features.

In one aspect, the compounds of the present invention relate to 3-(cyclohexanoheteroarylidenyl)-2-indolinone compounds having the chemical structure shown in Formula 1:

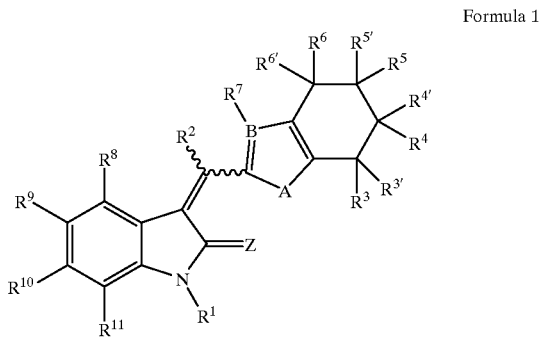

Formula 1

A is selected from the group consisting of carbon, nitrogen, oxygen and sulfur; when A is carbon, A has two additional hydrogen atoms bonded to it.

B is selected from the group consisting of carbon and nitrogen; and it is understood that, when B is nitrogen, $R^7$ does not exist.

Z is selected from the group consisting of oxygen, sulfur and $NR^{12}$. $R^{12}$ is selected from the group consisting of hydrogen, alkyl, cycloalkyl, aryl, hydroxy, alkoxy, aryloxy, carbonyl, C-carboxy, O-carboxy, C-amido, guanyl, sulfonyl and trihalomethanesulfonyl.

$R^1$ is selected from the group consisting of hydrogen, alkyl, cycloalkyl, alkenyl, alkynyl, aryl, hydroxy, C-carboxy, C-amido, trihalomethanecarbonyl, trihalomethanesulfonyl, and sulfonyl.

$R^2$ is selected from the group consisting of hydrogen, alkyl, cycloalkyl, aryl and halogen.

$R^3$, $R^{3'}$, $R^4$, $R^{4'}$, $R^5$, $R^{5'}$, $R^6$, and $R^{6'}$ are independently selected from the group consisting of hydrogen, alkyl, trihaloalkyl, cycloalkyl, alkenyl, alkynyl, aryl, heteroaryl, heteroalicyclic, alkoxy, aryloxy, thioalkoxy, thioaryloxy, heteroaryloxy, heteroalicycloxy, sulfinyl, sulfonyl, S-sulfonamido, N-Sulfonamido, trihalomethanesulfonyl, carbonyl, C-carboxy, O-carboxy, C-amido, N-amido, cyano, nitro, halo, O-carbamyl, N-carbamyl, O-thiocarbamyl, phosphonyl, N-thiocarbamyl, guanyl, guanidino, ureido, amino, trihalomethanesulfonamido, and $-NR^{13}R^{14}$.

$R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring containing at least one nitrogen.

When any of $R^3$, $R^4$, $R^5$, and $R^6$ are hydrogen, $R^{3'}$, $R^{4'}$, $R^{5'}$, and $R^{6'}$, respectively, in addition to being independently selected from the above group, may be independently selected from the group consisting of hydroxy and thiohydroxy.

Combined, $R^3$ and $R^{3'}$, $R^4$ and $R^{4'}$, $R^5$ and $R^{5'}$, and $R^5$ and $R^{6'}$ may be independently selected from the group consisting of keto, five-member spirocycloalkyl, five-member spiroheteroalicyclyl, six-member spirocycloalkyl and six member spiroheteroalicyclyl.

$R^7$, $R^8$, $R^9$, $R^{10}$, and $R^{11}$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheterarylogy, thioheteralicyloxy, halo, nitro, cyano, O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and $-NR^{13}R^{14}$, wherein, $R^{13}$ and $R^{14}$ are as defined previously herein. $R^7$ preferably is selected from the group consisting of hydrogen, alkyl, cycloalkyl, trihaloalkyl, alkenyl, alkynyl, aryl, heteroaryl, C-carboxy, O-carboxy, halo, cyano, nitro, hydroxy and alkoxy.

As used herein, the term "alkyl" refers to a saturated aliphatic hydrocarbon including straight chain and branched chain groups. Preferably, the alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and $NR^{13}R^{14}$, $R^{13}$ and $R^{14}$ are independently selected from the group consisting of hydrogen, alkyl, cycloalkyl, aryl, carbonyl, sulfonyl, trihalomethanesulfonyl and, combined, a five-member or six-member heteroalicyclic ring.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system.

Examples, without limitation, of aryl groups are phenyl, naphthalenyl and anthracenyl. The aryl group may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more selected from alkyl, cycloalkyl, aryl, heteroaryl, heteroalicyclic, hydroxy, alkoxy, aryloxy, heteroaryloxy, heteroalicylcoxy, thiohydroxy, thioalkoxy, thioaryloxy, thioheteroaryloxy, thioheteroalicyloxy, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfinyl, sulfonyl, sulfonamido, trihalomethanesulfonamido, trihalomethanesulfonyl, silyl, guanyl, guanidino, ureido, phosphonyl, amino and $NR^{13}R^{14}$ with $R^{13}$ and $R^{14}$ as defined above.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $X_3CC$(=O)— group with X as defined herein.

A "C-carboxy" group refers to a —C(=O)O—R" groups, with R" as defined herein.

An "O-carboxy" group refers to a R" C(=O)O— group, with R" as defined herein.

A "carboxyic acid" group refers to a C-carboxy group in which R" is hydrogen.

A "halo" group refers to fluorine, chlorine, bromine or iodine.

A "trihalomethyl" group refers to a —$CX_3$ group wherein X is a halo group as defined herein.

A "trihalomethanesulfonyl" group refers to a $X_3CS$(=O)$_2$— groups with X as defined above.

A "trihalomethanesulfonamido" group refers to a $X_3CS$(=O)$_2NR^{13}$— group with X and $R^{13}$ as defined herein.

A "sulfinyl" group refers to a —S(=O)—R" group, with R" as defined herein.

A "sulfonyl" group refers to a —S(=O)$_2$R" group, with R" as defined herein.

An "S-sulfonamido" group refers to a —S(=O)$_2NR^{13}R^{14}$, with $R^{13}$ and $R^{14}$ as defined herein.

An "N-Sulfonamido" group refers to a $R^{13}S$(=O)$_2NR^{14}$— group, with $R^{13}$ and $R^{14}$ as defined herein.

An "O-carbamyl" group refers to a —OC(=O)$NR^{13}R^{14}$ group with $R^{13}$ and $R^{14}$ as defined herein.

An "N-carbamyl" group refers to a $R^{13}OC$(=O)$NR^{14}$ group, with $R^{13}$ and $R^{14}$ as defined herein.

An "O-thiocarbamyl" group refers to a —OC(=S)$NR^{13}R^{14}$ group with $R^{12}$ and $R^{13}$ as defined herein.

An "N-thiocarbamyl" group refers to a $R^{13}OC$(=S)$NR^{14}$— group, with $R^{13}$ and $R^{14}$ as defined herein.

An "amino" group refers to an —$NH_2$ group.

A "C-amido" group refers to a —C(=O)$NR^{13}R^{14}$ group with $R^{13}$ and $R^{14}$ as defined herein.

An "N-amido" group refers to a $R^{13}C$(=O)$NR^{14}$, with $R^{13}$ and $R^{14}$ as defined herein.

A "quaternary ammonium" group refers to a -$^+NHR^{13}R^{14}$ group wherein $R^{13}$ and $R^{14}$ are independently selected from the group consisting of alkyl, cycloalkyl, aryl, and heteroaryl.

A "ureido" group refers to a —$NR^{13}C$(=O)$NR^{14}R^{15}$ group, with $R^{13}$ and $R^{14}$ as defined herein and $R^{15}$ defined the same as $R^{13}$ and $R^{14}$.

A "guanidino" group refers to a —$R^{13}NC$(=N)$NR^{14}R^{15}$ group, with $R^{13}$ and $R^{14}$ as defined herein and $R^{15}$ defined the same as $R^{13}$ and $R^{14}$.

A "guanyl" group refers to a $R^{13}R^{14}NC$(=N)— group, with $R^{13}$ and $R^{14}$. as defined herein.

A "nitro" group refers to a —$NO_2$ group.

A "cyano" group refers to a —C≡N group.

A "silyl" group refers to a —Si(R")$_3$, with R" as defined herein.

A "spirocycloalkyl" group refers to a cycloalkyl group which shares one ring carbon atom with another ring.

A "spiroheteroalicyclyl" group refers to a heteroalicyclic group which shares a ring carbon atom with another ring.

B. Preferred Structural Features.

Preferred structural features of this invention are those in which:

A is nitrogen;

B is carbon;

$R^7$ is selected from the group consisting of hydrogen, unsubstituted lower alkyl, unsubstituted aryl and unsubstituted heteroaryl; and/or $R^8$, $R^9$, $R^{10}$ and $R^{11}$ are independently selected from the groups consisting of halo, unsubstituted lower alkoxy, carbonyl, amino and S-sulfonamido, N-sulfonamido, sulfonyl, C-carboxy and O-carboxy.

Also preferred are structures in which:

A is oxygen;

B is carbon; and/or $R^7$ is selected from the group consisting of hydrogen, alkyl, cycloalkyl, aryl, C-carboxy and cyano.

Further preferred structural features are those in which:

A is sulfur;

B is carbon; and/or $R^7$ is selected from the group consisting of hydrogen, alkyl, cycloalkyl, alkenyl, C-carboxy, hydroxy, alkoxy, cycloalkoxy and aryloxy.

A still further preferred embodiment of the present invention are those in which:

$R^8$, $R^9$, $R^{10}$ and $R^{11}$ are independently selected from the group consisting of hydrogen, alkyl, trihalomethyl, alkoxy, amino, halo, nitro, C-carboxy, C-amido, O-carbamyl and S-sulfonamido.

In preferred embodiments:

A is nitrogen;

B is carbon;

Z is oxygen;

$R^1$, $R^2$, $R^3$, $R^{3'}$, $R^4$, $R^{4'}$, $R^5$, $R^{5'}$, $R^6$, $R^{6'}$ $R^7$, $R^8$, $R^{10}$ and $R^{11}$ are hydrogen; and/or $R^9$ is a S-sulfonamido wherein $R^{13}$ and $R^{14}$ are independently selected from the group of hydrogen or methyl and preferably are either both hydrogen or both methyl.

Finally, it is a preferred embodiment of this invention that "alkyl" be unsubstituted lower alkyl, or lower alkyl substituted with one or more halogens, carboxy, unsubstituted heteroaryl, unsubstituted heteroalicyclic.

The chemical formulae referred to herein may exhibit the phenomena of tautomerism and structural isomerism. For example, the compounds described herein may adopt a cis or trans configuration about the double bond connecting the 2-indolinone ring to the cyclohexanoheteroaryl moiety or they may be a mixture of cis and trans. In addition, the groups attached to the cyclohexanyl ring; i.e., $R^3$, $R^{3'}$, $R^4$, $R^{4'}$, $R^5$, $R^{5'}$, $R^6$ and $R^{6'}$ may each adopt the axial or equatorial orientation with respect to the cyclohexanyl ring. This invention encompasses any tautomeric or structural isomeric form and mixtures thereof which possess the ability to modulate RTK and/or CTK activity and is not limited to any one tautomeric or structural isomeric form.

As used herein, the term "cis" refers to the structural configuration wherein the cycohexanoheteroaryl group is on the same side of the double bond connecting it to the 2-indolinone ring as the keto oxygen of the 2-indolinone.

As used herein, the term "trans" refers to the structural configuration wherein the cyclohexanoheteroaryl group is on the opposite side of the double bond connecting it to the 2-indolinone ring as the keto oxygen of the 2-indolinone.

As used herein the term "axial" is a term well-known to those of ordinary skill in the chemical arts are refers to a conformation in which the "axial" bond is essentially perpendicular to the place of the cyclohexano group.

As used herein, the term "equitorial" is a term well-known to those of ordinary skill in the chemical arts and refers to confromation in which the "equatorial" bond is essentially parallel to the plane of the cyclohexano group.

As used herein, a "cyclohexano" group refers to that portion of Formula 1 consisting of the 6-carbon ring which shares two carbon atoms with the heteroaryl group.

Some preferred indolinone compounds of the invention are listed in Table 1, while other preferred compounds are selected from the group consisting of 6-methoxy-3-(4,5,6,7-tetrahydro-1H-indol-2-ylmethylene)-1,3-dihydro-indol-2-one, 5-(2-bromoethyl)-3-(4,5,6,7-tetrahydro-1H-indol-2-ylmethylene)-1,3-dihydro-indol-2-one, 5-acetyl-3-(4,5,6,7-tetrahydro-1H-indol-2-ylmethylene)-1,3-dihydro-indol-2-one, 6-chloro-3-(4,5,6,7-tetrahydro-1H-indol-2-ylmethylene)-1,3-dihydro-indol-2-one, 6-hydroxy-3-(4,5,6,7-tetrahydro-1H-indol-2-ylmethylene)-1,3-dihydro-indol-2-one, 6-(3-methoxyphenyl)-3-(4,5,6,7-tetrahydro-1H-indol-2-ylmethylene)-1,3-dihydro-indol-2-one, 6-bromo-3-(4,5,6,7-tetrahydro-1H-indol-2-ylmethylene)-1,3-dihydro-indol-2-one, 7-bromo-5-methyl-3-(4,5,6,7-tetrahydro-1H-indol-2-ylmethylene)-1,3-dihydro-indol-2-one, 6-bromo-3-(3-methyl-4,5,6,7-tetrahydro-1H-indol-2-ylmethylene)-1,3-dihydro-indol-2-one, 6-(3-methoxyphenyl)-3-(3-methyl-4,5,6,7-tetrahydro-1H-indol-2-ylmethylene)-1,3 -dihydro-indol-2-one, 6-(3-ethoxyphenyl)-3-(4,5,6,7-tetrahydro-1H-indol-2-ylmethylene)-1,3-dihydro-indol-2-one, 6-phenyl-3-(4,5,6,7-tetrahydro-1H-indol-2-ylmethylene)-1,3-dihydro-indol-2-one, 6-(4-methoxyphenyl)-3-(4,5,6,7-tetrahydro-1H-indol-2-ylmethylene)-1,3-dihydro-indol-2-one, 6-(4-methoxyphenyl)-3-(3-methyl-4,5,6,7-tetrahydro-1H-indol-2-ylmethylene)-1,3-dihydro-indol-2-one, 6-(2-methoxyphenyl)-3-(3-methyl-4,5,6,7-tetrahydro-1H-indol-2-ylmethylene)-1,3-dihydro-indol-2-one, and 2-oxo-3-(4,5,6,7-tetrahydro-1H-indol-2-ylmethylene)-2,3-dihydro-1H-indol-4-carboxylic acid. Two other preferred compounds of the invention include 3-(4,5,6,7-tetrahydroinden-2-methyidenyl)-5-[N,N-dimethylaminosulforyl]-2-indolinone and 3-(4,5,6,7-tetrahydroinden-2-methylidenyl)-5-[aminosulfonyl]-2-indolinone. It is understood that the present invention not only contemplates the compounds mentioned above, but that the pharmaceutically acceptable salts or prodrugs of the above compounds are also within the scope of the present invention.

C. Methods of Synthesis and Combinatorial Libraries

In another aspect, the invention provides a combinatorial library of at least 10 3-(cyclohexanoheteroarylidene)-2-indolinone compounds that can be formed by reacting an oxindole with an acyl compound. The oxindole has a structure set forth in formula 2

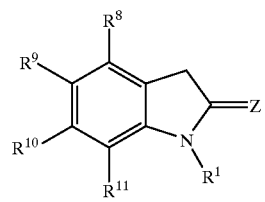

(2)

where

Z is selected from the group consisting of oxygen, sulfur and $NR^{12}$, where

R$^{12}$ is selected from the group consisting of hydrogen, alkyl, cycloalkyl, aryl, hydroxy, alkoxy, aryloxy, carbonyl, C-carboxy, O-carboxy, C-amido, guanyl, sulfonyl and trihalomethanesulfonyl;

R$^1$ is selected from the group consisting of hydrogen, alkyl, cycloalkyl, alkenyl, alkynyl, aryl, hydroxy, alkoxy, C-carboxy, C-amido, trihalomethanecarbonyl, trihalomethane- sulfonyl and sulfonyl; and R$^8$, R$^9$, R$^{10}$ and R$^{11}$ are independently selected from the group consisting of hydrogen, alkyl, trihaloalkyl, alkenyl, alkynyl, cycycloalkyl, aryl, heteroaryl, heteroalicyclic , hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicycloxy, halo, nitro, cyano, O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —NR$^{13}$R$^{14}$, where, R$^{13}$ and R$^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

and where the acyl compound has the structure set forth in formula 3

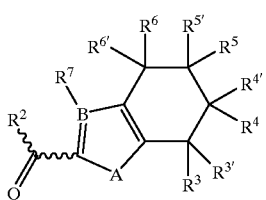

(3)

where

R$^2$ is selected from the group consisting of hydrogen, alkyl, cycloalkyl, aryl and halogen;

R$^3$, R$^{3'}$, R$^4$, R$^{4'}$, R$^5$, R$^{5'}$, R$^6$, and R$^{6'}$ are independently selected from the group consisting of hydrogen, alkyl, trihaloalkyl, cycloalkyl, alkenyl, alkynyl, aryl, heteroaryl, heteroalicyclic, alkoxy, aryloxy, thioalkoxy, thioaryloxy, heteroaryloxy, heteroalicycloxy, sulfinyl, sulfonyl, S-sulfonamido, N-Sulfonamido, trihalomethanesulfonyl, carbonyl, C-carboxy, O-carboxy, C-amido, N-amido, cyano, nitro, halo, O-carbamyl, N-carbamyl, O-thiocarbamyl, phosphonyl, N-thiocarbamyl, guanyl, guanidino, ureido, amino, trihalomethanesulfonamido, and —NR$^{12}$R$^{13}$;

where

R$^{12}$ and R$^{13}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

when any of R$^3$, R$^4$, R$^5$ and R6 are hydrogen, R$^{3'}$, R$^{4'}$, R$^{5'}$ and R$^{6'}$, respectively, in addition to being independently selected from the above group, may be indendently selected from the group consisting of hydroxy and thiohydroxy;

combined, R$^3$ and R$^{3'}$, R$^4$ and R$^{4'}$, R$^5$ and R$^{5'}$, and R$^6$ and R$^{6'}$ may be independently selected from the group consisting of keto, five-member spirocycloalkyl, five-member spiroheteroalicyclyl, six-member spirocycloalkyl and six member spiroheteroalicyclyl;

and

R$^7$ is selected from the group consisting of hydrogen, alkyl, cycloalkyl, trihaloalkyl alkenyl, alkynyl, aryl, heteroaryl, C-carboxy, O-carboxy, halo, cyano, nitro, hydroxy, alkoxy.

The oxindole used in the combinatorial library is preferably selected from the group consisting of 2-indolinone, 5-acetyl-2-indolinone, 5-amino-2-indolinone, 5-aminosulfonyl-2-indolinone, 5-bromo-2-indolinone, 6-bromo-2-indolinone, 7-bromo-5-chloro-2-indolinone, 5-bromo-4-methyl-2-indolinone, 7-bromo-5-methyl-2-indolinone, 5-(2-bromoethyl)-2-indolinone, 5-n-butyl-2-indolinone, 5-carboxy-2-indolinone, 5-(4-carboxybenzamido)-2-indolinone, 5-(2-carboxyethyl)-2-indolinone, 5-(2-carboxyethyl)-4-methyl-2-indolinone, 5-chloro-2-indolinone, 6-chloro-2-indolinone, 5-chloro-7-methyl-2-indolinone, 5-(2-chloroethyl)-2-indolinone, 5,7-dibromo-2-indolinone, 5,7-dibromo-4-methyl-2-indolinone, 5,6-dimethoxy-2-indolinone, 4,6-dimethyl-2-indolinone, 6-(3-ethoxyphenyl)-2-indolinone, 5-ethyl-2-indolinone, 5-fluoro-2-indolinone, 6-fluoro-2-indolinone, 7-fluoro-2-indolinone, 6-hydroxy-2-indolinone, 5-iodo-2-indolinone, 5-iodo-4-methyl-2-indolinone, 5-methoxy-2-indolinone, 6-methoxy-2-indolinone, 5-methoxycarbonyl-2-indolinone, 5-(4-methoxycarbonylbenzamido)-2-indolinone, 6-(2-methoxyphenyl)-2-indolinone, 6-(3-methoxyphenyl)-2-indolinone, 6-(4-methoxyphenyl)-2-indolinone, 4-methyl-2-indolinone, 5-methyl-2 -indolinone, 5-methylaminosulfonyl-2-indolinone, 5-(morpholin-4-sulfonyl)-2-indolinone, 5-(2-morpholin-4-ethyl)-2-indolinone, 5-nitro-2-indolinone, 6-phenyl-2-indolinone, 5-(piperidin-1-acetyl)-2-indolinone, 5-(2-piperidin-1-acetyl)-2-indolinone, 5-(2-piperidin-1-ethyl)-2-indolinone, 5-(2-pyrrolidin-1-ethyl)-2-indolinone, 5-trifluoromethyl-2-indolinone, 6-trifluoromethyl-2-indolinone, 5-[4-(trifluoromethyl)phenylaminosulfonyl]-2-indolinone, and 2-oxo-2,3-dihydro-1H-indole-4-carboxylic acid.

The acyl compound is preferably selected from the group consisting of 2-formyl-4,5,6,7-tetrahydrobenzofuran, 3-cyano-2-formyl-4,5,6,7-tetrahydrobenzofuran, 3-ethoxycarbonyl-2-formyl-4,5,6,7-tetrahydrobenzofuran, 3-ethyl-2-formyl-4,5,6,7-tetrahydrobenzofuran, 2-formyl-3-methyl-4,5,6,7-tetrahydrobenzofuran, 2-formyl-3-(4-methylphenyl)-4,5,6,7-tetrahydrobenzofuran, 2-formyl-3-n-pentyl-4,5,6,7-tetrahydrobenzofuran, 2-formyl-3-phenyl-4,5,6,7-tetrahydrobenzofuran, 2-formyl-3-phenylaminomethyl-4,5,6,7-tetrahydrobenzofuran, 2-formyl-3-phenylsulfonylmethyl-4,5,6,7-tetrahydrobenzofuran, 2-formyl-4,5,6,7-benzimidazol, 2-formyl-4,5,6,7-tetrahydrobenzoxazol, 2-formyl-4,5,6,7-tetrahydroindole, 2-formyl-3-ethyl-4,5,6,7-tetrahydroindole, 2-formyl-4-ethyl-4,5,6,7-tetrahydroindole, 2-formyl-3-methyl-4,5,6,7-tetrahydroindole, 2-formyl-4-methyl-4,5,6,7-tetrahydroindole, 2-formyl-4,4-dimethyl-4,5,6,7-tetrahydroindole, 3-carboxy-2-formyl-4,5,6,7-tetrahydroindole, 4-carboxymethyl-2-formyl-4,5,6,7-tetrahydroindole, 2-formyl-3-isopropyl-4,5,6,7-tetrahydroindole, 2-formyl-4-isopropyl-4,5,6,7-tetrahydroindole, 2-formyl-3-(isoquinoline-1-methyl)-4,5,6,7-tetrahydroindole, 2-formyl-3-hydroxy-4,5,6,7-tetrahydroindole, 2-formyl-4-phenyl-4,5,6,7-tetrahydroindole, 2-formyl-4,5,6,7-tetrahydrobenzothiene, 2-formyl-3-methoxycarbonyl-4,5,6,7- tetrahydrobenzothiene, 2-formyl-3-vinyl-4,5,6,7-tetrahydrobenzothiene, 3-carboxy-2-formyl-4,5,6,7-tetrahydrobenzothiene, 3-ethoxycarbonyl-2-formyl-4,5,6,7-tetrahydrobenzothiene, 3-(3-dimethylamino-n-propoxycarbonyl)-2-formyl-4,5,6,7-tetrahydrobenzothiene, 3-(2-methylaminoethyl)-2-formyl-4,5,6,7-tetrahydrobenzothiene, 3-(2-diethylaminoethoxycarbonyl)-2-formyl-4,5,6,7-tetrahydrobenzothiene, 3-cyclopropylmethoxy-2-formyl-4,5,6,7-tetrahydrobenzothiene, and 2-formyl-4,5,6,7-tetrahydrobenzothiazole.

A "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the acyl compounds of the invention. Each oxindole may be reacted with each and every acyl compound in order to form an indolinone compound. All indolinone compounds formed in this way are within the scope of the present invention. Also within the scope of the present invention are smaller combinatorial libraries formed by the reaction of some of the oxindoles with all of the acyl compounds, all of the oxindoles with some of the acyl compounds, or some of the oxindoles with some of the acyl compounds.

By "acyl compound" it is meant a compound of the formula R—C(O)—R', where R and R' can be independently organic groups or hydrogen. Thus, aldehydes and ketones are examples of acyl compounds.

Another aspect of the invention provides for a method for synthesizing an indolinone compound of formula 1, as described herein, comprising the step of reacting a first reactant with a second reactant in a solvent and in the presence of a base at elevated temperatures, where the first reactant is an oxindole having the structure set forth in formula 2 and the second reactant is an acyl compound, having a structure set forth in formula 3, as those formulae are described herein.

The first reactant is most preferably an oxindole selected from the group consisting of 2-indolinone, 5-acetyl-2-indolinone, 5-amino-2-indolinone, 5-aminosulfonyl-2-indolinone, 5-bromo-2-indolinone, 6-bromo-2-indolinone, 7-bromo-5-chloro-2-indolinone, 5-bromo-4-methyl-2-indolinone, 7-bromo-5-methyl-2-indolinone, 5-(2-bromoethyl)-2-indolinone, 5-n-butyl-2-indolinone, 5-carboxy-2-indolinone, 5-(4-carboxybenzamido)-2-indolinone, 5-(2-carboxyethyl)-2-indolinone, 5-(2-carboxyethyl)-4-methyl-2-indolinone, 5-chloro-2-indolinone, 6-chloro-2-indolinone, 5-chloro-7-methyl-2-indolinone, 5-(2-chloroethyl)-2-indolinone, 5,7-dibromo-2-indolinone, 5,7-dibromo-4-methyl-2-indolinone, 5,6-dimethoxy-2-indolinone, 4,6-dimethyl-2-indolinone, 6-(3-ethoxyphenyl)-2-indolinone, 5-ethyl-2-indolinone, 5-fluoro-2-indolinone, 6-fluoro-2-indolinone, 7-fluoro-2-indolinone, 6-hydroxy-2-indolinone, 5-iodo-2-indolinone, 5-iodo-4-methyl-2-indolinone, 5-methoxy-2-indolinone, 6-methoxy-2-indolinone, 5-methoxycarbonyl-2-indolinone, 5-(4-methoxycarbonylbenzamido)-2-indolinone, 6-(2-methoxyphenyl)-2-indolinone, 6-(3-methoxyphenyl)-2-indolinone, 6-(4-methoxyphenyl)-2-indolinone, 4-methyl-2-indolinone, 5-methyl-2-indolinone, 5-methylaminosulfonyl-2-indolinone, 5-(morpholin-4-sulfonyl)-2-indolinone, 5-(2-morpholin-4-ethyl)-2-indolinone, 5-nitro-2-indolinone, 6-phenyl-2-indolinone, 5-(piperidin-1-acetyl)-2-indolinone, 5-(2-piperidin-1-acetyl)-2-indolinone, 5-(2-piperidin-1-ethyl)-2-indolinone, 5-(2-pyrrolidin-1-ethyl)-2-indolinone, 5-trifluoromethyl-2-indolinone, 6-trifluoromethyl-2-indolinone, 5-[4-(trifluoromethyl)phenylaminosulfonyl]-2-indolinone, and 2-oxo-2,3-dihydro-1H-indole-4-carboxylic acid.

The second reactant is preferably an acyl compound selected from the group consisting of 2-formyl-4,5,6,7-tetrahydrobenzofuran, 3-cyano-2-formyl-4,5,6,7-tetrahydrobenzofuran, 3-ethoxycarbonyl-2-formyl-4,5,6,7-tetrahydrobenzofuran, 3-ethyl-2-formyl-4,5,6,7-tetrahydrobenzofuran, 2-formyl-3-methyl-4,5,6,7-tetrahydrobenzofuran, 2-formyl-3-(4-methylphenyl)-4,5,6,7-tetrahydrobenzofuran, 2-formyl-3-n-pentyl-4,5,6,7-tetrahydrobenzofuran, 2-formyl-3-phenyl-4,5,6,7-tetrahydrobenzofuran, 2-formyl-3-phenylaminomethyl-4,5,6,7-tetrahydrobenzofuran, 2-formyl-3-phenylsulfonylmethyl-4,5,6,7-tetrahydrobenzofuran, 2-formyl-4,5,6,7-benzimidazol, 2-formyl-4,5,6,7-tetrahydrobenzoxazol, 2-formyl-4,5,6,7-tetrahydroindole, 2-formyl-3-ethyl-4,5,6,7-tetrahydroindole, 2-formyl-4-ethyl-4,5,6,7-tetrahydroindole, 2-formyl-3-methyl-4,5,6,7-tetrahydroindole, 2-formyl-4-methyl-4,5,6,7-tetrahydroindole, 2-formyl-4,4-dimethyl-4,5,6,7-tetrahydroindole, 3-carboxy-2-formyl-4,5,6,7-tetrahydroindole, 4-carboxymethyl-2-formyl-4,5,6,7-tetrahydroindole, 2-formyl-3-isopropyl-4,5,6,7-tetrahydroindole, 2-formyl-4-isopropyl-4,5,6,7-tetrahydroindole, 2-formyl-3-(isoquinoline-1-methyl)-4,5,6,7-tetrahydroindole, 2-formyl-3-hydroxy-4,5,6,7-tetrahydroindole, 2-formyl-4-phenyl-4,5,6,7-tetrahydroindole, 2-formyl-4,5,6,7-tetrahydrobenzothiene, 2-formyl-3-methoxycarbonyl-4,5,6,7-tetrahydrobenzothiene, 2-formyl-3-vinyl-4,5,6,7-tetrahydrobenzothiene, 3-carboxy-2-formyl-4,5,6,7-tetrahydrobenzothiene, 3-ethoxycarbonyl-2-formyl-4,5,6,7-tetrahydrobenzothiene, 3-(3-dimethylamino-n-propoxycarbonyl)-2-formyl-4,5,6,7-tetrahydrobenzothiene, 3-(2-methylaminoethyl)-2-formyl-4,5,6,7-tetrahydrobenzothiene, 3-(2-diethylaminoethoxycarbonyl)-2-formyl-4,5,6,7-tetrahydrobenzothiene, 3-cyclopropylmethoxy-2-formyl-4,5,6,7-tetrahydrobenzothiene, and 2-formyl-4,5,6,7-tetrahydrobenzothiazole.

To synthesize the compounds of the invention a base may be used. The base is preferably a nitrogen base or an inorganic base. "Nitrogen bases" are commonly used in the art and are selected from acyclic and cyclic amines. Examples of nitrogen bases include, but are not limited to, ammonia, methylamine, trimethylamine, triethylamine, aniline, 1,8-diazabicyclo[5.4.0]undec-7-ene, diisopropylethylamine, pyrrolidine, and piperidine. "Inorganic bases" are bases that do not contain any carbon atoms. Examples of inorganic bases include, but are not limited to, hydroxide, phosphate, bisulfate, hydrosulfide, and amide anions. Those skilled in the art know which nitrogen base or inorganic base would match the requirements of the reaction conditions. In certain embodiments of the invention, the base used may be pyrrolidine or piperidine. In other embodiments the base may be the hydroxide anion, preferably used as its sodium or potassium salt.

The synthesis of the compounds of the invention takes place in a solvent. The solvent of the reaction is preferably a protic solvent or an aprotic solevent. "Protic solvents" are those that are capable of donating a proton to a solute. Examples of protic solvents include, but are not limited to, alcohols and water. "Aprotic solvents" are those solvents that, under normal reaction conditions, do not donate a proton to a solute. Typical organic solvents, such as hexane, toluene, benzene, methylene chloride, dimethylformamide, chloroform, tetrahydrofuran, are some of the examples of aprotic solvents. Other aprotic solvents are also within the scope of used by the present invention. In some preferred embodiments, the solvent of the reaction is an alcohol, which may preferably be isopropanol or most preferably ethanol. Water is another preferred protic solvent. Dimethylformamide, known in the chemistry art as DMF, is a preferred aprotic solvent.

The synthetic method of the invention calls for the reaction to take place at elevated temperatures which are temperatures that are greater than room temperature. More preferably, the elevated temperature is preferably about 30–150° C., more preferably is about 80–100° C., and most preferably is about 80–90° C., which is about the temperature at which ethanol boils (i.e., the boiling point of ethanol). By "about" a certain temperature it is meant that the temperature range is preferably within 10° C. of the listed temperature, more preferably within 5° C. of the listed temperature, and most preferably within 2° C. of the listed temperature. Therefore, by way of example, by "about 80° C." it is meant that the temperature range is preferably 80 ±10° C., more preferably 80±5° C., and most preferably 80±2° C.

The synthetic method of the invention may be accompanied by the step of screening a library for a compound of the desired activity and structure—thus, providing a method of synthesis of a compound by first screening for a compound having the desired properties and then chemically synthesizing that compound.

2. THE BIOCHEMISTRY

In yet another embodiment, this invention relates to a method for the modulation of the catalytic activity of PTKs comprising administering a compound of this invention or a physiologically acceptable salt or a prodrug thereof to a PTK.

By "PTK" is meant both RTKs and CTKs; i.e., the modulation of both RTK signal transduction and CTK signal transduction is contemplated by this invention.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmacological, biological, biochemical and medical arts.

As used herein, the term "modulation" or "modulating" refers to the alteration of the catalytic activity of RTKs and/or CTKs. In particular, modulating refers to the activation of the catalytic activity of RTKs and/or CTKs, more preferably the activation or inhibition of the catalytic activity of RTKs and/or CTKS, depending on the concentration of the compound administered or, more preferably still, the inhibition of the catalytic activity of RTKs and/or CTKs.

The term "catalytic activity" as used herein refers to the rate of phosphorylation of tyrosine under the influence, direct or indirect of RTKs and/or CTKs.

The term "administering" as used herein refers to a method for bringing a compound of this invention and a target PK together in such a manner that the compound can affect the catalytic activity of the PK either directly; i.e., by interacting with the kinase itself, or indirectly; i.e. by interacting with another molecule on which the catalytic activity of the kinase is dependent. As used herein, administration can be accomplished either in vitro, i.e. in a test tube, or in vivo, i.e. in cells or tissues of a living organism.

Thus, the TK mediated disorders which are the object of this invention can be studied, prevented or treated by the methods set forth herein whether the cells or tissues of the organism exist within the organism or outside the organism. Cells existing outside the organism can be maintained or grown in cell culture dishes. In this context, the ability of a particular compound to affect a PTK related disorder can be determined; i.e., the IC50 of the compound, defined below, before the use of the compounds in more complex living organisms is attempted. For cells outside the organism, multiple methods exist, and are well-known to those skilled in the art, to administer compounds including, but not limited to, direct cell microinjection and numerous transmembrane carrier techniques. For cells harbored within a living organism, myriad methods also exist, and are likewise well-known to those skilled in the art, to administer compounds including, but not limited to, oral, parenteral, dermal and aerosol applications.

RTK mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, *Neuron* 9:303–391.

It has been shown that tyrosine phosphorylation sites in growth factor receptors function as high-affinity binding sites for SH2 (src homology) domains of signaling molecules. Fantl et al., 1992, *Cell* 69:413–423; Songyang et al., 1994, *Mol. Cell. Biol.* 14:2777–2785); Songyang et al., 1993, *Cell* 72:767–778; and Koch et al., 1991, *Science* 252:668–678. Several intracellular substrate proteins that associate with RTKs have been identified. They may be divided into two principal groups: (1) substrates which have a catalytic domain; and (2) substrates which lack such domain but serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

PTK signal transduction results in, among other responses, cell proliferation, differentiation, growth and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

A precise understanding of the mechanism by which the compounds of this invention inhibit PTKs is not required in order to practice the present invention. However, while not being bound to any particular mechanism or theory, it is believed that the compounds interact with the amino acids of the catalytic region of PTKs. PTKs typically possess a bi-lobate structure wherein ATP appears to bind in the cleft between the two lobes in a region where the amino acids are conserved among PTKs. Inhibitors of PTKs are believed to bind by non-covalent interactions such as hydrogen bonding, van der Waals forces and ionic interactions in the same general region where the aforesaid ATP binds to the PTKs. More specifically, it is thought that the indolinone component of the compounds of this invention binds in the general space normally occupied by the adenine ring of ATP. Specificity of a particular molecule for a particular PTK could arise as the result of additional interactions between the various substituents on the indolinone core with amino acid domains specific to particular PTKs. Thus, different indolinone substituents may contribute to preferential binding to particular PTKs. The ability to select those compounds active at different ATP (or other nucleotide) binding sites makes the compounds useful for targeting any protein with such a site; i.e., not only PTKs but serine/threonine kinases and protein phosphatases as well. Thus, the compounds disclosed herein have utility for in vitro assays on such proteins and for in vivo therapeutic effects through such proteins.

Thus, in another aspect, this invention relates to a method for treating or preventing a PTK related disorder by administering a therapeutically effective amount of a compound of this invention or a salt or a prodrug thereof to an organism.

As used herein, "PTK related disorder," "PTK driven disorder," and "abnormal PTK activity" all refer to a disorder characterized by inappropriate or over-activity of PTKs, which can be either RTKs or CTKs. Inappropriate activity refers to either: (1) PTK expression in cells which normally do not express PTKs; (2) increased PTK expression leading to unwanted cell proliferation, differentiation and/or growth; or, (3) decreased PTK expression leading to unwanted reductions in cell proliferation, differentiation and/or growth. Overactivity of PTKs refers to either amplification of the gene encoding a particular PTK or production of a level of PTK activity which can correlate with a cell proliferation, differentiation and/or growth disorder (that is, as the level of the PTK increases, the severity of one or more of the symptoms of the cellular disorder increases).

As used herein, the terms "prevent", "preventing" and "prevention" refer to a method for barring an organism from the first place acquiring an PTK mediated cellular disorder.

As used herein, the terms "treat", "treating" and "treatment" refer to a method of alleviating or abrogating the PTK mediated cellular disorder and/or its attendant symptoms. With regard particularly to cancer, these terms simply mean that the life expectancy or an individual affected with a cancer will be increased or that one or more of the symptoms of the disease will be reduced.

As used herein, the term "cancer" refers to various types of malignant neoplasms, most of which can invade surrounding tissues, and may metastasize to different sites, as defined by Stedman's Medical Dictionary 25th edition (Hensyl ed. 1990). Examples of cancers which may be treated by the present invention include, but are not limited to, brain, ovarian, colon, prostate, kidney, bladder, breast, lung, oral and skin cancers which exhibit inappropriate PTK activity. These types of cancers can be further characterized. For example, brain cancers include glioblastoma multiforme, anaplastic astrocytoma, astrocytoma, ependymoma, oligodendroglioma, medulloblastoma, meningioma, sarcoma, hemangioblastoma, and pineal parenchymal. Skin cancers include melanoma and Kaposi's sarcoma.

The term "organism" refers to any living entity comprised of at least one cell. A living organism can be as simple as, for example, a single eukariotic cell or as complex as a mammal, including a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer.

This invention is therefore directed to compounds which modulate PTK signal transduction by affecting the enzymatic activity of the RTKs and/or CTKs and thereby interfering with the signal transduced by such proteins. More particularly, the present invention is directed to compounds which modulate the RTK and/or CTK mediated signal transduction pathways as a therapeutic approach to cure many kinds of solid tumors, including but not limited to carcinoma, sarcoma, erythroblastoma, glioblastoma, meningioma, astrocytoma, melanoma and myoblastoma. Indications may include, but are not limited to brain cancers, bladder cancers, ovarian-cancers, gastric cancers, pancreas cancers, colon cancers, blood cancers, lung cancers, bone cancers and leukemias.

Further examples, without limitation, of the types of disorders related to unregulated PTK activity that the compounds described herein may be useful in preventing, treating and studying, are cell proliferative disorders, fibrotic disorders and metabolic disorders. Specific disorders to be treated and/or prevented with the present invention include src kinase related disorders, lck kinase related disorders, cancer, arterial restenosis, transplant rejection, autoimmune diseases, osteoporosis, psoriasis, metastasis, rheumatoid arthritis, inflammatory disease, fibrosis, and sclerosis.

Cell proliferative disorders which may be prevented, treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. For instance, PDGFR has been implicated in the maintenance of mesangial cell proliferation. Floege et al., 1993, *Kidney International* 43:47S–54S.

As noted previously, PTKs have been associated with cell proliferative disorders. For example, some members of the RTK family have been associated with the development of cancer. Some of these receptors, like EGFR (Tuzi et al., 1991, *Br. J. Cancer* 63:227–233; Torp et al., 1992, *APMIS* 100:713–719); HER2/neu (Slamon et al., 1989, *Science* 244:707–712) and PDGFR (Kumabe et al., 1992, *Oncogene*, 7:627–633) are over-expressed in many tumors and/or are persistently activated by autocrine loops. In fact, in the most common and severe cancers these receptor over-expressions and autocrine loops have been demonstrated (Akbasak and Suner-Akbasak et al., 1992, *J. Neurol. Sci.*, 111:119–133; Dickson et al., 1992, *Cancer Treatment Res.* 61:249–273; Korc et al., 1992, *J. Clin. Invest.* 90:1352–1360); (Lee and Donoghue, 1992, *J. Cell. Biol.*, 118:1057–1070; Korc et al., supra; Akbasak and Suner-Akbasak et al., supra). For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma, lung, ovarian, melanoma and prostate. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkins disease, Burkitts disease, and the lymphoma cell line.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.*, 50:2511–2517). In addition, IGF-I, while being integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression,* 1:301–326. In a series of recent publications, Baserga even suggests that IGF-IR plays a central role in the mechanisms of transformation and, as such, could be a preferred target for therapeutic interventions for a broad spectrum of human malignancies. Baserga, 1995, *Cancer Res.*, 55:249–252; Baserga, 1994, *Cell* 79:927–930; Coppola et al., 1994, *Mol. Cell. Biol.,* 14:4588–4595.

The association between abnormal RTK activity and disease are not restricted to cancer, however. For example, RTKs have been associated with metabolic diseases like psoriasis, diabetes mellitus, wound healing, inflammation, and neurodegenerative diseases. For example, EGFR has been indicated in corneal and dermal wound healing. Defects in the Insulin-R and IGF-1R are indicated in type-II diabetes mellitus. A more complete correlation between specific RTKs and their therapeutic indications is set forth in Plowman et al., 1994, *DN&P* 7:334–339.

As noted previously, not only RTKs but CTKs as well including, but not limited to, src, abl, fps, yes, fyn, lyn, lck, blk, hck, fgr and yrk (reviewed by Bolen et al., 1992, *FASEB J.,* 6:3403–3409) are involved in the proliferative and metabolic signal transduction pathway and thus were expected, and have been shown, to be involved in many PTK-mediated disorders to which the present invention is directed. For example, mutated src (v-src) has been demonstrated as an oncoprotein ($pp60^{v\text{-}src}$) in chicken. Moreover, its cellular homolog, the proto-oncogene $pp60^{c\text{-}src}$ transmits oncogenic signals of many receptors. For example, over-expression of EGFR or HER2/neu in tumors leads to the constitutive activation of $pp60^{c\text{-}src}$, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders. Similarly, Zap70 is implicated in T-cell signaling.

Finally, both RTKs and CTKs are currently suspected as being involved in hyperimmune disorders.

DETAILED DESCRIPTION OF THE INVENTION

A compound of the present invention, or its physiologically acceptable salt or prodrug, can be administered to a human patient per se, or in pharmacological compositions where it is mixed with suitable carriers or excipient(s). Techniques for formulation and administration of drugs may be found in "Remington's Pharmaceutical Sciences," Mack Publishing Co., Easton, Pa., latest edition.

1. Routes Of Administration.

Suitable routes of administration may include, without limitation, oral, rectal, transmucosal or intestinal administration or intramuscular, subcutaneous, intramedullary, intrathecal, direct intraventricular, intravenous, intraperitoneal or intranasal injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

2. Composition/Formulation.

Pharmacological compositions of the compounds and the physiologically acceptable salts and prodrugs thereof are preferred embodiments of this invention. Pharmacological compositions of the present invention may be manufactured by processes well known in the art; e.g., by means of conventional mixing, dissolving, granulating, dragee-making, levigating, emulsifying, encapsulating, entrapping or lyophilizing processes.

Pharmacological compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmacological preparations for oral use can be made with the use of a solid excipient, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active -compound doses.

Pharmacological compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichloro-tetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmacological compositions for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmacological compositions herein also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate, etc. formed by the reaction of an amino group with the appropriate acid. Salts in which the compound forms the negatively charged species include, without limitation, the sodium, potassium, calcium and magnesium salts formed by the reaction of a carboxyic acid group in the molecule with the appropriate base (e.g. sodium hydroxide (NaOH), potassium hydroxide (KOH), Calcium hydroxide (Ca(OH)$_2$), etc.).

3. Dosage.

Pharmacological compositions suitable for use in the present invention include compositions wherein the active ingredients are contained in an amount effective to achieve its intended purpose.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging.

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

5. Brief Description of the Tables.

Table 1 shows a list of exemplary compounds of this invention. The compounds in Table 1 are not to be construed as limiting the scope of this invention in any manner.

Table 2 shows the results of several biological assays using certain preferred structures of the present invention. IC50 refers to the amount (in micromoles, $\mu$M) of compound required to achieve 50% inhibition of the activity of the particular kinase being tested as compared to the activity of an untreated control.

TABLE 2

| COMPOUND | FLK-1R $IC_{50}$ ($\mu$m) | PDGF R $IC_{50}$ ($\mu$m) | EGFR $IC_{50}$ ($\mu$m) | HUV-EC-C VEGF ($\mu$m) | ATCC aFGF ($\mu$m) | SRC ($\mu$m) | LCK ($\mu$m) | FAK ($\mu$m) |
|---|---|---|---|---|---|---|---|---|
| 3-(4,5,6,7-tetrahydroinden-2-methyldenyl)-5-[N,N-dimethylaminosulforyl]-2-indolinone | >100 | >100 | >100.0 | | | 0.1 | 0.5 | >10 |
| 3-(4,5,6,7-tetrahydroinden-2-methylidenyl)-5-[aminosulfonyl]-2-indolinone | >100.0 | 1 | >100.0 | 0.65 1.07 | 2.4 3.3 | 0.8 | 0.7 | >10 |

---

3-(3-cyano-4,5,6,7-tetrahydrobenzofuran-2-methylidenyl)-5-(2-piperidin-1-ethyl)-2-indolinone
3-(3-phenylaminomethyl-4,5,6,7-tetrahydrobenzofuran-2-methylidenyl)-5-(2-piperidin-1-ethyl)-2-indolinone
3-(3-phenyl-4,5,6,7-tetrahydrobenzofuran-2-methylidenyl)-5-(2-piperidin-1-ethyl)-2-indolinone
3-(4,5,6,7-tetrahydrobenzimidazol-2-methylidenyl)-5-(2-piperidin-1-ethyl)-2-indolinone
3-(4,5,6,7-tetrahydrobenzoxazol-2-methylidenyl)-5-(2-piperidin-1-ethyl)-2-indolinone
3-(3-methyl-4,5,6,7-tetrahydroindol-2-methylidenyl)-5-(2-piperidin-1-ethyl)-2-indolinone -continued 3-(3-carboxy-4,5,6,7-tetrahydroindol-2-methylidenyl)-5-(2-piperidin-1-ethyl)-2-indolinone
3-(3-isoquinolin-1-methyl)-4,5,6,7-tetrahydroindol-2-methylidenyl)-5-(2-piperidin-1-ethyl)-2-indolinone
3-(3-hydroxy-4,5,6,7-tetrahydroindol-2-methylidenyl)-5-(2-piperidin-1-ethyl)-2-indolinone
3-(3-methoxy-4,5,6,7-tetrahydroindol-2-methylidenyl)-5-(2-piperidin-1-ethyl)-2-indolinone
3-(4,5,6,7-tetrahydroindol-2-methylidenyl)-5-(2-piperidin-1-ethyl)-2-indolinone
3-(4,5,6,7-tetrahydrobenzothien-2-methylidenyl)-5-(2-piperidin-1-ethyl)-2-indolinone
3-(3-methoxycarbonyl-4,5,6,7-tetrahydrobenzothien-2-methylidenyl)-5-(2-piperidin-1-ethyl)-2-indolinone
3-(3-vinyl-4,5,6,7-tetrahydrobenzothien-2-methylidenyl)-5-(2-piperidin-1-ethyl)-2-indolinone
3-(3-carboxy-4,5,6,7-tetrahydrobenzothien-2-methylidenyl)-5-(2-piperidin-1-ethyl)-2-indolinone
3-(3-ethoxycarbonyl-4,5,6,7-tetrahydrobenzothien-2-methylidenyl)-5-(2-piperidin-1-ethyl)-2-indolinone
3-[3-(3-dimethylamino-n-propoxycarbonyl)-4,5,6,7-tetrahydrobenzothien-2-methylidenyl]-5-(2-piperidin-1-ethyl)-2-indolinone
3-[3-(2-diethylaminoethyoxycarbonyl)-4,5,6,7-tetrahydrobenzothien-2-methylidenyl]-5-(2-piperidin-1-ethyl)-2-indolinone
3-[3-(2-methylaminoethyl)-4,5,6,7-tetrahydrobenzothien-2-methylidenyl]-5-(2-piperidin-1-ethyl)-2-indolinone
3-(3-cyclopropylmethoxy-4,5,6,7-tetrahydrobenzothien-2-methylidenyl)-5-(2-piperidin-1-ethyl)-2-indolinone
3-(4,5,6,7-tetrahydrobenzothiazol-2-methylidenyl)-5-(2-piperidin-1-ethyl)-2-indolinone
3-(4-methyl-4,5,6,7-tetrahydroindol-2-methylidenyl)-5-(2-piperidin-1-ethyl)-2-indolinone
3-(4,4-dimethyl-4,5,6,7-tetrahydroindol-2-methylidenyl)-5-(2-piperidin-1-ethyl)-2-indolinone
3-(4-ethyl-4,5,6,7-tetrahydroindol-2-methylidenyl)-5-(2-piperidin-1-ethyl)-2-indolinone
3-(4-phenyl-4,5,6,7-tetrahydroindol-2-methylidenyl)-5-(2-piperidin-1-ethyl)-2-indolinone
3-(3-ethyl-4,5,6,7-tetrahydroindol-2-methylidenyl)-5-(2-piperidin-1-ethyl)-2-indolinone
3-(3-isopropyl-4,5,6,7-tetrahydroindol-2-methylidenyl)-5-(2-piperidin-1-ethyl)-2-indolinone
3-(4,5,6,7-tetrahydroindol-3-methylidenyl)-5-(2-piperidin-1-ethyl)-2-indolinone
3-(4-isopropyl-4,5,6,7-tetrahydroindol-2-methylidenyl)-5-(2-piperidin-1-ethyl)-2-indolinone
3-(4-carboxymethyl-4,5,6,7-tetrahydroindol-2-methylidenyl)-5-(2-piperidin-1-ethyl)-2-indolinone
3-(3-methyl-4,5,6,7-tetrahydroinden-2-methylidenyl)-5-(2-pyrrolidin-1-ethyl)-2-indolinone
3-(3-ethoxycarbonyl-4,5,6,7-tetrahydrobenzofuran-2-methylidenyl)-5-(2-pyrrolidin-1-ethyl)-2-indolinone
3-(3-n-pentyl-4,5,6,7-tetrahydrobenzofuran-2-methylidenyl)-5-(2-pyrrolidin-1-ethyl)-2-indolinone
3-(3-ethyl-4,5,6,7-tetrahydrobenzofuran-2-methylidenyl)-5-(2-pyrrolidin-1-ethyl)-2-indolinone
3-(4,5,6,7-tetrahydrobenzofuran-2-methylidenyl)-5-(2-pyrrolidin-1-ethyl)-2-indolinone
3-[3-(4-methylphenyl)-4,5,6,7-tetrahydrobenzofuran-2-methylidenyl]-5-(2-pyrrolidin-1-ethyl)-2-indolinone
3-(3-phenylsulfonylmethyl-4,5,6,7-tetrahydrobenzofuran-2-methylidenyl)-5-(2-pyrrolidin-1-ethyl)-2-indolinone
3-[3-(1-phenylaminoethyl-4,5,6,7-tetrahydrobenzofuran-2-methylidenyl]-5-(2-pyrrolidin-1-ethyl)-2-indolinone
3-(3-phenylaminomethyl-4,5,6,7-tetrahydrobenzofuran-2-methylidenyl)-5-(piperidin-1-acetyl)-2-indolinone
3-(3-phenyl-4,5,6,7-tetrahydrobenzofuran-2-methylidenyl)-5-(piperidin-1-acetyl)-2-indolinone
3-(4,5,6,7-tetrahydrobenzimidazol-2-methylidenyl)-5-(piperidin-1-acetyl)-2-indolinone
3-(4,5,6,7-tetrahydrobenzoxazol-2-methylidenyl)-5-(piperidin-1-acetyl-2-indolinone
3-(3-methyl-4,5,6,7-tetrahydroindol-2-methylidenyl)-5-(piperidin-1-acetyl)-2-indolinone
3-(3-carboxy-4,5,6,7-tetrahydroindol-2-methylidenyl)-5-(piperidin-1-acetyl)-2-indolinone
3-[(isoquinolin-1-methyl)-4,5,6,7-tetrahydroindol-2-methylidenyl]-5-(piperidin-1-acetyl)-2-indolinone
3-(3-hydroxy-4,5,6,7-tetrahydroindol-2-methylidenyl)-5-(piperidin-1-acetyl)-2-indolinone
3-(3-methoxy-4,5,6,7-tetrahydroindol-2-methylidenyl)-5-(piperidin-1-acetyl)-2-indolinone
3-(4,5,6,7-tetrahydroindol-2-methylidenyl)-5-(piperidin-1-acetyl)-2-indolinone
3-(4,5,6,7-tetrahydrobenzothien-2-methylidenyl)-5-(piperidin-1-acetyl)-2-indolinone
3-(3-methoxycarbonyl-4,5,6,7-tetrahydrobenzothien-2-methylidenyl)-5-(piperidin-1-acetyl)-2-indolinone
3-(3-vinyl-4,5,6,7-tetrahydrobenzothien-2-methylidenyl)-5-(piperidin-1-acetyl)-2-indolinone
3-(3-carboxy-4,5,6,7-tetrahydrobenzothien-2-methylidenyl)-5-(piperidin-1-acetyl)-2-indolinone
3-(3-ethoxycarbonyl-4,5,6,7-tetrahydrobenzothien-2-methylidenyl)-5-(piperidin-1-acetyl)-2-indolinone
3-[3-(3-dimethylamino-n-propoxycarbonyl)-4,5,6,7-tetrahydrobenzothien-2-methylidenyl]-5-(piperidin-1-acetyl)-2-indolinone
3-[3-(2-diethylaminoethoxycarbonyl)-4,5,6,7-tetrahydrobenzothien-2-methylidenyl]-5-(piperidin-1-acetyl)-2-indolinone
3-[3-(2-methylaminoethyl)-4,5,6,7-tetrahydrobenzothien-2-methylidenyl]-5-(piperidin-1-acetyl)-2-indolinone
3-(3-cyclopropylmethoxy-4,5,6,7-tetrahydrobenzothien-2-methylidenyl)-5-(piperidin-1-acetyl)-2-indolinone
3-(4,5,6,7-tetrahydrobenzothiazol-2-methylidenyl)-5-(piperidin-1-acetyl)-2-indolinone
3-(4-methyl-4,5,6,7-tetrahydroindol-2-methylidenyl)-5-(piperidin-1-acetyl)-2-indolinone
3-(4,4-dimethyl-4,5,6,7-tetrahydroindol-2-methylidenyl)-5-(piperidin-1-acetyl)-2-indolinone
3-(4-ethyl-4,5,6,7-tetrahydroindol-2-methylidenyl)-5-(piperidin-1-acetyl)-2-indolinone
3-(4-phenyl-4,5,6,7-tetrahydroindol-2-methylidenyl)-5-(piperidin-1-acetyl)-2-indolinone
3-(3-ethyl-4,5,6,7-tetrahydroindol-2-methylidenyl)-5-(piperidin-1-acetyl)-2-indolinone
3-(3-isopropyl-4,5,6,7-tetrahydroindol-2-methylidenyl)-5-(piperidin-1-acetyl)-2-indolinone
3-(4,5,6,7-tetrahydroindol-2-methylidenyl)-5-(piperidin-1-acetyl)-2-indolinone
3-(4-isopropyl-4,5,6,7-tetrahydroindol-2-methylidenyl)-5-(piperidin-1-acetyl)-2-indolinone
3-(4-carboxymethyl-4,5,6,7-tetrahydroindol-2-methylidenyl)-5-(piperidin-1-acetyl)-2-indolinone
3-(3-methyl-4,5,6,7-tetrahydroinden-2-methylidenyl)-5-(piperidin-1-ethyl)-2-indolinone
3-(4,5,6,7-tetrahydroinden-2-methylidenyl)-5-(piperidin-1-ethyl)-2-indolinone
3-(3-methyl-4,5,6,7-tetrahydrobenzofuran-2-methylidenyl)-5-(piperidin-1-ethyl)-2-indolinone
3-(3-ethoxycarbonyl-4,5,6,7-tetrahydrobenzofuran-2-methylidenyl)-5-(piperidin-1-ethyl)-2-indolinone
3-(3-n-pentyl-4,5,6,7-tetrahydrobenzofuran-2-methylidenyl)-5-(piperidin-1-ethyl)-2-indolinone
3-(3-ethyl-4,5,6,7-tetrahydrobenzofuran-2-methylidenyl)-5-(piperidin-1-ethyl)-2-indolinone
3-(4,5,6,7-tetrahydrobenzofuran-2-methylidenyl)-5-(piperidin-1-ethyl)-2-indolinone
3-[3-(4-methylphenyl)-4,5,6,7-tetrahydrobenzofuran-2-methylidenyl]-5-(piperidin-1-ethyl)-2-indolinone
3-(3-phenylsulfonylmethyl-4,5,6,7-tetrahydrobenzofuran-2-methylidenyl)-5-(piperidin-1-ethyl)-2-indolinone
3-[3-(1-phenylaminoethyl)-4,5,6,7-tetrahydrobenzofuran-2-methylidenyl]-5-(piperidin-1-ethyl)-2-indolinone
3-[3-(1-phenylaminobutyl)-4,5,6,7-tetrahydrobenzofuran-2-methylidenyl]-5-(piperidin-1-ethyl)-2-indolinone
3-[3-(1-phenylaminobutyl)-4,5,6,7-tetrahydrobenzofuran-2-methylidenyl]-5-(2-pyrrolidin-1-ethyl)-2-indolinone
3-(3-cyano-4,5,6,7-tetrahydrobenzofuran-2-methylidenyl)-5-(2-pyrrolidin-1-ethyl)-2-indolinone
3-(3-phenylaminomethyl-4,5,6,7-tetrahydrobenzofuran-2-methylidenyl)-5-(2-pyrrolidin-1-ethyl)-2-indolinone
3-(3-phenyl-4,5,6,7-tetrahydrobenzofuran-2-methylidenyl)-5-(2-pyrrolidin-1-ethyl)-2-indolinone
3-(4,5,6,7-tetrahydrobenzimidazol-2-methylidenyl)-5-(2-pyrrolidin-1-ethyl)-2-indolinone
3-(4,5,6,7-tetrahydrobenzoxazol-2-methylidenyl)-5-(2-pyrrolidin-1-ethyl)-2-indolinone
3-(3-methyl-4,5,6,7-tetrahydroindol-2-methylidenyl)-5-(2-pyrrolidin-1-ethyl)-2-indolinone -continued 3-(3-carboxy-4,5,6,7-tetrahydroindol-2-methylidenyl)-5-(2-pyrrolidin-1-ethyl)-2-indolinone
3-[3-(isoquinolin-1-methyl)-4,5,6,7-tetrahydroindol-2-methylidenyl]-5-(2-pyrrolidin-1-ethyl)-2-indolinone
3-(3-hydroxy-4,5,6,7-tetrahydroindol-2-methylidenyl)-5-(2-pyrrolidin-1-ethyl)-2-indolinone
3-(3-methoxy-4,5,6,7-tetrahydroindol-2-methylidenyl)-5-(2-pyrrolidin-1-ethyl)-2-indolinone
3-(4,5,6,7-tetrahydroindol-2-methylidenyl)-5-(2-pyrrolidin-1-ethyl)-2-indolinone
3-(4,5,6,7-tetrahydrobenzothien-2-methylidenyl)-5-(2-pyrrolidin-1-ethyl)-2-indolinone
3-(3-methoxycarbonyl-4,5,6,7-tetrahydrobenzothien-2-methylidenyl)-5-(2-pyrrolidin-1-ethyl)-2-indolinone
3-(3-vinyl-4,5,6,7-tetrahydrobenzothien-2-methylidenyl)-5-(2-pyrrolidin-1-ethyl)-2-indolinone
3-(3-carboxy-4,5,6,7-tetrahydrobenzothien-2-methylidenyl)-5-(2-pyrrolidin-1-ethyl)-2-indolinone
3-(3-ethoxycarbonyl-4,5,6,7-tetrahydrobenzothien-2-methylidenyl)-5-(2-pyrrolidin-1-ethyl)-2-indolinone
3-[3-(3-dimethylamino-n-propoxycarbonyl)-4,5,6,7-tetrahydrobenzothien-2-methylidenyl]-5-(2-pyrrolidin-1-ethyl)-2-indolinone
3-[3-(2-diethylaminoethoxycarbonyl)-4,5,6,7-tetrahydrobenzothien-2-methylidenyl]-5-(2-pyrrolidin-1-ethyl)-2-indolinone
3-[3-(2-methylaminoethyl)-4,5,6,7-tetrahydrobenzothien-2-methylidenyl]-5-(2-pyrrolidin-1-ethyl)-2-indolinone
3-(3-cyclopropylmethoxy-4,5,6,7-tetrahydrobenzothien-2-methylidenyl)-5-(2-pyrrolidin-1-ethyl)-2-indolinone
3-(4,5,6,7-tetrahydrobenzothiazol-2-methylidenyl)-5-(2-pyrrolidin-1-ethyl)-2-indolinone
3-(4-methyl-4,5,6,7-tetrahydroindol-2-methylidenyl)-5-(2-pyrrolidin-1-ethyl)-2-indolinone
3-(4,4-dimethyl-4,5,6,7-tetrahydroindol-2-methylidenyl)-5-(2-pyrrolidin-1-ethyl)-2-indolinone
3-(4-ethyl-4,5,6,7-tetrahydroindol-2-methylidenyl)-5-(2-pyrrolidin-1-ethyl)-2-indolinone
3-(4-phenyl-4,5,6,7-tetrahydroindol-2-methylidenyl)-5-(2-pyrrolidin-1-ethyl)-2-indolinone
3-(3-ethyl-4,5,6,7-tetrahydroindol-2-methylidenyl)-5-(2-pyrrolidin-1-ethyl)-2-indolinone
3-(3-isopropyl-4,5,6,7-tetrahydroindol-2-methylidenyl)-5-(2-pyrrolidin-1-ethyl)-2-indolinone
3-(4,5,6,7-tetrahydroindol-2-methylidenyl)-5-(2-pyrrolidin-1-ethyl)-2-indolinone
3-(4-isopropyl-4,5,6,7-tetrahydroindol-2-methylidenyl)-5-(2-pyrrolidin-1-ethyl)-2-indolinone
3-(4-carboxymethyl-4,5,6,7-tetrahydroindol-2-methylidenyl)-5-(2-pyrrolidin-1-ethyl)-2-indolinone
3-(3-phenyl-4,5,6,7-tetrahydrobenzofuran-2-methylidenyl)-5-trifluoromethyl-2-indolinone
3-(4,5,6,7-tetrahydrobenzimidazol-2-methylidenyl)-5-trifluoromethyl-2-indolinone
3-(4,5,6,7-tetrahydrobenzoxazol-2-methylidenyl)-5-trifluoromethyl-2-indolinone
3-(3-methyl-4,5,6,7-tetrahydroindol-2-methylidenyl)-5-trifluoromethyl-2-indolinone
3-(3-carboxy-4,5,6,7-tetrahydroindol-2-methylidenyl)-5-trifluoromethyl-2-indolinone
3-[3-(isoquinolin-1-methyl)-4,5,6,7-tetrahydroindol-2-methylidenyl]-5-trifluoromethyl-2-indolinone
3-(3-hydroxy-4,5,6,7-tetrahydroindol-2-methylidenyl)-5-trifluoromethyl-2-indolinone
3-(3-methoxy-4,5,6,7-tetrahydroindol-2-methylidenyl)-5-trifluoromethyl-2-indolinone
3-(4,5,6,7-tetrahydroindol-2-methylidenyl)-5-trifluoromethyl-2-indolinone
3-(4,5,6,7-tetrahydrobenzothien-2-methylidenyl)-5-trifluoromethyl-2-indolinone
3-(3-methoxycarbonyl-4,5,6,7-tetrahydrobenzothien-2-methylidenyl)-5-trifluoromethyl-2-indolinone
3-(3-vinyl-4,5,6,7-tetrahydrobenzothien-2-methylidenyl)-5-trifluoromethyl-2-indolinone
3-(3-carboxy-4,5,6,7-tetrahydrobenzothien-2-methylidenyl)-5-trifluoromethyl-2-indolinone
3-(3-ethoxycarbonyl-4,5,6,7-tetrahydrobenzothien-2-methylidenyl)-5-trifluoromethyl-2-indolinone
3-[3-(3-dimethylamino-n-propoxycarbonyl)-4,5,6,7-tetrahydrobenzothien-2-methylidenyl]-5-trifluoromethyl-2-indolinone
3-[3-(2-diethylaminoethoxycarbonyl)-4,5,6,7-tetrahydrobenzothien-2-methylidenyl]-5-trifluoromethyl-2-indolinone
3-[3-(2-methylaminoethyl)-4,5,6,7-tetrahydrobenzothien-2-methylidenyl]-5-trifluoromethyl-2-indolinone
3-(3-cyclopropylmethoxy-4,5,6,7-4,5,6,7-tetrahydrobenzothien-2-methylidenyl)-5-trifluoromethyl-2-indolinone
3-(4,5,6,7-tetrahydrobenzothiazol-2-methylidenyl)-5-trifluoromethyl-2-indolinone
3-(4-methyl-4,5,6,7-tetrahydroindol-2-methylidenyl)-5-trifluoromethyl-2-indolinone
3-(4,4-dimethyl-4,5,6,7-tetrahydroindol-2-methylidenyl)-5-trifluoromethyl-2-indolinone
3-(4-ethyl-4,5,6,7-tetrahydroindol-2-methylidenyl)-5-trifluoromethyl-2-indolinone
3-(4-phenyl-4,5,6,7-tetrahydroindol-2-methylidenyl)-5-trifluoromethyl-2-indolinone
3-(3-ethyl-4,5,6,7-tetrahydroindol-2-methylidenyl)-5-trifluoromethyl-2-indolinone
3-(3-isopropyl-4,5,6,7-tetrahydroindol-2-methylidenyl)-5-trifluoromethyl-2-indolinone
3-(4,5,6,7-tetrahydroindol-2-methylidenyl)-5-trifluoromethyl-2-indolinone
3-(4-isopropyl-4,5,6,7-tetrahydroindol-2-methylidenyl)-5-trifluoromethyl-2-indolinone
3-(4-carboxymethyl-4,5,6,7-tetrahydroindol-2-methylidenyl)-5-trifluoromethyl-2-indolinone
3-(3-methyl-4,5,6,7-tetrahydroinden-2-methylidenyl)-5-(piperidin-1-acetyl-2-indolinone
3-(4,5,6,7-tetrahydroinden-2-methylidenyl)-5-(piperidin-1-acetyl-2-indolinone
3-(3-methyl-4,5,6,7-tetrahydrobenzofuran-2-methylidenyl)-5-(piperidin-1-acetyl-2-indolinone
3-(3-ethoxycarbonyl-4,5,6,7-tetrahydrobenzofuran-2-methylidenyl)-5-(piperidin-1-acetyl-2-indolinone
3-(3-n-pentyl-4,5,6,7-tetrahydrobenzofuran-2-methylidenyl)-5-(piperidin-1-acetyl-2-indolinone
3-(3-ethyl-4,5,6,7-tetrahydrobenzofuran-2-methylidenyl)-5-(piperidin-1-acetyl-2-indolinone
3-(4,5,6,7-tetrahydrobenzofuran-2-methylidenyl)-5-(piperidin-1-acetyl-2-indolinone
3-[3-(4-methylphenyl)-4,5,6,7-tetrahydrobenzofuran-2-methylidenyl]-5-(piperidin-1-acetyl-2-indolinone
3-(3-phenylsulfonylmethyl-4,5,6,7-tetrahydrobenzofuran-2-methylidenyl)-5-(piperidin-1-acetyl-2-indolinone
3-[3-(1-phenylaminoethyl)-4,5,6,7-tetrahydrobenzofuran-2-methylidenyl]-5-(piperidin-1-acetyl-2-indolinone
3-[3-(1-phenylaminobutyl)4,5,6,7-tetrahydrobenzofuran-2-methylidenyl]-5-(piperidin-1-acetyl-2-indolinone
3-(3-cyano-4,5,6,7-tetrahydrobenzofuran-2-methylidenyl)-5-(piperidin-1-acetyl-2-indolinone
3-(4,5,6,7-tetrahydrobenzimidazol-2-methylidenyl)-5-methoxy-2-indolinone
3-(4,5,6,7-tetrahydrobenzoxazol-2-methylidenyl)-5-methoxy-2-indolinone
3-(3-methyl-4,5,6,7-tetrahydroindol-2-methylidenyl)-5-methoxy-2-indolinone
3-(3-carboxy-4,5,6,7-tetrahydroindol-2-methylidenyl)-5-methoxy-2-indolinone
3-[3-(isoquinolin-1-methyl)-4,5,6,7-tetrahydroindol-2-methylidenyl]-5-methoxy-2-indolinone
3-(3-hydroxy-4,5,6,7-tetrahydroindol-2-methylidenyl)-5-methoxy-2-indolinone
3-(3-methoxy-4,5,6,7-4,5,6,7-tetrahydroindol-2-methylidenyl)-5-methoxy-2-indolinone
3-(4,5,6,7-tetrahydroindol-2-methylidenyl)-5-methoxy-2-indolinone
3-(3-methoxycarbonyl-4,5,6,7-tetrahydrobenzothien-2-methylidenyl)-5-methoxy-2-indolinone
3-(3-vinyl-4,5,6,7-tetrahydrobenzothien-2-methylidenyl)-5-methoxy-2-indolinone
3-(3-carboxy-4,5,6,7-tetrahydrobenzothien-2-methylidenyl)-5-methoxy-2-indolinone
3-(3-ethoxycarbonyl-4,5,6,7-tetrahydrobenzothien-2-methylidenyl)-5-methoxy-2-indolinone
3-[3-(3-dimethylamino-n-propoxycarbonyl)-4,5,6,7-tetrahydrobenzothien-2-methylidenyl]-5-methoxy-2-indolinone
3-[3-(2-diethylaminoethoxycarbonyl)-4,5,6,7-tetrahydrobenzothien-2-methylidenyl]-5-methoxy-2-indolinone 3-[3-(2-methylaminoethyl)-4,5,6,7-tetrahydrobenzothien-2-methylidenyl]-5-methoxy-2-indolinone
3-(3-cyclopropylmethoxy-4,5,6,7-tetrahydrobenzothien-2-methylidenyl)-5-methoxy-2-indolinone
3-(4,5,6,7-tetrahydrobenzothiazol-2-methylidenyl)-5-methoxy-2-indolinone
3-(4-methyl-4,5,6,7-tetrahydroindol-2-methylidenyl)-5-methoxy-2-indolinone
3-(4,4-dimethyl-4,5,6,7-tetrahydroindol-2-methylidenyl)-5-methoxy-2-indolinone
3-(4-ethyl-4,5,6,7-4,5,6,7-tetrahydroindol-2-methylidenyl)-5-methoxy-2-indolinone
3-(4-phenyl-4,5,6,7-tetrahydroindol-2-methylidenyl)-5-methoxy-2-indolinone
3-(3-ethyl-4,5,6,7-tetrahydroindol-2-methylidenyl)-5-methoxy-2-indolinone
3-(3-isopropyl-4,5,6,7-tetrahydroindol-2-methylidenyl)-5-methoxy-2-indolinone
3-(4,5,6,7-tetrahydroindol-2-methylidenyl)-5-methoxy-2-indolinone
3-(4-isopropyl-4,5,6,7-tetrahydroindol-2-methylidenyl)-5-methoxy-2-indolinone
3-(4-carboxymethyl(4,5,6,7-tetrahydroindol-2-methylidenyl)-5-methoxy-2-indolinone
3-(3-methyl-4,5,6,7-tetrahydroinden-2-methylidenyl)-5-trifluoromethyl-2-indolinone
3-(4,5,6,7-tetrahydroinden-2-methylidenyl)-5-trifluoromethyl-2-indolinone
3-(3-methyl-4,5,6,7-tetrahydrobenzofuran-2-methylidenyl)-5-trifluoromethyl-2-indolinone
3-(3-ethoxycarbonyl-4,5,6,7-tetrahydrobenzofuran-2-methylidenyl)-5-trifluoromethyl-2-indolinone
3-(3-n-pentyl-4,5,6,7-tetrahydrobenzofuran-2-methylidenyl)-5-trifluoromethyl-2-indolinone
3-(3-ethyl-4,5,6,7-tetrahydrobenzofuran-2-methylidenyl)-5-trifluoromethyl-2-indolinone
3-(4,5,6,7-tetrahydrobenzofuran-2-methylidenyl)-5-trifluoromethyl-2-indolinone
3-[3-(4-methylphenyl)-4,5,6,7-tetrahydrobenzofuran-2-methylidenyl]-5-trifluoromethyl-2-indolinone
3-(3-phenylsulfonylmethyl-4,5,6,7-tetrahydrobenzofuran-2-methylidenyl)-5-trifluoromethyl-2-indolinone
3-[3-(1-phenylaminoethyl)-4,5,6,7-tetrahydrobenzofuran-2-methylidenyl]-5-trifluoromethyl-2-indolinone
3-[3-(1-phenylaminobutyl)-4,5,6,7-tetrahydrobenzofuran-2-methylidenyl]-5-trifluoromethyl-2-indolinone
3-(3-cyano-4,5,6,7-tetrahydrobenzofuran-2-methylidenyl)-5-trifluoromethyl-2-indolinone
3-(3-phenylaminomethyl-4,5,6,7-tetrahydrobenzofuran-2-methylidenyl)-5-trifluoromethyl-2-indolinone
3-(4,5,6,7-tetrahydrobenzoxazol-2-methylidenyl)-5-(4-carboxybenzamido)-2-indolinone
3-(3-methyl-4,5,6,7-tetrahydroindol-2-methylidenyl)-5-(4-carboxybenzamido)-2-indolinone
3-(3-carboxy-4,5,6,7-tetrahydroindol-2-methylidenyl)-5-(4-carboxybenzamido)-2-indolinone
3-[3-(isoquinolin-1-methyl)-4,5,6,7-tetrahydroindol-2-methylidenyl]-5-(4-carboxybenzamido)-2-indolinone
3-(3-hydroxy-4,5,6,7-tetrahydroindol-2-methylidenyl)-5-(4-carboxybenzamido)-2-indolinone
3-(3-methoxy-4,5,6,7-tetrahydroindol-2-methylidenyl)-5-(4-carboxybenzamido)-2-indolinone
3-(4,5,6,7-tetrahydroindol-2-methylidenyl)-5-(4-carboxybenzamido)-2-indolinone
3-(4,5,6,7-tetrahydrobenzothien-2-methylidenyl)-5-(4-carboxybenzamido)-2-indolinone
3-(3-methoxycarbonyl-4,5,6,7-tetrahydrobenzothien-2-methylidenyl)-5-(4-carboxybenzamido)-2-indolinone
3-(3-vinyl-4,5,6,7-tetrahydrobenzothien-2-methylidenyl)-5-(4-carboxybenzamido)-2-indolinone
3-(3-carboxy-4,5,6,7-tetrahydrobenzothien-2-methylidenyl)-5-(4-carboxybenzamido)-2-indolinone
3-(3-ethoxycarbonyl-4,5,6,7-tetrahydrobenzothien-2-methylidenyl)-5-(4-carboxybenzamido)-2-indolinone
3-[3-(3-dimethylamino-n-propoxycarbonyl)-4,5,6,7-tetrahydrobenzothien-2-methylidenyl]-5-(4-carboxybenzamido)-2-indolinone
3-[3-(2-diethylaminoethoxycarbonyl)-4,5,6,7-tetrahydrobenzothien-2-methylidenyl]-5-(4-carboxybenzamido)-2-indolinone
3-[3-(2-methylaminoethyl)-4,5,6,7-tetrahydrobenzothien-2-methylidenyl]-5-(4-carboxybenzamido)-2-indolinone
3-(3-cyclopropylmethoxy-4,5,6,7-tetrahydrobenzothien-2-methylidenyl)-5-(4-carboxybenzamido)-2-indolinone
3-(-4,5,6,7-tetrahydrobenzothiazol-2-methylidenyl)-5-(4-carboxybenzamido)-2-indolinone
3-(4-methyl-4,5,6,7-tetrahydroindol-2-methylidenyl)-5-(4-carboxybenzamido)-2-indolinone
3-(4,4-dimethyl-4,5,6,7-tetrahydroindol-2-methylidenyl)-5-(4-carboxybenzamido)-2-indolinone
3-(4-ethyl-4,5,6,7-tetrahydroindol-2-methylidenyl)-5-(4-carboxybenzamido)-2-indolinone
3-(4-phenyl-4,5,6,7-tetrahydroindol-2-methylidenyl)-5-(4-carboxybenzamido)-2-indolinone
3-(3-ethyl-4,5,6,7-tetrahydroindol-2-methylidenyl)-5-(4-carboxybenzamido)-2-indolinone
3-(3-isopropyl-4,5,6,7-tetrahydroindol-2-methylidenyl)-5-(4-carboxybenzamido)-2-indolinone
3-(4,5,6,7-tetrahydroindol-2-methylidenyl)-5-(4-carboxybenzamido)-2-indolinone
3-(4-isopropyl-4,5,6,7-tetrahydroindol-2-methylidenyl)-5-(4-carboxybenzamido)-2-indolinone
3-(4-carboxymethyl-4,5,6,7-tetrahydroindol-2-methylidenyl)-5-(4-carboxybenzamido)-2-indolinone
3-(3-methyl-4,5,6,7-tetrahydroinden-2-methylidenyl)-5-methoxy-2-indolinone
3-(4,5,6,7-tetrahydroinden-2-methylidenyl)-5-methoxy-2-indolinone
3-(3-methyl-4,5,6,7-tetrahydrobenzofuran-2-methylidenyl)-5-methoxy-2-indolinone
3-(3-ethoxycarbonyl-4,5,6,7-tetrahydrobenzofuran-2-methylidenyl)-5-methoxy-2-indolinone
3-(3-n-pentyl-4,5,6,7-tetrahydrobenzofuran-2-methylidenyl)-5-methoxy-2-indolinone
3-(3-ethyl-4,5,6,7-tetrahydrobenzofuran-2-methylidenyl)-5-methoxy-2-indolinone
3-(4,5,6,7-tetrahydrobenzofuran-2-methylidenyl)-5-methoxy-2-indolinone
3-[3-(4-methylphenyl)-4,5,6,7-tetrahydrobenzofuran-2-methylidenyl]-5-methoxy-2-indolinone
3-(3-phenylsulfonylmethyl-4,5,6,7-tetrahydrobenzofuran-2-methylidenyl)-5-methoxy-2-indolinone
3-[3-(1-phenylaminoethyl)-4,5,6,7-tetrahydrobenzofuran-2-methylidenyl]-5-methoxy-2-indolinone
3-[3-(1-phenylaminobutyl)-4,5,6,7-tetrahydrobenzofuran-2-methylidenyl]-5-methoxy-2-indolinone
3-(3-cyano-4,5,6,7-tetrahydrobenzofuran-2-methylidenyl)-5-methoxy-2-indolinone
3-(3-phenylaminomethyl-4,5,6,7-tetrahydrobenzofuran-2-methylidenyl)-5-methoxy-2-indolinone
3-(3-phenyl-4,5,6,7-tetrahydrobenzofuran-2-methylidenyl)-5-methoxy-2-indolinone
3-(4,5,6,7-tetrahydrobenzoxazol-2-methylidenyl)-5-(4-methoxycarbonylbenzamido)-2-indolinone
3-(3-methyl-4,5,6,7-tetrahydroindol-2-methylidenyl)-5-(4-methoxycarbonylbenzamido)-2-indolinone
3-(3-carboxy-4,5,6,7-tetrahydroindol-2-methylidenyl)-5-(4-methoxycarbonylbenzamido)-2-indolinone
3-[3-(isoquinolin-1-methyl)-4,5,6,7-tetrahydroindol-2-methylidenyl]-5-(4-methoxycarbonylbenzamido)-2-indolinone
3-(3-hydroxy-4,5,6,7-tetrahydroindol-2-methylidenyl)-5-(4-methoxycarbonylbenzamido)-2-indolinone
3-(3-methoxy-4,5,6,7-tetrahydroindol-2-methylidenyl)-5-(4-methoxycarbonylbenzamido)-2-indolinone
3-(4,5,6,7-tetrahydroindol-2-methylidenyl)-5-(4-methoxycarbonylbenzamido)-2-indolinone
3-(4,5,6,7-tetrahydrobenzothien-2-methylidenyl)-5-(4-methoxycarbonylbenzamido)-2-indolinone
3-(3-methoxycarbonyl-4,5,6,7-tetrahydrobenzothien-2-methylidenyl)-5-(4-methoxycarbonylbenzamido)-2-indolinone
3-(3-vinyl-4,5,6,7-tetrahydrobenzothien-2-methylidenyl)-5-(4-methoxycarbonylbenzamido)-2-indolinone
3-(3-carboxy-4,5,6,7-tetrahydrobenzothien-2-methylidenyl)-5-(4-methoxycarbonylbenzamido)-2-indolinone
3-(3-ethoxycarbonyl-4,5,6,7-tetrahydrobenzothien-2-methylidenyl)-5-(4-methoxycarbonylbenzamido)-2-indolinone
3-[3-(3-dimethylamino-n-propoxycarbonyl)-4,5,6,7-tetrahydrobenzothien-2-methylidenyl]-5-(4-methoxycarbonylbenzamido)-2-indolinone
3-[3-(2-diethylaminoethoxycarbonyl)-4,5,6,7-tetrahydrobenzothien-2-methylidenyl]-5-(4-methoxycarbonylbenzamido)-2-indolinone -continued 3-[3-(2-methylaminoethyl)-4,5,6,7-tetrahydrobenzothien-2-methylidenyl]-5-(4-methoxycarbonylbenzamido)-2-indolinone
3-(3-cyclopropylmethoxy-4,5,6,7-tetrahydrobenzothien-2-methylidenyl)-5-(4-methoxycarbonylbenzamido)-2-indolinone
3-(4,5,6,7-tetrahydrobenzothiazol-2-methylidenyl)-5-(4-methoxycarbonylbenzamido)-2-indolinone
3-(4-methyl-4,5,6,7-tetrahydroindol-2-methylidenyl)-5-(4-methoxycarbonylbenzamido)-2-indolinone
3-(4,4-dimethyl-4,5,6,7-tetrahydroindol-2-methylidenyl)-5-(4-methoxycarbonylbenzamido)-2-indolinone
3-(4-ethyl-4,5,6,7-tetrahydroindol-2-methylidenyl)-5-(4-methoxycarbonylbenzamido)-2-indolinone
3-(4-phenyl-4,5,6,7-tetrahydroindol-2-methylidenyl)-5-(4-methoxycarbonylbenzamido)-2-indolinone
3-(3-ethyl-4,5,6,7-tetrahydroindol-2-methylidenyl)-5-(4-methoxycarbonylbenzamido)-2-indolinone
3-(3-isopropyl-4,5,6,7-tetrahydroindol-2-methylidenyl)-5-(4-methoxycarbonylbenzamido)-2-indolinone
3-(4,5,6,7-tetrahydroindol-2-methylidenyl)-5-(4-methoxycarbonylbenzamido)-2-indolinone
3-(4-isopropyl-4,5,6,7-tetrahydroindol-2-methylidenyl)-5-(4-methoxycarbonylbenzamido)-2-indolinone
3-(4-carboxymethyl-4,5,6,7-tetrahydroindol-2-methylidenyl)-5-(4-methoxycarbonylbenzamido)-2-indolinone
3-(3-methyl-4,5,6,7-tetrahydroinden-2-methylidenyl)-5-(4-carboxybenzamido)-2-indolinone
3-(4,5,6,7-tetrahydroinden-2-methylidenyl)-5-(4-carboxybenzamido)-2-indolinone
3-(3-methyl-4,5,6,7-tetrahydrobenzofuran-2-methylidenyl)-5-(4-carboxybenzamido)-2-indolinone
3-(3-ethoxycarbonyl-4,5,6,7-tetrahydrobenzofuran-2-methylidenyl)-5-(4-carboxybenzamido)-2-indolinone
3-(3-pentyl-4,5,6,7-tetrahydrobenzofuran-2-methylidenyl)-5-(4-carboxybenzamido)-2-indolinone
3-(3-ethyl-4,5,6,7-tetrahydrobenzofuran-2-methylidenyl)-5-(4-carboxybenzamido)-2-indolinone
3-(4,5,6,7-tetrahydrobenzofuran-2-methylidenyl)-5-(4-carboxybenzamido)-2-indolinone
3-[3-(4-methylphenyl)-4,5,6,7-tetrahydrobenzofuran-2-methylidenyl]-5-(4-carboxybenzamido)-2-indolinone
3-(3-phenylsulfonylmethyl-4,5,6,7-tetrahydrobenzofuran-2-methylidenyl)-5-(4-carboxybenzamido)-2-indolinone
3-[3-(1-phenylaminoethyl)-4,5,6,7-tetrahydrobenzofuran-2-methylidenyl]-5-(4-carboxybenzamido)-2-indolinone
3-[3-(1-phenylaminobutyl)-4,5,6,7-tetrahydrobenzofuran-2-methylidenyl]-5-(4-carboxybenzamido)-2-indolinone
3-(3-cyano-4,5,6,7-tetrahydrobenzofuran-2-methylidenyl)-5-(4-carboxybenzamido)-2-indolinone
3-(3-phenylaminomethyl-4,5,6,7-tetrahydrobenzofuran-2-methylidenyl)-5-(4-carboxybenzamido)-2-indolinone
3-(3-phenyl-4,5,6,7-tetrahydrobenzofuran-2-methylidenyl)-5-(4-carboxybenzamido)-2-indolinone
3-(4,5,6,7-tetrahydrobenzimidazol-2-methylidenyl)-5-(4-carboxybenzamido)-2-indolinone
3-(4,5,6,7-tetrahydrobenzoxazol-2-methylidenyl)-5-(2-morpholin-4-ethyl)-2-indolinone
3-(3-methyl-4,5,6,7-tetrahydroindol-2-methylidenyl)-5-(2-morpholin-4-ethyl)-2-indolinone
3-(3-carboxy-4,5,6,7-tetrahydroindol-2-methylidenyl)-5-(2-morpholin-4-ethyl)-2-indolinone
3-[3-(isoquinolin-1-methyl)-4,5,6,7-tetrahydroindol-2-methylidenyl]-5-(2-morpholin-4-ethyl)-2-indolinone
3-(3-hydroxy-4,5,6,7-tetrahydroindol-2-methylidenyl)-5-(2-morpholin-4-ethyl)-2-indolinone
3-(4,5,6,7-tetrahydroindol-2-methylidenyl)-5-(2-morpholin-4-ethyl)-2-indolinone
3-(4,5,6,7-tetrahydrobenzothien-2-methylidenyl)-5-(2-morpholin-4-ethyl)-2-indolinone
3-(3-methoxycarbonyl-4,5,6,7-tetrahydrobenzothien-2-methylidenyl)-5-(2-morpholin-4-ethyl)-2-indolinone
3-(3-vinyl-4,5,6,7-tetrahydrobenzothien-2-methylidenyl)-5-(2-morpholin-4-ethyl)-2-indolinone
3-(3-carboxy-4,5,6,7-tetrahydrobenzothien-2-methylidenyl)-5-(2-morpholin-4-ethyl)-2-indolinone
3-(3-ethoxycarbonyl-4,5,6,7-tetrahydrobenzothien-2-methylidenyl)-5-(2-morpholin-4-ethyl)-2-indolinone
3-[3-(3-dimethylamino-n-propoxycarbonyl)-4,5,6,7-tetrahydrobenzothien-2-methylidenyl]-5-(2-morpholin-4-ethyl)-2-indolinone
3-[3-(2-diethylaminoethoxycarbonyl)-4,5,6,7-tetrahydrobenzothien-2-methylidenyl]-5-(2-morpholin-4-ethyl)-2-indolinone
3-[3-(2-methylaminoethyl)-4,5,6,7-tetrahydrobenzothien-2-methylidenyl]-5-(2-morpholin-4-ethyl)-2-indolinone
3-(3-cyclopropylmethoxy-4,5,6,7-tetrahydrobenzothien-2-methylidenyl)-5-(2-morpholin-4-ethyl)-2-indolinone
3-(4,5,6,7-tetrahydrobenzothiazol-2-methylidenyl)-5-(2-morpholin-4-ethyl)-2-indolinone
3-(4-methyl-4,5,6,7-tetrahydroindol-2-methylidenyl)-5-(2-morpholin-4-ethyl)-2-indolinone
3-(4,4-dimethyl-4,5,6,7-tetrahydroindol-2-methylidenyl)-5-(2-morpholin-4-ethyl)-2-indolinone
3-(4-ethyl-4,5,6,7-tetrahydroindol-2-methylidenyl)-5-(2-morpholin-4-ethyl)-2-indolinone
3-(4-phenyl-4,5,6,7-tetrahydroindol-2-methylidenyl)-5-(2-morpholin-4-ethyl)-2-indolinone
3-(3-ethyl-4,5,6,7-tetrahydroindol-2-methylidenyl)-5-(2-morpholin-4-ethyl)-2-indolinone
3-(3-isopropyl-4,5,6,7-tetrahydroindol-2-methylidenyl)-5-(2-morpholin-4-ethyl)-2-indolinone
3-(4,5,6,7-tetrahydroindol-2-methylidenyl)-5-(2-morpholin-4-ethyl)-2-indolinone
3-(4-isopropyl-4,5,6,7-tetrahydroindol-2-methylidenyl)-5-(2-morpholin-4-ethyl)-2-indolinone
3-(4-carboxymethyl-4,5,6,7-tetrahydroindol-2-methylidenyl)-5-(2-morpholin-4-ethyl)-2-indolinone
3-(3-methyl-4,5,6,7-tetrahydroinden-2-methylidenyl)-5-(4-methoxycarbonylbenzamido)-2-indolinone
3-(4,5,6,7-tetrahydroinden-2-methylidenyl)-5-(4-methoxycarbonylbenzamido)-2-indolinone
3-(3-methyl-4,5,6,7-tetrahydrobenzofuran-2-methylidenyl)-5-(4-methoxycarbonylbenzamido)-2-indolinone
3-(3-ethoxycarbonyl-4,5,6,7-tetrahydrobenzofuran-2-methylidenyl)-5-(4-methoxycarbonylbenzamido)-2-indolinone
3-(3-n-pentyl-4,5,6,7-tetrahydrobenzofuran-2-methylidenyl)-5-(4-methoxycarbonylbenzamido)-2-indolinone
3-(3-ethyl-4,5,6,7-tetrahydrobenzofuran-2-methylidenyl)-5-(4-methoxycarbonylbenzamido)-2-indolinone
3-(3-(4-methylphenyl)-4,5,6,7-tetrahydrobenzofuran-2-methylidenyl)-5-(4-methoxycarbonylbenzamido)-2-indolinone
3-(3-phenylsulfonylmethyl-4,5,6,7-tetrahydrobenzofuran-2-methylidenyl)-5-(4-methoxycarbonylbenzamido)-2-indolinone
3-[3-(1-phenylaminoethyl)-4,5,6,7-tetrahydrobenzofuran-2-methylidenyl]-5-(4-methoxycarbonylbenzamido)-2-indolinone
3-[3-(1-phenylaminobutyl)-4,5,6,7-tetrahydrobenzofuran-2-methylidenyl]-5-(4-methoxycarbonylbenzamido)-2-indolinone
3-(3-cyano-4,5,6,7-tetrahydrobenzofuran-2-methylidenyl)-5-(4-methoxycarbonylbenzamido)-2-indolinone
3-(3-phenylaminomethyl-4,5,6,7-tetrahydrobenzofuran-2-methylidenyl)-5-(4-methoxycarbonylbenzamido)-2-indolinone
3-(3-phenyl-4,5,6,7-tetrahydrobenzofuran-2-methylidenyl)-5-(4-methoxycarbonylbenzamido)-2-indolinone
3-(4,5,6,7-tetrahydrobenzimidazol-2-methylidenyl)-5-(4-methoxycarbonylbenzamido)-2-indolinone
3-(3-methyl-4,5,6,7-tetrahydroindol-2-methylidenyl)-5-ethyl-2-indolinone
3-(3-carboxy-4,5,6,7-tetrahydroindol-2-methylidenyl)-5-ethyl-2-indolinone
3-[3-(isoquinolin-1-methyl)-4,5,6,7-tetrahydroindol-2-methylidenyl]-5-ethyl-2-indolinone
3-(3-hydroxy-4,5,6,7-tetrahydroindol-2-methylidenyl)-5-ethyl-2-indolinone
3-(3-methoxy-4,5,6,7-tetrahydroindol-2-methylidenyl)-5-ethyl-2-indolinone
3-(4,5,6,7-tetrahydroindol-2-methylidenyl)-5-ethyl-2-indolinone
3-(4,5,6,7-tetrahydrobenzothien-2-methylidenyl)-5-ethyl-2-indolinone
3-(3-methoxycarbonyl-4,5,6,7-tetrahydrobenzothien-2-methylidenyl)-5-ethyl-2-indolinone
3-(3-vinyl-4,5,6,7-tetrahydrobenzothien-2-methylidenyl)-5-ethyl-2-indolinone
3-(3-carboxy-4,5,6,7-tetrahydrobenzothien-2-methylidenyl)-5-ethyl-2-indolinone
3-(3-ethoxycarbonyl-4,5,6,7-tetrahydrobenzothien-2-methylidenyl)-5-ethyl-2-indolinone
3-[3-(3-dimethylamino-n-propoxycarbonyl)-4,5,6,7-tetrahydrobenzothien-2-methylidenyl]-5-ethyl-2-indolinone
3-[3-(2-diethylaminoethoxycarbonyl)-4,5,6,7-tetrahydrobenzothien-2-methylidenyl]-5-ethyl-2-indolinone -continued 3-[3-(2-methylaminoethyl)-4,5,6,7-tetrahydrobenzothien-2-methylidenyl)-5-ethyl-2-indolinone
3-(3-cyclopropylmethoxy-4,5,6,7-tetrahydrobenzothien-2-methylidenyl)-5-ethyl-2-indolinone
3-(4,5,6,7-tetrahydrobenzothiazol-2-methylidenyl)-5-ethyl-2-indolinone
3-(4-methyl-4,5,6,7-tetrahydroindol-2-methylidenyl)-5-ethyl-2-indolinone
3-(4,4-dimethyl-4,5,6,7-tetrahydroindol-2-methylidenyl)-5-ethyl-2-indolinone
3-(4-ethyl-4,5,6,7-tetrahydroindol-2-methylidenyl)-5-ethyl-2-indolinone
3-(4-phenyl-4,5,6,7-tetrahydroindol-2-methylidenyl)-5-ethyl-2-indolinone
3-(3-ethyl-4,5,6,7-tetrahydroindol-2-methylidenyl)-5-ethyl-2-indolinone
3-(4,5,6,7-tetrahydroindol-2-methylidenyl)-5-ethyl-2-indolinone
3-(4-isopropyl-4,5,6,7-tetrahydroindol-2-methylidenyl)-5-ethyl-2-indolinone
3-(4-carboxymethyl-4,5,6,7-tetrahydroindol-2-methylidenyl)-5-ethyl-2-indolinone
3-(3-methyl-4,5,6,7-tetrahydroinden-2-methylidenyl)-5-(2-morpholin-4-ethyl)-2-indolinone
3-(4,5,6,7-tetrahydroinden-2-methylidenyl)-5-(2-morpholin-4-ethyl)-2-indolinone
3-(3-methyl-4,5,6,7-tetrahydrobenzofuran-2-methylidenyl)-5-(2-morpholin-4-ethyl)-2-indolinone
3-(3-ethoxycarbonyl-4,5,6,7-tetrahydrobenzofuran-2-methylidenyl)-5-(2-morpholin-4-ethyl)-2-indolinone
3-(3-n-pentyl-4,5,6,7-tetrahydrobenzofuran-2-methylidenyl)-5-(2-morpholin-4-ethyl)-2-indolinone
3-(3-ethyl-4,5,6,7-tetrahydrobenzofuran-2-methylidenyl)-5-(2-morpholin-4-ethyl)-2-indolinone
3-(4,5,6,7-tetrahydrobenzofuran-2-methylidenyl)-5-(2-morpholin-4-ethyl)-2-indolinone
3-[3-(4-methylphenyl)-4,5,6,7-tetrahydrobenzofuran-2-methylidenyl]-5-(2-morpholin-4-ethyl)-2-indolinone
3-(3-phenylsulfonylmethyl-4,5,6,7-tetrahydrobenzofuran-2-methylidenyl)-5-(2-morpholin-4-ethyl)-2-indolinone
3-[3-(1-phenylaminoethyl)-4,5,6,7-tetrahydrobenzofuran-2-methylidenyl]-5-(2-morpholin-4-ethyl)-2-indolinone
3-[3-(1-phenylaminobutyl)-4,5,6,7-tetrahydrobenzofuran-2-methylidenyl]-5-(2-morpholin-4-ethyl)-2-indolinone
3-(3-cyano-4,5,6,7-tetrahydrobenzofuran-2-methylidenyl)-5-(2-morpholin-4-ethyl)-2-indolinone
3-(3-phenylaminomethyl-4,5,6,7-tetrahydrobenzofuran-2-methylidenyl)-5-(2-morpholin-4-ethyl)-2-indolinone
3-(3-phenyl-4,5,6,7-tetrahydrobenzofuran-2-methylidenyl)-5-(2-morpholin-4-ethyl)-2-indolinone
3-(4,5,6,7-tetrahydrobenzimidazol-2-methylidenyl)-5-(2-morpholin-4-ethyl)-2-indolinone
3-(3-methyl-4,5,6,7-tetrahydroindol-2-methylidenyl)-5-n-butyl-2-indolinone
3-(3-carboxy-4,5,6,7-tetrahydroindol-2-methylidenyl)-5-n-butyl-2-indolinone
3-[3-(isoquinolin-1-methyl)-4,5,6,7-tetrahydroindol-2-methylidenyl]-5-n-butyl-2-indolinone
3-(3-hydroxy-4,5,6,7-tetrahydroindol-2-methylidenyl)-5-n-butyl-2-indolinone
3-(3-methoxy-4,5,6,7-tetrahydroindol-2-methylidenyl)-5-n-butyl-2-indolinone
3-(4,5,6,7-tetrahydroindol-2-methylidenyl)-5-n-butyl-2-indolinone
3-(4,5,6,7-tetrahydrobenzothien-2-methylidenyl)-5-n-butyl-2-indolinone
3-(3-methoxycarbonyl-4,5,6,7-tetrahydrobenzothien-2-methylidenyl)-5-n-butyl-2-indolinone
3-(3-vinyl-4,5,6,7-tetrahydrobenzothien-2-methylidenyl)-5-n-butyl-2-indolinone
3-(3-carboxy-4,5,6,7-tetrahydrobenzothien-2-methylidenyl)-5-n-butyl-2-indolinone
3-(3-ethoxycarbonyl-4,5,6,7-tetrahydrobenzothien-2-methylidenyl)-5-n-butyl-2-indolinone
3-[3-(3-dimethylamino-n-propoxycarbonyl)-4,5,6,7-tetrahydrobenzothien-2-methylidenyl]-5-n-butyl-2-indolinone
3-[3-(2-diethylaminoethoxycarbonyl)-4,5,6,7-tetrahydrobenzothien-2-methylidenyl]-5-n-butyl-2-indolinone
3-[3-(2-methylaminoethyl)-4,5,6,7-tetrahydrobenzothien-2-methylidenyl]-5-n-butyl-2-indolinone
3-(3-cyclopropylmethoxy-4,5,6,7-tetrahydrobenzothien-2-methylidenyl)-5-n-butyl-2-indolinone
3-(4,5,6,7-tetrahydrobenzothiazol-2-methylidenyl)-5-n-butyl-2-indolinone
3-(4-methyl-4,5,6,7-tetrahydroindol-2-methylidenyl)-5-n-butyl-2-indolinone
3-(4,4-dimethyl-4,5,6,7-tetrahydroindol-2-methylidenyl)-5-n-butyl-2-indolinone
3-(4-ethyl-4,5,6,7-tetrahydroindol-2-methylidenyl)-5-n-butyl-2-indolinone
3-(4-phenyl-4,5,6,7-tetrahydroindol-2-methylidenyl)-5-n-butyl-2-indolinone
3-(4-ethyl-4,5,6,7-tetrahydroindol-2-methylidenyl)-5-n-butyl-2-indolinone
3-3-isopropyl-4,5,6,7-tetrahydroindol-2-methylidenyl)-5-n-butyl-2-indolinone
3-(4,5,6,7-tetrahydroindol-2-methylidenyl)-5-n-butyl-2-indolinone
3-(4-isopropyl-4,5,6,7-tetrahydroindol-2-methylidenyl)-5-n-butyl-2-indolinone
3-(4-carboxymethyl-4,5,6,7-tetrahydroindol-2-methylidenyl)-5-n-butyl-2-indolinone
3-(3-methyl-4,5,6,7-tetrahydroinden-2-methylidenyl-5-ethyl-2-indolinone
3-(4,5,6,7-tetrahydroinden-2-methylidenyl)-5-ethyl-2-indolinone
3-(3-methyl-4,5,6,7-tetrahydrobenzofuran-2-methylidenyl)-5-ethyl-2-indolinone
3-(3-ethoxycarbonyl-4,5,6,7-tetrahydrobenzofuran-2-methylidenyl)-5-ethyl-2-indolinone
3-(3-n-pentyl-4,5,6,7-tetrahydrobenzofuran-2-methylidenyl)-5-ethyl-2-indolinone
3-(3-ethyl-4,5,6,7-tetrahydrobenzofuran-2-methylidenyl)-5-ethyl-2-indolinone
3-(4,5,6,7-tetrahydrobenzofuran-2-methylidenyl)-5-ethyl-2-indolinone
3-[3-(4-methylphenyl)-4,5,6,7-tetrahydrobenzofuran-2-methylidenyl]-5-ethyl-2-indolinone
3-(3-phenylsulfonylmethyl-4,5,6,7-tetrahydrobenzofuran-2-methylidenyl)-5-ethyl-2-indolinone
3-[3-(1-phenylaminoethyl)-4,5,6,7-tetrahydrobenzofuran-2-methylidenyl]-5-ethyl-2-indolinone
3-[3-(1-phenylaminobutyl)-4,5,6,7-tetrahydrobenzofuran-2-methylidenyl]-5-ethyl-2-indolinone
3-(3-cyano-4,5,6,7-tetrahydrobenzofuran-2-methylidenyl)-5-ethyl-2-indolinone
3-(3-phenylaminomethyl-4,5,6,7-tetrahydrobenzofuran-2-methylidenyl)-5-ethyl-2-indolinone
3-(3-phenyl-4,5,6,7-tetrahydrobenzofuran-2-methylidenyl)-5-ethyl-2-indolinone
3-(4,5,6,7-tetrahydrobenzimidazol-2-methylidenyl)-5-ethyl-2-indolinone
3-(4,5,6,7-tetrahydrobenzoxazol-2-methylidenyl)-5-ethyl-2-indolinone
3-(3-carboxy-4,5,6,7-tetrahydroindol-2-methylidenyl)-5,7-dibromo-4-methyl-2-indolinone
3-[3-(isoquinolin-1-methyl)-4,5,6,7-tetrahydroindol-2-methylidenyl]-5,7-dibromo-4-methyl-2-indolinone
3-(3-hydroxy-4,5,6,7-tetrahydroindol-2-methylidenyl)-5,7-dibromo-4-methyl-2-indolinone
3-(3-methoxy-4,5,6,7-tetrahydroindol-2-methylidenyl)-5,7-dibromo-4-methyl-2-indolinone
3-(4,5,6,7-tetrahydroindol-2-methylidenyl)-5,7-dibromo-4-methyl-2-indolinone
3-(4,5,6,7-tetrahydrobenzothien-2-methylidenyl)-5,7-dibromo-4-methyl-2-indolinone
3-(3-methoxycarbonyl-4,5,6,7-tetrahydrobenzothien-2-methylidenyl)-5,7-dibromo-4-methyl-2-indolinone
3-(3-vinyl-4,5,6,7-tetrahydrobenzothien-2-methylidenyl)-5,7-dibromo-4-methyl-2-indolinone
3-(3-carboxy-4,5,6,7-tetrahydrobenzothien-2-methylidenyl)-5,7-dibromo-4-methyl-2-indolinone
3-(3-ethoxycarbonyl-4,5,6,7-tetrahydrobenzothien-2-methylidenyl)-5,7-dibromo-4-methyl-2-indolinone
3-[3-(3-dimethylamino-n-propoxycarbonyl)-4,5,6,7-tetrahydrobenzothien-2-methylidenyl]-5,7-dibromo-4-methyl-2-indolinone
3-[3-(2-diethylaminoethoxycarbonyl)-4,5,6,7-tetrahydrobenzothien-2-methylidenyl]-5,7-dibromo-4-methyl-2-indolinone -continued 3-[3-(2-methylaminoethyl)-4,5,6,7-tetrahydrobenzothien-2-methylidenyl]-5,7-dibromo-4-methyl-2-indolinone
3-(3-cyclopropylmethoxy-4,5,6,7-tetrahydrobenzothien-2-methylidenyl)-5,7-dibromo-4-methyl-2-indolinone
3-(4,5,6,7-tetrahydrobenzothiazol-2-methylidenyl)-5,7-dibromo-4-methyl-2-indolinone
3-(4-methyl-4,5,6,7-tetrahydroindol-2-methylidenyl)-5,7-dibromo-4-methyl-2-indolinone
3-(4,4-dimethyl-4,5,6,7-tetrahydroindol-2-methylidenyl)-5,7-dibromo-4-methyl-2-indolinone
3-(4-ethyl-4,5,6,7-tetrahydroindol-2-methylidenyl)-5,7-dibromo-4-methyl-2-indolinone
3-(4-phenyl-4,5,6,7-tetrahydroindol-2-methylidenyl)-5,7-dibromo-4-methyl-2-indolinone
3-(3-ethyl-4,5,6,7-tetrahydroindol-2-methylidenyl)-5,7-dibromo-4-methyl-2-indolinone
3-(3-isopropyl-4,5,6,7-tetrahydroindol-2-methylidenyl)-5,7-dibromo-4-methyl-2-indolinone
3-(4,5,6,7-tetrahydroindol-3-methylidenyl)-5,7-dibromo-4-methyl-2-indolinone
3-(4-isopropyl-4,5,6,7-tetrahydroindol-2-methylidenyl)-5,7-dibromo-4-methyl-2-indolinone
3-(4-carboxymethyl-4,5,6,7-tetrahydroindol-2-methylidenyl)-5,7-dibromo-4-methyl-2-indolinone
3-(3-methyl-4,5,6,7-tetrahydroinden-2-methylidenyl)-5-n-butyl-2-indolinone
3-(4,5,6,7-tetrahydroinden-2-methylidenyl)-5-n-butyl-2-indolinone
3-(3-methyl-4,5,6,7-tetrahydrobenzofuran-2-methylidenyl)-5-n-butyl-2-indolinone
3-(3-ethoxycarbonyl-4,5,6,7-tetrahydrobenzofuran-2-methylidenyl)-5-n-butyl-2-indolinone
3-(3-n-pentyl-4,5,6,7-tetrahydrobenzofuran-2-methylidenyl)-5-n-butyl-2-indolinone
3-(3-ethyl-4,5,6,7-tetrahydrobenzofuran-2-methylidenyl)-5-n-butyl-2-indolinone
3-(4,5,6,7-tetrahydrobenzofuran-2-methylidenyl)-5-n-butyl-2-indolinone
3-[3-(4-methylphenyl)-4,5,6,7-tetrahydrobenzofuran-2-methylidenyl]-5-n-butyl-2-indolinone
3-(3-phenylsulfonylmethyl-4,5,6,7-tetrahydrobenzofuran-2-methylidenyl)-5-n-butyl-2-indolinone
3-[3-(1-phenylaminoethyl)-4,5,6,7-tetrahydrobenzofuran-2-methylidenyl]-5-n-butyl-2-indolinone
3-[3-(1-phenylaminobutyl)-4,5,6,7-tetrahydrobenzofuran-2-methylidenyl]-5-n-butyl-2-indolinone
3-(3-cyano-4,5,6,7-tetrahydrobenzofuran-2-methylidenyl)-5-n-butyl-2-indolinone
3-(3-phenylaminomethyl-4,5,6,7-tetrahydrobenzofuran-2-methylidenyl)-5-n-butyl-2-indolinone
3-(3-phenyl-4,5,6,7-tetrahydrobenzofuran-2-methylidenyl)-5-n-butyl-2-indolinone
3-(4,5,6,7-tetrahydrobenzimidazol-2-methylidenyl)-5-n-butyl-2-indolinone
3-(4,5,6,7-tetrahydrobenzoxazol-2-methylidenyl)-5-n-butyl-2-indolinone
3-[3-(isoquinolin-1-methyl)-4,5,6,7-tetrahydroindol-2-methylidenyl]-5-iodo-4-methyl-2-indolinone
3-(3-hydroxy-4,5,6,7-tetrahydroindol-2-methylidenyl)-5-iodo-4-methyl-2-indolinone
3-(3-methoxy-4,5,6,7-tetrahydroindol-2-methylidenyl)-5-iodo-4-methyl-2-indolinone
3-(4,5,6,7-tetrahydroindol-2-methylidenyl)-5-iodo-4-methyl-2-indolinone
3-(4,5,6,7-tetrahydrobenzothien-2-methylidenyl)-5-iodo-4-methyl-2-indolinone
3-(3-methoxycarbonyl-4,5,6,7-tetrahydrobenzothien-2-methylidenyl)-5-iodo-4-methyl-2-indolinone
3-(3-vinyl-4,5,6,7-tetrahydrobenzothien-2-methylidenyl)-5-iodo-4-methyl-2-indolinone
3-(3-carboxy-4,5,6,7-tetrahydrobenzothien-2-methylidenyl)-5-iodo-4-methyl-2-indolinone
3-(3-ethoxycarbonyl-4,5,6,7-tetrahydrobenzothien-2-methylidenyl)-5-iodo-4-methyl-2-indolinone
3-[3-(3-dimethylamino-n-propoxycarbonyl)-4,5,6,7-tetrahydrobenzothien-2-methylidenyl]-5-iodo-4-methyl-2-indolinone
3-[3-(2-diethylaminoethoxycarbonyl)-4,5,6,7-tetrahydrobenzothien-2-methylidenyl]-5-iodo-4-methyl-2-indolinone
3-[3-(2-methylaminoethyl)-4,5,6,7-tetrahydrobenzothien-2-methylidenyl]-5-iodo-4-methyl-2-indolinone
3-(3-cyclopropylmethoxy-4,5,6,7-tetrahydrobenzothien-2-methylidenyl)-5-iodo-4-methyl-2-indolinone
3-(4,5,6,7-tetrahydrobenzothiazol-2-methylidenyl)-5-iodo-4-methyl-2-indolinone
3-(4-methyl-4,5,6,7-tetrahydroindol-2-methylidenyl)-5-iodo-4-methyl-2-indolinone
3-(4,4-dimethyl-4,5,6,7-tetrahydroindol-2-methylidenyl)-5-iodo-4-methyl-2-indolinone
3-(4-ethyl-4,5,6,7-tetrahydroindol-2-methylidenyl)-5-iodo-4-methyl-2-indolinone
3-(4-phenyl-4,5,6,7-tetrahydroindol-2-methylidenyl)-5-iodo-4-methyl-2-indolinone
3-(3-ethyl-4,5,6,7-tetrahydroindol-2-methylidenyl)-5-iodo-4-methyl-2-indolinone
3-(3-isopropyl-4,5,6,7-tetrahydroindol-2-methylidenyl)-5-iodo-4-methyl-2-indolinone
3-(4,5,6,7-tetrahydroindol-3-methylidenyl)-5-iodo-4-methyl-2-indolinone
3-(4-isopropyl-4,5,6,7-tetrahydroindol-2-methylidenyl)-5-iodo-4-methyl-2-indolinone
3-(4-carboxymethyl-4,5,6,7-tetrahydroindol-2-methylidenyl)-5-iodo-4-methyl-2-indolinone
3-(3-methyl-4,5,6,7-tetrahydroinden-2-methylidenyl)-5,7-dibromo-4-methyl-2-indolinone
3-(4,5,6,7-tetrahydroinden-2-methylidenyl)-5,7-dibromo-4-methyl-2-indolinone
3-(3-methyl-4,5,6,7-tetrahydrobenzofuran-2-methylidenyl)-5,7-dibromo-4-methyl-2-indolinone
3-(3-ethoxycarbonyl-4,5,6,7-tetrahydrobenzofuran-2-methylidenyl)-5,7-dibromo-4-methyl-2-indolinone
3-(3-n-pentyl-4,5,6,7-tetrahydrobenzofuran-2-methylidenyl)-5,7-dibromo-4-methyl-2-indolinone
3-(3-ethyl-4,5,6,7-tetrahydrobenzofuran-2-methylidenyl)-5,7-dibromo-4-methyl-2-indolinone
3-(4,5,6,7-tetrahydrobenzofuran-2-methylidenyl)-5,7-dibromo-4-methyl-2-indolinone
3-[3-(4-methylphenyl)-4,5,6,7-tetrahydrobenzofuran-2-methylidenyl]-5,7-dibromo-4-methyl-2-indolinone
3-(3-phenylsulfonylmethyl-4,5,6,7-tetrahydrobenzofuran-2-methylidenyl)-5,7-dibromo-4-methyl-2-indolinone
3-[3-(1-phenylaminoethyl)-4,5,6,7-tetrahydrobenzofuran-2-methylidenyl]-5,7-dibromo-4-methyl-2-indolinone
3-[3-(1-phenylaminobutyl)-4,5,6,7-tetrahydrobenzofuran-2-methylidenyl]-5,7-dibromo-4-methyl-2-indolinone
3-(3-cyano-4,5,6,7-tetrahydrobenzofuran-2-methylidenyl)-5,7-dibromo-4-methyl-2-indolinone
3-(3-phenylaminomethyl-4,5,6,7-tetrahydrobenzofuran-2-methylidenyl)-5,7-dibromo-4-methyl-2-indolinone
3-(3-phenyl-4,5,6,7-tetrahydrobenzofuran-2-methylidenyl)-5,7-dibromo-4-methyl-2-indolinone
3-(4,5,6,7-tetrahydrobenzimidazol-2-methylidenyl)-5,7-dibromo-4-methyl-2-indolinone
3-(4,5,6,7-tetrahydrobenzoxazol-2-methylidenyl)-5,7-dibromo-4-methyl-2-indolinone
3-(3-methyl-4,5,6,7-tetrahydroindol-2-methylidenyl)-5,7-dibromo-4-methyl-2-indolinone
3-(3-hydroxy-4,5,6,7-tetrahydroindol-2-methylidenyl)-5-(2-carboxyethyl)-2-indolinone
3-(3-methoxy-4,5,6,7-tetrahydroindol-2-methylidenyl)-5-(2-carboxyethyl)-2-indolinone
3-(4,5,6,7-tetrahydroindol-2-methylidenyl)-5-(2-carboxyethyl)-2-indolinone
3-(4,5,6,7-tetrahydrobenzothien-2-methylidenyl)-5-(2-carboxyethyl)-2-indolinone
3-(3-methoxycarbonyl-4,5,6,7-tetrahydrobenzothien-2-methylidenyl)-5-(2-carboxyethyl)-2-indolinone
3-(3-vinyl-4,5,6,7-tetrahydrobenzothien-2-methylidenyl)-5-(2-carboxyethyl)-2-indolinone
3-(3-carboxy-4,5,6,7-tetrahydrobenzothien-2-methylidenyl)-5-(2-carboxyethyl)-2-indolinone
3-(3-ethoxycarbonyl-4,5,6,7-tetrahydrobenzothien-2-methylidenyl)-5-(2-carboxyethyl)-2-indolinone
3-[3-(3-dimethylamino-n-propoxycarbonyl)-4,5,6,7-tetrahydrobenzothien-2-methylidenyl]-5-(2-carboxyethyl)-2-indolinone
3-[3-(2-diethylaminoethoxycarbonyl)-4,5,6,7-tetrahydrobenzothien-2-methylidenyl]-5-(2-carboxyethyl)-2-indolinone
3-[3-(2-methylaminoethyl)-4,5,6,7-tetrahydrobenzothien-2-methylidenyl]-5-(2-carboxyethyl)-2-indolinone -continued 3-(3-cyclopropylmethoxy-4,5,6,7-tetrahydrobenzothien-2-methylidenyl)-5-(2-carboxyethyl)-2-indolinone
3-(4,5,6,7-tetrahydrobenzothiazol-2-methylidenyl)-5-(2-carboxyethyl)-2-indolinone
3-(4-methyl-4,5,6,7-tetrahydroindol-2-methylidenyl)-5-(2-carboxyethyl)-2-indolinone
3-(4,4-dimethyl-4,5,6,7-tetrahydroindol-2-methylidenyl)-5-(2-carboxyethyl)-2-indolinone
3-(4-ethyl-4,5,6,7-tetrahydroindol-2-methylidenyl)-5-(2-carboxyethyl)-2-indolinone
3-(4-phenyl-4,5,6,7-tetrahydroindol-2-methylidenyl)-5-(2-carboxyethyl)-2-indolinone
3-(3-ethyl-4,5,6,7-tetrahydroindol-2-methylidenyl)-5-(2-carboxyethyl)-2-indolinone
3-(3-isopropyl-4,5,6,7-tetrahydroindol-2-methylidenyl)-5-(2-carboxyethyl)-2-indolinone
3-(4,5,6,7-tetrahydroindol-2-methylidenyl)-5-(2-carboxyethyl)-2-indolinone
3-(4-isopropyl-4,5,6,7-tetrahydroindol-2-methylidenyl)-5-(2-carboxyethyl)-2-indolinone
3-(4-carboxymethyl-4,5,6,7-tetrahydroindol-2-methylidenyl)-5-(2-carboxyethyl)-2-indolinone
3-(3-methyl-4,5,6,7-tetrahydroinden-2-methylidenyl)-5-iodo-4-methyl-2-indolinone
3-(4,5,6,7-tetrahydroinden-2-methylidenyl)-5-iodo-4-methyl-2-indolinone
3-(3-methyl-4,5,6,7-tetrahydrobenzofuran-2-methylidenyl)-5-iodo-4-methyl-2-indolinone
3-(3-ethoxycarbonyl-4,5,6,7-tetrahydrobenzofuran-2-methylidenyl)-5-iodo-4-methyl-2-indolinone
3-(3-n-pentyl-4,5,6,7-tetrahydrobenzofuran-2-methylidenyl)-5-iodo-4-methyl-2-indolinone
3-(3-ethyl-4,5,6,7-tetrahydrobenzofuran-2-methylidenyl)-5-iodo-4-methyl-2-indolinone
3-(4,5,6,7-tetrahydrobenzofuran-2-methylidenyl)-5-iodo-4-methyl-2-indolinone
3-[3-(4-methylphenyl)4,5,6,7-tetrahydrobenzofuran-2-methylidenyl]-5-iodo-4-methyl-2-indolinone
3-(3-phenylsulfonylmethyl-4,5,6,7-tetrahydrobenzofuran-2-methylidenyl)-5-iodo-4-methyl-2-indolinone
3-[3-(1-phenylaminoethyl)-4,5,6,7-tetrahydrobenzofuran-2-methylidenyl]-5-iodo-4-methyl-2-indolinone
3-[3-(1-phenylaminobutyl)-4,5,6,7-tetrahydrobenzofuran-2-methylidenyl]-5-iodo-4-methyl-2-indolinone
3-(3-cyano-4,5,6,7-tetrahydrobenzofuran-2-methylidenyl)-5-iodo-4-methyl-2-indolinone
3-(3-phenylaminomethyl-4,5,6,7-tetrahydrobenzofuran-2-methylidenyl)-5-iodo-4-methyl-2-indolinone
3-(3-phenyl-4,5,6,7-tetrahydrobenzofuran-2-methylidenyl)-5-iodo-4-methyl-2-indolinone
3-(4,5,6,7-tetrahydrobenzimidazol-2-methylidenyl)-5-iodo-4-methyl-2-indolinone
3-(4,5,6,7-tetrahydrobenzoxazol-2-methylidenyl)-5-iodo-4-methyl-2-indolinone
3-(3-methyl-4,5,6,7-tetrahydroindol-2-methylidenyl)-5-iodo-4-methyl-2-indolinone
3-(3-carboxy-4,5,6,7-tetrahydroindol-2-methylidenyl)-5-iodo-4-methyl-2-indolinone
3-(3-methoxy-4,5,6,7-tetrahydroindol-2-methylidenyl)-5-carboxy-2-indolinone
3-(4,5,6,7-tetrahydroindol-2-methylidenyl)-5-carboxy-2-indolinone
3-(4,5,6,7-tetrahydrobenzothien-2-methylidenyl)-5-carboxy-2-indolinone
3-(3-methoxycarbonyl-4,5,6,7-tetrahydrobenzothien-2-methylidenyl)-5-carboxy-2-indolinone
3-(3-vinyl-4,5,6,7-tetrahydrobenzothien-2-methylidenyl)-5-carboxy-2-indolinone
3-(3-carboxy-4,5,6,7-tetrahydrobenzothien-2-methylidenyl)-5-carboxy-2-indolinone
3-(3-ethoxycarbonyl-4,5,6,7-tetrahydrobenzothien-2-methylidenyl)-5-carboxy-2-indolinone
3-[3-(3-dimethylamino-n-propoxycarbonyl)-4,5,6,7-tetrahydrobenzothien-2-methylidenyl]-5-carboxy-2-indolinone
3-[3-(2-diethylaminoethoxycarbonyl)-4,5,6,7-tetrahydrobenzothien-2-methylidenyl]-5-carboxy-2-indolinone
3-[-(2-methylaminoethyl)-4,5,6,7-tetrahydrobenzothien-2-methylidenyl]-5-carboxy-2-indolinone
3-(3-cyclopropylmethoxy-4,5,6,7-tetrahydrobenzothien-2-methylidenyl)-5-carboxy-2-indolinone
3-(4,5,6,7-tetrahydrobenzothiazol-2-methylidenyl)-5-carboxy-2-indolinone
3-(4-methyl-4,5,6,7-tetrahydroindol-2-methylidenyl)-5-carboxy-2-indolinone
3-(4,4-dimethyl-4,5,6,7-tetrahydroindol-2-methylidenyl)-5-carboxy-2-indolinone
3-(4-ethyl-4,5,6,7-tetrahydroindol-2-methylidenyl)-5-carboxy-2-indolinone
3-(4-phenyl-4,5,6,7-tetrahydroindol-2-methylidenyl)-5-carboxy-2-indolinone
3-(3-ethyl-4,5,6,7-tetrahydroindol-2-methylidenyl)-5-carboxy-2-indolinone
3-(3-isopropyl-4,5,6,7-tetrahydroindol-2-methylidenyl)-5-carboxy-2-indolinone
3-(4,5,6,7-tetrahydroindol-2-methylidenyl)-5-carboxy-2-indolinone
3-(4-isopropyl-4,5,6,7-tetrahydroindol-2-methylidenyl)-5-carboxy-2-indolinone
3-(4-carboxymethyl-4,5,6,7-tetrahydroindol-2-methylidenyl)-5-carboxy-2-indolinone
3-(3-methyl-4,5,6,7-tetrahydroinden-2-methylidenyl)-5-(2-carboxyethyl)-2-indolinone
3-(4,5,6,7-tetrahydroinden-2-methylidenyl)-5-(2-carboxyethyl)-2-indolinone
3-(3-methyl-4,5,6,7-tetrahydrobenzofuran-2-methylidenyl)-5-(2-carboxyethyl))-2-indolinone
3-(3-ethoxycarbonyl-4,5,6,7-tetrahydrobenzofuran-2-methylidenyl)-5-(2-carboxyethyl)-2-indolinone
3-(3-n-pentyl-4,5,6,7-tetrahydrobenzofuran-2-methylidenyl)-5-(2-carboxyethyl)-2-indolinone
3-(3-ethyl-4,5,6,7-tetrahydrobenzofuran-2-methylidenyl)-5-(2-carboxyethyl)-2-indolinone
3-(4,5,6,7-tetrahydrobenzofuran-2-methylidenyl)-5-(2-carboxyethyl)-2-indolinone
3-[3-(4-methylphenyl)-4,5,6,7-tetrahydrobenzofuran-2-methylidenyl]-5-(2-carboxyethyl)-2-indolinone
3-(3-phenylsulfonylmethyl-4,5,6,7-tetrahydrobenzofuran-2-methylidenyl)-5-(2-carboxyethyl)-2-indolinone
3-[3-(1-phenylaminoethyl)-4,5,6,7-tetrahydrobenzofuran-2-methylidenyl]-5-(2-carboxyethyl)-2-indolinone
3-[3-(1-phenylaminobutyl)-4,5,6,7-tetrahydrobenzofuran-2-methylidenyl]-5-(2-carboxyethyl)-2-indolinone
3-(3-cyano-4,5,6,7-tetrahydrobenzofuran-2-methylidenyl)-5-(2-carboxyethyl)-2-indolinone
3-(3-phenylaminomethyl-4,5,6,7-tetrahydrobenzofuran-2-methylidenyl)-5-(2-carboxyethyl))-2-indolinone
3-(3-phenyl-4,5,6,7-tetrahydrobenzofuran-2-methylidenyl)-5-(2-carboxyethyl)-2-indolinone
3-(4,5,6,7-tetrahydrobenzimidazol-2-methylidenyl)-5-(2-carboxyethyl))-2-indolinone
3-(4,5,6,7-tetrahydrobenzoxazol-2-methylidenyl)-5-(2-carboxyethyl)-2-indolinone
3-(3-methyl-4,5,6,7-tetrahydroindol-2-methylidenyl)-5-(2-carboxyethyl)-2-indolinone
3-(3-carboxy-4,5,6,7-tetrahydroindol-2-methylidenyl)-5-(2-carboxyethyl)-2-indolinone
3-[3-(isoquinolin-1-methyl)-4,5,6,7-tetrahydroindol-2-methylidenyl]-5-(2-carboxyethyl)-2-indolinone
3-(4,5,6,7-tetrahydroindol-2-methylidenyl]-5-(2-carboxyethyl)-2-indolinone
3-(4,5,6,7-tetrahydrobenzothien-2-methylidenyl)-5-methoxycarbonyl-2-indolinone
3-(3-methoxycarbonyl-4,5,6,7-tetrahydrobenzothien-2-methylidenyl)-5-methoxycarbonyl-2-indolinone
3-(3-vinyl-4,5,6,7-tetrahydrobenzothien-2-methylidenyl)-5-methoxycarbonyl-2-indolinone
3-(3-carboxy-4,5,6,7-tetrahydrobenzothien-2-methylidenyl)-5-methoxycarbonyl-2-indolinone
3-(3-ethoxycarbonyl-4,5,6,7-tetrahydrobenzothien-2-methylidenyl)-5-methoxycarbonyl-2-indolinone
3-[3-(3-dimethylamino-n-propoxycarbonyl)-4,5,6,7-tetrahydrobenzothien-2-methylidenyl]-5-methoxycarbonyl-2-indolinone
3-[3-(2-diethylaminoethoxycarbonyl)-4,5,6,7-tetrahydrobenzothien-2-methylidenyl]-5-methoxycarbonyl-2-indolinone
3-[3-(2-methylaminoethyl)-4,5,6,7-tetrahydrobenzothien-2-methylidenyl]-5-methoxycarbonyl-2-indolinone
3-(3-cyclopropylmethoxy-4,5,6,7-tetrahydrobenzothien-2-methylidenyl)-5-methoxycarbonyl-2-indolinone 3-(4,5,6,7-tetrahydrobenzothiazol-2-methylidenyl)-5-methoxycarbonyl-2-indolinone
3-(4-methyl-4,5,6,7-tetrahydroindol-2-methylidenyl)-5-methoxycarbonyl-2-indolinone
3-(4,4-dimethyl-4,5,6,7-tetrahydroindol-2-methylidenyl)-5-methoxycarbonyl-2-indolinone
3-(4-ethyl-4,5,6,7-tetrahydroindol-2-methylidenyl)-5-methoxycarbonyl-2-indolinone
3-(4-phenyl-4,5,6,7-tetrahydroindol-2-methylidenyl)-5-methoxycarbonyl-2-indolinone
3-(3-ethyl-4,5,6,7-tetrahydroindol-2-methylidenyl)-5-methoxycarbonyl-2-indolinone
3-(3-isopropyl-4,5,6,7-tetrahydroindol-2-methylidenyl)-5-methoxycarbonyl-2-indolinone
3-(4,5,6,7-tetrahydroindol-2-methylidenyl)-5-methoxycarbonyl-2-indolinone
3-(4-isopropyl-4,5,6,7-tetrahydroindol-2-methylidenyl)-5-methoxycarbonyl-2-indolinone
3-(4-carboxymethyl-4,5,6,7-tetrahydroindol-2-methylidenyl)-5-methoxycarbonyl-2-indolinone
3-(3-methyl-4,5,6,7-tetrahydroinden-2-methylidenyl)-5-carboxy-2-indolinone
3-(4,5,6,7-tetrahydroinden-2-methylidenyl)-5-carboxy-2-indolinone
3-(3-methyl-4,5,6,7-tetrahydrobenzofuran-2-methylidenyl)-5-carboxy-2-indolinone
3-(3-ethoxycarbonyl-4,5,6,7-tetrahydrobenzofuran-2-methylidenyl)-5-carboxy-2-indolinone
3-(3-n-pentyl-4,5,6,7-tetrahydrobenzofuran-2-methylidenyl)-5-carboxy-2-indolinone
3-(3-ethyl-4,5,6,7-tetrahydrobenzofuran-2-methylidenyl)-5-carboxy-2-indolinone
3-(4,5,6,7-tetrahydrobenzofuran-2-methylidenyl)-5-carboxy-2-indolinone
3-[3-(4-methylphenyl)-4,5,6,7-tetrahydrobenzofuran-2-methylidenyl]-5-carboxy-2-indolinone
3-(3-phenylsulfonylmethyl-4,5,6,7-tetrahydrobenzofuran-2-methylidenyl)-5-carboxy-2-indolinone
3-[3-(1-phenylaminoethyl)-4,5,6,7-tetrahydrobenzofuran-2-methylidenyl]-5-carboxy-2-indolinone
3-[3-(1-phenylaminobutyl)-4,5,6,7-tetrahydrobenzofuran-2-methylidenyl]-5-carboxy-2-indolinone
3-(3-cyano-4,5,6,7-tetrahydrobenzofuran-2-methylidenyl)-5-carboxy-2-indolinone
3-(3-phenylaminomethyl-4,5,6,7-tetrahydrobenzofuran-2-methylidenyl)-5-carboxy-2-indolinone
3-(3-phenyl-4,5,6,7-tetrahydrobenzofuran-2-methylidenyl)-5-carboxy-2-indolinone
3-(4,5,6,7-tetrahydrobenzimidazol-2-methylidenyl)-5-carboxy-2-indolinone
3-(4,5,6,7-tetrahydrobenzoxazol-2-methylidenyl)-5-carboxy-2-indolinone
3-(3-methyl-4,5,6,7-tetrahydroindol-2-methylidenyl)-5-carboxy-2-indolinone
3-(3-carboxy-4,5,6,7-tetrahydroindol-2-methylidenyl)-5-carboxy-2-indolinone
3-[3-(isoquinolin-1-methyl)-4,5,6,7-tetrahydroindol-2-methylidenyl]-5-carboxy-2-indolinone
3-(3-hydroxy-4,5,6,7-tetrahydroindol-2-methylidenyl)-5-carboxy-2-indolinone
3-(4,5,6,7-tetrahydrobenzothien-2-methylidenyl)-5-(2-chloroethyl)-2-indolinone
3-(3-methoxycarbonyl-4,5,6,7-tetrahydrobenzothien-2-methylidenyl)-5-(2-chloroethyl)-2-indolinone
3-(3-vinyl-4,5,6,7-tetrahydrobenzothien-2-methylidenyl)-5-(2-chloroethyl)-2-indolinone
3-(3-carboxy-4,5,6,7-tetrahydrobenzothien-2-methylidenyl)-5-(2-chloroethyl)-2-indolinone
3-(3-ethoxycarbonyl-4,5,6,7-tetrahydrobenzothien-2-methylidenyl)-5-(2-chloroethyl)-2-indolinone
3-[3-(3-dimethylamino-n-propoxycarbonyl)-4,5,6,7-tetrahydrobenzothien-2-methylidenyl]-5-(2-chloroethyl)-2-indolinone
3-[3-(2-diethylaminoethoxycarbonyl)-4,5,6,7-tetrahydrobenzothien-2-methylidenyl]-5-(2-chloroethyl)-2-indolinone
3-[3-(2-methylaminoethyl)-4,5,6,7-tetrahydrobenzothien-2-methylidenyl]-5-(2-chloroethyl)-2-indolinone
3-(3-cyclopropylmethoxy-4,5,6,7-tetrahydrobenzothien-2-methylidenyl)-5-(2-chloroethyl)-2-indolinone
3-(4,5,6,7-tetrahydrobenzothiazol-2-methylidenyl)-5-(2-chloroethyl)-2-indolinone
3-(4-methyl-4,5,6,7-tetrahydroindol-2-methylidenyl)-5-(2-chloroethyl)-2-indolinone
3-(4,4-dimethyl-4,5,6,7-tetrahydroindol-2-methylidenyl)-5-(2-chloroethyl)-2-indolinone
3-(4-ethyl-4,5,6,7-tetrahydroindol-2-methylidenyl)-5-(2-chloroethyl)-2-indolinone
3-(4-phenyl-4,5,6,7-tetrahydroindol-2-methylidenyl)-5-(2-chloroethyl)-2-indolinone
3-(3-ethyl-4,5,6,7-tetrahydroindol-2-methylidenyl)-5-(2-chloroethyl)-2-indolinone
3-(3-isopropyl-4,5,6,7-tetrahydroindol-2-methylidenyl)-5-(2-chloroethyl)-2-indolinone
3-(4,5,6,7-tetrahydroindol-2-methylidenyl)-5-(2-chloroethyl)-2-indolinone
3-(4-isopropyl-4,5,6,7-tetrahydroindol-2-methylidenyl)-5-(2-chloroethyl)-2-indolinone
3-(4-carboxymethyl-4,5,6,7-tetrahydroindol-2-methylidenyl)-5-(2-chloroethyl)-2-indolinone
3-(3-methyl-4,5,6,7-tetrahydroinden-2-methylidenyl)-5-methoxycarbonyl-2-indolinone
3-(4,5,6,7-tetrahydroinden-2-methylidenyl)-5-methoxycarbonyl-2-indolinone
3-(3-methyl-4,5,6,7-tetrahydrobenzofuran-2-methylidenyl)-5-methoxycarbonyl-2-indolinone
3-(3-ethoxycarbonyl-4,5,6,7-tetrahydroinden-2-methylidenyl)-5-methoxycarbonyl-2-indolinone
3-(3-n-pentyl-4,5,6,7-tetrahydrobenzofuran-2-methylidenyl)-5-methoxycarbonyl-2-indolinone
3-(3-ethyl-4,5,6,7-tetrahydrobenzofuran-2-methylidenyl)-5-methoxycarbonyl-2-indolinone
3-(4,5,6,7-tetrahydrobenzofuran-2-methylidenyl)-5-methoxycarbonyl-2-indolinone
3-[3-(4-methylphenyl)-4,5,6,7-tetrahydrobenzofuran-2-methylidenyl]-5-methoxycarbonyl-2-indolinone
3-(3-phenylsulfonylmethyl-4,5,6,7-tetrahydrobenzofuran-2-methylidenyl)-5-methoxycarbonyl-2-indolinone
3-[3-(1-phenylaminoethyl)-4,5,6,7-tetrahydrobenzofuran-2-methylidenyl]-5-methoxycarbonyl-2-indolinone
3-[3-(1-phenylaminobutyl)-4,5,6,7-tetrahydrobenzofuran-2-methylidenyl]-5-methoxycarbonyl-2-indolinone
3-(3-cyano-4,5,6,7-tetrahydrobenzofuran-2-methylidenyl)-5-methoxycarbonyl-2-indolinone
3-(3-phenylaminomethyl-4,5,6,7-tetrahydrobenzofuran-2-methylidenyl)-5-methoxycarbonyl-2-indolinone
3-(3-phenyl-4,5,6,7-tetrahydrobenzofuran-2-methylidenyl)-5-methoxycarbonyl-2-indolinone
3-(4,5,6,7-tetrahydrobenzimidazol-2-methylidenyl)-5-methoxycarbonyl-2-indolinone
3-(4,5,6,7-tetrahydrobenzoxazol-2-methylidenyl)-5-methoxycarbonyl-2-indolinone
3-(3-methyl-4,5,6,7-tetrahydroindol-2-methylidenyl)-5-methoxycarbonyl-2-indolinone
3-(3-carboxy-4,5,6,7-tetrahydroindol-2-methylidenyl)-5-methoxycarbonyl-2-indolinone
3-[3-(isoquinolin-1-methyl)-4,5,6,7-tetrahydroindol-2-methylidenyl]-5-methoxycarbonyl-2-indolinone
3-(3-hydroxy-4,5,6,7-tetrahydroindol-2-methylidenyl)-5-methoxycarbonyl-2-indolinone
3-(3-methoxy-4,5,6,7-tetrahydroindol-2-methylidenyl)-5-methoxycarbonyl-2-indolinone
3-(3-methoxycarbonyl-4,5,6,7-tetrahydrobenzothien-2-methylidenyl)-6-trifluoromethyl-2-indolinone
3-(3-vinyl-4,5,6,7-4,5,6,7-tetrahydrobenzothien-2-methylidenyl)-6-trifluoromethyl-2-indolinone
3-(3-carboxy-4,5,6,7-tetrahydrobenzothien-2-methylidenyl)-6-trifluoromethyl-2-indolinone
3-(3-ethoxycarbonyl-4,5,6,7-tetrahydrobenzothien-2-methylidenyl)-6-trifluoromethyl-2-indolinone
3-[3-(3-dimethylamino-n-propoxycarbonyl)-4,5,6,7-tetrahydrobenzothien-2-methylidenyl]-6-trifluoromethyl-2-indolinone
3-[3-(2-diethylaminoethoxycarbonyl)-4,5,6,7-tetrahydrobenzothien-2-methylidenyl]-6-trifluoromethyl-2-indolinone
3-[3-(2-methylaminoethyl)-4,5,6,7-tetrahydrobenzothien-2-methylidenyl]-6-trifluoromethyl-2-indolinone
3-(3-cyclopropylmethoxy-4,5,6,7-tetrahydrobenzothien-2-methylidenyl)-6-trifluoromethyl-2-indolinone
3-(4,5,6,7-tetrahydrobenzothiazol-2-methylidenyl)-6-trifluoromethyl-2-indolinone -continued 3-(4-methyl-4,5,6,7-tetrahydroindol-2-methylidenyl)-6-trifluoromethyl-2-indolinone
3-(4,4-dimethyl-4,5,6,7-tetrahydroindol-2-methylidenyl)-6-trifluoromethyl-2-indolinone
3-(4-ethyl-4,5,6,7-tetrahydroindol-2-methylidenyl)-6-trifluoromethyl-2-indolinone
3-(4-phenyl-4,5,6,7-tetrahydroindol-2-methylidenyl)-6-trifluoromethyl-2-indolinone
3-(4-ethyl-4,5,6,7-tetrahydroindol-2-methylidenyl)-6-trifluoromethyl-2-indolinone
3-(3-isopropyl-4,5,6,7-tetrahydroindol-2-methylidenyl)-6-trifluoromethyl-2-indolinone
3-(4,5,6,7-tetrahydroindol-3-methylidenyl)-6-trifluoromethyl-2-indolinone
3-(4-isopropyl-4,5,6,7-tetrahydroindol-2-methylidenyl)-6-trifluoromethyl-2-indolinone
3-(4-carboxymethyl-4,5,6,7-tetrahydroindol-2-methylidenyl)-6-trifluoromethyl-2-indolinone
3-(3-methyl-4,5,6,7-tetrahydroinden-2-methylidenyl)-5-(2-chloroethyl)-2-indolinone
3-(4,5,6,7-tetrahydroinden-2-methylidenyl)-5-(2-chloroethyl)-2-indolinone
3-(3-methyl-4,5,6,7-tetrahydrobenzofuran-2-methylidenyl)-5-(2-chloroethyl)-2-indolinone
3-(3-ethoxycarbonyl-4,5,6,7-tetrahydrobenzofuran-2-methylidenyl)-5-(2-chloroethyl)-2-indolinone
3-(3-n-pentyl-4,5,6,7-tetrahydrobenzofuran-2-methylidenyl)-5-(2-chloroethyl)-2-indolinone
3-(3-ethyl-4,5,6,7-tetrahydrobenzofuran-2-methylidenyl)-5-(2-chloroethyl)-2-indolinone
3-(4,5,6,7-tetrahydrobenzofuran-2-methylidenyl)-5-(2-chloroethyl)-2-indolinone
3-[3-(4-methylphenyl)-4,5,6,7-tetrahydrobenzofuran-2-methylidenyl]-5-(2-chloroethyl)-2-indolinone
3-(3-phenylsulfonylmethyl-4,5,6,7-tetrahydrobenzofuran-2-methylidenyl)-5-(2-chloroethyl)-2-indolinone
3-[3-(1-phenylaminoethyl)-4,5,6,7-tetrahydrobenzofuran-2-methylidenyl]-5-(2-chloroethyl)-2-indolinone
3-[3-(1-phenylaminobutyl)-4,5,6,7-tetrahydrobenzofuran-2-methylidenyl]-5-(2-chloroethyl)-2-indolinone
3-(3-cyano-4,5,6,7-tetrahydrobenzofuran-2-methylidenyl)-5-(2-chloroethyl)-2-indolinone
3-(3-phenylaminomethyl(4,5,6,7-tetrahydrobenzofuran-2-methylidenyl)-5-(2-chloroethyl)-2-indolinone
3-(3-phenyl-4,5,6,7-tetrahydrobenzofuran-2-methylidenyl)-5-(2-chloroethyl)-2-indolinone
3-(4,5,6,7-tetrahydrobenzimidazol-2-methylidenyl)-5-(2-chloroethyl)-2-indolinone
3-(4,5,6,7-tetrahydrobenzoxazol-2-methylidenyl)-5-(2-chloroethyl)-2-indolinone
3-(3-methyl-4,5,6,7-tetrahydroindol-2-methylidenyl)-5-(2-chloroethyl)-2-indolinone
3-(3-carboxy-4,5,6,7-tetrahydroindol-2-methylidenyl)-5-(2-chloroethyl)-2-indolinone
3-[3-(isoquinolin-1-methyl)-4,5,6,7-tetrahydroindol-2-methylidenyl]-5-(2-chloroethyl)-2-indolinone
3-(3-hydroxy-4,5,6,7-tetrahydroindol-2-methylidenyl)-5-(2-chloroethyl)-2-indolinone
3-(3-methoxy-4,5,6,7-tetrahydroindol-2-methylidenyl)-5-(2-chloroethyl)-2-indolinone
3-(4,5,6,7-tetrahydroindol-2-methylidenyl)-5-(2-chloroethyl)-2-indolinone
3-(3-vinyl-4,5,6,7-tetrahydrobenzothien-2-methylidenyl)-5-(morpholin-4-sulfonyl)-2-indolinone
3-(3-carboxy-4,5,6,7-tetrahydrobenzothien-2-methylidenyl)-5-(morpholin-4-sulfonyl)-2-indolinone
3-(3-ethoxycarbonyl-4,5,6,7-tetrahydrobenzothien-2-methylidenyl)-5-(morpholin-4-sulfonyl)-2-indolinone
3-[3-(3-dimethylamino-n-propoxycarbonyl)-4,5,6,7-tetrahydrobenzothien-2-methylidenyl]-5-(morpholin-4-sulfonyl)-2-indolinone
3-[3-(2-diethylaminoethoxycarbonyl)-4,5,6,7-tetrahydrobenzothien-2-methylidenyl]-5-(morpholin-4-sulfonyl)-2-indolinone
3-[3-(2-methylaminoethyl)-4,5,6,7-tetrahydrobenzothien-2-methylidenyl]-5-(morpholin-4-sulfonyl)-2-indolinone
3-(3-cyclopropylmethoxy-4,5,6,7-tetrahydrobenzothien-2-methylidenyl)-5-(morpholin-4-sulfonyl)-2-indolinone
3-(4,5,6,7-tetrahydrobenzothiazol-2-methylidenyl)-5-(morpholin-4-sulfonyl)-2-indolinone
3-(4-methyl-4,5,6,7-tetrahydroindol-2-methylidenyl)-5-(morpholin-4-sulfonyl)-2-indolinone
3-(4,4-dimethyl-4,5,6,7-tetrahydroindol-2-methylidenyl)-5-(morpholin-4-sulfonyl)-2-indolinone
3-(4-ethyl-4,5,6,7-tetrahydroindol-2-methylidenyl)-5-(morpholin-4-sulfonyl)-2-indolinone
3-(4-phenyl-4,5,6,7-tetrahydroindol-2-methylidenyl)-5-(morpholin-4-sulfonyl)-2-indolinone
3-(4-ethyl-4,5,6,7-tetrahydroindol-2-methylidenyl)-5-(morpholin-4-sulfonyl)-2-indolinone
3-(3-isopropyl-4,5,6,7-tetrahydroindol-2-methylidenyl)-5-(morpholin-4-sulfonyl)-2-indolinone
3-(4,5,6,7-tetrahydroindol-2-methylidenyl)-5-(morpholin-4-sulfonyl)-2-indolinone
3-(4-isopropyl-4,5,6,7-tetrahydroindol-2-methylidenyl)-5-(morpholin-4-sulfonyl)-2-indolinone
3-(4-carboxymethyl-4,5,6,7-tetrahydroindol-2-methylidenyl)-5-(morpholin-4-sulfonyl)-2-indolinone
3-(3-methyl-4,5,6,7-tetrahydroinden-2-methylidenyl)-6-trifluoromethyl-2-indolinone
3-(4,5,6,7-tetrahydroinden-2-methylidenyl)-6-trifluoromethyl-2-indolinone
3-(3-methyl-4,5,6,7-tetrahydrobenzofuran-2-methylidenyl)-6-trifluoromethyl-2-indolinone
3-(3-ethoxycarbonyl-4,5,6,7-tetrahydrobenzofuran-2-methylidenyl)-6-trifluoromethyl-2-indolinone
3-(3-n-pentyl-4,5,6,7-tetrahydrobenzofuran-2-methylidenyl)-6-trifluoromethyl-2-indolinone
3-(3-ethyl-4,5,6,7-tetrahydrobenzofuran-2-methylidenyl)-6-trifluoromethyl-2-indolinone
3-(4,5,6,7-tetrahydrobenzofuran-2-methylidenyl)-6-trifluoromethyl-2-indolinone
3-[3-(4-methylphenyl)-4,5,6,7-tetrahydrobenzofuran-2-methylidenyl]-6-trifluoromethyl-2-indolinone
3-(3-phenylsulfonylmethyl-4,5,6,7-tetrahydrobenzofuran-2-methylidenyl)-6-trifluoromethyl-2-indolinone
3-[3-(1-phenylaminoethyl)-4,5,6,7-tetrahydrobenzofuran-2-methylidenyl]-6-trifluoromethyl-2-indolinone
3-[3-(1-phenylaminobutyl)-4,5,6,7-tetrahydrobenzofuran-2-methylidenyl]-6-trifluoromethyl-2-indolinone
3-(3-cyano-4,5,6,7-tetrahydrobenzofuran-2-methylidenyl)-6-trifluoromethyl-2-indolinone
3-(3-phenylaminomethyl-4,5,6,7-tetrahydrobenzofuran-2-methylidenyl)-6-trifluoromethyl-2-indolinone
3-(3-phenyl-4,5,6,7-tetrahydrobenzofuran-2-methylidenyl)-6-trifluoromethyl-2-indolinone
3-(4,5,6,7-tetrahydrobenzimidazol-2-methylidenyl)-6-trifluoromethyl-2-indolinone
3-(4,5,6,7-tetrahydrobenzoxazol-2-methylidenyl)-6-trifluoromethyl-2-indolinone
3-(3-methyl-4,5,6,7-tetrahydroindol-2-methylidenyl)-6-trifluoromethyl-2-indolinone
3-(3-carboxy-4,5,6,7-tetrahydroindol-2-methylidenyl)-6-trifluoromethyl-2-indolinone
3-[3-(isoquinolin-1-methyl)-4,5,6,7-tetrahydroindol-2-methylidenyl]-6-trifluoromethyl-2-indolinone
3-(3-hydroxy-4,5,6,7-tetrahydroindol-2-methylidenyl)-6-trifluoromethyl-2-indolinone
3-(3-methoxy-4,5,6,7-tetrahydroindol-2-methylidenyl)-6-trifluoromethyl-2-indolinone
3-(4,5,6,7-tetrahydroindol-2-methylidenyl)-6-trifluoromethyl-2-indolinone
3-(4,5,6,7-tetrahydrobenzothien-2-methylidenyl)-6-trifluoromethyl-2-indolinone
3-(3-carboxy-4,5,6,7-tetrahydrobenzothien-2-methylidenyl)-5-[4-(trifluoromethyl)phenylaminosulfonyl]-2-indolinone
3-(3-ethoxycarbonyl-4,5,6,7-tetrahydrobenzothien-2-methylidenyl)-5-[4-(trifluoromethyl)phenylaminosulfonyl]-2-indolinone
3-[3-(3-dimethylamino-n-propoxycarbonyl)-4,5,6,7-tetrahydrobenzothien-2-methylidenyl]-5-[4-(trifluoromethyl)phenylaminosulfonyl]-2-indolinone
3-[3-(2-diethylaminoethoxycarbonyl)-4,5,6,7-tetrahydrobenzothien-2-methylidenyl]-5-[4-(trifluoromethyl)phenylaminosulfonyl]-2-indolinone
3-[3-(2-methylaminoethyl)-4,5,6,7-tetrahydrobenzothien-2-methylidenyl]-5-[4-(trifluoromethyl)phenylaminosulfonyl]-2-indolinone
3-(3-cyclopropylmethoxy-4,5,6,7-tetrahydrobenzothien-2-methylidenyl)-5-[4-(trifluoromethyl)phenylaminosulfonyl]-2-indolinone
3-(4,5,6,7-tetrahydrobenzothiazol-2-methylidenyl)-5-[4-(trifluoromethyl)phenylaminosulfonyl]-2-indolinone
3-(4-methyl-4,5,6,7-tetrahydroindol-2-methylidenyl)-5-[4-(trifluoromethyl)phenylaminosulfonyl]-2-indolinone -continued 3-(4,4-dimethyl-4,5,6,7-tetrahydroindol-2-methylidenyl)-5-[4-(trifluoromethyl)phenylaminosulfonyl]-2-indolinone
3-(4-ethyl-4,5,6,7-tetrahydroindol-2-methylidenyl)-5-[4-(trifluoromethyl)phenylaminosulfonyl]-2-indolinone
3-(4-phenyl-4,5,6,7-tetrahydroindol-2-methylidenyl)-5-[4-(trifluoromethyl)phenylaminosulfonyl]-2-indolinone
3-(3-ethyl-4,5,6,7-tetrahydroindol-2-methylidenyl)-5-[4-(trifluoromethyl)phenylaminosulfonyl]-2-indolinone
3-3-isopropyl-4,5,6,7-tetrahydroindol-2-methylidenyl)-5-[4-(trifluoromethyl)phenylaminosulfonyl]-2-indolinone
3-(4,5,6,7-tetrahydroindol-3-methylidenyl)-5-[4-(trifluoromethyl)phenylaminosulfonyl]-2-indolinone
3-(4-isopropyl-4,5,6,7-tetrahydroindol-2-methylidenyl)-5-[4-(trifluoromethyl)phenylaminosulfonyl]-2-indolinone
3-(4-carboxymethyl-4,5,6,7-tetrahydroindol-2-methylidenyl)-5-[4-(trifluoromethyl)phenylaminosulfonyl]-2-indolinone
3-(3-methyl-4,5,6,7-tetrahydroinden-2-methylidenyl)-5-morpholin-4-sulfonyl)-2-indolinone
3-(4,5,6,7-tetrahydroinden-2-methylidenyl)-5-(morpholin-4-sulfonyl)-2-indolinone
3-(3-methyl-4,5,6,7-tetrahydrobenzofuran-2-methylidenyl)-5-(morpholin-4-sulfonyl)-2-indolinone
3-(3-ethoxycarbonyl-4,5,6,7-tetrahydrobenzofuran-2-methylidenyl)-5-(morpholin-4-sulfonyl)-2-indolinone
3-(3-n-pentyl-4,5,6,7-tetrahydrobenzofuran-2-methylidenyl)-5-(morpholin-4-sulfonyl)-2-indolinone
3-(3-ethyl-4,5,6,7-tetrahydrobenzofuran-2-methylidenyl)-5-(morpholin-4-sulfonyl)-2-indolinone
3-(4,5,6,7-tetrahydrobenzofuran-2-methylidenyl)-5-(morpholin-4-sulfonyl)-2-indolinone
3-[3-(4-methylphenyl)-4,5,6,7-tetrahydrobenzofuran-2-methylidenyl]-5-(morpholin-4-sulfonyl)-2-indolinone
3-(3-phenylsulfonylmethyl-4,5,6,7-tetrahydrobenzofuran-2-methylidenyl)-5-(morpholin-4-sulfonyl)-2-indolinone
3-[3-(1-phenylaminoethyl)-4,5,6,7-tetrahydrobenzofuran-2-methylidenyl]-5-(morpholin-4-sulfonyl)-2-indolinone
3-[3-(1-phenylaminobutyl)-4,5,6,7-tetrahydrobenzofuran-2-methylidenyl]-5-(morpholin-4-sulfonyl)-2-indolinone
3-(3-cyano-4,5,6,7-tetrahydrobenzofuran-2-methylidenyl)-5-(morpholin-4-sulfonyl)-2-indolinone
3-(3-phenylaminomethyl-4,5,6,7-tetrahydrobenzofuran-2-methylidenyl)-5-(morpholin-4-sulfonyl)-2-indolinone
3-(3-phenyl-4,5,6,7-tetrahydrobenzofuran-2-methylidenyl)-5-(morpholin-4-sulfonyl)-2-indolinone
3-(4,5,6,7-tetrahydrobenzimidazol-2-methylidenyl)-5-(morpholin-4-sulfonyl)-2-indolinone
3-(4,5,6,7-tetrahydrobenzoxazol-2-methylidenyl)-5-(morpholin-4-sulfonyl)-2-indolinone
3-(3-methyl-4,5,6,7-tetrahydroindol-2-methylidenyl)-5-(morpholin-4-sulfonyl)-2-indolinone
3-(3-carboxy-4,5,6,7-tetrahydroindol-2-methylidenyl)-5-(morpholin-4-sulfonyl)-2-indolinone
3-[3-(isoquinolin-1-methyl)-4,5,6,7-tetrahydroindol-2-methylidenyl]-5-(morpholin-4-sulfonyl)-2-indolinone
3-(3-hydroxy-4,5,6,7-tetrahydroindol-2-methylidenyl)-5-(morpholin-4-sulfonyl)-2-indolinone
3-(3-methoxy-4,5,6,7-tetrahydroindol-2-methylidenyl)-5-(morpholin-4-sulfonyl)-2-indolinone
3-(4,5,6,7-tetrahydroindol-2-methylidenyl)-5-(morpholin-4-sulfonyl)-2-indolinone
3-(4,5,6,7-tetrahydrobenzothien-2-methylidenyl)-5-(morpholin-4-sulfonyl)-2-indolinone
3-(3-methoxycarbonyl-4,5,6,7-tetrahydrobenzothien-2-methylidenyl)-5-(morpholin-4-sulfonyl)-2-indolinone
3-(3-ethoxycarbonyl-4,5,6,7-tetrahydrobenzothien-2-methylidenyl)-5-methylaminosulfonyl-2-indolinone
3-[3-(3-dimethylamino-n-propoxycarbonyl)-4,5,6,7-tetrahydrobenzothien-2-methylidenyl]-5-methylaminosulfonyl-2-indolinone
3-[3-(2-diethylaminoethoxycarbonyl)-4,5,6,7-tetrahydrobenzothien-2-methylidenyl]-5-methylaminosulfonyl-2-indolinone
3-[3-(2-methylaminoethyl)-4,5,6,7-tetrahydrobenzothien-2-methylidenyl]-5-methylaminosulfonyl-2-indolinone
3-(3-cyclopropylmethoxy-4,5,6,7-tetrahydrobenzothien-2-methylidenyl)-5-methylaminosulfonyl-2-indolinone
3-(4,5,6,7-tetrahydrobenzothiazol-2-methylidenyl)-5-methylaminosulfonyl-2-indolinone
3-(4-methyl-4,5,6,7-tetrahydroindol-2-methylidenyl)-5-methylaminosulfonyl-2-indolinone
3-(4,4-dimethyl-4,5,6,7-tetrahydroindol-2-methylidenyl)-5-methylaminosulfonyl-2-indolinone
3-(4-ethyl-4,5,6,7-tetrahydroindol-2-methylidenyl)-5-methylaminosulfonyl-2-indolinone
3-(4-phenyl-4,5,6,7-tetrahydroindol-2-methylidenyl)-5-methylaminosulfonyl-2-indolinone
3-(3-ethyl-4,5,6,7-tetrahydroindol-2-methylidenyl)-5-methylaminosulfonyl-2-indolinone
3-3-isopropyl-4,5,6,7-tetrahydroindol-2-methylidenyl)-5-methylaminosulfonyl-2-indolinone
3-(4,5,6,7-tetrahydroindol-3-methylidenyl)-5-methylaminosulfonyl-2-indolinone
3-(4-isopropyl-4,5,6,7-tetrahydroindol-2-methylidenyl)-5-methylaminosulfonyl-2-indolinone
3-(4-carboxymethyl-4,5,6,7-tetrahydroindol-2-methylidenyl)-5-methylaminosulfonyl-2-indolinone
3-(3-methyl-4,5,6,7-tetrahydroinden-2-methylidenyl)-5-[4-(trifluoromethyl)phenylaminosulfonyl]-2-indolinone
3-(4,5,6,7-tetrahydroinden-2-methylidenyl)-5-[4-(trifluoromethyl)phenylaminosulfonyl]-2-indolinone
3-(3-methyl-4,5,6,7-tetrahydrobenzofuran-2-methylidenyl)-5-[4-(trifluoromethyl)phenylaminosulfonyl]-2-indolinone
3-(3-ethoxycarbonyl-4,5,6,7-tetrahydrobenzofuran-2-methylidenyl)-5-[4-(trifluoromethyl)phenylaminosulfonyl]-2-indolinone
3-(3-n-pentyl-4,5,6,7-tetrahydrobenzofuran-2-methylidenyl)-5-[4-(trifluoromethyl)phenylaminosulfonyl]-2-indolinone
3-(3-ethyl-4,5,6,7-tetrahydrobenzofuran-2-methylidenyl)-5-[4-(trifluoromethyl)phenylaminosulfonyl]-2-indolinone
3-(4,5,6,7-tetrahydrobenzofuran-2-methylidenyl)-5-[4-(trifluoromethyl)phenylaminosulfonyl]-2-indolinone
3-[3-(4-methylphenyl)-4,5,6,7-tetrahydrobenzofuran-2-methylidenyl]-5-[4-(trifluoromethyl)phenylaminosulfonyl]-2-indolinone
3-(3-phenylsulfonylmethyl-4,5,6,7-tetrahydrobenzofuran-2-methylidenyl)-5-[4-(trifluoromethyl)phenylaminosulfonyl]-2-indolinone
3-[3-(1-phenylaminoethyl)-4,5,6,7-tetrahydrobenzofuran-2-methylidenyl]-5-[4-(trifluoromethyl)phenylaminosulfonyl]-2-indolinone
3-[3-(1-phenylaminobutyl)-4,5,6,7-tetrahydrobenzofuran-2-methylidenyl]-5-[4-(trifluoromethyl)phenylaminosulfonyl]-2-indolinone
3-(3-cyano-4,5,6,7-tetrahydrobenzofuran-2-methylidenyl)-5-[4-(trifluoromethyl)phenylaminosulfonyl]-2-indolinone
3-(3-phenylaminomethyl-4,5,6,7-tetrahydrobenzofuran-2-methylidenyl)-5-[4-(trifluoromethyl)phenylaminosulfonyl]-2-indolinone
3-(3-phenyl-4,5,6,7-tetrahydrobenzofuran-2-methylidenyl)-5-[4-(trifluoromethyl)phenylaminosulfonyl]-2-indolinone
3-(4,5,6,7-tetrahydrobenzimidazol-2-methylidenyl)-5-[4-(trifluoromethyl)phenylaminosulfonyl]-2-indolinone
3-(4,5,6,7-tetrahydrobenzoxazol-2-methylidenyl)-5-[4-(trifluoromethyl)phenylaminosulfonyl]-2-indolinone
3-(3-methyl-4,5,6,7-tetrahydroindol-2-methylidenyl)-5-[4-(trifluoromethyl)phenylaminosulfonyl]-2-indolinone
3-[3-(isoquinolin-1-methyl)-4,5,6,7-tetrahydroindol-2-methylidenyl]-5-[4-(trifluoromethyl)phenylaminosulfonyl]-2-indolinone
3-(3-hydroxy-4,5,6,7-tetrahydroindol-2-methylidenyl)-5-[4-(trifluoromethyl)phenylaminosulfonyl]-2-indolinone
3-(3-methoxy-4,5,6,7-tetrahydroindol-2-methylidenyl)-5-[4-(trifluoromethyl)phenylaminosulfonyl]-2-indolinone
3-(4,5,6,7-tetrahydroindol-2-methylidenyl)-5-[4-(trifluoromethyl)phenylaminosulfonyl]-2-indolinone
3-(4,5,6,7-tetrahydrobenzothien-2-methylidenyl)-5-[4-(trifluoromethyl)phenylaminosulfonyl]-2-indolinone
3-(3-methoxycarbonyl-4,5,6,7-tetrahydrobenzothien-2-methylidenyl)-5-[4-(trifluoromethyl)phenylaminosulfonyl]-2-indolinone
3-(3-vinyl-4,5,6,7-tetrahydrobenzothien-2-methylidenyl)-5-[4-(trifluoromethyl)phenylaminosulfonyl]-2-indolinone
3-[3-(3-dimethylamino-n-propoxycarbonyl)-4,5,6,7-tetrahydrobenzothien-2-methylidenyl]-5-aminosulfonyl-2-indolinone
3-[3-(2-diethylaminoethoxycarbonyl)-4,5,6,7-tetrahydrobenzothien-2-methylidenyl]-5-aminosulfonyl-2-indolinone
3-[3-(2-methylaminoethyl)-4,5,6,7-tetrahydrobenzothien-2-methylidenyl]-5-aminosulfonyl-2-indolinone
3-(3-cyclopropylmethoxy-4,5,6,7-tetrahydrobenzothien-2-methylidenyl)-5-aminosulfonyl-2-indolinone
3-(4,5,6,7-tetrahydrobenzothiazol-2-methylidenyl)-5-aminosulfonyl-2-indolinone
3-(4-methyl-4,5,6,7-tetrahydroindol-2-methylidenyl)-5-aminosulfonyl-2-indolinone
3-(4,4-dimethyl-4,5,6,7-tetrahydroindol-2-methylidenyl)-5-aminosulfonyl-2-indolinone
3-(4-ethyl-4,5,6,7-tetrahydroindol-2-methylidenyl)-5-aminosulfonyl-2-indolinone -continued 3-(4-phenyl-4,5,6,7-tetrahydroindol-2-methylidenyl)-5-aminosulfonyl-2-indolinone
3-(3-ethyl-4,5,6,7-tetrahydroindol-2-methylidenyl)-5-aminosulfonyl-2-indolinone
3-(3-isopropyl-4,5,6,7-tetrahydroindol-2-methylidenyl)-5-aminosulfonyl-2-indolinone
3-(4,5,6,7-tetrahydroindol-3-methylidenyl)-5-aminosulfonyl-2-indolinone
3-(4-isopropyl-4,5,6,7-tetrahydroindol-2-methylidenyl)-5-aminosulfonyl-2-indolinone
3-(4-carboxymethyl-4,5,6,7-tetrahydroindol-2-methylidenyl)-5-aminosulfonyl-2-indolinone
3-(3-methyl-4,5,6,7-tetrahydroinden-2-methylidenyl)-5-methylaminosulfonyl-2-indolinone
3-(4,5,6,7-tetrahydroinden-2-methylidenyl)-5-methylaminosulfonyl-2-indolinone
3-(3-methyl-4,5,6,7-tetrahydrobenzofuran-2-methylidenyl)-5-methylaminosulfonyl-2-indolinone
3-(3-ethoxycarbonyl-4,5,6,7-tetrahydrobenzofuran-2-methylidenyl)-5-methylaminosulfonyl-2-indolinone
3-(3-n-pentyl-4,5,6,7-tetrahydrobenzofuran-2-methylidenyl)-5-methylaminosulfonyl-2-indolinone
3-(3-ethyl-4,5,6,7-tetrahydrobenzofuran-2-methylidenyl)-5-methylaminosulfonyl-2-indolinone
3-(4,5,6,7-tetrahydrobenzofuran-2-methylidenyl)-5-methylaminosulfonyl-2-indolinone
3-[3-(4-methylphenyl)-4,5,6,7-tetrahydrobenzofuran-2-methylidenyl]-5-methylaminosulfonyl-2-indolinone
3-(3-phenylsulfonylmethyl-4,5,6,7-tetrahydrobenzofuran-2-methylidenyl)-5-methylaminosulfonyl-2-indolinone
3-[3-(1-phenylaminoethyl)-4,5,6,7-tetrahydrobenzofuran-2-methylidenyl]-5-methylaminosulfonyl-2-indolinone
3-[3-(1-phenylaminobutyl)-4,5,6,7-tetrahydrobenzofuran-2-methylidenyl]-5-methylaminosulfonyl-2-indolinone
3-(3-cyano-4,5,6,7-tetrahydrobenzofuran-2-methylidenyl)-5-methylaminosulfonyl-2-indolinone
3-(3-phenylaminomethyl-4,5,6,7-tetrahydrobenzofuran-2-methylidenyl)-5-methylaminosulfonyl-2-indolinone
3-(3-phenyl-4,5,6,7-tetrahydrobenzofuran-2-methylidenyl)-5-methylaminosulfonyl-2-indolinone
3-(4,5,6,7-tetrahydrobenzimidazol-2-methylidenyl)-5-methylaminosulfonyl-2-indolinone
3-(4,5,6,7-tetrahydrobenzoxazol-2-methylidenyl)-5-methylaminosulfonyl-2-indolinone
3-(3-methyl-4,5,6,7-tetrahydroindol-2-methylidenyl)-5-methylaminosulfonyl-2-indolinone
3-(3-carboxy-4,5,6,7-tetrahydroindol-2-methylidenyl)-5-methylaminosulfonyl-2-indolinone
3-[3-(isoquinolin-1-methyl)-4,5,6,7-tetrahydroindol-2-methylidenyl]-5-methylaminosulfonyl-2-indolinone
3-(3-hydroxy-4,5,6,7-tetrahydroindol-2-methylidenyl)-5-methylaminosulfonyl-2-indolinone
3-(3-methoxy-4,5,6,7-tetrahydroindol-2-methylidenyl)-5-methylaminosulfonyl-2-indolinone
3-(4,5,6,7-tetrahydroindol-2-methylidenyl)-5-methylaminosulfonyl-2-indolinone
3-(4,5,6,7-tetrahydrobenzothien-2-methylidenyl)-5-methylaminosulfonyl-2-indolinone
3-(3-methoxycarbonyl-4,5,6,7-tetrahydrobenzothien-2-methylidenyl)-5-methylaminosulfonyl-2-indolinone
3-(3-vinyl-4,5,6,7-tetrahydrobenzothien-2-methylidenyl)-5-methylaminosulfonyl-2-indolinone
3-(3-carboxy-4,5,6,7-tetrahydrobenzothien-2-methylidenyl)-5-methylaminosulfonyl-2-indolinone
3-[3-(2-diethylaminoethoxycarbonyl)-4,5,6,7-tetrahydrobenzothien-2-methylidenyl]-5-(2-carboxyethyl)-4-methyl-2-indolinone
3-[3-(2-methylaminoethyl)-4,5,6,7-tetrahydrobenzothien-2-methylidenyl]-5-(2-carboxyethyl)-4-methyl-2-indolinone
3-(3-cyclopropylmethoxy-4,5,6,7-tetrahydrobenzothien-2-methylidenyl)-5-(2-carboxyethyl)-4-methyl-2-indolinone
3-(4,5,6,7-tetrahydrobenzothiazol-2-methylidenyl)-5-(2-carboxyethyl)-4-methyl-2-indolinone
3-(4-methyl-4,5,6,7-tetrahydroindol-2-methylidenyl)-5-(2-carboxyethyl)-4-methyl-2-indolinone
3-(4,4-dimethyl-4,5,6,7-tetrahydroindol-2-methylidenyl)-5-(2-carboxyethyl)-4-methyl-2-indolinone
3-(4-ethyl-4,5,6,7-tetrahydroindol-2-methylidenyl)-5-(2-carboxyethyl)-4-methyl-2-indolinone
3-(4-phenyl-4,5,6,7-tetrahydroindol-2-methylidenyl)-5-(2-carboxyethyl)-4-methyl-2-indolinone
3-(3-ethyl-4,5,6,7-tetrahydroindol-2-methylidenyl)-5-(2-carboxyethyl)-4-methyl-2-indolinone
3-(3-isopropyl-4,5,6,7-tetrahydroindol-2-methylidenyl)-5-(2-carboxyethyl)-4-methyl-2-indolinone
3-(4,5,6,7-tetrahydroindol-3-methylidenyl)-5-(2-carboxyethyl)-4-methyl-2-indolinone
3-(4-isopropyl-4,5,6,7-tetrahydroindol-2-methylidenyl)-5-(2-carboxyethyl)-4-methyl-2-indolinone
3-(4-carboxymethyl-4,5,6,7-tetrahydroindol-2-methylidenyl)-5-(2-carboxyethyl)-4-methyl-2-indolinone
3-(3-methyl-4,5,6,7-tetrahydroinden-2-methylidenyl)-5-aminosulfonyl-2-indolinone
3-(4,5,6,7-tetrahydroinden-2-methylidenyl)-5-aminosulfonyl-2-indolinone
3-(3-methyl-4,5,6,7-tetrahydrobenzofuran-2-methylidenyl)-5-aminosulfonyl-2-indolinone
3-(3-ethoxycarbonyl-4,5,6,7-tetrahydrobenzofuran-2-methylidenyl)-5-aminosulfonyl-2-indolinone
3-(3-n-pentyl-4,5,6,7-tetrahydrobenzofuran-2-methylidenyl)-5-aminosulfonyl-2-indolinone
3-(3-ethyl-4,5,6,7-tetrahydrobenzofuran-2-methylidenyl)-5-aminosulfonyl-2-indolinone
3-(4,5,6,7-tetrahydrobenzofuran-2-methylidenyl)-5-aminosulfonyl-2-indolinone
3-[3-(4-methylphenyl)-4,5,6,7-tetrahydrobenzofuran-2-methylidenyl]-5-aminosulfonyl-2-indolinone
3-(3-phenylsulfonylmethyl-4,5,6,7-tetrahydrobenzofuran-2-methylidenyl)-5-aminosulfonyl-2-indolinone
3-[3-(1-phenylaminoethyl)-4,5,6,7-tetrahydrobenzofuran-2-methylidenyl]-5-aminosulfonyl-2-indolinone
3-[3-(1-phenylaminobutyl)-4,5,6,7-tetrahydrobenzofuran-2-methylidenyl]-5-aminosulfonyl-2-indolinone
3-(3-cyano-4,5,6,7-tetrahydrobenzofuran-2-methylidenyl)-5-aminosulfonyl-2-indolinone
3-(3-phenylaminomethyl-4,5,6,7-tetrahydrobenzofuran-2-methylidenyl)-5-aminosulfonyl-2-indolinone
3-(3-phenyl-4,5,6,7-tetrahydrobenzofuran-2-methylidenyl)-5-aminosulfonyl-2-indolinone
3-(4,5,6,7-tetrahydrobenzimidazol-2-methylidenyl)-5-aminosulfonyl-2-indolinone
3-(4,5,6,7-tetrahydrobenzoxazol-2-methylidenyl)-5-aminosulfonyl-2-indolinone
3-(3-methyl-4,5,6,7-tetrahydroindol-2-methylidenyl)-5-aminosulfonyl-2-indolinone
3-(3-carboxy-4,5,6,7-tetrahydroindol-2-methylidenyl)-5-aminosulfonyl-2-indolinone
3-[3-(isoquinolin-1-methyl)-4,5,6,7-tetrahydroindol-2-methylidenyl]-5-aminosulfonyl-2-indolinone
3-(3-hydroxy-4,5,6,7-tetrahydroindol-2-methylidenyl)-5-aminosulfonyl-2-indolinone
3-(3-methoxy-4,5,6,7-tetrahydroindol-2-methylidenyl)-5-aminosulfonyl-2-indolinone
3-(4,5,6,7-tetrahydroindol-2-methylidenyl)-5-aminosulfonyl-2-indolinone
3-(4,5,6,7-tetrahydrobenzothien-2-methylidenyl)-5-aminosulfonyl-2-indolinone
3-(3-methoxycarbonyl-4,5,6,7-tetrahydrobenzothien-2-methylidenyl)-5-aminosulfonyl-2-indolinone
3-(3-vinyl-4,5,6,7-tetrahydrobenzothien-2-methylidenyl)-5-aminosulfonyl-2-indolinone
3-(3-carboxy-4,5,6,7-tetrahydrobenzothien-2-methylidenyl)-5-aminosulfonyl-2-indolinone
3-(3-ethoxycarbonyl-4,5,6,7-tetrahydrobenzothien-2-methylidenyl)-5-aminosulfonyl-2-indolinone
3-[3-(2-methylaminoethyl)-4,5,6,7-tetrahydrobenzothien-2-methylidenyl]-6-fluoro-2-indolinone
3-(3-cyclopropylmethoxy-4,5,6,7-tetrahydrobenzothien-2-methylidenyl)-6-fluoro-2-indolinone
3-(4,5,6,7-tetrahydrobenzothiazol-2-methylidenyl)-6-fluoro-2-indolinone
3-(4-methyl-4,5,6,7-tetrahydroindol-2-methylidenyl)-6-fluoro-2-indolinone
3-(4,4-dimethyl-4,5,6,7-tetrahydroindol-2-methylidenyl)-6-fluoro-2-indolinone
3-(4-ethyl-4,5,6,7-tetrahydroindol-2-methylidenyl)-6-fluoro-2-indolinone
3-(4-phenyl-4,5,6,7-tetrahydroindol-2-methylidenyl)-6-fluoro-2-indolinone 3-(3-ethyl-4,5,6,7-tetrahydroindol-2-methylidenyl)-6-fluoro-2-indolinone
3-(3-isopropyl-4,5,6,7-tetrahydroindol-2-methylidenyl)-6-fluoro-2-indolinone
3-(4,5,6,7-tetrahydroindol-3-methylidenyl)-6-fluoro-2-indolinone
3-(4-isopropyl-(4,5,6,7-tetrahydroindol-3-methylidenyl)-6-fluoro-2-indolinone
3-(4-carboxymethyl-(4,5,6,7-tetrahydroindol-3-methylidenyl)-6-fluoro-2-indolinone
3-(3-methyl-4,5,6,7-tetrahydroinden-2-methylidenyl)-5-(2-carboxyethyl)-4-methyl-2-indolinone
3-(4,5,6,7-tetrahydroinden-2-methylidenyl)-5-(2-carboxyethyl)-4-methyl-2-indolinone
3-(3-methyl-4,5,6,7-tetrahydrobenzofuran-2-methylidenyl)-5-(2-carboxyethyl)-4-methyl-2-indolinone
3-(3-ethoxycarbonyl-4,5,6,7-tetrahydrobenzofuran-2-methylidenyl)-5-(2-carboxyethyl)-4-methyl-2-indolinone
3-(3-n-pentyl-4,5,6,7-tetrahydrobenzofuran-2-methylidenyl)-5-(2-carboxyethyl)-4-methyl-2-indolinone
3-(3-ethyl-4,5,6,7-tetrahydrobenzofuran-2-methylidenyl)-5-(2-carboxyethyl)-4-methyl-2-indolinone
3-(4,5,6,7-tetrahydrobenzofuran-2-methylidenyl)-5-(2-carboxyethyl)-4-methyl-2-indolinone
3-[3-(4-methylphenyl)-4,5,6,7-tetrahydrobenzofuran-2-methylidenyl]-5-(2-carboxyethyl)-4-methyl-2-indolinone
3-(3-phenylsulfonylmethyl-4,5,6,7-tetrahydrobenzofuran-2-methylidenyl)-5-(2-carboxyethyl)-4-methyl-2-indolinone
3-[3-(1-phenylaminoethyl)-4,5,6,7-tetrahydrobenzofuran-2-methylidenyl]-5-(2-carboxyethyl)-4-methyl-2-indolinone
3-[3-(1-phenylaminobutyl)-4,5,6,7-tetrahydrobenzofuran-2-methylidenyl]-5-(2-carboxyethyl)-4-methyl-2-indolinone
3-(3-cyano-4,5,6,7-tetrahydrobenzofuran-2-methylidenyl)-5-(2-carboxyethyl)-4-methyl-2-indolinone
3-(3-phenylaminomethyl-4,5,6,7-tetrahydrobenzofuran-2-methylidenyl)-5-(2-carboxyethyl)-4-methyl-2-indolinone
3-(3-phenyl-4,5,6,7-tetrahydrobenzofuran-2-methylidenyl)-5-(2-carboxyethyl)-4-methyl-2-indolinone
3-(4,5,6,7-tetrahydrobenzimidazol-2-methylidenyl)-5-(2-carboxyethyl)-4-methyl-2-indolinone
3-(4,5,6,7-tetrahydrobenzoxazol-2-methylidenyl)-5-(2-carboxyethyl)-4-methyl-2-indolinone
3-(3-methyl-4,5,6,7-tetrahydroindol-2-methylidenyl)-5-(2-carboxyethyl)-4-methyl-2-indolinone
3-(3-carboxy-4,5,6,7-tetrahydroindol-2-methylidenyl)-5-(2-carboxyethyl)-4-methyl-2-indolinone
3-[3-(isoquinolin-1-methyl)-4,5,6,7-tetrahydroindol-2-methylidenyl]-5-(2-carboxyethyl)-4-methyl-2-indolinone
3-(3-hydroxy-4,5,6,7-tetrahydroindol-2-methylidenyl)-5-(2-carboxyethyl)-4-methyl-2-indolinone
3-(3-methoxy-4,5,6,7-tetrahydroindol-2-methylidenyl)-5-(2-carboxyethyl)-4-methyl-2-indolinone
3-(4,5,6,7-tetrahydroindol-2-methylidenyl)-5-(2-carboxyethyl)-4-methyl-2-indolinone
3-(4,5,6,7-tetrahydrobenzothien-2-methylidenyl)-5-(2-carboxyethyl)-4-methyl-2-indolinone
3-(3-methoxycarbonyl-4,5,6,7-tetrahydrobenzothien-2-methylidenyl)-5-(2-carboxyethyl)-4-methyl-2-indolinone
3-(3-vinyl-4,5,6,7-tetrahydrobenzothien-2-methylidenyl)-5-(2-carboxyethyl)-4-methyl-2-indolinone
3-(3-carboxy-4,5,6,7-tetrahydrobenzothien-2-methylidenyl)-5-(2-carboxyethyl)-4-methyl-2-indolinone
3-(3-ethoxycarbonyl-4,5,6,7-tetrahydrobenzothien-2-methylidenyl)-5-(2-carboxyethyl)-4-methyl-2-indolinone
3-[3-(3-dimethylamino-n-propoxycarbonyl)-4,5,6,7-tetrahydrobenzothien-2-methylidenyl]-5-(2-carboxyethyl)-4-methyl-2-indolinone
3-(3-cyclopropylmethoxy-4,5,6,7-tetrahydrobenzothien-2-methylidenyl)-7-fluoro-2-indolinone
3-(4,5,6,7-tetrahydrobenzothiazol-2-methylidenyl)-7-fluoro-2-indolinone
3-(4-methyl-4,5,6,7-tetrahydroindol-2-methylidenyl)-7-fluoro-2-indolinone
3-(4,4-dimethyl-4,5,6,7-tetrahydroindol-2-methylidenyl)-7-fluoro-2-indolinone
3-(4-ethyl-4,5,6,7-tetrahydroindol-2-methylidenyl)-7-fluoro-2-indolinone
3-(4-phenyl-4,5,6,7-tetrahydroindol-2-methylidenyl)-7-fluoro-2-indolinone
3-(3-ethyl-4,5,6,7-tetrahydroindol-2-methylidenyl)-7-fluoro-2-indolinone
3-(3-isopropyl-4,5,6,7-tetrahydroindol-2-methylidenyl)-7-fluoro-2-indolinone
3-(4,5,6,7-tetrahydroindol-3-methylidenyl)-7-fluoro-2-indolinone
3-(4-isopropyl-4,5,6,7-tetrahydroindol-2-methylidenyl)-7-fluoro-2-indolinone
3-(4-carboxymethyl-4,5,6,7-tetrahydroindol-2-methylidenyl)-7-fluoro-2-indolinone
3-(3-methyl-4,5,6,7-tetrahydroinden-2-methylidenyl)-6-fluoro-2-indolinone
3-(4,5,6,7-tetrahydroinden-2-methylidenyl)-6-fluoro-2-indolinone
3-(3-methyl-4,5,6,7-tetrahydrobenzofuran-2-methylidenyl)-6-fluoro-2-indolinone
3-(3-ethoxycarbonyl-4,5,6,7-tetrahydrobenzofuran-2-methylidenyl)-6-fluoro-2-indolinone
3-(3-n-pentyl-4,5,6,7-tetrahydrobenzofuran-2-methylidenyl)-6-fluoro-2-indolinone
3-(3-ethyl-4,5,6,7-tetrahydrobenzofuran-2-methylidenyl)-6-fluoro-2-indolinone
3-(4,5,6,7-tetrahydrobenzofuran-2-methylidenyl)-6-fluoro-2-indolinone
3-[3-(4-methylphenyl)-4,5,6,7-tetrahydrobenzofuran-2-methylidenyl]-6-fluoro-2-indolinone
3-(3-phenylsulfonylmethyl-4,5,6,7-tetrahydrobenzofuran-2-methylidenyl)-6-fluoro-2-indolinone
3-[3-(1-phenylaminoethyl)-4,5,6,7-tetrahydrobenzofuran-2-methylidenyl]-6-fluoro-2-indolinone
3-[3-(1-phenylaminobutyl)-4,5,6,7-tetrahydrobenzofuran-2-methylidenyl]-6-fluoro-2-indolinone
3-(3-cyano-4,5,6,7-tetrahydrobenzofuran-2-methylidenyl)-6-fluoro-2-indolinone
3-(3-phenylaminomethyl-4,5,6,7-tetrahydrobenzofuran-2-methylidenyl)-6-fluoro-2-indolinone
3-(3-phenyl-4,5,6,7-tetrahydrobenzofuran-2-methylidenyl)-6-fluoro-2-indolinone
3-(4,5,6,7-tetrahydrobenzimidazol-2-methylidenyl)-6-fluoro-2-indolinone
3-(4,5,6,7-tetrahydrobenzoxazol-2-methylidenyl)-6-fluoro-2-indolinone
3-(3-methyl-4,5,6,7-tetrahydroindol-2-methylidenyl)-6-fluoro-2-indolinone
3-(3-carboxy-4,5,6,7-tetrahydroindol-2-methylidenyl)-6-fluoro-2-indolinone
3-[3-(isoquinolin-1-methyl)-4,5,6,7-tetrahydroindol-2-methylidenyl]-6-fluoro-2-indolinone
3-(3-hydroxy-4,5,6,7-tetrahydroindol-2-methylidenyl)-6-fluoro-2-indolinone
3-(3-methoxy-4,5,6,7-tetrahydroindol-2-methylidenyl)-6-fluoro-2-indolinone
3-(4,5,6,7-tetrahydroindol-2-methylidenyl)-6-fluoro-2-indolinone
3-(4,5,6,7-tetrahydrobenzothien-2-methylidenyl)-6-fluoro-2-indolinone
3-(3-methoxycarbonyl-4,5,6,7-tetrahydrobenzothien-2-methylidenyl)-6-fluoro-2-indolinone
3-(3-vinyl-4,5,6,7-tetrahydrobenzothien-2-methylidenyl)-6-fluoro-2-indolinone
3-(3-carboxy-4,5,6,7-tetrahydrobenzothien-2-methylidenyl)-6-fluoro-2-indolinone
3-(3-ethoxycarbonyl-4,5,6,7-tetrahydrobenzothien-2-methylidenyl)-6-fluoro-2-indolinone
3-[3-(3-dimethylamino-n-propoxycarbonyl)-4,5,6,7-tetrahydrobenzothien-2-methylidenyl]-6-fluoro-2-indolinone
3-[3-(2-diethylaminoethoxycarbonyl)-4,5,6,7-tetrahydrobenzothien-2-methylidenyl]-6-fluoro-2-indolinone
3-(4,5,6,7-tetrahydrobenzothiazol-2-methylidenyl)-5-bromo-4-methyl-2-indolinone
3-(4-methyl-4,5,6,7-tetrahydroindol-2-methylidenyl)-5-bromo-4-methyl-2-indolinone
3-(4,4-dimethyl-4,5,6,7-tetrahydroindol-2-methylidenyl)-5-bromo-4-methyl-2-indolinone
3-(4-ethyl-4,5,6,7-tetrahydroindol-2-methylidenyl)-5-bromo-4-methyl-2-indolinone
3-(4-phenyl-4,5,6,7-tetrahydroindol-2-methylidenyl)-5-bromo-4-methyl-2-indolinone
3-(3-ethyl-4,5,6,7-tetrahydroindol-2-methylidenyl)-5-bromo-4-methyl-2-indolinone -continued 3-(3-isopropyl-4,5,6,7-tetrahydroindol-2-methylidenyl)-5-bromo-4-methyl-2-indolinone
3-(4,5,6,7-tetrahydroindol-3-methylidenyl)-5-bromo-4-methyl-2-indolinone
3-(4-isopropyl-4,5,6,7-tetrahydroindol-2-methylidenyl)-5-bromo-4-methyl-2-indolinone
3-(4-carboxymethyl-4,5,6,7-tetrahydroindol-2-methylidenyl)-5-bromo-4-methyl-2-indolinone
3-(3-methyl-4,5,6,7-tetrahydroinden-2-methylidenyl)-7-fluoro-2-indolinone
3-(4,5,6,7-tetrahydroinden-2-methylidenyl)-7-fluoro-2-indolinone
3-(3-methyl-4,5,6,7-tetrahydrobenzofuran-2-methylidenyl)-7-fluoro-2-indolinone
3-(3-ethoxycarbonyl-4,5,6,7-tetrahydrobenzofuran-2-methylidenyl)-7-fluoro-2-indolinone
3-(3-n-pentyl-4,5,6,7-tetrahydrobenzofuran-2-methylidenyl)-7-fluoro-2-indolinone
3-(3-ethyl-4,5,6,7-tetrahydrobenzofuran-2-methylidenyl)-7-fluoro-2-indolinone
3-(4,5,6,7-tetrahydrobenzofuran-2-methylidenyl)-7-fluoro-2-indolinone
3-[3-(4-methylphenyl)-4,5,6,7-tetrahydrobenzofuran-2-methylidenyl]-7-fluoro-2-indolinone
3-(3-phenylsulfonylmethyl-4,5,6,7-tetrahydrobenzofuran-2-methylidenyl)-7-fluoro-2-indolinone
3-[3-(1-phenylaminoethyl)-4,5,6,7-tetrahydrobenzofuran-2-methylidenyl]-7-fluoro-2-indolinone
3-[3-(1-phenylaminobutyl)-4,5,6,7-tetrahydrobenzofuran-2-methylidenyl]-7-fluoro-2-indolinone
3-(3-cyano-4,5,6,7-tetrahydrobenzofuran-2-methylidenyl)-7-fluoro-2-indolinone
3-(3-phenylaminomethyl-4,5,6,7-tetrahydrobenzofuran-2-methylidenyl)-7-fluoro-2-indolinone
3-(3-phenyl-4,5,6,7-tetrahydrobenzofuran-2-methylidenyl)-7-fluoro-2-indolinone
3-(4,5,6,7-tetrahydrobenzimidazol-2-methylidenyl)-7-fluoro-2-indolinone
3-(4,5,6,7-tetrahydrobenzoxazol-2-methylidenyl)-7-fluoro-2-indolinone
3-(3-methyl-4,5,6,7-tetrahydroindol-2-methylidenyl)-7-fluoro-2-indolinone
3-(3-carboxy-4,5,6,7-tetrahydroindol-2-methylidenyl)-7-fluoro-2-indolinone
3-[3-(isoquinolin-1-methyl)-4,5,6,7-tetrahydroindol-2-methylidenyl]-7-fluoro-2-indolinone
3-(3-hydroxy-4,5,6,7-tetrahydroindol-2-methylidenyl)-7-fluoro-2-indolinone
3-(3-methoxy-4,5,6,7-tetrahydroindol-2-methylidenyl)-7-fluoro-2-indolinone
3-(4,5,6,7-tetrahydroindol-2-methylidenyl)-7-fluoro-2-indolinone
3-(4,5,6,7-tetrahydrobenzothien-2-methylidenyl)-7-fluoro-2-indolinone
3-(3-methoxycarbonyl-4,5,6,7-tetrahydrobenzothien-2-methylidenyl)-7-fluoro-2-indolinone
3-(3-vinyl-4,5,6,7-tetrahydrobenzothien-2-methylidenyl)-7-fluoro-2-indolinone
3-(3-carboxy-4,5,6,7-tetrahydrobenzothien-2-methylidenyl)-7-fluoro-2-indolinone
3-(3-ethoxycarbonyl-4,5,6,7-tetrahydrobenzothien-2-methylidenyl)-7-fluoro-2-indolinone
3-[3-(3-dimethylamino-n-propoxycarbonyl)-4,5,6,7-tetrahydrobenzothien-2-methylidenyl]-7-fluoro-2-indolinone
3-[3-(2-diethylaminoethoxycarbonyl)-4,5,6,7-tetrahydrobenzothien-2-methylidenyl]-7-fluoro-2-indolinone
3-[3-(2-methylaminoethyl)-4,5,6,7-tetrahydrobenzothien-2-methylidenyl]-7-fluoro-2-indolinone
3-(4-methyl-4,5,6,7-tetrahydroindol-2-methylidenyl)-5-methyl-2-indolinone
3-(4,4-dimethyl-4,5,6,7-tetrahydroindol-2-methylidenyl)-5-methyl-2-indolinone
3-(4-ethyl-4,5,6,7-tetrahydroindol-2-methylidenyl)-5-methyl-2-indolinone
3-(4-phenyl-4,5,6,7-tetrahydroindol-2-methylidenyl)-5-methyl-2-indolinone
3-(3-ethyl-4,5,6,7-tetrahydroindol-2-methylidenyl)-5-methyl-2-indolinone
3-(3-isopropyl-4,5,6,7-tetrahydroindol-2-methylidenyl)-5-methyl-2-indolinone
3-(4,5,6,7-tetrahydroindol-3-methylidenyl)-5-methyl-2-indolinone
3-(4-isopropyl-4,5,6,7-tetrahydroindol-2-methylidenyl)-5-methyl-2-indolinone
3-(4-carboxymethyl-4,5,6,7-tetrahydroindol-2-methylidenyl)-5-methyl-2-indolinone
3-(3-methyl-4,5,6,7-tetrahydroinden-2-methylidenyl)-5-bromo-4-methyl-2-indolinone
3-(4,5,6,7-tetrahydroinden-2-methylidenyl)-5-bromo-4-methyl-2-indolinone
3-(3-methyl-4,5,6,7-tetrahydrobenzofuran-2-methylidenyl)-5-bromo-4-methyl-2-indolinone
3-(3-ethoxycarbonyl-4,5,6,7-tetrahydrobenzofuran-2-methylidenyl)-5-bromo-4-methyl-2-indolinone
3-(3-n-pentyl-4,5,6,7-tetrahydrobenzofuran-2-methylidenyl)-5-bromo-4-methyl-2-indolinone
3-(3-ethyl-4,5,6,7-tetrahydrobenzofuran-2-methylidenyl)-5-bromo-4-methyl-2-indolinone
3-(4,5,6,7-tetrahydrobenzofuran-2-methylidenyl)-5-bromo-4-methyl-2-indolinone
3-[3-(4-methylphenyl)-4,5,6,7-tetrahydrobenzofuran-2-methylidenyl]-5-bromo-4-methyl-2-indolinone
3-(3-phenylsulfonylmethyl-4,5,6,7-tetrahydrobenzofuran-2-methylidenyl)-5-bromo-4-methyl-2-indolinone
3-[3-(1-phenylaminoethyl)-4,5,6,7-tetrahydrobenzofuran-2-methylidenyl]-5-bromo-4-methyl-2-indolinone
3-[3-(1-phenylaminobutyl)-4,5,6,7-tetrahydrobenzofuran-2-methylidenyl]-5-bromo-4-methyl-2-indolinone
3-(3-cyano-4,5,6,7-tetrahydrobenzofuran-2-methylidenyl)-5-bromo-4-methyl-2-indolinone
3-(3-phenylaminomethyl-4,5,6,7-tetrahydrobenzofuran-2-methylidenyl)-5-bromo-4-methyl-2-indolinone
3-(3-phenyl-4,5,6,7-tetrahydrobenzofuran-2-methylidenyl)-5-bromo-4-methyl-2-indolinone
3-(4,5,6,7-tetrahydrobenzimidazol-2-methylidenyl)-5-bromo-4-methyl-2-indolinone
3-(4,5,6,7-tetrahydrobenzoxazol-2-methylidenyl)-5-bromo-4-methyl-2-indolinone
3-(3-methyl-4,5,6,7-tetrahydroindol-2-methylidenyl)-5-bromo-4-methyl-2-indolinone
3-(3-carboxy-4,5,6,7-tetrahydroindol-2-methylidenyl)-5-bromo-4-methyl-2-indolinone
3-[3-(isoquinolin-1-methyl)-4,5,6,7-tetrahydroindol-2-methylidenyl]-5-bromo-4-methyl-2-indolinone
3-(3-hydroxy-4,5,6,7-tetrahydroindol-2-methylidenyl)-5-bromo-4-methyl-2-indolinone
3-(3-methoxy-4,5,6,7-tetrahydroindol-2-methylidenyl)-5-bromo-4-methyl-2-indolinone
3-(4,5,6,7-tetrahydroindol-2-methylidenyl)-5-bromo-4-methyl-2-indolinone
3-(4,5,6,7-tetrahydrobenzothien-2-methylidenyl)-5-bromo-4-methyl-2-indolinone
3-(3-methoxycarbonyl-4,5,6,7-tetrahydrobenzothien-2-methylidenyl)-5-bromo-4-methyl-2-indolinone
3-(3-vinyl-4,5,6,7-tetrahydrobenzothien-2-methylidenyl)-5-bromo-4-methyl-2-indolinone
3-(3-carboxy-4,5,6,7-tetrahydrobenzothien-2-methylidenyl)-5-bromo-4-methyl-2-indolinone
3-(3-ethoxycarbonyl-4,5,6,7-tetrahydrobenzothien-2-methylidenyl)-5-bromo-4-methyl-2-indolinone
3-[3-(3-dimethylamino-n-propoxycarbonyl)-4,5,6,7-tetrahydrobenzothien-2-methylidenyl]-5-bromo-4-methyl-2-indolinone
3-[3-(2-diethylaminoethoxycarbonyl)-4,5,6,7-tetrahydrobenzothien-2-methylidenyl]-5-bromo-4-methyl-2-indolinone
3-[3-(2-methylaminoethyl)-4,5,6,7-tetrahydrobenzothien-2-methylidenyl]-5-bromo-4-methyl-2-indolinone
3-(3-cyclopropylmethoxy-4,5,6,7-tetrahydrobenzothien-2-methylidenyl)-5-bromo-4-methyl-2-indolinone
3-(4,4-dimethyl-4,5,6,7-tetrahydroindol-2-methylidenyl)-5-chloro-7-methyl-2-indolinone
3-(4-ethyl-4,5,6,7-tetrahydroindol-2-methylidenyl)-5-chloro-7-methyl-2-indolinone
3-(4-phenyl-4,5,6,7-tetrahydroindol-2-methylidenyl)-5-chloro-7-methyl-2-indolinone
3-(4-ethyl-4,5,6,7-tetrahydroindol-2-methylidenyl)-5-chloro-7-methyl-2-indolinone
3-(3-isopropyl-4,5,6,7-tetrahydroindol-2-methylidenyl)-5-chloro-7-methyl-2-indolinone 3-(4,5,6,7-tetrahydroindol-2-methylidenyl)-5-chloro-7-methyl-2-indolinone
3-(4-isopropyl-4,5,6,7-tetrahydroindol-2-methylidenyl)-5-chloro-7-methyl-2-indolinone
3-(4-carboxymethyl-4,5,6,7-tetrahydroindol-2-methylidenyl)-5-chloro-7-methyl-2-indolinone
3-(3-methyl-4,5,6,7-tetrahydroinden-2-methylidenyl)-5-methyl-2-indolinone
3-(4,5,6,7-tetrahydroinden-2-methylidenyl)-5-methyl-2-indolinone
3-(3-methyl-4,5,6,7-tetrahydrobenzofuran-2-methylidenyl)-5-methyl-2-indolinone
3-(3-ethoxycarbonyl-4,5,6,7-tetrahydrobenzofuran-2-methylidenyl)-5-methyl-2-indolinone
3-(3-n-pentyl-4,5,6,7-tetrahydrobenzofuran-2-methylidenyl)-5-methyl-2-indolinone
3-(3-ethyl-4,5,6,7-tetrahydrobenzofuran-2-methylidenyl)-5-methyl-2-indolinone
3-(4,5,6,7-tetrahydrobenzofuran-2-methylidenyl)-5-methyl-2-indolinone
3-[3-(4-methylphenyl)-4,5,6,7-tetrahydrobenzofuran-2-methylidenyl]-5-methyl-2-indolinone
3-(3-phenylsulfonylmethyl-4,5,6,7-tetrahydrobenzofuran-2-methylidenyl)-5-methyl-2-indolinone
3-[3-(1-phenylaminoethyl)-4,5,6,7-tetrahydrobenzofuran-2-methylidenyl]-5-methyl-2-indolinone
3-[3-(1-phenylaminobutyl)-4,5,6,7-tetrahydrobenzofuran-2-methylidenyl]-5-methyl-2-indolinone
3-(3-cyano-4,5,6,7-tetrahydrobenzofuran-2-methylidenyl)-5-methyl-2-indolinone
3-(3-phenylaminomethyl-4,5,6,7-tetrahydrobenzofuran-2-methylidenyl)-5-methyl-2-indolinone
3-(3-phenyl-4,5,6,7-tetrahydrobenzofuran-2-methylidenyl)-5-methyl-2-indolinone
3-(4,5,6,7-tetrahydrobenzimidazol-2-methylidenyl)-5-methyl-2-indolinone
3-(4,5,6,7-tetrahydrobenzoxazol-2-methylidenyl)-5-methyl-2-indolinone
3-(3-methyl-4,5,6,7-tetrahydroindol-2-methylidenyl)-5-methyl-2-indolinone
3-(3-carboxy-4,5,6,7-tetrahydroindol-2-methylidenyl)-5-methyl-2-indolinone
3-[3-(isoquinolin-1-methyl)-4,5,6,7-tetrahydroindol-2-methylidenyl]-5-methyl-2-indolinone
3-(3-hydroxy-4,5,6,7-tetrahydroindol-2-methylidenyl)-5-methyl-2-indolinone
3-(3-methoxy-4,5,6,7-tetrahydroindol-2-methylidenyl)-5-methyl-2-indolinone
3-(4,5,6,7-tetrahydroindol-2-methylidenyl)-5-methyl-2-indolinone
3-(4,5,6,7-tetrahydrobenzothien-2-methylidenyl)-5-methyl-2-indolinone
3-(3-methoxycarbonyl-4,5,6,7-tetrahydrobenzothien-2-methylidenyl)-5-methyl-2-indolinone
3-(3-vinyl-4,5,6,7-tetrahydrobenzothien-2-methylidenyl)-5-methyl-2-indolinone
3-(3-carboxy-4,5,6,7-tetrahydrobenzothien-2-methylidenyl)-5-methyl-2-indolinone
3-(3-ethoxycarbonyl-4,5,6,7-tetrahydrobenzothien-2-methylidenyl)-5-methyl-2-indolinone
3-[3-(3-dimethylamino-n-propoxycarbonyl)-4,5,6,7-tetrahydrobenzothien-2-methylidenyl]-5-methyl-2-indolinone
3-[3-(2-diethylaminoethoxycarbonyl)-4,5,6,7-tetrahydrobenzothien-2-methylidenyl]-5-methyl-2-indolinone
3-[3-(2-methylaminoethyl)-4,5,6,7-tetrahydrobenzothien-2-methylidenyl]-5-methyl-2-indolinone
3-(3-cyclopropylmethoxy-4,5,6,7-tetrahydrobenzothien-2-methylidenyl)-5-methyl-2-indolinone
3-(4,5,6,7-tetrahydrobenzothiazol-2-methylidenyl)-5-methyl-2-indolinone
3-(4-ethyl-4,5,6,7-tetrahydroindol-2-methylidenyl)-5-iodo-2-indolinone
3-(4-phenyl-4,5,6,7-tetrahydroindol-2-methylidenyl)-5-iodo-2-indolinone
3-(3-ethyl-4,5,6,7-tetrahydroindol-2-methylidenyl)-5-iodo-2-indolinone
3-(3-isopropyl-4,5,6,7-tetrahydroindol-2-methylidenyl)-5-iodo-2-indolinone
3-(4,5,6,7-tetrahydroindol-2-methylidenyl)-5-iodo-2-indolinone
3-(4-isopropyl-4,5,6,7-tetrahydroindol-2-methylidenyl)-5-iodo-2-indolinone
3-(4-carboxymethyl-4,5,6,7-tetrahydroindol-2-methylidenyl)-5-iodo-2-indolinone
3-(3-methyl-4,5,6,7-tetrahydroinden-2-methylidenyl)-5-chloro-7-methyl-2-indolinone
3-(4,5,6,7-tetrahydroinden-2-methylidenyl)-5-chloro-7-methyl-2-indolinone
3-(3-methyl-4,5,6,7-tetrahydrobenzofuran-2-methylidenyl)-5-chloro-7-methyl-2-indolinone
3-(3-ethoxycarbonyl-4,5,6,7-tetrahydrobenzofuran-2-methylidenyl)-5-chloro-7-methyl-2-indolinone
3-(3-n-pentyl-4,5,6,7-tetrahydrobenzofuran-2-methylidenyl)-5-chloro-7-methyl-2-indolinone
3-(3-ethyl-4,5,6,7-tetrahydrobenzofuran-2-methylidenyl)-5-chloro-7-methyl-2-indolinone
3-(4,5,6,7-tetrahydrobenzofuran-2-methylidenyl)-5-chloro-7-methyl-2-indolinone
3-[3-(4-methylphenyl)-4,5,6,7-tetrahydrobenzofuran-2-methylidenyl]-5-chloro-7-methyl-2-indolinone
3-(3-phenylsulfonylmethyl-4,5,6,7-tetrahydrobenzofuran-2-methylidenyl)-5-chloro-7-methyl-2-indolinone
3-[3-(1-phenylaminoethyl)-4,5,6,7-tetrahydrobenzofuran-2-methylidenyl]-5-chloro-7-methyl-2-indolinone
3-[3-(2-phenylaminobutyl)-4,5,6,7-tetrahydrobenzofuran-2-methylidenyl]-5-chloro-7-methyl-2-indolinone
3-(3-cyano-4,5,6,7-tetrahydrobenzofuran-2-methylidenyl)-5-chloro-7-methyl-2-indolinone
3-(3-phenylaminomethyl-4,5,6,7-tetrahydrobenzofuran-2-methylidenyl)-5-chloro-7-methyl-2-indolinone
3-(3-phenyl-4,5,6,7-tetrahydrobenzofuran-2-methylidenyl)-5-chloro-7-methyl-2-indolinone
3-(4,5,6,7-tetrahydrobenzimidazol-2-methylidenyl)-5-chloro-7-methyl-2-indolinone
3-(4,5,6,7-tetrahydrobenzoxazol-2-methylidenyl)-5-chloro-7-methyl-2-indolinone
3-(3-methyl-4,5,6,7-tetrahydroindol-2-methylidenyl)-5-chloro-7-methyl-2-indolinone
3-(3-carboxy-4,5,6,7-tetrahydroindol-2-methylidenyl)-5-chloro-7-methyl-2-indolinone
3-[3-(isoquinolin-1-methyl)-4,5,6,7-tetrahydroindol-2-methylidenyl]-5-chloro-7-methyl-2-indolinone
3-(3-hydroxy-4,5,6,7-tetrahydroindol-2-methylidenyl)-5-chloro-7-methyl-2-indolinone
3-(3-methoxy-4,5,6,7-tetrahydroindol-2-methylidenyl)-5-chloro-7-methyl-2-indolinone
3-(4,5,6,7-tetrahydroindol-2-methylidenyl)-5-chloro-7-methyl-2-indolinone
3-(4,5,6,7-tetrahydrobenzothien-2-methylidenyl)-5-chloro-7-methyl-2-indolinone
3-(3-methoxycarbonyl-4,5,6,7-tetrahydrobenzothien-2-methylidenyl)-5-chloro-7-methyl-2-indolinone
3-(3-vinyl-4,5,6,7-tetrahydrobenzothien-2-methylidenyl)-5-chloro-7-methyl-2-indolinone
3-(3-carboxy-4,5,6,7-tetrahydrobenzothien-2-methylidenyl)-5-chloro-7-methyl-2-indolinone
3-(3-ethoxycarbonyl-4,5,6,7-tetrahydrobenzothien-2-methylidenyl)-5-chloro-7-methyl-2-indolinone
3-[3-(3-dimethylamino-n-propoxy/carbonyl)-4,5,6,7-tetrahydrobenzothien-2-methylidenyl]-5-chloro-7-methyl-2-indolinone
3-[3-(2-diethylaminoethoxycarbonyl)-4,5,6,7-tetrahydrobenzothien-2-methylidenyl]-5-chloro-7-methyl-2-indolinone
3-[3-(2-methylaminoethyl)-4,5,6,7-tetrahydrobenzothien-2-methylidenyl]-5-chloro-7-methyl-2-indolinone
3-(3-cyclopropylmethoxy-4,5,6,7-tetrahydrobenzothien-2-methylidenyl)-5-chloro-7-methyl-2-indolinone
3-(4,5,6,7-tetrahydrobenzothiazol-2-methylidenyl)-5-chloro-7-methyl-2-indolinone
3-(4-methyl-4,5,6,7-tetrahydroindol-2-methylidenyl)-5-chloro-7-methyl-2-indolinone
3-(4-phenyl-4,5,6,7-tetrahydroindol-2-methylidenyl)-5-nitro-2-indolinone
3-(3-ethyl-4,5,6,7-tetrahydroindol-2-methylidenyl)-5-nitro-2-indolinone
3-(3-isopropyl-4,5,6,7-tetrahydroindol-2-methylidenyl)-5-nitro-2-indolinone
3-(4,5,6,7-tetrahydroindol-3-methylidenyl)-5-nitro-2-indolinone -continued 3-(4-isopropyl-4,5,6,7-tetrahydroindol-2-methylidenyl)-5-nitro-2-indolinone
3-(4-carboxymethyl-4,5,6,7-tetrahydroindol-2-methylidenyl)-5-nitro-2-indolinone
3-(3-methyl-4,5,6,7-tetrahydroinden-2-methylidenyl)-5-iodo-2-indolinone
3-(4,5,6,7-tetrahydroinden-2-methylidenyl)-5-iodo-2-indolinone
3-(3-methyl-4,5,6,7-tetrahydrobenzofuran-2-methylidenyl)-5-iodo-2-indolinone
3-(3-ethoxycarbonyl-4,5,6,7-tetrahydrobenzofuran-2-methylidenyl)-5-iodo-2-indolinone
3-(3-n-pentyl-4,5,6,7-tetrahydrobenzofuran-2-methylidenyl)-5-iodo-2-indolinone
3-(3-ethyl-4,5,6,7-tetrahydrobenzofuran-2-methylidenyl)-5-iodo-2-indolinone
3-(4,5,6,7-tetrahydrobenzofuran-2-methylidenyl)-5-iodo-2-indolinone
4-[3-(4-methylphenyl)-4,5,6,7-tetrahydrobenzofuran-2-methylidenyl]-5-iodo-2-indolinone
3-(3-phenylsulfonylmethyl-4,5,6,7-tetrahydrobenzofuran-2-methylidenyl)-5-iodo-2-indolinone
3-[3-(1-phenylaminoethyl)-4,5,6,7-tetrahydrobenzofuran-2-methylidenyl]-5-iodo-2-indolinone
3-[3-(1-phenylaminobutyl)-4,5,6,7-tetrahydrobenzofuran-2-methylidenyl]-5-iodo-2-indolinone
3-(3-cyano-4,5,6,7-tetrahydrobenzofuran-2-methylidenyl)-5-iodo-2-indolinone
3-(3-phenylaminomethyl-4,5,6,7-tetrahydrobenzofuran-2-methylidenyl)-5-iodo-2-indolinone
3-(3-phenyl-4,5,6,7-tetrahydrobenzofuran-2-methylidenyl)-5-iodo-2-indolinone
3-(4,5,6,7-tetrahydrobenzimidazol-2-methylidenyl)-5-iodo-2-indolinone
3-(4,5,6,7-tetrahydrobenzoxazol-2-methylidenyl)-5-iodo-2-indolinone
3-(3-methyl-4,5,6,7-tetrahydroindol-2-methylidenyl)-5-iodo-2-indolinone
3-(3-carboxy-4,5,6,7-tetrahydroindol-2-methylidenyl)-5-iodo-2-indolinone
3-[3-(isoquinolin-1-methyl)-4,5,6,7-tetrahydroindol-2-methylidenyl]-5-iodo-2-indolinone
3-(3-hydroxy-4,5,6,7-tetrahydroindol-2-methylidenyl)-5-iodo-2-indolinone
3-(3-methoxy-4,5,6,7-tetrahydroindol-2-methylidenyl)-5-iodo-2-indolinone
3-(4,5,6,7-tetrahydroindol-2-methylidenyl)-5-iodo-2-indolinone
3-(4,5,6,7-tetrahydrobenzothien-2-methylidenyl)-5-iodo-2-indolinone
3-(3-methoxycarbonyl-4,5,6,7-tetrahydrobenzothien-2-methylidenyl)-5-iodo-2-indolinone
3-(3-vinyl-4,5,6,7-tetrahydrobenzothien-2-methylidenyl)-5-iodo-2-indolinone
3-(3-carboxy-4,5,6,7-tetrahydrobenzothien-2-methylidenyl)-5-iodo-2-indolinone
3-(3-ethoxycarbonyl-4,5,6,7-tetrahydrobenzothien-2-methylidenyl)-5-iodo-2-indolinone
3-[3-(3-dimethylamino-n-propoxycarbonyl)-4,5,6,7-tetrahydrobenzothien-2-methylidenyl]-5-iodo-2-indolinone
3-[3-(2-diethylaminoethoxycarbonyl)-4,5,6,7-tetrahydrobenzothien-2-methylidenyl]-5-iodo-2-indolinone
3-[3-(2-methylaminoethyl)-4,5,6,7-tetrahydrobenzothien-2-methylidenyl]-5-iodo-2-indolinone
3-(3-cyclopropylmethoxy-4,5,6,7-tetrahydrobenzothien-2-methylidenyl)-5-iodo-2-indolinone
3-(4,5,6,7-tetrahydrobenzothiazol-2-methylidenyl)-5-iodo-2-indolinone
3-(4-methyl-4,5,6,7-tetrahydroindol-2-methylidenyl)-5-iodo-2-indolinone
3-(4,4-dimethyl-4,5,6,7-tetrahydroindol-2-methylidenyl)-5-iodo-2-indolinone
3-(3-ethyl-4,5,6,7-tetrahydroindol-2-methylidenyl)-5-fluoro-2-indolinone
3-(3-isopropyl-4,5,6,7-tetrahydroindol-2-methylidenyl)-5-fluoro-2-indolinone
3-(4,5,6,7-tetrahydroindol-3-methylidenyl)-5-fluoro-2-indolinone
3-(4-isopropyl-4,5,6,7-tetrahydroindol-2-methylidenyl)-5-fluoro-2-indolinone
3-(4-carboxymethyl-4,5,6,7-tetrahydroindol-2-methylidenyl)-5-fluoro-2-indolinone
3-(3-methyl-4,5,6,7-tetrahydroinden-2-methylidenyl)-5-nitro-2-indolinone
3-(4,5,6,7-tetrahydroinden-2-methylidenyl)-5-nitro-2-indolinone
3-(3-methyl-4,5,6,7-tetrahydrobenzofuran-2-methylidenyl)-5-nitro-2-indolinone
3-(3-n-pentyl-4,5,6,7-tetrahydrobenzofuran-2-methylidenyl)-5-nitro-2-indolinone
3-(3-ethyl-4,5,6,7-tetrahydrobenzofuran-2-methylidenyl)-5-nitro-2-indolinone
3-(4,5,6,7-tetrahydrobenzofuran-2-methylidenyl)-5-nitro-2-indolinone
3-[3-(4-methylphenyl)-4,5,6,7-tetrahydrobenzofuran-2-methylidenyl]-5-nitro-2-indolinone
3-(3-phenylsulfonylmethyl-4,5,6,7-tetrahydrobenzofuran-2-methylidenyl)-5-nitro-2-indolinone
3-[3-(1-phenylaminoethyl)-4,5,6,7-tetrahydrobenzofuran-2-methylidenyl]-5-nitro-2-indolinone
3-[3-(1-phenylaminobutyl)-4,5,6,7-tetrahydrobenzofuran-2-methylidenyl]-5-nitro-2-indolinone
3-(3-cyano-4,5,6,7-tetrahydrobenzofuran-2-methylidenyl)-5-nitro-2-indolinone
3-(3-phenylaminomethyl-4,5,6,7-tetrahydrobenzofuran-2-methylidenyl)-5-nitro-2-indolinone
3-(3-phenyl-4,5,6,7-tetrahydrobenzofuran-2-methylidenyl)-5-nitro-2-indolinone
3-(4,5,6,7-tetrahydrobenzimidazol-2-methylidenyl)-5-nitro-2-indolinone
3-(4,5,6,7-tetrahydrobenzoxazol-2-methylidenyl)-5-nitro-2-indolinone
3-(3-methyl-4,5,6,7-tetrahydroindol-2-methylidenyl)-5-nitro-2-indolinone
3-(3-carboxy-4,5,6,7-tetrahydroindol-2-methylidenyl)-5-nitro-2-indolinone
3-[3-(isoquinolin-1-methyl)-4,5,6,7-tetrahydroindol-2-methylidenyl]-5-nitro-2-indolinone
3-(3-hydroxy-4,5,6,7-tetrahydroindol-2-methylidenyl)-5-nitro-2-indolinone
3-(3-methoxy-4,5,6,7-tetrahydroindol-2-methylidenyl)-5-nitro-2-indolinone
3-(4,5,6,7-tetrahydroindol-2-methylidenyl)-5-nitro-2-indolinone
3-(4,5,6,7-tetrahydrobenzothien-2-methylidenyl)-5-nitro-2-indolinone
3-(3-methoxycarbonyl-4,5,6,7-tetrahydrobenzothien-2-methylidenyl)-5-nitro-2-indolinone
3-(3-vinyl-4,5,6,7-tetrahydrobenzothien-2-methylidenyl)-5-nitro-2-indolinone
3-(3-carboxy-4,5,6,7-tetrahydrobenzothien-2-methylidenyl)-5-nitro-2-indolinone
3-(3-ethoxycarbonyl-4,5,6,7-tetrahydrobenzothien-2-methylidenyl)-5-nitro-2-indolinone
3-[3-(3-dimethylamino-n-propoxycarbonyl)-4,5,6,7-tetrahydrobenzothien-2-methylidenyl]-5-nitro-2-indolinone
3-[3-(2-diethylaminoethoxycarbonyl)-4,5,6,7-tetrahydrobenzothien-2-methylidenyl]-5-nitro-2-indolinone
3-[3-(2-methylaminoethyl)-4,5,6,7-tetrahydrobenzothien-2-methylidenyl]-5-nitro-2-indolinone
3-(3-cyclopropylmethoxy-4,5,6,7-tetrahydrobenzothien-2-methylidenyl)-5-nitro-2-indolinone
3-(4,5,6,7-tetrahydrobenzothiazol-2-methylidenyl)-5-nitro-2-indolinone
3-(4-methyl-4,5,6,7-tetrahydroindol-2-methylidenyl)-5-nitro-2-indolinone
3-(4,4-dimethyl-4,5,6,7-tetrahydroindol-2-methylidenyl)-5-nitro-2-indolinone
3-(4-ethyl-4,5,6,7-tetrahydroindol-2-methylidenyl)-5-nitro-2-indolinone
3-(3-isopropyl-4,5,6,7-tetrahydroindol-2-methylidenyl)-7-bromo-5-chloro-2-indolinone
3-(4,5,6,7-tetrahydroindol-3-methylidenyl)-7-bromo-5-chloro-2-indolinone
3-(4-isopropyl-4,5,6,7-tetrahydroindol-2-methylidenyl)-7-bromo-5-chloro-2-indolinone
3-(4-carboxymethyl-4,5,6,7-tetrahydroindol-2-methylidenyl)-7-bromo-5-chloro-2-indolinone 3-(3-methyl-4,5,6,7-tetrahydroinden-2-methylidenyl)-5-fluoro-2-indolinone
3-(4,5,6,7-tetrahydroinden-2-methylidenyl)-5-fluoro-2-indolinone
3-(3-methyl-4,5,6,7-tetrahydrobenzofuran-2-methylidenyl)-5-fluoro-2-indolinone
3-(3-ethoxycarbonyl-4,5,6,7-tetrahydrobenzofuran-2-methylidenyl)-5-fluoro-2-indolinone
3-(3-n-pentyl-4,5,6,7-tetrahydrobenzofuran-2-methylidenyl)-5-fluoro-2-indolinone
3-(3-ethyl-4,5,6,7-tetrahydrobenzofuran-2-methylidenyl)-5-fluoro-2-indolinone
3-(4,5,6,7-tetrahydrobenzofuran-2-methylidenyl)-5-fluoro-2-indolinone
3-[3-(4-methylphenyl)-4,5,6,7-tetrahydrobenzofuran-2-methylidenyl]-5-fluoro-2-indolinone
3-(3-phenylsulfonylmethyl-4,5,6,7-tetrahydrobenzofuran-2-methylidenyl)-5-fluoro-2-indolinone
3-[3-(1-phenylaminoethyl)-4,5,6,7-tetrahydrobenzofuran-2-methylidenyl]-5-fluoro-2-indolinone
3-[3-(1-phenylaminobutyl)-4,5,6,7-tetrahydrobenzofuran-2-methylidenyl]-5-fluoro-2-indolinone
3-(3-cyano-4,5,6,7-tetrahydrobenzofuran-2-methylidenyl)-5-fluoro-2-indolinone
3-(3-phenylaminomethyl-4,5,6,7-tetrahydrobenzofuran-2-methylidenyl)-5-fluoro-2-indolinone
3-(3-phenyl-4,5,6,7-tetrahydrobenzofuran-2-methylidenyl)-5-fluoro-2-indolinone
3-(4,5,6,7-tetrahydrobenzimidazol-2-methylidenyl)-5-fluoro-2-indolinone
3-(4,5,6,7-tetrahydrobenzoxazol-2-methylidenyl)-5-fluoro-2-indolinone
3-(3-methyl-4,5,6,7-tetrahydroindol-2-methylidenyl)-5-fluoro-2-indolinone
3-(3-carboxy-4,5,6,7-tetrahydroindol-2-methylidenyl)-5-fluoro-2-indolinone
3-[3-(isoquinolin-1-methyl)-4,5,6,7-tetrahydroindol-2-methylidenyl]-5-fluoro-2-indolinone
3-(3-hydroxy-4,5,6,7-tetrahydroindol-2-methylidenyl)-5-fluoro-2-indolinone
3-(3-methoxy-4,5,6,7-tetrahydroindol-2-methylidenyl)-5-fluoro-2-indolinone
3-(4,5,6,7-tetrahydroindol-2-methylidenyl)-5-fluoro-2-indolinone
3-(4,5,6,7-tetrahydrobenzothien-2-methylidenyl)-5-fluoro-2-indolinone
3-(3-methoxycarbonyl-4,5,6,7-tetrahydrobenzothien-2-methylidenyl)-5-fluoro-2-indolinone
3-(3-vinyl-4,5,6,7-tetrahydrobenzothien-2-methylidenyl)-5-fluoro-2-indolinone
3-(3-carboxy-4,5,6,7-tetrahydrobenzothien-2-methylidenyl)-5-fluoro-2-indolinone
3-(3-ethoxycarbonyl-4,5,6,7-tetrahydrobenzothien-2-methylidenyl)-5-fluoro-2-indolinone
3-[3-(3-dimethylamino-n-propoxycarbonyl)-4,5,6,7-tetrahydrobenzothien-2-methylidenyl]-5-fluoro-2-indolinone
3-[3-(2-diethylaminoethoxycarbonyl)-4,5,6,7-tetrahydrobenzothien-2-methylidenyl]-5-fluoro-2-indolinone
3-[3-(2-methylaminoethyl)-4,5,6,7-tetrahydrobenzothien-2-methylidenyl]-5-fluoro-2-indolinone
3-(3-cyclopropylmethoxy-4,5,6,7-tetrahydrobenzothien-2-methylidenyl)-5-fluoro-2-indolinone
3-(4,5,6,7-tetrahydrobenzothiazol-2-methylidenyl)-5-fluoro-2-indolinone
3-(4-methyl-4,5,6,7-tetrahydroindol-2-methylidenyl)-5-fluoro-2-indolinone
3-(4,4-dimethyl-4,5,6,7-tetrahydroindol-2-methylidenyl)-5-fluoro-2-indolinone
3-(4-ethyl-4,5,6,7-tetrahydroindol-2-methylidenyl)-5-fluoro-2-indolinone
3-(4-phenyl-4,5,6,7-tetrahydroindol-2-methylidenyl)-5-fluoro-2-indolinone
3-(4,5,6,7-tetrahydroindol-3-methylidenyl)-5,7-dibromo-2-indolinone
3-(4-isopropyl-4,5,6,7-tetrahydroindol-2-methylidenyl)-5,7-dibromo-2-indolinone
3-(4-carboxymethyl-4,5,6,7-tetrahydroindol-3-methylidenyl)-5,7-dibromo-2-indolinone
3-(3-methyl-4,5,6,7-tetrahydroinden-2-methylidenyl)-7-bromo-5-chloro-2-indolinone
3-(4,5,6,7-tetrahydroinden-2-methylidenyl)-7-bromo-5-chloro-2-indolinone
3-(3-methyl-4,5,6,7-tetrahydrobenzofuran-2-methylidenyl)-7-bromo-5-chloro-2-indolinone
3-(3-ethoxycarbonyl-4,5,6,7-tetrahydrobenzofuran-2-methylidenyl)-7-bromo-5-chloro-2-indolinone
3-(3-n-pentyl-4,5,6,7-tetrahydrobenzofuran-2-methylidenyl)-7-bromo-5-chloro-2-indolinone
3-(3-ethyl-4,5,6,7-tetrahydrobenzofuran-2-methylidenyl)-7-bromo-5-chloro-2-indolinone
3-(4,5,6,7-tetrahydrobenzofuran-2-methylidenyl)-7-bromo-5-chloro-2-indolinone
3-[3-(4-methylphenyl)-4,5,6,7-tetrahydrobenzofuran-2-methylidenyl]-7-bromo-5-chloro-2-indolinone
3-(3-phenylsulfonylmethyl-4,5,6,7-tetrahydrobenzofuran-2-methylidenyl)-7-bromo-5-chloro-2-indolinone
3-[3-(1-phenylaminoethyl)-4,5,6,7-tetrahydrobenzofuran-2-methylidenyl]-7-bromo-5-chloro-2-indolinone
3-[3-(1-phenylaminobutyl)-4,5,6,7-tetrahydrobenzofuran-2-methylidenyl]-7-bromo-5-chloro-2-indolinone
3-(3-cyano-4,5,6,7-tetrahydrobenzofuran-2-methylidenyl)-7-bromo-5-chloro-2-indolinone
3-(3-phenylaminomethyl-4,5,6,7-tetrahydrobenzofuran-2-methylidenyl)-7-bromo-5-chloro-2-indolinone
3-(3-phenyl-4,5,6,7-tetrahydrobenzofuran-2-methylidenyl)-7-bromo-5-chloro-2-indolinone
3-(4,5,6,7-tetrahydrobenzimidazol-2-methylidenyl)-7-bromo-5-chloro-2-indolinone
3-(4,5,6,7-tetrahydrobenzoxazol-2-methylidenyl)-7-bromo-5-chloro-2-indolinone
3-(3-methyl-4,5,6,7-tetrahydroindol-2-methylidenyl)-7-bromo-5-chloro-2-indolinone
3-(3-carboxy-4,5,6,7-tetrahydroindol-2-methylidenyl)-7-bromo-5-chloro-2-indolinone
3-[3-(isoquinolin-1-methyl)-4,5,6,7-tetrahydroindol-2-methylidenyl]-7-bromo-5-chloro-2-indolinone
3-(3-hydroxy-4,5,6,7-tetrahydroindol-2-methylidenyl)-7-bromo-5-chloro-2-indolinone
3-(3-methoxy-4,5,6,7-tetrahydroindol-2-methylidenyl)-7-bromo-5-chloro-2-indolinone
3-(4,5,6,7-tetrahydroindol-2-methylidenyl)-7-bromo-5-chloro-2-indolinone
3-(4,5,6,7-tetrahydrobenzothien-2-methylidenyl)-7-bromo-5-chloro-2-indolinone
3-(3-methoxycarbonyl-4,5,6,7-tetrahydrobenzothien-2-methylidenyl)-7-bromo-5-chloro-2-indolinone
3-(3-vinyl-4,5,6,7-tetrahydrobenzothien-2-methylidenyl)-7-bromo-5-chloro-2-indolinone
3-(3-carboxy-4,5,6,7-tetrahydrobenzothien-2-methylidenyl)-7-bromo-5-chloro-2-indolinone
3-(3-ethoxycarbonyl-4,5,6,7-tetrahydrobenzothien-2-methylidenyl)-7-bromo-5-chloro-2-indolinone
3-[3-(3-dimethylamino-n-propoxycarbonyl)-4,5,6,7-tetrahydrobenzothien-2-methylidenyl]-7-bromo-5-chloro-2-indolinone
3-[3-(2-diethylaminoethoxycarbonyl)-4,5,6,7-tetrahydrobenzothien-2-methylidenyl]-7-bromo-5-chloro-2-indolinone
3-[3-(2-methylaminoethyl)-4,5,6,7-tetrahydrobenzothien-2-methylidenyl]-7-bromo-5-chloro-2-indolinone
3-(3-cyclopropylmethoxy-4,5,6,7-tetrahydrobenzothien-2-methylidenyl)-7-bromo-5-chloro-2-indolinone
3-(4,5,6,7-tetrahydrobenzothiazol-2-methylidenyl)-7-bromo-5-chloro-2-indolinone
3-(4-methyl-4,5,6,7-tetrahydroindol-2-methylidenyl)-7-bromo-5-chloro-2-indolinone
3-(4,4-dimethyl-4,5,6,7-tetrahydroindol-2-methylidenyl)-7-bromo-5-chloro-2-indolinone
3-(4-ethyl-4,5,6,7-tetrahydroindol-2-methylidenyl)-7-bromo-5-chloro-2-indolinone
3-(4-phenyl-4,5,6,7-tetrahydroindol-2-methylidenyl)-7-bromo-5-chloro-2-indolinone
3-(3-ethyl-4,5,6,7-tetrahydroindol-2-methylidenyl)-7-bromo-5-chloro-2-indolinone
3-(4-isopropyl-4,5,6,7-tetrahydroindol-2-methylidenyl)-4-methyl-2-indolinone
3-(4-carboxymethyl-4,5,6,7-tetrahydroindol-2-methylidenyl)-4-methyl-2-indolinone
3-(3-methyl-4,5,6,7-tetrahydroinden-2-methylidenyl)-5,7-dibromo-2-indolinone -continued 3-(4,5,6,7-tetrahydroinden-2-methylidenyl)-5,7-dibromo-2-indolinone
3-(3-methyl-4,5,6,7-tetrahydrobenzofuran-2-methylidenyl)-5,7-dibromo-2-indolinone
3-(3-ethoxycarbonyl-4,5,6,7-tetrahydrobenzofuran-2-methylidenyl)-5,7-dibromo-2-indolinone
3-(3-n-pentyl-4,5,6,7-tetrahydrobenzofuran-2-methylidenyl)-5,7-dibromo-2-indolinone
3-(3-ethyl-4,5,6,7-tetrahydrobenzofuran-2-methylidenyl)-5,7-dibromo-2-indolinone
3-(4,5,6,7-tetrahydrobenzofuran-2-methylidenyl)-5,7-dibromo-2-indolinone
3-[3-(4-methylphenyl)-4,5,6,7-tetrahydrobenzofuran-2-methylidenyl]-5,7-dibromo-2-indolinone
3-(3-phenylsulfonylmethyl-4,5,6,7-tetrahydrobenzofuran-2-methylidenyl)-5,7-dibromo-2-indolinone
3-[3-(1-phenylaminoethyl)-4,5,6,7-tetrahydrobenzofuran-2-methylidenyl]-5,7-dibromo-2-indolinone
3-[3-(1-phenylaminobutyl)-4,5,6,7-tetrahydrobenzofuran-2-methylidenyl]-5,7-dibromo-2-indolinone
3-(3-cyano-4,5,6,7-tetrahydrobenzofuran-2-methylidenyl)-5,7-dibromo-2-indolinone
3-(3-phenylaminomethyl-4,5,6,7-tetrahydrobenzofuran-2-methylidenyl)-5,7-dibromo-2-indolinone
3-(3-phenyl-4,5,6,7-tetrahydrobenzofuran-2-methylidenyl)-5,7-dibromo-2-indolinone
3-(4,5,6,7-tetrahydrobenzimidazol-2-methylidenyl)-5,7-dibromo-2-indolinone
3-(4,5,6,7-tetrahydrobenzoxazol-2-methylidenyl)-5,7-dibromo-2-indolinone
3-(3-methyl-4,5,6,7-tetrahydroindol-2-methylidenyl)-5,7-dibromo-2-indolinone
3-(3-carboxy-4,5,6,7-tetrahydroindol-2-methylidenyl)-5,7-dibromo-2-indolinone
3-[3-(isoquinolin-1-methyl)-4,5,6,7-tetrahydroindol-2-methylidenyl]-5,7-dibromo-2-indolinone
3-(3-hydroxy-4,5,6,7-tetrahydroindol-2-methylidenyl)-5,7-dibromo-2-indolinone
3-(3-methoxy-4,5,6,7-tetrahydroindol-2-methylidenyl)-5,7-dibromo-2-indolinone
3-(4,5,6,7-tetrahydroindol-2-methylidenyl)-5,7-dibromo-2-indolinone
3-(4,5,6,7-tetrahydrobenzothien-2-methylidenyl)-5,7-dibromo-2-indolinone
3-(3-methoxycarbonyl-(4,5,6,7-tetrahydrobenzothien-2-methylidenyl)-5,7-dibromo-2-indolinone
3-(3-vinyl-(4,5,6,7-tetrahydrobenzothien-2-methylidenyl)-5,7-dibromo-2-indolinone
3-(3-carboxy-(4,5,6,7-tetrahydrobenzothien-2-methylidenyl)-5,7-dibromo-2-indolinone
3-(3-ethoxycarbonyl-(4,5,6,7-tetrahydrobenzothien-2-methylidenyl)-5,7-dibromo-2-indolinone
3-[3-(3-dimethylamino-n-proxycarbonyl)-(4,5,6,7-tetrahydrobenzothien-2-methylidenyl]-5,7-dibromo-2-indolinone
3-[3-(2-diethylaminoethoxycarbonyl)(4,5,6,7-tetrahydrobenzothien-2-methylidenyl]-5,7-dibromo-2-indolinone
3-[3-(2-methylaminoethyl)-(4,5,6,7-tetrahydrobenzothien-2-methylidenyl]-5,7-dibromo-2-indolinone
3-(3-cyclopropylmethoxy-(4,5,6,7-tetrahydrobenzothien-2-methylidenyl)-5,7-dibromo-2-indolinone
3-(4,5,6,7-tetrahydrobenzothiazol-2-methylidenyl)-5,7-dibromo-2-indolinone
3-(4-methyl-tetrahydroindol-2-methylidenyl)-5,7-dibromo-2-indolinone
3-(4,4-dimethyl-tetrahydroindol-2-methylidenyl)-5,7-dibromo-2-indolinone
3-(4-ethyl-tetrahydroindol-2-methylidenyl)-5,7-dibromo-2-indolinone
3-(4-phenyl-tetrahydroindol-2-methylidenyl)-5,7-dibromo-2-indolinone
3-(3-ethyl-tetrahydroindol-2-methylidenyl)-5,7-dibromo-2-indolinone
3-(3-isopropyl-tetrahydroindol-2-methylidenyl)-5,7-dibromo-2-indolinone
3-(4-carboxymethyl-4,5,6,7-tetrahydroindol-2-methylidenyl)-2-indolinone
3-(3-methyl-4,5,6,7-tetrahydroinden-2-methylidenyl)-4-methyl-2-indolinone
3-(4,5,6,7-tetrahydroinden-2-methylidenyl)-4-methyl-2-indolinone
3-(3-methyl-4,5,6,7-tetrahydrobenzofuran-2-methylidenyl)-4-methyl-2-indolinone
3-(3-ethoxycarbonyl-4,5,6,7-tetrahydrobenzofuran-2-methylidenyl)-4-methyl-2-indolinone
3-(3-n-pentyl-4,5,6,7-tetrahydrobenzofuran-2-methylidenyl)-4-methyl-2-indolinone
3-(3-ethyl-4,5,6,7-tetrahydrobenzofuran-2-methylidenyl)-4-methyl-2-indolinone
3-(4,5,6,7-tetrahydrobenzofuran-2-methylidenyl)-4-methyl-2-indolinone
3-[3-(4-methylphenyl)-4,5,6,7-tetrahydrobenzofuran-2-methylidenyl]-4-methyl-2-indolinone
3-(3-phenylsulfonylmethyl-4,5,6,7-tetrahydrobenzofuran-2-methylidenyl)-4-methyl-2-indolinone
3-[3-(1-phenylaminoethyl)-4,5,6,7-tetrahydrobenzofuran-2-methylidenyl]-4-methyl-2-indolinone
3-[3-(1-phenylaminobutyl)-4,5,6,7-tetrahydrobenzofuran-2-methylidenyl]-4-methyl-2-indolinone
3-(3-cyano-4,5,6,7-tetrahydrobenzofuran-2-methylidenyl)-4-methyl-2-indolinone
3-(3-phenylaminomethyl-4,5,6,7-tetrahydrobenzofuran-2-methylidenyl)-4-methyl-2-indolinone
3-(3-phenyl-4,5,6,7-tetrahydrobenzofuran-2-methylidenyl)-4-methyl-2-indolinone
3-(4,5,6,7-tetrahydrobenzimidazol-2-methylidenyl)-4-methyl-2-indolinone
3-(4,5,6,7-tetrahydrobenzoxazol-2-methylidenyl)-4-methyl-2-indolinone
3-(3-methyl-4,5,6,7-tetrahydroindol-2-methylidenyl)-4-methyl-2-indolinone
3-(3-carboxy-4,5,6,7-tetrahydroindol-2-methylidenyl)-4-methyl-2-indolinone
3-[3-(isoquinolin-1-methyl)-4,5,6,7-tetrahydroindol-2-methylidenyl]-4-methyl-2-indolinone
3-(3-hydroxy-4,5,6,7-tetrahydroindol-2-methylidenyl)-4-methyl-2-indolinone
3-(3-methoxy-4,5,6,7-tetrahydroindol-2-methylidenyl)-4-methyl-2-indolinone
3-(4,5,6,7-tetrahydroindol-2-methylidenyl)-4-methyl-2-indolinone
3-(4,5,6,7-tetrahydrobenzothien-2-methylidenyl)-4-methyl-2-indolinone
3-(3-methoxycarbonyl-4,5,6,7-tetrahydrobenzothien-2-methylidenyl)-4-methyl-2-indolinone
3-(3-vinyl-4,5,6,7-tetrahydrobenzothien-2-methylidenyl)-4-methyl-2-indolinone
3-(3-carboxy-4,5,6,7-tetrahydrobenzothien-2-methylidenyl)-4-methyl-2-indolinone
3-(3-ethoxycarbonyl-4,5,6,7-tetrahydrobenzothien-2-methylidenyl)-4-methyl-2-indolinone
3-[3-(3-dimethylamino-n-propoxycarbonyl)-4,5,6,7-tetrahydrobenzothien-2-methylidenyl]-4-methyl-2-indolinone
3-[3-(2-diethylaminoethoxycarbonyl)-4,5,6,7-tetrahydrobenzothien-2-methylidenyl]-4-methyl-2-indolinone
3-[3-(2-methylaminoethyl)-4,5,6,7-tetrahydrobenzothien-2-methylidenyl]-4-methyl-2-indolinone
3-(3-cyclopropylmethoxy-4,5,6,7-tetrahydrobenzothien-2-methylidenyl)-4-methyl-2-indolinone
3-(4,5,6,7-tetrahydrobenzothiazol-2-methylidenyl)-4-methyl-2-indolinone
3-(4-methyl-4,5,6,7-tetrahydroindol-2-methylidenyl)-4-methyl-2-indolinone
3-(4,4-dimethyl-4,5,6,7-tetrahydroindol-2-methylidenyl)-4-methyl-2-indolinone
3-(4-ethyl-4,5,6,7-tetrahydroindol-2-methylidenyl)-4-methyl-2-indolinone
3-(4-phenyl-4,5,6,7-tetrahydroindol-2-methylidenyl)-4-methyl-2-indolinone
3-(3-ethyl-4,5,6,7-tetrahydroindol-2-methylidenyl)-4-methyl-2-indolinone
3-(3-isopropyl-4,5,6,7-tetrahydroindol-2-methylidenyl)-4-methyl-2-indolinone
3-(4,5,6,7-tetrahydroindol-3-methylidenyl)-4-methyl-2-indolinone
3-(3-methyl-4,5,6,7-tetrahydroinden-2-methylidenyl)-2-indolinone
3-(4,5,6,7-tetrahydroinden-2-methylidenyl)-2-indolinone 3-(3-methyl-4,5,6,7-tetrahydrobenzofuran-2-methylidenyl)-2-indolinone
3-(3-ethoxycarbonyl-4,5,6,7-tetrahydrobenzofuran-2-methylidenyl)-2-indolinone
3-(3-n-pentyl-4,5,6,7-tetrahydrobenzofuran-2-methylidenyl)-2-indolinone
3-(3-ethyl-4,5,6,7-tetrahydrobenzofuran-2-methylidenyl)-2-indolinone
3-(4,5,6,7-tetrahydrobenzofuran-2-methylidenyl)-2-indolinone
3-[3-(4-methylphenyl)-4,5,6,7-tetrahydrobenzofuran-2-methylidenyl]-2-indolinone
3-(3-phenylsulfonylmethyl-4,5,6,7-tetrahydrobenzofuran-2-methylidenyl)-2-indolinone
3-[3-(1-phenylaminoethyl)-4,5,6,7-tetrahydrobenzofuran-2-methylidenyl]-2-indolinone
3-[3-(1-phenylaminobutyl)-4,5,6,7-tetrahydrobenzofuran-2-methylidenyl]-2-indolinone
3-(3-cyano-4,5,6,7-tetrahydrobenzofuran-2-methylidenyl)-2-indolinone
3-(3-phenylaminomethyl-4,5,6,7-tetrahydrobenzofuran-2-methylidenyl)-2-indolinone
3-(3-phenyl-4,5,6,7-tetrahydrobenzofuran-2-methylidenyl)-2-indolinone
3-(4,5,6,7-tetrahydrobenzimidazol-2-methylidenyl)-2-indolinone
3-(4,5,6,7-tetrahydrobenzoxazol-2-methylidenyl)-2-indolinone
3-(3-methyl-4,5,6,7-tetrahydroindol-2-methylidenyl)-2-indolinone
3-(3-carboxy-4,5,6,7-tetrahydroindol-2-methylidenyl)-2-indolinone
3-[3-(isoquinolin-1-methyl)-4,5,6,7-tetrahydroindol-2-methylidenyl]-2-indolinone
3-(3-hydroxy-4,5,6,7-tetrahydroindol-2-methylidenyl)-2-indolinone
3-(3-methoxy-4,5,6,7-tetrahydroindol-2-methylidenyl)-2-indolinone
3-(4,5,6,7-tetrahydroindol-2-methylidenyl)-2-indolinone
3-(4,5,6,7-tetrahydrobenzothien-2-methylidenyl)-2-indolinone
3-(3-methoxycarbonyl-4,5,6,7-tetrahydrobenzothien-2-methylidenyl)-2-indolinone
3-(3-vinyl-4,5,6,7-tetrahydrobenzothien-2-methylidenyl)-2-indolinone
3-(3-carboxy-4,5,6,7-tetrahydrobenzothien-2-methylidenyl)-2-indolinone
3-(3-ethoxycarbonyl-4,5,6,7-tetrahydrobenzothien-2-methylidenyl)-2-indolinone
3-[3-(3-dimethylamino-n-propoxycarbonyl)-4,5,6,7-tetrahydrobenzothien-2-methylidenyl]-2-indolinone
3-[3-(2-diethylaminoethoxycarbonyl)-4,5,6,7-tetrahydrobenzothien-2-methylidenyl]-2-indolinone
3-[3-(2-methylaminoethyl)-4,5,6,7-tetrahydrobenzothien-2-methylidenyl]-2-indolinone
3-(3-cyclopropylmethoxy-4,5,6,7-tetrahydrobenzothien-2-methylidenyl)-2-indolinone
3-(4,5,6,7-tetrahydrobenzothiazol-2-methylidenyl)-2-indolinone
3-(4-methyl-4,5,6,7-tetrahydroindol-2-methylidenyl)-2-indolinone
3-(4,4-dimethyl-4,5,6,7-tetrahydroindol-2-methylidenyl)-2-indolinone
3-(4-ethyl-4,5,6,7-tetrahydroindol-2-methylidenyl)-2-indolinone
3-(4-phenyl-4,5,6,7-tetrahydroindol-2-methylidenyl)-2-indolinone
3-(3-ethyl-4,5,6,7-tetrahydroindol-2-methylidenyl)-2-indolinone
3-(3-isopropyl-4,5,6,7-tetrahydroindol-2-methylidenyl)-2-indolinone
3-(4,5,6,7-tetrahydroindol-3-methylidenyl)-2-indolinone
3-(4-isopropyl-4,5,6,7-tetrahydroindol-2-methylidenyl)-2-indolinone
3-(3-methyl-4,5,6,7-tetrahydroinden-2-methylidenyl)-5,6-dimethoxy-2-indolinone
3-(4,5,6,7-tetrahydroinden-2-methylidenyl)-5,6-dimethoxy-2-indolinone
3-(3-methyl-4,5,6,7-tetrahydrobenzofuran-2-methylidenyl)-5,6-dimethoxy-2-indolinone
3-(3-ethoxycarbonyl-4,5,6,7-tetrahydrobenzofuran-2-methylidenyl)-5,6-dimethoxy-2-indolinone
3-(3-n-pentyl-4,5,6,7-tetrahydrobenzofuran-2-methylidenyl)-5,6-dimethoxy-2-indolinone
3-(3-ethyl-4,5,6,7-tetrahydrobenzofuran-2-methylidenyl)-5,6-dimethoxy-2-indolinone
3-(3-4,5,6,7-tetrahydrobenzofuran-2-methylidenyl)-5,6-dimethoxy-2-indolinone
3-[3-(4-methylphenyl)-4,5,6,7-tetrahydrobenzofuran-2-methylidenyl]-5,6-dimethoxy-2-indolinone
3-(3-phenylsulfonylmethyl-4,5,6,7-tetrahydrobenzofuran-2-methylidenyl)-5,6-dimethoxy-2-indolinone
3-[3-(1-phenylaminoethyl)-4,5,6,7-tetrahydrobenzofuran-2-methylidenyl]-5,6-dimethoxy-2-indolinone
3-[3-(1-phenylaminobutyl)-4,5,6,7-tetrahydrobenzofuran-2-methylidenyl]-5,6-dimethoxy-2-indolinone
3-(3-phenylaminomethyl-4,5,6,7-tetrahydrobenzofuran-2-methylidenyl)-5,6-dimethoxy-2-indolinone
3-(3-cyano-4,5,6,7-tetrahydrobenzofuran-2-methylidenyl)-5,6-dimethoxy-2-indolinone
3-(3-phenylaminomethyl-4,5,6,7-tetrahydrobenzofuran-2-methylidenyl)-5,6-dimethoxy-2-indolinone
3-(3-phenyl-4,5,6,7-tetrahydrobenzofuran-2-methylidenyl)-5,6-dimethoxy-2-indolinone
3-(4,5,6,7-tetrahydrobenzimidazol-2-methylidenyl)-5,6-dimethoxy-2-indolinone
3-(4,5,6,7-tetrahydrobenzoxazol-2-methylidenyl)-5,6-dimethoxy-2-indolinone
3-(3-methyl-4,5,6,7-tetrahydroindol-2-methylidenyl)-5,6-dimethoxy-2-indolinone
3-(3-carboxy-4,5,6,7-tetrahydroindol-2-methylidenyl)-5,6-dimethoxy-2-indolinone
3-[3-(isoquinolin-1-methyl)-4,5,6,7-tetrahydroindol-2-methylidenyl]-5,6-dimethoxy-2-indolinone
3-(3-hydroxy-4,5,6,7-tetrahydroindol-2-methylidenyl)-5,6-dimethoxy-2-indolinone
3-(3-methoxy-4,5,6,7-tetrahydroindol-2-methylidenyl)-5,6-dimethoxy-2-indolinone
3-(4,5,6,7-tetrahydroindol-2-methylidenyl)-5,6-dimethoxy-2-indolinone
3-(4,5,6,7-tetrahydrobenzothien-2-methylidenyl)-5,6-dimethoxy-2-indolinone
3-(3-methoxycarbonyl-4,5,6,7-tetrahydrobenzothien-2-methylidenyl)-5,6-dimethoxy-2-indolinone
3-(vinyl-4,5,6,7-tetrahydrobenzothien-2-methylidenyl)-5,6-dimethoxy-2-indolinone
3-(3-carboxy-4,5,6,7-tetrahydrobenzothien-2-methylidenyl)-5,6-dimethoxy-2-indolinone
3-(3-ethoxycarbonyl-4,5,6,7-tetrahydrobenzothien-2-methylidenyl)-5,6-dimethoxy-2-indolinone
3-[3-(3-dimethylamino-n-propoxycarbonyl)-4,5,6,7-tetrahydrobenzothien-2-methylidenyl]-5,6-dimethoxy-2-indolinone
3-[3-(2-diethylaminoethoxycarbonyl)-4,5,6,7-tetrahydrobenzothien-2-methylidenyl]-5,6-dimethoxy-2-indolinone
3-[3-(2-methylaminoethyl)-4,5,6,7-tetrahydrobenzothien-2-methylidenyl]-5,6-dimethoxy-2-indolinone
3-(3-cyclopropylmethoxy-4,5,6,7-tetrahydrobenzothien-2-methylidenyl)-5,6-dimethoxy-2-indolinone
3-(4,5,6,7-tetrahydrobenzothiazol-2-methylidenyl)-5,6-dimethoxy-2-indolinone
3-(4-methyl-4,5,6,7-tetrahydroindol-2-methylidenyl)-5,6-dimethoxy-2-indolinone
3-(4,4-dimethyl-4,5,6,7-tetrahydroindol-2-methylidenyl)-5,6-dimethoxy-2-indolinone
3-(4-ethyl-4,5,6,7-tetrahydroindol-2-methylidenyl)-5,6-dimethoxy-2-indolinone
3-(4-phenyl-4,5,6,7-tetrahydroindol-2-methylidenyl)-5,6-dimethoxy-2-indolinone
3-(3-ethyl-4,5,6,7-tetrahydroindol-2-methylidenyl)-5,6-dimethoxy-2-indolinone
3-(3-isopropyl-4,5,6,7-tetrahydroindol-2-methylidenyl)-5,6-dimethoxy-2-indolinone
3-(4,5,6,7-tetrahydroindol-3-methylidenyl)-5,6-dimethoxy-2-indolinone
3-(4-isopropyl-4,5,6,7-tetrahydroindol-2-methylidenyl)-5,6-dimethoxy-2-indolinone -continued 3-(4-carboxymethyl-4,5,6,7-tetrahydroindol-2-methylidenyl)-5,6-dimethoxy-2-indolinone
3-(4,5,6,7-tetrahydroinden-2-methylidenyl)-4,6-dimethyl-2-indolinone
3-(3-methyl-4,5,6,7-tetrahydrobenzofuran-2-methylidenyl)-4,6-dimethyl-2-indolinone
3-(3-ethoxycarbonyl)-4,5,6,7-tetrahydrobenzofuran-2-methylidenyl)-4,6-dimethyl-2-indolinone
3-(3-n-pentyl-4,5,6,7-tetrahydrobenzofuran-2-methylidenyl)-4,6-dimethyl-2-indolinone
3-(3-ethyl-4,5,6,7-tetrahydrobenzofuran-2-methylidenyl)-4,6-dimethyl-2-indolinone
3-(4,5,6,7-tetrahydrobenzofuran-2-methylidenyl)-4,6-dimethyl-2-indolinone
3-[3-(4-methylphenyl)-4,5,6,7-tetrahydrobenzofuran-2-methylidenyl]-4,6-dimethyl-2-indolinone
3-(3-phenylsulfonylmethyl-4,5,6,7-tetrahydrobenzofuran-2-methylidenyl)-4,6-dimethyl-2-indolinone
3-[3-(1-phenylaminoethyl)-4,5,6,7-tetrahydrobenzofuran-2-methylidenyl]-4,6-dimethyl-2-indolinone
3-[3-(1-phenylaminobutyl)-4,5,6,7-tetrahydrobenzofuran-2-methylidenyl]-4,6-dimethyl-2-indolinone
3-(3-cyano-4,5,6,7-tetrahydrobenzofuran-2-methylidenyl)-4,6-dimethyl-2-indolinone
3-(3-phenylaminomethyl-4,5,6,7-tetrahydrobenzofuran-2-methylidenyl)-4,6-dimethyl-2-indolinone
3-(3-phenyl-4,5,6,7-tetrahydrobenzofuran-2-methylidenyl)-4,6-dimethyl-2-indolinone
3-(4,5,6,7-tetrahydrobenzimidazol-2-methylidenyl)-4,6-dimethyl-2-indolinone
3-(4,5,6,7-tetrahydrobenzoxazol-2-methylidenyl)-4,6-dimethyl-2-indolinone
3-(3-methyl-4,5,6,7-tetrahydroindol-2-methylidenyl)-4,6-dimethyl-2-indolinone
3-(3-carboxy-4,5,6,7-tetrahydroindol-2-methylidenyl)-4,6-dimethyl-2-indolinone
3-[3-(isoquinolin-1-methyl)-4,5,6,7-tetrahydroindol-2-methylidenyl]-4,6-dimethyl-2-indolinone
3-(3-hydroxy-4,5,6,7-tetrahydroindol-2-methylidenyl)-4,6-dimethyl-2-indolinone
3-(3-methoxy-4,5,6,7-tetrahydroindol-2-methylidenyl)-4,6-dimethyl-2-indolinone
3-(4,5,6,7-tetrahydroindol-2-methylidenyl)-4,6-dimethyl-2-indolinone
3-(4,5,6,7-tetrahydrobenzothien-2-methylidenyl)-4,6-dimethyl-2-indolinone
3-(3-methoxycarbonyl-4,5,6,7-tetrahydrobenzothien-2-methylidenyl)-4,6-dimethyl-2-indolinone
3-(3-vinyl-4,5,6,7-tetrahydrobenzothien-2-methylidenyl)-4,6-dimethyl-2-indolinone
3-(3-carboxy-4,5,6,7-tetrahydrobenzothien-2-methylidenyl)-4,6-dimethyl-2-indolinone
3-(3-ethoxycarbonyl-4,5,6,7-tetrahydrobenzothien-2-methylidenyl)-4,6-dimethyl-2-indolinone
3-[3-(3-dimethylamino-n-propoxycarbonyl)-4,5,6,7-tetrahydrobenzothien-2-methylidenyl]-4,6-dimethyl-2-indolinone
3-[3-(2-diethylaminoethoxycarbonyl)-4,5,6,7-tetrahydrobenzothien-2-methylidenyl]-4,6-dimethyl-2-indolinone
3-[3-(2-methylaminoethyl)-4,5,6,7-tetrahydrobenzothien-2-methylidenyl]-4,6-dimethyl-2-indolinone
3-(3-cyclopropylmethoxy-4,5,6,7-tetrahydrobenzothien-2-methylidenyl)-4,6-dimethyl-2-indolinone
3-(4,5,6,7-tetrahydrobenzothiazol-2-methylidenyl)-4,6-dimethyl-2-indolinone
3-(4-methyl-4,5,6,7-tetrahydrodroindol-2-methylidenyl)-4,6-dimethyl-2-indolinone
3-(4,4-dimethyl-4,5,6,7-tetrahydrodroindol-2-methylidenyl)-4,6-dimethyl-2-indolinone
3-(4-ethyl-4,5,6,7-tetrahydrodroindol-2-methylidenyl)-4,6-dimethyl-2-indolinone
3-(4-phenyl-4,5,6,7-tetrahydrodroindol-2-methylidenyl)-4,6-dimethyl-2-indolinone
3-(3-ethyl-4,5,6,7-tetrahydrodroindol-2-methylidenyl)-4,6-dimethyl-2-indolinone
3-(3-isopropyl-4,5,6,7-tetrahydrodroindol-2-methylidenyl)-4,6-dimethyl-2-indolinone
3-(4,5,6,7-tetrahydrodroindol-3-methylidenyl)-4,6-dimethyl-2-indolinone
3-(4-isopropyl-4,5,6,7-tetrahydrodroindol-2-methylidenyl)-4,6-dimethyl-2-indolinone
3-(4-carboxymethyl-4,5,6,7-tetrahydrodroindol-2-methylidenyl)-4,6-dimethyl-2-indolinone
3-(3-methyl-4,5,6,7-tetrahydrobenzofuran-2-methylidenyl)-5-chloro-2-indolinone
3-(3-ethoxycarbonyl-4,5,6,7-tetrahydrobenzofuran-2-methylidenyl)-5-chloro-2-indolinone
3-(3-n-pentyl-4,5,6,7-tetrahydrobenzofuran-2-methylidenyl)-5-chloro-2-indolinone
3-(3-ethyl-4,5,6,7-tetrahydrobenzofuran-2-methylidenyl)-5-chloro-2-indolinone
3-(4,5,6,7-tetrahydrobenzofuran-2-methylidenyl)-5-chloro-2-indolinone
3-[3-(4-methylphenyl)-4,5,6,7-tetrahydrobenzofuran-2-methylidenyl]-5-chloro-2-indolinone
3-(3-phenylsulfonylmethyl-4,5,6,7-tetrahydrobenzofuran-2-methylidenyl)-5-chloro-2-indolinone
3-[3-(1-phenylaminoethyl)-4,5,6,7-tetrahydrobenzofuran-2-methylidenyl]-5-chloro-2-indolinone
3-[3-(1-phenylaminobutyl)-4,5,6,7-tetrahydrobenzofuran-2-methylidenyl]-5-chloro-2-indolinone
3-(3-cyano-4,5,6,7-tetrahydrobenzofuran-2-methylidenyl)-5-chloro-2-indolinone
3-(3-phenylaminomethyl-4,5,6,7-tetrahydrobenzofuran-2-methylidenyl)-5-chloro-2-indolinone
3-(3-phenyl-4,5,6,7-tetrahydrobenzofuran-2-methylidenyl)-5-chloro-2-indolinone
3-(4,5,6,7-tetrahydrobenzimidazol-2-methylidenyl)-5-chloro-2-indolinone
3-(4,5,6,7-tetrahydrobenzoxazol-2-methylidenyl)-5-chloro-2-indolinone
3-(3-methyl-4,5,6,7-tetrahydroindol-2-methylidenyl)-5-chloro-2-indolinone
3-(3-carboxy-4,5,6,7-tetrahydroindol-2-methylidenyl)-5-chloro-2-indolinone
3-[-(isoquinolin-1-methyl)-4,5,6,7-tetrahydroindol-2-methylidenyl]-5-chloro-2-indolinone
3-(3-hydroxy-4,5,6,7-tetrahydroindol-2-methylidenyl)-5-chloro-2-indolinone
3-(3-methoxy-4,5,6,7-tetrahydroindol-2-methylidenyl)-5-chloro-2-indolinone
3-(4,5,6,7-tetrahydroindol-2-methylidenyl)-5-chloro-2-indolinone
3-(4,5,6,7-tetrahydrobenzothien-2-methylidenyl)-5-chloro-2-indolinone
3-(3-methoxycarbonyl-4,5,6,7-tetrahydrobenzothien-2-methylidenyl)-5-chloro-2-indolinone
3-(3-vinyl-4,5,6,7-tetrahydrobenzothien-2-methylidenyl)-5-chloro-2-indolinone
3-(3-carboxy-4,5,6,7-tetrahydrobenzothien-2-methylidenyl)-5-chloro-2-indolinone
3-(3-ethoxycarbonyl-4,5,6,7-tetrahydrobenzothien-2-methylidenyl)-5-chloro-2-indolinone
3-[3-(3-dimethylamino-n-propoxycarbonyl)-4,5,6,7-tetrahydrobenzothien-2-methylidenyl]-5-chloro-2-indolinone
3-[3-(2-diethylaminoethoxycarbonyl)-4,5,6,7-tetrahydrobenzothien-2-methylidenyl]-5-chloro-2-indolinone
3-[3-(2-methylaminoethyl)-4,5,6,7-tetrahydrobenzothien-2-methylidenyl]-5-chloro-2-indolinone
3-(3-cyclopropylmethoxy-4,5,6,7-tetrahydrobenzothien-2-methylidenyl)-5-chloro-2-indolinone
3-(4,5,6,7-tetrahydrobenzothiazol-2-methylidenyl)-5-chloro-2-indolinone
3-(4-methyl-4,5,6,7-tetrahydroindol-2-methylidenyl)-5-chloro-2-indolinone
3-(4,4-dimethyl-4,5,6,7-tetrahydroindol-2-methylidenyl)-5-chloro-2-indolinone
3-(4-ethyl-4,5,6,7-tetrahydroindol-2-methylidenyl)-5-chloro-2-indolinone
3-(4-phenyl-4,5,6,7-tetrahydroindol-2-methylidenyl)-5-chloro-2-indolinone
3-(3-ethyl-4,5,6,7-tetrahydroindol-2-methylidenyl)-5-chloro-2-indolinone
3-(3-isopropyl-4,5,6,7-tetrahydroindol-2-methylidenyl)-5-chloro-2-indolinone
3-(4,5,6,7-tetrahydroindol-3-methylidenyl)-5-chloro-2-indolinone
3-(4-isopropyl-4,5,6,7-tetrahydroindol-2-methylidenyl)-5-chloro-2-indolinone -continued 3-(4-carboxymethyl-4,5,6,7-tetrahydroindol-2-methylidenyl)-5-chloro-2-indolinone
3-(3-methyl-4,5,6,7-tetrahydroinden-2-methylidenyl)-4,6-dimethyl-2-indolinone
3-(3-ethoxycarbonyl-4,5,6,7-tetrahydrobenzofuran-2-methylidenyl)-5-bromo-2-indolinone
3-(3-n-pentyl-4,5,6,7-tetrahydrobenzofuran-2-methylidenyl)-5-bromo-2-indolinone
3-(3-ethyl-4,5,6,7-tetrahydrobenzofuran-2-methylidenyl)-5-bromo-2-indolinone
3-(4,5,6,7-tetrahydrobenzofuran-2-methylidenyl)-5-bromo-2-indolinone
3-[3-(4-methylphenyl)-4,5,6,7-tetrahydrobenzofuran-2-methylidenyl]-5-bromo-2-indolinone
3-(3-phenylsulfonylmethyl-4,5,6,7-tetrahydrobenzofuran-2-methylidenyl)-5-bromo-2-indolinone
3-[3-(1-phenylaminoethyl)-4,5,6,7-tetrahydrobenzofuran-2-methylidenyl]-5-bromo-2-indolinone
3-[3-(1-phenylaminobutyl)-4,5,6,7-tetrahydrobenzofuran-2-methylidenyl]-5-bromo-2-indolinone
3-(3-cyano-4,5,6,7-tetrahydrobenzofuran-2-methylidenyl)-5-bromo-2-indolinone
3-(3-phenylaminomethyl-4,5,6,7-tetrahydrobenzofuran-2-methylidenyl)-5-bromo-2-indolinone
3-(3-phenyl-4,5,6,7-tetrahydrobenzofuran-2-methylidenyl)-5-bromo-2-indolinone
3-(4,5,6,7-tetrahydrobenzimidazol-2-methylidenyl)-5-bromo-2-indolinone
3-(4,5,6,7-tetrahydrobenzoxazol-2-methylidenyl)-5-bromo-2-indolinone
3-(3-methyl-4,5,6,7-tetrahydroindol-2-methylidenyl)-5-bromo-2-indolinone
3-(3-carboxy-4,5,6,7-tetrahydroindol-2-methylidenyl)-5-bromo-2-indolinone
3-[3-(isoquinolin-1-methyl)-4,5,6,7-tetrahydroindol-2-methylidenyl)-5-bromo-2-indolinone
3-(3-hydroxy-4,5,6,7-tetrahydroindol-2-methylidenyl)-5-bromo-2-indolinone
3-(3-methoxy-4,5,6,7-tetrahydroindol-2-methylidenyl)-5-bromo-2-indolinone
3-(4,5,6,7-tetrahydroindol-2-methylidenyl)-5-bromo-2-indolinone
3-(4,5,6,7-tetrahydrobenzothien-2-methylidenyl)-5-bromo-2-indolinone
3-(3-methoxycarbonyl-4,5,6,7-tetrahydrobenzothien-2-methylidenyl)-5-bromo-2-indolinone
3-(3-vinyl-4,5,6,7-tetrahydrobenzothien-2-methylidenyl)-5-bromo-2-indolinone
3-(3-carboxy-4,5,6,7-tetrahydrobenzothien-2-methylidenyl)-5-bromo-2-indolinone
3-(3-ethoxycarbonyl-4,5,6,7-tetrahydrobenzothien-2-methylidenyl)-5-bromo-2-indolinone
3-[3-(3-dimethylamino-n-propoxycarbonyl)-4,5,6,7-tetrahydrobenzothien-2-methylidenyl]-5-bromo-2-indolinone
3-[3-(2-diethylaminoethoxycarbonyl)-4,5,6,7-tetrahydrobenzothien-2-methylidenyl]-5-bromo-2-indolinone
3-[3-(2-methylaminoethyl)-4,5,6,7-tetrahydrobenzothien-2-methylidenyl]-5-bromo-2-indolinone
3-(3-cyclopropylmethoxy-4,5,6,7-tetrahydrobenzothien-2-methylidenyl)-5-bromo-2-indolinone
3-(4,5,6,7-tetrahydrobenzothiazol-2-methylidenyl)-5-bromo-2-indolinone
3-(4-methyl-4,5,6,7-tetrahydroindol-2-methylidenyl)-5-bromo-2-indolinone
3-(4,4-dimethyl-4,5,6,7-tetrahydroindol-2-methylidenyl)-5-bromo-2-indolinone
3-(4-ethyl-4,5,6,7-tetrahydroindol-2-methylidenyl)-5-bromo-2-indolinone
3-(4-phenyl-4,5,6,7-tetrahydroindol-2-methylidenyl)-5-bromo-2-indolinone
3-(3-ethyl-4,5,6,7-tetrahydroindol-2-methylidenyl)-5-bromo-2-indolinone
3-(3-isopropyl-4,5,6,7-tetrahydroindol-2-methylidenyl)-5-bromo-2-indolinone
3-(4,5,6,7-tetrahydroindol-2-methylidenyl)-5-bromo-2-indolinone
3-(4-isopropyl-4,5,6,7-tetrahydroindol-2-methylidenyl)-5-bromo-2-indolinone
3-(4-carboxymethyl-4,5,6,7-tetrahydroindol-2-methylidenyl)-5-bromo-2-indolinone
3-(3-methyl-4,5,6,7-tetrahydroinden-2-methylidenyl)-5-chloro-2-indolinone
3-(4,5,6,7-tetrahydroinden-2-methylidenyl)-5-chloro-2-indolinone
3-(3-n-pentyl-4,5,6,7-tetrahydrobenzofuran-2-methylidenyl)-5-amino-2-indolinone
3-(3-ethyl-4,5,6,7-tetrahydrobenzofuran-2-methylidenyl)-5-amino-2-indolinone
3-(4,5,6,7-tetrahydrobenzofuran-2-methylidenyl)-5-amino-2-indolinone
3-[3-(4-methylphenyl)4,5,6,7-tetrahydrobenzofuran-2-methylidenyl]-5-amino-2-indolinone
3-(3-phenylsulfonylmethyl-4,5,6,7-tetrahydrobenzofuran-2-methylidenyl)-5-amino-2-indolinone
3-[3-(1-phenylaminoethyl)-4,5,6,7-tetrahydrobenzofuran-2-methylidenyl)-5-amino-2-indolinone
3-[3-(1-phenylaminobutyl)-4,5,6,7-tetrahydrobenzofuran-2-methylidenyl)-5-amino-2-indolinone
3-(3-cyano-4,5,6,7-tetrahydrobenzofuran-2-methylidenyl)-5-amino-2-indolinone
3-(3-phenylaminomethyl-4,5,6,7-tetrahydrobenzofuran-2-methylidenyl)-5-amino-2-indolinone
3-(3-phenyl-4,5,6,7-tetrahydrobenzofuran-2-methylidenyl)-5-amino-2-indolinone
3-(4,5,6,7-tetrahydrobenzimidazol-2-methylidenyl)-5-amino-2-indolinone
3-(4,5,6,7-tetrahydrobenzoxazol-2-methylidenyl)-5-amino-2-indolinone
3-(3-methyl-4,5,6,7-tetrahydroindol-2-methylidenyl)-5-amino-2-indolinone
3-(3-carboxy-4,5,6,7-tetrahydroindol-2-methylidenyl)-5-amino-2-indolinone
3-[3-(isoquinolin-1-methyl)-4,5,6,7-tetrahydroindol-2-methylidenyl)-5-amino-2-indolinone
3-(3-hydroxy-4,5,6,7-tetrahydroindol-2-methylidenyl)-5-amino-2-indolinone
3-(3-methoxy-4,5,6,7-tetrahydroindol-2-methylidenyl)-5-amino-2-indolinone
3-(4,5,6,7-tetrahydroindol-2-methylidenyl)-5-amino-2-indolinone
3-(4,5,6,7-tetrahydrobenzothien-2-methylidenyl)-5-amino-2-indolinone
3-(3-methoxycarbonyl-4,5,6,7-tetrahydrobenzothien-2-methylidenyl)-5-amino-2-indolinone
3-(3-vinyl-4,5,6,7-tetrahydrobenzothien-2-methylidenyl)-5-amino-2-indolinone
3-(3-carboxy-4,5,6,7-tetrahydrobenzothien-2-methylidenyl)-5-amino-2-indolinone
3-(3-ethoxycarbonyl-4,5,6,7-tetrahydrobenzothien-2-methylidenyl)-5-amino-2-indolinone
3-[3-(3-dimethylamino-n-propoxycarbonyl)-4,5,6,7-tetrahydrobenzothien-2-methylidenyl]-5-amino-2-indolinone
3-[3-(2-diethylaminoethoxycarbonyl)-4,5,6,7-tetrahydrobenzothien-2-methylidenyl]-5-amino-2-indolinone
3-[3-(2-methylaminoethyl)-4,5,6,7-tetrahydrobenzothien-2-methylidenyl]-5-amino-2-indolinone
3-(3-cyclopropylmethoxy-4,5,6,7-tetrahydrobenzothien-2-methylidenyl)-5-amino-2-indolinone
3-(4,5,6,7-tetrahydrobenzothiazol-2-methylidenyl)-5-amino-2-indolinone
3-(4-methyl-4,5,6,7-tetrahydroindol-2-methylidenyl)-5-amino-2-indolinone
3-(4,4-dimethyl-4,5,6,7-tetrahydroindol-2-methylidenyl)-5-amino-2-indolinone
3-(4-ethyl-4,5,6,7-tetrahydroindol-2-methylidenyl)-5-amino-2-indolinone
3-(4-phenyl-4,5,6,7-tetrahydroindol-2-methylidenyl)-5-amino-2-indolinone
3-(3-ethyl-4,5,6,7-tetrahydroindol-2-methylidenyl)-5-amino-2-indolinone
3-(3-isopropyl-4,5,6,7-tetrahydroindol-2-methylidenyl)-5-amino-2-indolinone
3-(4,5,6,7-tetrahydroindol-3-methylidenyl)-5-amino-2-indolinone
3-(4-isopropyl-4,5,6,7-tetrahydroindol-2-methylidenyl)-5-amino-2-indolinone
3-(4-carboxymethyl-4,5,6,7-tetrahydroindol-2-methylidenyl)-5-amino-2-indolinone -continued

| | |
|---|---|
| 3-(3-methyl-4,5,6,7-tetrahydroinden-2-methylidenyl)-5-bromo-2-indolinone | |
| 3-(4,5,6,7-tetrahydroinden-2-methylidenyl)-5-bromo-2-indolinone | |
| 3-(3-methyl-4,5,6,7-tetrahydrobenzofuran-2-methylidenyl)-5-bromo-2-indolinone | |
| 5-amino-2-indolinone | X |
| 5-bromo-2-indolinone | X |
| 5-chloro-2-indolinone | X |
| 4,6-dimethyl-2-indolinone | X |
| 5,6-dimethoxy-2-indolinone | X |
| 2-indolinone | X |
| 4-methyl-2-indolinone | X |
| 5,7-dibromo-2-indolinone | X |
| 7-bromo-5-chloro-2-indolinone | X |
| 5-fluoro-2-indolinone | X |
| 5-nitro-2-indolinone | X |
| 5-iodo-2-indolinone | X |
| 6-chloro-7-methyl-2-indolinone | X |
| 5-methyl-2-indolinone | X |
| 5-bromo-4-methyl-2-indolinone | X |
| 7-fluoro-2-indolinone | X |
| 6-fluoro-2-indolinone | X |
| 6-(2-carboxyethyl)-4-methyl-2-indolinone | X |
| 6-aminosulfonyl-2-indolinone | X |
| 5-methylaminosulfonyl-2-indolinone | X |
| 5-[4-(trifluoromethyl)phenylaminosulfonyl]-2-indolinon | X |
| 5-(morpholin-4-sulfonyl)-2-indolinone | X |
| 6-trifluoromethyl-2-indolinone | X |
| 5-(2-chloroethyl)-2-indolinone | X |
| 5-methoxycarbonyl-2-indolinone | X |
| 5-carboxy-2-indolinone | X |
| 5-(2-carboxyethyl)-2-indolinone | X |
| 5-iodo-4-methyl-2-indolinone | X |
| 5,7-dibromo-4-methyl-2-indolinone | X |
| 5-n-butyl-2-indolinone | X |
| 5-ethyl-2-indolinone | X |
| 5-(2-morpholin-4-ethyl)-2-indolinone | X |
| 5-(4-methoxycarbonylbenzamido)-2-indolinone | X |
| 5-(4-carboxybenzamido)-2-indolinone | X |
| 5-methoxy-2-indolinone | X |
| 5-trifluoromethyl-2-indolinone | X |
| 5-(piperidin-1-acetyl)-2-indolinone | X |
| 5-(2-piperidin-1-ethyl)-2-indolinone | X |
| 5-(2-pyrrolidin-1-ethyl)-2-indolinone | X |
| 3-(3-methyl-4,5,6,7-tetrahydroinden-2-methylidenyl)-5-amino-2-indolinone | |
| 3-(4,5,6,7-tetrahydroinden-2-methylidenyl)-5-amino-2-indolinone | |
| 3-(3-methyl-4,5,6,7-tetrahydrobenzofuran-2-methylidenyl)-5-amino-2-indolinone | |
| 3-(3-ethoxycarbonyl-4,5,6,7-tetrahydrobenzofuran-2-methylidenyl)-5-amino-2-indolinone | |

EXAMPLES

The examples below are non-limiting and are merely representative of various aspects and features of the present invention. The examples describe methods for synthesizing compounds of the invention and methods for measuring an effect of a compound on the function of protein tyrosine kinases.

Example 1

PROCEDURES FOR SYNTHESIZING THE SUBSTITUTED INDOLINONE COMPOUNDS OF THE INVENTION

The compounds of this invention, as well as the precursor 2-indolinones and the acyl compounds, may be readily synthesized using techniques well known in the chemical arts. It will be appreciated by those skilled in the art that other synthetic pathways for forming the compounds of the invention are available and that the following is offered by way of example and not limitation.

A. General synthetic procedure.

The following general methodology may be employed to prepare the compounds of this invention:

The appropriately substituted 2-indolinone, the appropriately substituted acyl compound and piperidine are mixed with ethanol and the mixture is then heated at elevated temperatures for 3 to 5 hours After cooling, the precipitate is filtered, washed with cold ethanol and dried to yield the target compound.

B. 2-oxindoles

The following examples show representative syntheses of several of the 2-oxindole precursors to the compounds of this invention. These 2-oxindoles, as well as the others claimed, will form the claimed compounds by reaction with an appropriately substituted acyl compound under the conditions described above. It is to be understood that the following syntheses are provided by way of example only and are not to be construed as limiting as to synthetic procedure or as to the compounds described.

5-Amino-2-oxindole

5-Nitro-2-oxindole (6.3 g) was hydrogenated in methanol over 10% palladium on carbon to give 3.0 g (60% yield) of the title compound as a white solid.

5-Bromo-2-oxindole

2-Oxindole (1.3 g) in 20 mL acetonitrile was cooled to −10° C. and 2.0 g N-bromosuccinimide was slowly added with stirring.

The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried under vacuum oven afford the title compound.

5-Nitro-2-oxindole

2-Oxindole (6.5 g) was dissolved in 25 mL concentrated sulfuric acid and the mixture maintained at −10 to −15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-nitro-2-oxindole.

5-Iodo-2-oxindole

2-Oxindole (82.9 g) was suspended in 630 mL of acetic acid with mechanical stirring and the mixture cooled to 10° C. in an ice water bath. Solid N-iodosuccinimide (175 g) was added in portions over 10 minutes. After the addition was complete the mixture was stirred for 1.0 hour at 10° C. The suspended solid which had always present became very thick at this time. The solid was collected by vacuum filtration, washed with 100 mL of 50% acetic acid in water and then with 200 mL of water and sucked dry for 20 minutes in the funnel. The product was dried under vacuum to give 93.5 g (36%) of 5-iodo-2-oxindole containing about 5% 2-oxindole by proton NMR.

5-Methyl-2-oxindole

5-Methylisatin (15.0 g) and 60 mL of hydrazine hydrate were heated at 140 to 160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6N hydrochloric acid. After standing at room temperature for 2 days the precipitate was collected by vacuum filtration, washed with water and dried under vacuum to give 6.5 g (47% yield) of 5-methyl-2-oxindole.

5-Bromo-4-methyloxindole and 5,7-Dibromo-4-methyloxindole

4-Methyl-2-oxindole (5 g) in 40 mL of acetonitrile was treated with 7.26 g of N-bromosuccinimide and stirred at room temperature for 4 hours. Thin layer chromatography (ethyl acetate:hexane 1:2, silica gel) showed a mixture of 5-bromo (Rf 0.3) and 5,7-dibromo (Rf 0.5) products. Another 7.26 g of N-bromosuccinimide was added and the mixture stirred for 4 additional hours. The solid was collected by vacuum filtration, washed with 20 mL of acetonitrile and dried to give a 1:1 mixture of mono and dibromo compounds. The filtrate was concentrated and chromatographed on silica gel (ethyl acetate:hexane (1:2)) to give 1.67 g of 5-bromo-4-methyl-2-oxindole as a beige solid. The remaining 1:1 mixture of solids was recrystallized twice from glacial acetic acid to give 3.2 g of 5,7-dibromo-4-methyl-2-oxindole as a light orange solid. The filtrates from this material were chromatographed as above to give 0.6 g of 5-bromo-4-methyl-2-oxindole and 0.5 g of 5,7-dibromo-4-methyl-2-oxindole.

6-Fluoro-2-oxindole

Sodium hydride (2.6 g) and 14.5 g of dimethylmalonate was stirred and heated to 100° C. in 160 mL dimethylsulfoxide for 1.0 hour. The mixture was cooled to room temperature, 7.95 g of 2,5-difluoronitrobenzene were added and mixture stirred for 30 minutes. The mixture was then heated to 100° C. for 1.0 hour, cooled to room temperature and poured into 400 mL of saturated ammonium chloride solution. The mixture was extracted with 200 mL of ethyl acetate and the organic layer washed with brine, dried over anhydrous sodium sulfate and concentrated under vacuum. The residue was crystallized from methanol to give 24.4 g (80% yield) of dimethyl 4-fluoro-2-nitrophenylmalonate as a white solid, Rf 0.2 on thin layer chromatography (ethyl acetate:hexane 1:6, silica gel). The filtrate was concentrated and chromatographed on a column of silica gel (ethyl acetate:hexane 1:8) to give an additional 5.03 g of dimethyl 4-fluoro-2-nitro- phenylmalonate, for a total of 29.5 g (96% yield).

Dimethyl 4-fluoro-2-nitrophenylmalonate (5.0 g) was refluxed in 20 mL of 6N hydrochloric acid for 24 hours. The reaction was cooled and the white solid collected by vacuum filtration, washed with water and dried to give 3.3 g (87% yield) of 4-fluoro-2nitrophenylacetic acid, Rf 0.6 on thin layer chromatography (ethyl acetate:hexane 1:2, silica gel).

4-Fluoro-2-nitrophenylacetatic acid (3.3 g) dissolved in 15 mL of acetic acid was hydrogenated over 0.45 g of 10% palladium on carbon at 60 psi $H_2$ for 2 hours. The catalyst was removed by filtration and washed with 15 mL of methanol. The combined filtrates were concentrated and diluted with water. The precipitate was collected by vacuum filtration, washed with water and dried to give 1.6 g (70% yield) of 6-fluoro-2-oxindole, Rf 0.24 on thin layer chromatography. The filtrate was concentrated to give a purple solid with an NNM spectrum similar to the first crop. Chromatography of the purple solid (ethyl acetate:hexane 1:2, silica gel) gave a second crop of 6-fluoro-2-oxindole as a white solid.

5-Aminosulfonyl-2-oxindole

To a 100 mL flask charged with 27 mL of chlorosulfonic acid as added slowly 13.3 g of 2-oxindole. The reaction temperature was maintained below 30° C. during the addition. After the addition, the reaction mixture was stirred at room temperature for 1.5 hr. heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Methylaminosulfonyl-2-oxindole

A suspension of 3.38 g of 5-chlorosulfonyl-2-oxindole in 10 mL 2M methylamine in tetrahydrofuran was stirred at room temperature for 4 hours during which time a white solid formed. The precipitate was collected by vacuum filtration, washed twice with 5 mL of water and dried under vacuum at 40° C. overnight to give 3.0 g (88% yield) of 5-methylaminosulfonyl-2-oxindole.

5-(4-Trifluoromethylphenylaminosulfonyl)-2-oxindole

A suspension of 2.1 g of 5-chlorosulfonyl-2-oxindole, 1.6 g of 4-trifluoromethylaniline and 1.4 g of pyridine in 20 mL of dichloromethane was stirred at room temperature for 4 hours. The precipitate which formed was collected by vacuum filtration, washed twice with 5 mL of water and dried under vacuum at 40° C. overnight to give 2.4 g of crude product containing some impurities by thin layer chromatography. The crude product was chromatographed on silica gel eluting with ethyl acetate:hexane (1:2) to give 1.2 g (37% yield) of 5-(4-trifluoromethylphenyl-aminosulfonyl)-2-oxindole.

5-(Morpholinosulfonyl)-2-oxindole

A suspension of 2.3 g of 5-chlorosulfonyl-2-oxindole and 2.2 g of morpholine in 50 mL of dichloromethane was stirred at room temperature for 3 hours. The white precipitate was collected by vacuum filtration, washed with ethyl acetate and hexane and dried under vacuum at 40° C. overnight to give 2.1 g (74% yield) of 5-(morpholinosulfonyl)-2-oxindole.

6-Trifluoromethyl-2-oxindole

Dimethylsulfoxide (330 mL) was added to 7.9 g of sodium hydride followed by dropwise addition of 43.6 g diethyloxalate. The mixture was heated to 100° C. for 1.0 hour and cooled to room temperature. 2-Nitro-4-trifluoromethyltoluene (31.3 g) was added, the reaction stirred for 30 minutes at room temperature and then heated to 100° C. for 1 hour. The reaction was cooled and poured into a mixture of saturated aqueous ammonium chloride, ethyl acetate and hexane. The organic layer was washed with saturated ammonium chloride, water and brine, dried, and concentrated to give dimethyl 2-(2-nitro-4-trifluoromethylphenyl)malonate.

The diester was dissolved in a mixture of 6.4 g of lithium chloride and 2.7 mL of water in 100 mL of dimethylsulfoxide and heated to 100° C. for 3 hours. The reaction was cooled and poured into a mixture of ethyl acetate and brine. The organic phase was washed with brine, dried with sodium sulfate, concentrated and chromatographed on silica gel (10% ethyl acetate in hexane). The fractions containing product were evaporated to give 25.7 g of methyl 2-nitro-4-trifluoromethylphenylacetate.

Methyl 2-nitro-4-trifluoromethylphenylacetate (26 mg) was hydrogenated over 10% palladium on carbon and then heated at 100° C. for 3 hours. The catalyst was removed by filtration and the solvent evaporated to give the title compound.

5-(2-Chloroethyl)oxindole

5-Chloroacetyl-2-oxindole (4.18 g) in 30 mL of trifluoroacetic acid in an ice bath was treated with 4.65 g of triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-2-oxindole as a reddish-brown solid.

5-Methoxycarbonyl-2-oxindole

5-Iodo-2-oxindole (17 g) was refluxed with 2 g of palladium diacetate, 18.2 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on silica gel (30% ethyl acetate in hexane). The fractions containing product were concentrated and allowed to stand. The precipitated product was collected by vacuum filtration to give 0.8 g (7%) of the title compound as an off-white solid.

4-Carboxy-2-oxindole

A solution of trimethylsilyldiazomethane in hexane (2M) was added dropwise to a solution of 2.01 g of 2-chloro-3-carboxynitrobenzene in 20 mL methanol at room temperature until no further gas evolution occurred. The excess trimethylsilyldiazo-methane was quenched with acetic acid. The reaction mixture was dried by rotary pump and the residue was further dried in a vacuum oven overnight. The product (2-chloro-3-methoxycarbonylnitrobenzene) was pure enough for the following reaction.

Dimethyl malonate (6.0 mL) was added to an ice-cold suspension of 2.1 g of sodium hydride in 15 mL of DMSO. The reaction mixture was then stirred at 100° C. for 1.0 h and then cooled to room temperature. 2-Chloro-3-methoxycarbonyl-nitrobenzene (2.15 g) was added to the above mixture in one portion and the mixture was heated to 100° C. for 1.5 h. The reaction mixture was then cooled to room temperature and poured into ice water, acidified to pH 5, and extracted with ethyl acetate. The organic layer was washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 mL of 6 N hydrochloric acid overnight. The mixture was concentrated to dryness and refluxed for 2 hours with 1.1 g of tin(II) chloride in 20 mL of ethanol. The mixture was filtered through Celite, concentrated and chromatographed on silica gel (ethyl acetate-:hexane:acetic acid) to give 0.65 g (37% yield) of 4-carboxy-2-oxindole as a white solid.

5-Carboxy-2-oxindole

2-Oxindole (6.7 g) was added to a stirred suspension of 23 g of aluminum chloride in 30 mL of dichloroethane in an ice bath. Chloroacetyl chloride (11.3 g) was slowly added and hydrogen chloride gas was evolved. After ten minutes of stirring, the reaction was warmed at 40 to 50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g of 5-chloroacetyl-2-oxindole was stirred in 90 mL pyridine at 80 to 90° C. for 3 hours then cooled to room temperature. The precipitate was collected by vacuum filtration and washed with 20 mL ethanol. The solid was dissolved in 90 mL 2.5N sodium hydroxide and stirred at 70 to 80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

5-Carboxyethyl-2-oxindole

5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

5-Iodo-4-methyl-2-oxindole

To 2 g of 4-methyl-2-oxindole in 40 mL of glacial acetic acid in an ice bath was added 3.67 g N-iodosuccinimide. The mixture was stirred for 1 hour, diluted with 100 mL 50% acetic acid in water and filtered. The resulting white solid was dried under high vacuum to give 3.27 g (88% yield) of the title compound as an off-white solid.

5-Chloro-4-methyl-2-oxindole

A suspension of 3.0 g of 4-methyl-2-oxindole was stirred in 50 mL of acetonitrile at room temperature while 3.3 g of N-chlorosuccinimide was added in portions. Trifluoroacetic acid (1 mL) was then added. The suspension was stirred at room temperature for 3 days during which time solid was always present. The white solid was collected by vacuum filtration, washed with a small amount of cold acetone and dried overnight in a vacuum oven at 40° C. to give 2.5 g (68%) of 5-chloro-4-methyl-2-oxindole.

5-Butyl-2-oxindole

Triethylsilane (2.3 g) was added to 2 g 4-butanoyl-2-oxindole in 20 mL of trifluoroacetic acid at room temperature and the solution stirred for 3 hours. The reaction was poured into ice water to give a red oil which solidified after standing. The solid was collected by vacuum filtration, washed with water and hexane and dried to give 1.7 g (91% yield) of the title compound as an off-white solid.

5-Ethyl-2-oxindole

To 5-Acetyl-2-oxindole (2 g) in 15 mL of trifluoroacetic acid in an ice bath was slowly added 1.8 g of triethylsilane; the reaction was then stirred at room temperature for 5 hours. One mL of triethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.

5-(Morpholin-4-ethyl)-2-oxindole

5-Chloroethyl-2-oxindole (2.3 g), 1.2 mL of morpholine and 1.2 mL of diisopropylethylamine were heated overnight at 100° C. in 10 mL of dimethylsulfoxide. The mixture ws cooled, poured into water and extacted with ethyl acetate. The organic layer was washed with brine, dried and evaporated. The residue was chromatographed on silica gel (5% methanol in chloroform) to give 0.9 g (31%) of the title compound as a white solid.

5-(4-Methoxycarbonylbenzamido)-2-oxindole

A mixture of 82.0 mg 5-amino-2-oxindole and 131.0 mg 4-methoxycarbonylbenzoyl chloride in pyridine was stirred at room temperature for 3 hr and poured into ice water. The precipitate was filtered, washed with water and dried in a vacuum oven to give 138.0 mg of 5-(4-methoxycarbonylbenzamido)-2-oxindole (81% yield).

5-(4-Carboxybenzamido)-2-oxindole 5-(4-Methoxycarbonylbenzamido)-2-oxindole (0.9 g) and 0.4 g of sodium hydroxide in 25 mL of methanol were refluxed for 3 hours. The mixture was concentrated, water added, and the mixture acidified with 6N hydrochloric acid. The precipitate was collected by vacuum filtration to give 0.75 g (87%) of the title compound as a white solid.

5-Methoxy-2-oxindole

Chloral hydrate (9.6 g) was dissolved in 200 mL of water containing 83 g of sodium sulfate. The solution was warmed to 60° C., a solution of 11.4 g of hydroxylamine hydrochloride in 50 mL of water was added and the mixture was held at 60° C. In a separate flask, 6.4 g of 4-anisidine and 4.3 mL of concentrated hydrochloric acid in 80 mL of water was warmed to 80° C. The first solution was added to the second and the mixture refluxed for 2 minutes after which it was cooled slowly to room temperature and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL of water was warmed to 60° C. and 8.6 g of N-(2-hydroximinoacetyl)anisidine was added in one portion. The stirred mixture was heated to 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid. 5-Methoxyisatin (5.0 g) and 30 mL of hydrazine hydrate were heated to reflux for 15 minutes. The reaction mixture was cooled to room temperature and 50 mL of water was added. The mixture was extracted 3 times with 25 mL of ethyl acetate each time, the organic layers combined, dried over anhydrous sodium sulfate and concentrated to give a yellow solid.

The solid was stirred in ethyl acetate and 1.1 g of insoluble material was removed by vacuum filtration and saved. This material proved to be 2-hydrazinocarbonylmethyl-4-anisidine. The filtrate was concentrated and chromatographed on silica gel eluting with ethyl acetate:hexane (1:1) to give 0.7 g of 5-methoxy-2-oxindole as a yellow solid. The 1.1 g of 2-hydrazinocarbonylmethyl-4-anisidine was refluxed for 1 hour in 20 mL of 1 N sodium hydroxide. The mixture was cooled, acidified to pH 2 with concentrated hydrochloric acid and extracted 3 times with 25 mL of ethyl acetate each time. The organic extracts were combined, washed with brine, dried over anhydrous sodium sulfate and concentrated to give 0.8 g of 5-methoxy-2-oxindole as a yellow solid. The combined yield was 1.5 g or 33%.

7-Azaoxindole 3,3-Dibromo-7-azaoxindole (2.9 g) was dissolved in a mixture of 20 mL of acetic acid and 30 mL of acetonitrile. To the solution was added 6.5 g of zinc dust. The mixture was stirred for 2 hrs at room temperature. The solid was filtered from the mixture and the solvent evaporated. The residue was slurried with ethyl acetate. The ethyl acetate solution containing insoluble solid was passed through a short column of silica gel. The collected ethyl acetate solution was evaporated and the residue dried under vacuum to give 1.8 g (yield 91%) of 7-azaoxindole acetic acid salt.

5-Dimethylaminosulfonyl-2-oxindole

A suspension of 2.3 g 5-chlorosulfonyl-2-oxindole in 10 mL 2M dimethylamine in methanol was stirred at room temperature for 4 hours at which time a white solid formed. The precipitate was collected by vacuum filtration, washed with 5 mL of 1 N sodium hydroxide and 5 mL of 1 N hydrochloric acid and dried under vacuum at 40° C. overnight to give 1.9 g (79% yield) of 5-dimethylaminosulfonyl-2-oxindole.

6-Phenyl-2-oxindole

Dimethyl malonate (10 mL) in 25 mL of dimethylsulfoxide was added dropwise to 3.5 g sodium hydride suspended in 25 mL dimethylsulfoxide and the mixture heated at 100° C. for 10 minutes. The mixture was cooled to room temperature and 4.7 g of 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give, as a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g of 3-nitrobiphenyl-4-acetic acid as a cream colored solid.

Iron powder (2.6 g) was added all at once to 4.5 g of 3-nitrobiphenyl-4-acetic acid in 40 mL of acetic acid. The mixture was refluxed for 2 hours, concentrated to dryness and taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

6-(2-Methoxyphenyl)-2-oxindole

Tetrakis(triphenylphosphine)palladium (1 g) was added to a mixture of 5 g 2-methoxyphenylboronic acid, 6.6 g 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, then dried, and concentrated to give a dark green oil which solidified on standing, crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was heated at 100° C. for 15 minutes and cooled to room temperature. Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated sodium chloride solution and extracted twice with ethyl acetate. The extracts were combined, washed with saturated ammonium chloride, water and brine, dried over anhydrous sodium sulfate and concentrated to give crude dimethyl 2'-methoxy-3-nitrobiphenyl-4-malonate as a yellow oil.

Crude dimethyl 2'-methoxy-3-nitrobiphenyl-4-malonate was heated at 100° C. in 50 mL of 6 N hydrochloric acid for 24 hours and cooled. The precipitate was collected by filtration, washed with water and hexane, and dried to give 9.8 of 2'-methoxy-2-nitrobiphenyl-4acetic acid as a light tan solid.

Iron powder (5 g) was added in one portion to 9.8 g of 2'-methoxy-3-nitrobiphenyl-4-acetic acid in 50 mL of glacial acetic acid was heated to 100° C. for 3 hours. The reaction mixture was concentrated to dryness, sonicated in ethyl acetate and filtered to remove the insolubles. The filtrate was washed twice with 1N hydrochloric acid, water and then brine, dried over anhydrous sodium sulfate and concentrated. The residue was chromatographed on silica gel in ethyl acetate:hexane (1:2) to give 5.4 g of 6-(2-methoxyphenyl)-2-oxindole as a rose colored solid.

6-(3-Methoxyphenyl)-2-oxindole

Tetrakis(triphenylphosphine)palladium (0.8 g) was added to a mixture of 5 g 3-methoxyphenylboronic acid, 5 g 5-bromo-2-fluoronitrobenzene and 11 mL of 2 M sodium carbonate solution in 100 mL of toluene. The mixture was refluxed for 2 hours, diluted with water and extracted with ethyl acetate. The ethyl acetate was washed with saturated sodium bicarbonate and brine and then dried and concentrated to give an oily solid. The solid was chromatographed on silica gel (ethyl acetate:hexane (1:6)) to give 4.3 g (77% yield) of 4-fluoro-3'-methoxy-3-nitrobiphenyl.

Dimethyl malonate (9.7 mL) was added dropwise to 2.0 g sodium hydride suspended in 50 mL dimethylsulfoxide. The mixture was heated to 100° C. for 35 minutes and cooled to room temperature. 4-Fluoro-2'-methoxy-3-nitrobiphenyl (4.2 g) in 50 mL dimethylsulfoxide was added and the mixture was heated at 100° C. for 1 hour. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude dimethyl 3'-methoxy-3-nitro-biphenyl-4-malonate was heated at 110° C. in 45 mL 6N hydrochloric acid for 4 days and then cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid (33:66:1) to give 3.0 g of 6-(3-methoxypheny)-2-oxindole as a pink solid.

6-(4-Methoxyphenyl)-2-oxindole

Tetrakis(triphenylphosphine)palladium (1 g) was added to a mixture of 5 g of 4methoxyphenylboronic acid, 6.6 g of 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, dried, and concentrated to give a brown oily solid. The solid was chromatographed on silica gel (5% ethyl acetate in hexane) to give crude 4-fluoro-4'-methoxy-3-nitrobiphenyl as a pale yellow solid.

Dimethyl malonate (10 mL) was added dropwise to 2.0 g of sodium hydride suspended in 60 mL of dimethylsulfoxide. The mixture was heated to 100° C. for 10 minutes and cooled to room temperature. Crude 4-fluoro-2'-methoxy-3-nitrobiphenyl (5.2 g) in 50 mL dimethylsulfoxide was added and the mixture was heated at 100° C. for 2 hours. The reaction mixture was cooled and quenched with 300 mL of saturated sodium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4malonate as a yellow oil.

Crude dimethyl 4'-methoxy-3-nitro-biphenyl-4-malonate was heated at 100° C. in 60 mL of 6 N hydrochloric acid for 15 hours and cooled. The precipitate was collected by filtration, washed with water and hexane, and dried to give 7.2 g of crude 4'-methoxy-3-nitrobiphenyl-4-acetic acid as a light tan solid.

Iron powder (3.6 g) was added in one portion to 7.2 g of 4'-methoxy-3-nitrobiphenyl-4-acetic acid in 50 mL of glacial acetic acid and heated at 100° C. overnight. The reaction mixture was concentrated to dryness, sonicated in ethyl acetate and filtered to remove the insolubles. The filtrate was washed twice with 1 N hydrochloric acid and brine, dried over anhydrous sodium sulfate and concentrated to give 2.7 g of 6-(4-methoxyphenyl)-2-oxindole as a rose colored solid.

6-(3-Ethoxyphenyl)-2-oxindole

Tetrakis(triphenylphosphine)palladium (0.8 g) was added to a mixture of 4.2 g of 3-ethoxyphenylboronic acid, 5.0 g of 5-bromo-2-fluoronitrobenzene and 22 mL of 2 M sodium carbonate solution in 50 mL of toluene and 50 mL of ethanol. The mixture was refluxed for 2 hours, concentrated, water was added and the mixture was extracted twice with ethyl acetate. The ethyl acetate layer was washed with water and brine, then dried, and concentrated. The residue was chromatographed on silica gel (5% ethyl acetate in hexane) to give 5.3 g (90% yield) of crude 4-fluoro-3'-ethoxy-3-nitrobiphenyl as a yellow oil.

Dimethyl malonate (11.4 mL) was added dropwise to 4.0 g sodium hydride suspended in 20 mL dimethylsulfoxide. The mixture was heated to 100° C. for 10 minutes and then cooled to room temperature. Crude 4-fluoro-3'-ethoxy-3-nitrobiphenyl (5.3 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with water and brine and then dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate was heated at 100° C. in 60 mL of 6 N hydrochloric acid for 4 days and then cooled. The precipitate was collected by filtration, washed with water and hexane, and dried to give 4.7 g of crude 3'-ethoxy-3-nitrobiphenyl-4-acetic acid as a light tan solid.

Iron powder (2.4 g) was added in one portion to 4.6 g of 3'-ethoxy-3-nitrobiphenyl-4-acetic acid in 40 mL of glacial acetic acid and refluxed for 2 hours. The reaction mixture was concentrated to dryness, treated repeatedly with ethyl acetate and filtered to remove the insolubles. The filtrate was washed twice with 1 N hydrochloric acid and brine and then dried over anhydrous sodium sulfate and concentrated to give 3.5 g (91% yield) of 6-(3-ethoxyphenyl)-2-oxindole as a light brown solid.

6-Bromo-2-oxindole

Dimethyl malonate (13 mL) was added dropwise to 2.7 g sodium hydride suspended in 20 mL dimethylsulfoxide. The mixture was heated to 100° C. for 10 minutes and then cooled to room temperature. 5-Bromo-2-fluoronitrobenzene (5.0 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate as a pale yellow oil.

Crude dimethyl 4-bromo-2-nitrophenylmalonate was heated at 110° C. in 40 mL of 6 N hydrochloric acid for 24 hours and then cooled. The precipitate was collected by filtration, washed with water and dried to give 5.3 g (89% yield) of 4-bromo-2-nitrophenylacetic acid as an off white solid.

4-Bromo-2-nitrophenylacetic acid (0.26 g), 0.26 g zinc powder and 3 mL 50% sulfuric acid in 5 mL of ethanol were heated at 100° C. overnight. The reaction mixture was filtered, diluted with a little acetic acid, concentrated to remove ethanol, diluted with water and extracted twice with ethyl acetate. The combined extracts were washed with brine, dried over anhydrous sodium sulfate and concentrated to give 0.19 g (90% yield) of 6-bromo-2-oxindole as a yellow solid.

5-Acetyl-2-oxindole

2-Oxindole (3 g) was suspended in 1,2-dichloroethane and 3.2 mL acetyl chloride were slowly added. The resulting suspension was heated to 50° C. for 5 hours, cooled, and poured into water. The resulting precipitate was collected by vacuum filtration, washed copiously with water and dried under vacuum to give 2.9 g (73% yield) of the title compound as a brown solid.

5-Butanoyl-2-oxindole

To 15 g aluminum chloride suspended in 30 mL 1,2-dichloro-ethane in an ice bath was added 7.5 g of 2-oxindole and then 12 g of butanoyl chloride. The resulting suspension was heated to 50° C. overnight. The mixture was poured into ice water and extracted 3 times with ethyl acetate. The combined ethyl acetate layers were washed with brine, dried over sodium sulfate, and concentrated to dryness to give a brown solid. The solid was chromatographed on silica gel (50% ethyl acetate in hexane) to give 3 g (25%) of the title compound as a yellow solid.

5-Cyanoethyl-2-oxindole

Potassium cyanide (2.0 g) was added to 15 mL of dimethyl-sulfoxide and heated to 90° C. 5-Chloroethyl-2-oxindole (3.0 g) dissolved in 5 mL dimethyl sulfoxide was added slowly with stirring, and the reaction heated to 150° C. for 2 hours. The mixture was cooled, poured into ice water and the precipitate collected by vacuum filtration, washed with water, dried and then chromatographed on silica gel (5% methanol in chloroform) to give 1.2 g (42% yield) of the title compound.

6-Morpholin-4-yl)-2-oxindole

6-Amino-2-oxindole (2.2 g), 4.0 g 2,2'-dibromoethyl ether and 7.9 g sodium carbonate were refluxed in 20 mL ethanol overnight, concentrated and diluted with 50 mL of water. The mixture was extracted three times with 50 mL of ethyl acetate and the organic extracts combined, washed with 20 mL of brine, dried over anhydrous sodium sulfate and concentrated to dryness. The solid was chromatographed on a column of silica gel (ethyl acetate:hexane (1:1) containing 0.7% acetic acid) to give 1.2 g (37% yield) of the title compound as a beige solid.

6-(3-Trifluoroacetylphenyl)-2-oxindole

3-Aminophenylboronic acid (3.9 g), 5 g 5-bromo-2-fluoronitrobenzene, 0.8 g tetrakis(triphenylphosphine) palladium and 23 mL of 2 M sodium bicarbonate solution in 50 mL of toluene were refluxed under nitrogen for 2.5 hours. The reaction mixture was poured into 200 mL of ice water and the mixture extracted three times with 50 mL of ethyl acetate. The combined organic layers were washed with 50 mL of water and 20 mL of brine, dried over anhydrous sodium sulfate and concentrated to give 9.7 g (92% yield) of 2-fluoro-5-(3-aminophenyl)nitrobenzene as a dark brown oil.

Trifluoroacetic anhydride (5.4 mL) was slowly added to a stirred solution of 9.7 g 2-fluoro-5-(3-aminophenyl)-nitrobenzene and 5.3 mL of triethylamine in 50 mL of dichloromethane at 0° C. and the mixture was stirred for an additional 20 minutes. The mixture was concentrated and the residue chromatographed on a column of silica gel (10% ethyl acetate in hexane) to give 8.6 g (65% yield) of 2-fluoro-5-(3-trifluoroacetamidophenyl)-nitrobenzene as a pale orange oil which solidified on standing.

Dimethyl malonate (9.6 mL) was added dropwise to a stirred suspension of 3.2 g of 60% sodium hydride in mineral oil in 40 mL anhydrous dimethylsulfoxide under nitrogen. The mixture was stirred for 10 minutes and 2-fluoro-5-(3-trifluoroacetamidophenyl)nitrobenzene in 20 mL dimethylsulfoxide was added. The resulting dark red mixture was heated to 100° C. for 2 hours. The reaction was quenched by pouring into 100 mL of saturated ammnonium chloride solution and extracted twice with 50 mL of ethyl acetate. The organic phase was washed with 50 mL each of saturated ammonium chloride solution, water, and brine, dried over anhydrous sodium sulfate and concentrated to a yellow oil. The oil was chromatographed on a column of silica gel (ethyl acetate:hexane (1:4)) to give 4.4 g (50% yield) of dimethyl 2-[2-nitro-4-(3-trifluoroacetamidophenyl)phenyl]malonate as a pale yellow solid.

Dimethyl 2-[2-nitro-4-(3-trifluoroacetamidophenyl) phenyl]malonate (4.4 g) was refluxed overnight in 50 mL 6 N hydrochloric acid. The reaction mixture was cooled to room temperature and the solids were collected by vacuum filtration, washed with water, and dried under vacuum to give 2.7 g (73% yield) of 2-[2-nitro-4-(3-trifluoroacetamidophenyl)phenyl]acetic acid.

2-[2-Nitro-4-(3-trifluoroacetamidophenyl)phenyl]acetic acid (100 mg) and 50 mg iron powder in 3 mL acetic acid was heated at 100° C. for 2 hours. The reaction mixture was concentrated and the residue sonicated in 5 mL ethyl acetate. The insoluble solids were removed by vacuum filtration and the filtrate washed with 1 N hydrochloric acid, water and brine, dried over anhydrous sodium sulfate and concentrated to give 10 mg (14% yield) of the title compound as a rose-colored solid.

5-Acetyl-2-oxindole

2-Oxindole (3 g) was suspended in 1,2-dichloroethane and slowly treated with 3.2 mL of acetyl chloride. The resulting suspension was heated to 50° C. for 5 hours, cooled, and poured into water. The resulting precipitate was collected by vacuum filtration washed copiously with water and dried under vacuum to give 2.9 g (73% yield) of 5-acetyl-2-oxindole as a brown solid.

$^1$HNMR (360 MHz, DMSO-d6) δ 10.75 (s, br, NH), 7.83 (d, J=8Hz, 1H), 7.78 (s, 1H, H-4) 6.88 (d, J=8Hz, 1H), .3.53 (s, 2H, CH$_2$), 2.49 (s, 3H, CH$_3$).

6-Hydroxy-2-oxindole

The solution of 3.26 of 6-methoxy-2-oxindole in 60 mL of dischloromethane was coold at −3° C. and 10 mL of 1 M boron tribromide solution in dichloromethane was added dropwise. The reaction mixture was stirred in ice-bath for 1 hour, room temperature for 1 hour, poured into ice water, and extracted with ethyl acetate. The organic layer was washed with water and brine, dried over anhydrous sodium sulfate, concentrated, and dried in a vacuum oven overnight to give 2.56 g of the 6-hydroxy-2-oxindole (86% yield), $^1$HNMR (360 MHz, DMSO-d6) δ 10.13 (s, 1H, NH-1), 9.22 (s, 1H, OH 6.93 (d, J=8Hz, 1H, H-4), 6.27–6.31 (M, 2H, H-5, 7) and 3.29 (s, 2H, H-3). MS m/z 150 [M+1]$^+$.

4-Carboxy-2-oxindole

A solution of trimethylsilyldiazomethane in hexane (2 M) was added dropwise to the solution of 2.01 g of 2-chloro-3-carboxynitrobenzene in 20 mL of methanol at room temperature until no gas evolution occurred. The excess trimethylsilyldiazomethane was quenched with acetic acid. The reaction mixture was dried by rotary pump and the residue was further dried in oven for overnight. The product (2-chloro-3-methoxycarbonyl-nitrobenzene) was pure enough for the following reaction.

Dimethyl malonate (6.0 mL) was added dropwise to the ice-cold suspension of 2.1 g of sodium hydride in 16 mL of DMSO. The reaction mixture was then stirred at 100° C. for 1 hour and cooled to room temperature. 2-chloro-3-methoxycarbonyl-nitrobenzene (2.15 g) was added to the above mixture in one portion and the mixture was heated to 100° C. for 1.5 hours. The reaction mixture was then cooled to room temperature and poured into ice water, acidified to pH of 5, and extracted with ethyl acetate. The organic layer was then washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 mL of 6 N hydrochloric acid overnight. The mixture was concentrated to dryness and refluxed for 2 hours with 1.1 g of tin (11) chloride in 20 mL of ethanol. The mixture was filtered through Celite, concentrated and chromatographed on silica gel in ethyl acetate-:hexane;acetic acid to give 0.65 g (37% yield) of 4-carboxy-2-oxindole as a while solid.

$^1$HNMR (360 MHz, DMSO-d6) δ 12.96 (s, br, 1H, COOH), 10.74 (s, br, 1H, NH) 7.53 (d, J=8Hz, 1H), 7.39 (t, J=8Hz, 1H, H-6), 7.12 (d, J=8Hz, 1H, H-7) 3.67 (s, 2H, H-3).

7-Bromo-5methyl-2-oxindole

5-Methyl-2-oxindole (147 mg) and 214 mg of N-bromosuccinimide in 5 mL of acetonitrate washed with acetonitrilee and dried to give 150 mg (66% yield) of 7-bromo-5-methyl-2-oxindole as a beige solid.

$^1$HNMR (360 MHz, DMSO-d6) δ 10.47 (s, br, 1H, NH-1), 7.16 (s, 1H 7.0 (s, 1H), 3.55 (s, 2H, CH$_2$), 2.22 (s, 2H, CH$_3$).

BIOLOGICAL EVALUATION

It will be appreciated that, in any given series of compounds, a spectrum of biological activity will be afforded.

In its most preferred embodiments, this invention relates to novel 3-(cyclohexanoheteroarylidenyl)-2-indolinones demonstrating the ability to modulate RTK and CTK activity. The following assays are employed to select those compounds demonstrating the optimal degree of the desired activity.

As used herein, the phrase "optimal degree of the desired activity" refers to the lowest IC$_{50}$, defined elsewhere herein, against a PTK related to a particular disorder so as to provide an organism, preferably a human, with a therapeutically effective amount of a compound of this invention at the lowest possible dosage.

The in vitro assays in the following Examples may be used to determine the level of activity and effect of the different compounds of the present invention on one or more of the RTKs. Similar assays can be designed along the same lines for any PTK using techniques well known in the art.

The cellular/catalytic assays described herein are performed in an ELISA format. The general procedure is a follows: a compound is introduced to cells expressing the test kinase, either naturally or recombinantly, for some period of time after which, if the test kinase is a receptor, a ligand known to activate the receptor's activity is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound.

The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for some period of time after which, if the test kinase is a receptor, a ligand known to activate the receptor's activity is added. After incubation at least overnight, a DNA labeling reagent such as Bromodeoxy-uridine (BrdU) or 3H-thymidine is added. The amount of labeled DNA is detected with either an anti-BrdU antibody or by measuring radioactivity and is compared to control cells not contacted with a test compound.

Enzyme linked immunosorbent assays (ELISA) may be used to detect and measure the presence of PTK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific RTK. For example, the preferred protocols for conducting the ELISA experiments for specific RTKs is provided below. Adaptation of these protocols for determining a compound's activity for other members of the RTK family, as well as for CTKs, is well within the scope of knowledge of those skilled in the art.

Example 2

FLK-1

An ELISA assay is conducted to measure the kinase activity of the FLK-1 receptor and more specifically, the inhibition or activation of TK activity on the FLK-1 receptor. Specifically, the following assay can be conducted to measure kinase activity of the FLK-1 receptor in cells genetically engineered to express Flk-1.

Materials And Methods

Materials. The following reagents and supplies are used:

a. Corning 96-well ELISA plates (Corning Catalog No. 25805-96);

b. Cappel goat anti-rabbit IgG (catalog no. 55641);

c. PBS (Gibco Catalog No. 450-1300EB);

d. TBSW Buffer (50 mM Tris (pH 7.2), 150 mM NaCl and 0.1% Tween-20);

e. Ethanolamine stock (10% ethanolamine (pH 7.0), stored at 4° C.);

f. HNTG buffer (20 mM HEPES buffer (pH 7.5), 150 mM NaCl, 0.2% Triton X-100, and 10% glycerol);

g. EDTA (0.5 M (pH 7.0) as a 100×stock);

h. Sodium orthovanadate (0.5 M as a 100×stock);

i. Sodium pyrophosphate (0.2 M as a 100×stock);

j. NUNC 96 well V bottom polypropylene plates (Applied Scientific Catalog No. AS-72092);

k. NIH3T3 C7#3 Cells (FLK-1 expressing cells);

l. DMEM with 1× high glucose L-Glutamine (catalog No. 11965-050);

m. FBS, Gibco (catalog no. 16000-028);

n. L-glutamine, Gibco (catalog no. 25030-016);

o. VEGF, PeproTech, Inc. (catalog no. 100-20)(kept as 1 g/100 $\mu$L stock in Milli-Q dH$_2$O and stored at −20° C.;

p. Affinity purified anti-FLK-1 antiserum;

q. UB40 monoclonal antibody specific for phosphotyrosine (see, Fendley, et al., 1990, *Cancer Research* 50:1550–1558);

r. EIA grade Goat anti-mouse IgG-POD (BioRad catalog no. 172-1011);

s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/mL ABTS (Sigma catalog no. A-1888)), solution should be stored in dark at 4° C. until ready for use;

t. H$_2$O$_2$ (30% solution) (Fisher catalog no. H325);

u. ABTS/H$_2$O$_2$ (15 mL ABTS solution, 2 $\mu$L H$_2$O$_2$) prepared 5 minutes before use and left at room temperature;

v. 0.2 M HCl stock in H$_2$O;

w. dimethylsulfoxide (100%) (Sigma Catalog No. D-8418); and y. Trypsin-EDTA (Gibco BRL Catalog No. 25200-049).

Protocol. The following protocol can be used for conducting the assay:

1. Coat Corning 96-well ELISA plates with 1.0 $\mu$g per well Cappel Anti-rabbit IgG antibody in 0.1 M Na$_2$CO$_3$ pH 9.6. Bring final volume to 150 $\mu$L per well. Coat plates overnight at 4° C. Plates can be kept up to two weeks when stored at 4° C.

2. Grow cells in Growth media(DMEM, supplemented with 2.0 mM L-Glutamine, 10% FBS) in suitable culture dishes until confluent at 37° C., 5% CO$_2$.

3. Harvest cells by trypsinization and seed in Corning 25850 polystyrene 96-well round bottom cell plates, 25.000 cells/well in 200 $\mu$L of growth media.

4. Grow cells at least one day at 37° C., 5% CO$_2$.

5. Wash cells with D-PBS 1×.

6. Add 200 $\mu$L/well of starvation media (DMEM, 2.0 mM 1-Glutamine, 0.1% FBS). Incubate overnight at 37° C., 5% CO$_2$.

7. Dilute Compounds 1:20 in polypropylene 96 well plates using starvation media. Dilute dimethylsulfoxide 1:20 for use in control wells.

8. Remove starvation media from 96 well cell culture plates and add 162 $\mu$L of fresh starvation media to each well.

9. Add 18 μL of 1:20 diluted Compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.

10. Remove unbound antibody from ELISA plates by inverting plate to remove liquid. Wash 3 times with TBSW+0.5% ethanolamine, pH 7.0. Pat the plate on a paper towel to remove excess liquid and bubbles.

11. Block plates with TBSW+0.5% Ethanolamine, pH 7.0, 150 μL per well. Incubate plate thirty minutes while shaking on a microtiter plate shaker.

12. Wash plate 3 times as described in step 10.

13. Add 0.5 μg/well affinity purified anti-FLU-1 polyclonal rabbit antiserum. Bring final volume to 150 μL/well with TBSW+0.5% ethanolamine pH 7.0. Incubate plate for thirty minutes while shaking.

14. Add 180 μL starvation medium to the cells and stimulate cells with 20 μL/well 10.0 mM sodium ortho vanadate and 500 ng/mL VEGF (resulting in a final concentration of 1.0 mM sodium ortho vanadate and 50 ng/mL VEGF per well) for eight minutes at 37° C., 5% $CO_2$. Negative control wells receive only starvation medium.

15. After eight minutes, media should be removed from the cells and washed one time with 200 μL/well PBS.

16. Lyse cells in 150 μL/well HNTG while shaking at room temperature for five minutes. HNTG formulation includes sodium ortho vanadate, sodium pyrophosphate and EDTA.

17. Wash ELISA plate three times as described in step 10.

18. Transfer cell lysates from the cell plate to ELISA plate and incubate while shaking for two hours. To transfer cell lysate pipette up and down while scrapping the wells.

19. Wash plate three times as described in step 10.

20. Incubate ELISA plate with 0.02 μg/well UB40 in TBSW+05% ethanolamine. Bring final volume to 150 μL/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW+0.5% ethanolamine, pH 7.0. Bring final volume to 150 μL/well. Incubate while shaking for thirty minutes.

23. Wash plate as described in step 10.

24. Add 100 μL of $ABTS/H_2O_2$ solution to well. Incubate ten minutes while shaking.

25. Add 100 μL of 0.2 M HCl for 0.1 M HCl final to stop the color development reaction. Shake 1 minute at room temperature. Remove bubbles with slow stream of air and read the ELISA plate in an ELISA plate reader at 410 nm.

The $IC_{50}$ values were measured for several of the compounds of the invention. These values are shown in Table 3.

TABLE 3

| Compound | $IC_{50}$ (μM) |
| --- | --- |
| 6-hydroxy-3-(4,5,6,7-tetrahydro-1H-indol-2-ylmethylene)-1, 3-dihydro-indol-2-one | 17.1 |
| 6-(3-methoxyphenyl)-3-(4,5,6,7-tetrahydro-1H-indol-2-ylmethylene)-1, 3-dihydro-indol-2-one | >20 |
| 7-bromo-5-methyl-3-(4,5,6,7-tetrahydro-1H-indol-2-ylmethylene)-1,3-dihydro-indol-2-one | >2.5 |
| 6-bromo-3-(3-methyl-4,5,6,7-tetrahydro-1H-indol-2-ylmethylene)-1,3-dihydro-indol-2-one | 2.19 |
| 6-(3-methoxyphenyl)-3-(3-methyl-4,5,6,7-tetrahydro-1H-indol-2-ylmethylene)-1,3-dihydro-indol-2-one | >5 |

Example 3

HER-2 ELISA

Assay 1: EGF Receptor-HER2 Chimeric Receptor Assay In Whole Cells

HER2 kinase activity in whole EGFR-NIH3T3 cells are measured as described below:

Materials and Reagents. The following materials and reagents can be used to conduct the assay:

a. EGF: stock concentration: 16.5 ILM; EGF 201, TOYOBO, Co., Ltd. Japan.

b. 05-101 (UBI) (a monoclonal antibody recognizing an EGFR extracellular domain).

c. Anti-phosphotyrosine antibody (anti-Ptyr) (polyclonal) (see, Fendley, et al., supra).

d. Detection antibody: Goat anti-rabbit IgG horse radish peroxidase conjugate, TAGO, Inc., Burlingame, Calif.

e. TBST buffer:

| Tris-HCl, pH 7.2 | 50 mM |
| --- | --- |
| NaCl | 150 mM |
| Triton X-100 | 0.1 | f. HNTG 5×stock:

| HEPES | 0.1M |
| --- | --- |
| NaCl | 0.75M |
| Glycerol | 50% |
| Triton X-100 | 1.0% | g. ABTS stock:

| Citric Acid | 100 mM |
| --- | --- |
| $Na_2HPO_4$ | 250 mM |
| HCl, conc. | 0.5 pM |
| ABTS* | 0.5 mg/mL |

*(2,2'-azinobis(3-ethylbenzthiazolinesulfonic acid)). Keep solution in dark at 4° C. until use.

h. Stock reagents of:

| EDTA 100 mM | pH 7.0 |
| --- | --- |
| $Na_3VO_4$ | 0.5M |
| $Na_4(P_2O_7)$ | 0.2M |

Procedure. The following protocol is used:

A. Pre-coat ELISA Plate

1. Coat ELISA plates (Corning, 96 well, Cat. #25805-96) with 05-101 antibody at 0.5 g per well in PBS, 100 μL final volume/well, and store overnight at 4° C. Coated plates are good for up to 10 days when stored at 4° C.
2. On day of use, remove coating buffer and replace with 100 μL blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells

1. An NIH3T3 cell line overexpressing a chimeric receptor containing the EGFR extracellular domain and intracellular HER2 kinase domain can be used for this assay.
2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.
3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

C. Assay Procedures

1. Check seeded cells for contamination using an inverted microscope. Dilute drug stock (10 mg/mL in DMSO) 1:10 in DMEM medium, then transfer 5 μL to a TBST well for a final drug dilution of 1:200 and a final DMSO concentration of 1%. Control wells receive DMSO alone. Incubate in 5% $CO_2$ at 37° C. for two hours.
2. Prepare EGF ligand: dilute stock EGF in DMEM so that upon transfer of 10 μl dilute EGF (1:12 dilution), 100 nM final concentration is attained.
3. Prepare fresh HNTG* sufficient for 100 μl per well; and place on ice.

| HNTG* (10 mL): | |
|---|---|
| HNTG stock | 2.0 mL |
| milli-Q $H_2O$ | 7.3 mL |
| EDTA, 100 mM, pH 7.0 | 0.5 mL |
| $Na_3VO_4$, 0.5M | 0.1 mL |
| $Na_4(P_2O_7)$, 0.2M | 0.1 mL |

4. After 120 minutes incubation with drug, add prepared SGF ligand to cells, 10 μl per well, to a final concentration of 100 nM. Control wells receive DMEM alone. Incubate, shaking, at room temperature, for 5 minutes.
5. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.
6. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
7. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).
8. Remove the anti-Ptyr antibody and wash 4 times with TBST. Transfer the freshly diluted TAGO anti-rabbit IgG antibody to the ELISA plate at 100 μl per well. Incubate shaking at room temperature for 30 minutes (anti-rabbit IgG antibody: 1:3000 dilution in TBST).
9. Remove TAGO detection antibody and wash 4 times with TBST. Transfer freshly prepared $ABTS/H_2O_2$ solution to ELISA plate, 100 μl per well. Incubate shaking at room temperature for 20 minutes. (ABTS/$H_2O_2$ solution: 1.0 μl 30% $H_2O_2$ in 10 mL ABTS stock).
10. Stop reaction by adding 50 μl 5N $H_2SO_4$ (optional), and determine O.D. at 410 nm.
11. The maximal phosphotyrosine signal is determined by subtracting the value of the negative controls from the positive controls. The percent inhibition of phosphotyrosine content for extract-containing wells is then calculated, after subtraction of the negative controls.

Example 4

PDGF-R ELISA

All cell culture media, glutamine, and fetal bovine serum can be purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

For ELISA assays, cells (U1242, obtained from Joseph Schlessinger, NYU) are grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells are changed to serum-free medium and treated with test compound for 2 hr in a 5% $CO_2$, 37° C. incubator. Cells are then stimulated with ligand for 5–10 minute followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) are transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates are incubated with shaking for 1 hour at room temperature. The plates are washed with TBST four times and then incubated with polyclonal anti-phosphotyrosine antibody at room temperature for 30 minutes. Excess anti-phosphotyrosine antibody is removed by rinsing the plate with TBST four times. Goat anti-rabbit IgG antibody is added to the ELISA plate for 30 min at room temperature followed by rinsing with TBST four more times. ABTS (100 mM citric acid, 250 mM $Na_2HPO_4$ and 0.5 mg/mL 2,2-azino-bis(3-ethylbenzthiazoline-6-sulfonic acid)) plus $H_2O_2$ (1.2 mL 30% $H_2O_2$ to 10 mL ABTS) is added to the ELISA plates to start color development. Absorbance at 410 nm with a reference wavelength of 630 nm is recorded about 15 to 30 min after ABTS addition.

The $IC_{50}$ values were measured for several of the compounds of the invention. These values are shown in Table 4.

TABLE 4

| Compound | IC$_{50}$ ($\mu$M) |
|---|---|
| 6-methoxy-3-(4,5,6,7-tetrahydro-1H-indol-2-ylmethylene)-1,3-dihydro-indol-2-one | 2.3 |
| 5-acetyl-3-(4,5,6,7-tetrahydro-1H-indol-2-ylmethylene)-1, 3-dihydro-indol-2-one | >100 |
| 6-chloro-3-(4,5,6,7-tetrahydro-1H-indol-2-ylmethylene)-1, 3-dihydro-indol-2-one | >100 |
| 6-hydroxy-3-(4,5,6,7-tetrahydro-1H-indol-2-ylmethylene)-1,3-dihydro-indol-2-one | 47.22 |
| 6-bromo-3-(4,5,6,7-tetrahydro-1H-indol-2-ylmethylene)-1,3-dihydro-indol-2-one | >100 |
| 6-(3-methoxyphenyl)-3-(4,5,6,7-tetrahydro-1H-indol-2-ylmethylene)-1,3-dihydro-indol-2-one | >100 |
| 7-bromo-5-methyl-3-(4,5,6,7-tetrahydro-1H-indol-2-ylmethylene)-1,3-dihydro-indol-2-one | 5.56 |
| 6-bromo-3-(3-methyl-4,5,6,7-tetrahydro-1H-indol-2-ylmethylene)-1,3-dihydro-indol-2-one | 40.05 |
| 6-(3-methoxyphenyl)-3-(3-methyl-4,5,6,7-tetrahydro-1H-indol-2-ylmethylene)-1,3-dihydro-indol-2-one | 5.83 |
| 6-(3-ethoxyphenyl)-3-(4,5,6,7-tetrahydro-1H-indol-2-ylmethylene)-1,3-dihydro-indol-2-one | >100 |
| 6-phenyl-3-(4,5,6,7-tetrahydra-1H-indol-2-ylmethylene)-1,3-dihydro-indol-2-one | 70.63 |
| 6-(4-methoxyphenyl)-3-(4,5,6,7-tetrahydro-1H-indol-2-ylmethylene)-1,3-dihydro-indol-2-one | 94.01 |
| 6-(4-methoxyphenyl)-3-(3-methyl-4,5,6,7-tetrahydro-1H-indol-2-ylmethylene)-1,3-dihydro-indol-2-one | >100 |
| 6-(2-methoxyphenyl)-3-(4,5,6,7-tetrahydro-1H-indol-2-ylmethylene)-1,3-dihydro-indol-2-one | 12.25 |
| 6-(2-methoxyphenyl)-3-(3-methyl-4,5,6,7-tetrahydro-1H-indol-2-ylmethylene)-1,3-dihydro-indol-2-one | 95.66 |

Example 5

IGF-I RECEPTOR ELISA

The following protocol may be used to measure phosphotyrosine level on IGF-I receptor, which indicates IGF-I receptor tyrosine kinase activity.

Materials And Reagents. The following materials and reagents are used:

a. The cell line used in this assay is 3T3/IGF-1R, a cell line genetically engineered to overexpresses IGF-1 receptor.
b. NIH3T3/IGF-1R is grown in an incubator with 5% CO$_2$ at 37° C. The growth media is DMEM+10% FBS (heat inactivated)+2 mM L-glutamine.
c. Affinity purified anti-IGF-1R antibody 17-69.
d. D-PBS:

| KH$_2$PO$_4$ | 0.20 g/L |
| K$_2$HPO$_4$ | 2.16 g/L |
| KCl | 0.20 g/L |
| NaCl | 8.00 g/L (pH 7.2) | e. Blocking Buffer: TBST plus 5% Milk (Carnation Instant Non-Fat Dry Milk).
f. TBST buffer:

| Tris-HCl | 50 mM |
| NaCl | 150 mM (pH 7.2/HCl 10N) |
| Triton X-100 | 0.1% |

Stock solution of TBS (10×) is prepared, and Triton X-100 is added to the buffer during dilution.

g. HNTG buffer:

| HEPES | 20 mM |
| NaCl | 150 mM (pH 7.2/HCl 1N) |
| Glycerol | 10% |
| Triton X-100 | 0.2% |

Stock solution (5×) is prepared and kept at 4° C.

h. EDTA/HCl: 0.5 M pH 7.0 (NaOH) as 100×stock.
i. Na$_3$VO$_4$: 0.5 M as 100×stock and aliquots are kept in −80° C.
j. Na$_4$P$_2$O$_7$: 0.2 M as 100×stock.
k. Insulin-like growth factor-1 from Promega (Cat# G5111).
l. Rabbit polyclonal anti-phosphotyrosine antiserum.
m. Goat anti-rabbit IgG, POD conjugate (detection antibody), Tago (Cat. No. 4520, Lot No. 1802): Tago, Inc., Burlingame, Calif.
n. ABTS (2,2'-azinobis(3-ethylbenzthiazolinesulfonic acid)) solution:

| Citric acid | 100 mM |
| Na$_2$HPO$_4$ | 250 mM (pH 4.0/1N HCl) |
| ABTS | 0.5 mg/mL |

ABTS solution should be kept in dark and 4° C. The solution should be discarded when it turns green.

o. Hydrogen Peroxide: 30% solution is kept in the dark and at 4° C.

Procedure. All the following steps are conducted at room temperature unless it is specifically indicated. All ELISA plate washings are performed by rinsing the plate with tap water three times, followed by one TBST rinse. Pat plate dry with paper towels.

A. Cell Seeding

1. The cells, grown in tissue culture dish (Corning 25020-100) to 80–90% confluence, are harvested with Trypsin-EDTA (0.25%, 0.5 mL/D-100, GIBCO).
2. Resuspend the cells in fresh DMEM+10% FBS+2 mM L-Glutamine, and transfer to 96-well tissue culture plate (Corning, 25806-96) at 20,000 cells/well (100 $\mu$L/well). Incubate for 1 day then replace medium to serum-free medium (90/$\mu$L) and incubate in 5% CO$_2$ and 37° C. overnight.

B. ELISA Plate Coating and Blocking

1. Coat the ELISA plate (Corning 25805-96) with Anti-IGF-1R Antibody at 0.5 $\mu$g/well in 100 $\mu$L PBS at least 2 hours.
2. Remove the coating solution, and replace with 100 $\mu$L Blocking Buffer., and shake for 30 minutes. Remove the blocking buffer and wash the plate just before adding lysate.

C. Assay Procedures
1. The drugs are tested in serum-free condition.
2. Dilute drug stock (in 100% DMSO) 1:10 with DMEM in 96-well poly-propylene plate, and transfer 10 μL/well of this solution to the cells to achieve final drug dilution 1:100, and final DMSO concentration of 1.0%. Incubate the cells in 5% $CO_2$ at 37° C. for 2 hours.
3. Prepare fresh cell lysis buffer (HNTG*)

|  |  |
|---|---|
| HNTG | 2 mL |
| EDTA | 0.1 mL |
| $Na_3VO_4$ | 0.1 mL |
| $Na_4(P_2O_7)$ | 0.1 mL |
| $H_2O$ | 7.3 mL |

4. After drug incubation for two hours, transfer 10 μL/well of 200 nM IGF-1 Ligand in PBS to the cells (Final Conc.=20 nM), and incubate at 5% $CO_2$ at 37° C. for 10 minutes.
5. Remove media and add 100 μL/well HNTG* and shake for 10 minutes. Look at cells under microscope to see if they are adequately lysed.
6. Use a 12-channel pipette to scrape the cells from the plate, and homogenize the lysate by repeated aspiration and dispensing. Transfer all the lysate to the antibody coated ELISA plate, and shake for 1 hour.
7. Remove the lysate, wash the plate, transfer anti-pTyr (1:3,000 with TBST) 100 μL/well, and shake for 30 minutes.
8. Remove anti-pTyr, wash the plate, transfer TAGO (1:3,000 with TBST) 100 μL/well, and shake for 30 minutes.
9. Remove detection antibody, wash the plate, and transfer fresh $ABTS/H_2O_2$ (1.2 μL $H_2O_2$ to 10 mL ABTS) 100 μL/well to the plate to start color development.
10. Measure OD at 410 nm with a reference wavelength of 630 nm in Dynatec MR5000.

Example 6

EGF RECEPTOR ELISA

EGF Receptor kinase activity in cells genetically engineered to express human EGF-R can be measured as described below:

Materials and Reagents. The following materials and reagents are used a. EGF Ligand: stock concentration 16.5 μM; EGF 201, TOYOBO, Co., Ltd. Japan.
b. 05-101 (UBI) (a monoclonal antibody recognizing an EGFR extracellular domain).
c. Anti-phosphotyosine antibody (anti-Ptyr) (polyclonal).
d. Detection antibody: Goat anti-rabbit lgG horse radish peroxidase conjugate, TAGO, Inc., Burlingame, Calif.
e. TBST buffer:

|  |  |
|---|---|
| Tris-HCl, pH 7 | 50 mM |
| NaCl | 150 mM |
| Triton X-100 | 0.1 | f. HNTG 5×stock:

|  |  |
|---|---|
| HEPES | 0.1M |
| NaCl | 0.75M |
| Glycerol | 50 |
| Triton X-100 | 1.0% | g. ABTS stock:

|  |  |
|---|---|
| Citric Acid | 100 mM |
| $Na_2HPO_4$ | 250 mM |
| HCl, conc. | 4.0 pH |
| ABTS* | 0.5 mg/mL |

Keep solution in dark at 4 C until used.
h. Stock reagents of:
   EDTA 100 mM pH 7.0
   $Na_3VO_4$ 0.5 M
   $Na_4(P_2O_7)$ 0.2 M
Procedure. The following protocol is used:
A. Pre-coat ELISA Plate
1. Coat ELISA plates (Corning, 96 well, Cat. #25805-96) with 05-101 antibody at 0.5 μg per well in PBS, 150 μL final volume/well, and store overnight at 4° C. Coated plates are good for up to 10 days when stored at 4° C.
2. On day of use, remove coating buffer and replace with blocking buffer (5% Carnation Instant NonFat Dry Milk in PBS). Incubate the plate, shaking, at room temperature
   (about 23° C. to 25° C.) for 30 minutes. Just prior to use, remove blocking buffer and wash plate 4 times with TBST buffer.
B. Seeding Cells
1. NIH 3T3/C7 cell line (Honegger, et al., Cell 51:199–209, 1987) can be use for this assay.
2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm at room temperature for 5 minutes.
3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μL per well, in a 96 well microtiter plate. Incubate seeded cells in 5% $CO_2$ at 37° C. for about 40 hours.
C. Assay Procedures
1. Check seeded cells for contamination using an inverted microscope. Dilute drug stock (10 mg/mL in DMSO) 1:10 in DMEM medium, then transfer 5 μL to a test well for a final drug dilution of 1:200 and a final DMSO concentration of 1%. Control wells receive DMSO alone. Incubate in 5% $CO_2$ at 37° C. for one hour.
2. Prepare EGF ligand: dilute stock EGF in DMEM so that upon transfer of 10 μL dilute EGF (1:12 dilution), 25 nM final concentration is attained.
3. Prepare fresh 10 mL HNTG* sufficient for 100 μL per well wherein HNTG* comprises: HNTG stock (2.0 mL), milli-Q $H_2O$ (7.3 mL), EDTA, 100 mM, pH 7.0 (0.5 mL), $Na_3VO_4$ 0.5 M (0.1 mL) and $Na_4(P_2O_7)$, 0.2 M (0.1 mL).

4. Place on ice.
5. After two hours incubation with drug, add prepared EGF ligand to cells, 10 μL per well, to yield a final concentration of 25 nM. Control wells receive DMEM alone. Incubate, shaking, at room temperature, for 5 minutes.
6. Remove drug, EGF, and DMEM. Wash cells twice with PBS. Transfer HNTG* to cells, 100 μL per well. Place on ice for 5 minutes. Meanwhile, remove blocking buffer from other ELISA plate and wash with TBST as described above.
7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
8. Remove lysate and wash 4 times with TBST. Transfer freshly diluted anti-Ptyr antibody to ELISA plate at 100 μL per well. Incubate shaking at room temperature for 30 minutes in the presence of the anti-Ptyr antiserum (1:3000 dilution in TBST).
9. Remove the anti-Ptyr antibody and wash 4 times with TBST. Transfer the freshly diluted TAGO 30 anti-rabbit IgG antibody to the ELISA plate at 100 μL per well. Incubate shaking at room temperature for 30 minutes (anti-rabbit IgG antibody: 1:3000 dilution in TBST).
10. Remove detection antibody and wash 4 times with TBST. Transfer freshly prepared ABTS/$H_2O_2$ solution to ELISA plate, 100 μl per well. Incubate at room temperature for 20 minutes. ABTS/$H_2O_2$ solution: 1.2 μL 30% $H_2O_2$ in 10 mL ABTS stock.
11. Stop reaction by adding 50 μL 5 N $H_2SO_4$ (optional), and determine O.D. at 410 nm.
12. The maximal phosphotyrosine signal is determined by subtracting the value of the negative controls from the positive controls. The percent inhibition of phosphotyrosine content for extract-containing wells is then calculated, after subtraction of the negative controls.

Example 7

ASSAY MEASURING THE KINASE ACTIVITY OF THE FGF RECEPTOR

The following protocol describes the reagents and procedures used to analyze protein tyrosine kinase activity of the Myc-GyrB-FGFR fusion protein.

Materials and Reagents
1. HNTG

| HEPES buffer pH 7.5 | 20 mM |
| --- | --- |
| NaCl | 150 mM |
| Triton X-100 | 0.2% |
| Glycerol | 10% |
| Aprotenin | 0.5 mg/mL |
| PMSF | 1 mM |

2. Kinase Buffer

| HEPES pH 7.2 | 50 mM |
| --- | --- |
| $MnCl_2$ | 10 mM |
| Triton-X-100 | 0.1% |
| DTT | 1.0 mM |

3. PBS (Phosphate Buffered Saline)

| KCL | 2.7 mM |
| --- | --- |
| $KH_2PO_4$ | 1.1 mM |
| $MgCl_2$ (anhydrous) | 0.5 mM |
| NaCl | 138 mM |
| $Na_2HPO_4$ | 8.1 mM |

4. Blocking Buffer: TBB (Terrene's Blocking Buffer)

| Tris pH 7.0–7.2 | 10 mM |
| --- | --- |
| NaCl | 100 mM |
| Tween-20 | 0.1% |
| BSA | 1.0% |

Note: One can make up this solution as a 10×stock, provided that it is sterile, filtered, and kept at 4° C.

5. PMSF Sigma Catalog # P-7626 Make up as a 100 mM stock solution in 100% Ethanol
6. ATP (Bacterial source): Sigma Catalog # A-7699 Make up as a 10M stock adiquot and store in −20° C.
7. Biotin conjugated anti-phosphotyrosine mab: Upstate Biotechnology Inc. (Clone 4G10 cat. # 16-103 ser. # 14495)
8. Voctastain Elite ABC reagent (Avidin peroxidase conjugate). Vector Laboratories (PK-6100).
9. ABTS (2.2'-azino-bist 3-ethylbeazthiazoline-6-sulfonic acid) Sigma CatalogA-1888

| Citric Acid | 100 mM |
| --- | --- |
| $Na_2HPO_4$ | 250 mM |
| pH to 4.0 with phosphoric acid | |
| ABTS | 0.5 mg/mL |

10. Hydrogen peroxide 30% solution: Fisher Catalog # H325. Store in the dark at 4° C. until ready to use.
11. ABTS/$H_2O_3$

| 15 mL ABTS solution (above) |
| --- |
| 2 μL $H_2O_2$ |

Prepare 5 minutes before use and leave at room temperature.

12. 0.2 M HCl
13. TRIS HCl: Fischer Catalog # BP 152-5
14. NaCl: Fischer Catalog # S271-10
15. HEPES Fischer Catalog # BP310-500

16. TBST Buffer (Tris buffered Saline with Triton X-100)

| Tris pH 7.2 | 50 mM |
|---|---|
| NaCl | 150 mM |
| Triton X-100 | 0.1% |

17. DTT (Dichiothreitol) Fischer Catalog # BP172-25
Make up as a IM stock aliquot and store in −20° C. Use once then discard remainder
18. MnCl$_2$: Manganese Chloride
Make up as a IM stock.
19. Triton X-100
20. Affinity purified Rabbit α GST GyrB: purified by Biochemistry Lab SUGEN, Inc.
21. Corning 96-well ELISA plates (Corning cat. # 25805-96)
22. DMSO (Dimethylsulfoxide): Sigma cat. # D-8418
23. Nunc Polypropylene 96-well V bottom plates.
Procedure
All of the following steps are conducted at room temperature unless it is specifically indicated. All ELISA plate washing is by rinsing 4× with TBST.
1. Coat Corning 96 well ELISA plates with 1.0 μg/well of Rabbit αGyrB antibody in PBS for a total well volume of 100 μL. Store overnight at 4° C.
2. Remove unbound Rabbit antibody by inverting plate to remove liquid. Pat plate on a paper towel to remove excess liquid and bubbles
3. Add 100 μL of Blocking Buffer (TBB) to each well. Incubate while shaking on a microliter plate shaker at room temperature for 30 min.
4. Wash 4× with TBST. Pat plate on a paper towel to remove excess liquid and bubbles.
5. Add 15 μg COS/FGFR cell lysate Myc-GyrB-FGFR sources per well in HNTG for a final volume of 100 μL per well. Incubate while shaking on a micro-liter plate shaker at room temperature for 2 hours.
6. Wash 4× with TBST as described in step 4.
7. Add 80 μL of 1×kinase buffer per well.
8. Dilute compunds/extracts 1:10 (or as stated otherwise) in 1×kinase buffer+1% DMSO in a polypropylene 96 well plate.
9. At this point diluted Compounds/Extracts are added to the ELISA plate. Transfer 10 μL of diluted test and control wells from the polypropylene plate wells to the corresponding ELISA plate wells. Incubate while shaking on a micro-liter plate shaker at room temperature for 20 minutes.
10. Add 10 μL of 70 μM ATP diluted in kinase buffer to positive control and test wells (Final ATP concentration is 7 μM/well.) Add 10 μL of 1×kinase buffer to negative control wells. Incubate while shaking on a micro-liter plate shaker at room temperature for 15 min.
11. It is also critical to change pipette tips between each ATP addition. This will eliminate any chance of samples being carried over to other wells.
12. Stop Kinase reaction with the addition of 5 μL of 0.5 MEDTA pH 8.0 to all wells.
13. Wash 4× with TBST as described in step 4.
14. Add 100 μL per well of biotin conjugated α-phosphotyrosine mab (b-4G10) diluted in TBST.

Incubate while shaking on a microliter plate shaker 30 minutes at room temperature while shaking.
15. Make up Vectastain ABC reagent. This step requires 30 min. for complete coupling of the avidin with the biotinylated HRP. Add on drop reagent A to 15 mL TBST. Mix by inverting tube several times. Then add one drop reagent B and mix again. Allow ABC reagent to mix at room temperature while the biotin-4G10 anti-phosphotyrosine is incubating in the assay plate.
16. Wash 4× with TBST as described in step 4.
17. Add 100 μl per well of ABC HRP reagent. Incubate while shaking on a micro-liter plate shaker at room temperature for 30 minutes.
18. Wash 4× with TBST and 1× with PBS
19. Add 100 μL of ABTS/H$_2$O$_2$ solution to each well.
20. Incubate 5 to 15 minutes while shaking. Remove any bubbles.
21. If necessary stop reaction with the addition of 10 μL of 0.2 M HCl/well.
22. Read assay on Dynatech MR7000 ELISA Plate Reader.

The IC$_{50}$ values were measured for several of the compounds of the invention. These values are shown in Table 5.

TABLE 5

| Compound | IC$_{50}$ (μM) |
|---|---|
| 5-acetyl-3-(4,5,6,7-tetrahydro-1H-indol-2-ylmethylene)-1,3-dihydro-indol-2-one | >20 |
| 6-chloro-3-(4,5,6,7-tetrahydro-1H-indol-2-ylmethylene)-1,3-dihydro-indol-2-one | >20 |
| 6-bromo-3-(4,5,6,7-tetrahydro-1H-indol-2-ylmethylene)-1,3-dihydro-indol-2-one | >20 |
| 6-bromo-3-(3-methyl-4,5,6,7-tetrahydro-1H-indol-2-ylmethylene)-1,3-dihydro-indol-2-one | >20 |
| 6-(3-methoxyphenyl)-3-(3-methyl-4,5,6,7-tetrahydro-1H-indol-2-ylmethylene)-1,3-dihydro-indol-2-one | >20 |
| 6-(3-ethoxyphenyl)-3-(4,5,6,7-tetrahydro-1H-indol-2-ylmethylene)-1,3-dihydro-indol-2-one | >20 |
| 6-phenyl-3-(4,5,6,7-tetrahydro-1H-indol-2-ylmethylene)-1,3-dihydro-indol-2-one | >100 |
| 6-(4-methoxyphenyl)-3-(4,5,6,7-tetrahydro-1H-indol-2-ylmethylene)-1,3-dihydro-indol-2-one | >100 |
| 6-(4-methoxyohenyl)-3-(3-methyl-4,5,6,7-tetrahydro-1H-indol-2-ylmethylene)-1,3-dihydro-indol-2-one | >100 |
| 6-(2-methoxyphenyl)-3-(4,5,6,7-tetrahydro-1H-indol-2-ylmethylene)-1,3-dihydro-indol-2-one | >100 |
| 6-(2-methoxyphenyl)-3-(3-methyl-4,5,6,7-tetrahydro-1H-indol-2-ylmethylene)-1,3-dihydro-indol-2-one | >100 |

Example 8

MET AUTOPHOSPHORYLATION ASSAY— ELISA

This assay determines Met tyrosine kinase activity by analyzing Met protein tyrosine kinase levels on the Met receptor.
1. Reagents
a. HNTG (5×stock solution): Dissolve 23.83 g HEPES and 43.83 g NaCl in about 350 mL dH$_2$O. Adjust pH to 7.2 with HCl or NaOH, add 500 mL glycerol and 10 mL Triton X-100, mix, add dH$_2$O to 1 L total volume. To make 1 L of 1×working solution add 200 mL 5×stock solution to 800 mL dH$_2$O, check and adjust pH as necessary, store at 4° C.

b. PBS (Dulbecco's Phosphate-Buffered Saline), Gibco Cat. # 450-1300EB (1×solution).
c. Blocking Buffer: in 500 mL dH$_2$O place 100 g BSA, 12.1 g Tris-pH7.5, 58.44 g NaCl and 10 mL Tween-20, dilute to 1 L total volume.
d. Kinase Buffer: To 500 mL dH$_2$O add 12.1 g TRIS pH7.2, 58.4 g NaCl, 40.7 g MgCl$_2$ and 1.9 g EGTA; bring to 1 L total volume with dH$_2$O.
e. PMSF (Phenylmethylsulfonyl fluoride), Sigma Cat. # P-7626, to 435.5 mg, add 100% ethanol to 25 mL total volume, vortex.
f. ATP (Bacterial Source), Sigma Cat. # A-7699, store powder at −20° C.; to make up solution for use, dissolve 3.31 mg in 1 mL dH$_2$O.
g. RC-20H HRPO Conjugated Anti-Phosphotyrosine, Transduction Laboratories Cat. # E120H.
h. Pierce 1-Step (TM) Turbo TMB-ELISA (3,3',5,5'-tetramethylbenzidine, Pierce Cat. # 34022.
i. H$_2$SO$_4$, add 1 mL conc. (18N) to 35 mL dH$_2$O.
j. TRIS HCL, Fischer Cat. # BP152-5; to 121.14 g of material, add 600 mL MilliQ H$_2$O, adjust pH to 7.5 (or 7.2) with HCl, bring volume to 1 L with MilliQ H$_2$O.
k. NaCl, Fischer Cat. # S271-10, make up 5M solution.
l. Tween-20, Fischer Cat. # S337-500.
m. Na$_3$VO$_4$, Fischer Cat. # S454-50, to 1.8 g material add 80 mL MilliQ H$_2$O, adjust pH to 10.0 with HCl or NaOH, boil in microwave, cool, check pH, repeat procedure until pH stable at 10.0, add MilliQ H$_2$O to 100 mL total volume, make 1 mL aliquots and store at −80° C.
n. MgCl$_2$, Fischer Cat. # M33-500, make up 1M solution.
o. HEPES, Fischer Cat. # BP310-500, to 200 mL MilliQ H$_2$O, add 59.6 g material, adjust pH to 7.5, bring volume to 250 mL total, sterile filter.
p. Albumin, Bovine (BSA), Sigma Cat. # A-4503, to 30 grams material add sterile distilled water to make total volume of 300 mL, store at 4° C.
q. TBST Buffer: to approx. 900 mL dH$_2$O in a 1 L graduated cylinder add 6.057 g TRIS and 8.766 g NaCl, when dissolved, adjust pH to 7.2 with HCl, add 1.0 mL Triton X-100 and bring to 1 L total volume with dH$_2$O.
r. Goat Affinity purified antibody Rabbit IgG (whole molecule), Cappel Cat. # 55641.
s. Anti h-Met (C-28) rabbit polyclonal IgG antibody, Santa Cruz Chemical Cat. # SC-161.
t. Transiently Transfected EGFR/Met chimeric cells (EMR) (Komada, et al., *Oncogene*, 8:2381–2390 (1993).
u. Sodium Carbonate Buffer, (Na$_2$CO$_4$, Fischer Cat. # S495): to 10.6 g material add 800 mL MilliQ H$_2$O, when dissolved adjust pH to 9.6 with NaOH, bring up to 1 L total volume with MilliQ H$_2$O, filter, store at 4° C.

2. Procedure

All of the following steps are conducted at room temperature unless it is specifically indicated otherwise. All ELISA plate washing is by rinsing 4× with TBST.

A. EMR Lysis

This procedure can be performed the night before or immediately prior to the start of receptor capture.

1. Quick thaw lysates in a 37° C. waterbath with a swirling motion until the last crystals disappear.
2. Lyse cell pellet with 1×HNTG containing 1 mM PMSF. Use 3 mL of HNTG per 15 cm dish of cells. Add ½ the calculated HNTG volume, vortex the tube for 1 min., add the remaining amount of HNTG, vortex for another min.
3. Balance tubes, centrifuge at 10,000×g for 10 min at 4° C.
4. Pool supernatants, remove an aliquot for protein determination.
5. Quick freeze pooled sample in dry ice/ethanol bath. This step is performed regardless of whether lysate will be stored overnight or used immediately following protein determination.
6. Perform protein determination using standard bicinchoninic acid (BCA) method (BCA Assay Reagent Kit from Pierce Chemical Cat. # 23225).

B. ELISA Procedure

1. Coat Corning 96 well ELISA plates with 5 µg per well Goat anti-Rabbit antibody in Carbonate Buffer for a total well volume of 50 µl. Store overnight at 4° C.
2. Remove unbound Goat anti-rabbit antibody by inverting plate to remove liquid.
3. Add 150 µL of Blocking Buffer to each well. Incubate for 30 min. at room temperature with shaking.
4. Wash 4× with TBST. Pat plate on a paper towel to remove excess liquid and bubbles.
5. Add 1 µg per well of Rabbit anti-Met antibody diluted in TBST for a total well volume of 100 µL.
6. Dilute lysate in HNTG (90 µg lysate/100 µL)
7. Add 100 µL of diluted lysate to each well. Shake at room temperature for 60 min.
8. Wash 4× with TBST. Pat on paper towel to remove excess liquid and bubbles.
9. Add 50 µL of 1×lysate buffer per well.
10. Dilute compounds/extracts 1:10 in 1×Kinase Buffer in a polypropylene 96 well plate.
11. Transfer 5.5 µL of diluted drug to ELISA plate wells. Incubate at room temperature with shaking for 20 min.
12. Add 5.5 µL of 60 µM ATP solution per well. Negative controls do not receive any ATP. Incubate at room temperature for 90 min., with shaking.
13. Wash 4× with TBST. Pat plate on paper towel to remove excess liquid and bubbles.
14. Add 100 µL per well of RC20 (1:3000 dilution in Blocking Buffer). Incubate 30 min. at room temperature with shaking.
15. Wash 4× with TBST. Pat plate on paper towel to remove excess liquid and bubbles.
16. Add 100 µL per well of Turbo-TMB. Incubate with shaking for 30–60 min.
17. Add 100 µL per well of 1M H$_2$SO$_4$ to stop reaction.
18. Read assay on Dynatech MR7000 ELISA reader. Test Filter=450 nm, reference filter=410 nm.

Example 9

BIOCHEMICAL SRC ASSAY—ELISA

This assay is used to determine src protein kinase activity measuring phosphorylation of a biotinylated peptide as the readout.

1. Materials and Reagents
a. Yeast transformed with src from Courtneidge Laboratory (Sugen, Inc., Redwood City, Calif.).
b. Cell lysates: Yeast cells expressing src are pelleted, washed once with water, re-pelleted and stored at −80° C. until use.

c. N-terminus biotinylated EEEYEEYEEEYEEEYEEEY is prepared by standard procedures well known to those skilled in the art.
d. DMSO: Sigma, St. Louis, Mo.
e. 96 Well ELISA Plate: Corning 96 Well Easy Wash, Modified flat Bottom Plate, Corning Cat. #25805-96.
f. NUNC 96-well V-bottom polypropylene plates for dilution of compounds: Applied Scientific Cat. # A-72092.
g. Vecastain ELITE ABC reagent: Vector, Burlingame, Calif.
h. Anti-src (327) mab: Schizosaccharomyces Pombe is used to express recombinant Src (Superti-Furga, et al., *EMBO J.*, 12:2625–2634; Superti-Furga, et al., *Nature Biochem.*, 14:600–605). S. Pombe strain SP200 (h-s leu1.32 ura4 ade210) is grown as described and transformations are pRSP expression plasmids are done by the lithium acetate method (Superti-Furga, supra). Cells are grown in the presence of 1 $\mu$M thiamine to repress expression from the nmtl promoter or in the absence of thiamine to induce expression.
i. Monoclonal anti-phosphotyrosine, UBI 05-321 (UB40 may be used instead).
j. Turbo TMB-ELISA peroxidase substrate: Pierce Chemical.
2. Buffer Solutions
a. PBS (Dulbecco's Phosphate-Buffered Saline): GIBCO PBS, GIBCO Cat. # 450-1300EB.
b. Blocking Buffer: 5% Non-fat milk (Carnation) in PBS.
c. Carbonate Buffer: $Na_2CO_4$ from Fischer, Cat. # S495, make up 100 mM stock solution.
d. Kinase Buffer: 1.0 mL (from 1 M stock solution) $MgCl_2$; 0.2 mL (from a 1M stock solution) $MnCl_2$; 0.2 mL (from a 1 M stock solution) DTT; 5.0 mL (from a 1 M stock solution) HEPES; 0.1 mL TX-100; bring to 10 mL total volume with MilliQ $H_2O$.
e. Lysis Buffer: 5.0 HEPES (from 1 M stock solution.); 2.74 mL NaCl (from 5M stock solution); 10 mL glycerol; 1.0 mL TX-100; 0.4 mL EDTA (from a 100 mM stock solution); 1.0 mL PMSF (from a 100 mM stock solution); 0.1 mL $Na_3VO_4$ (from a 0.1 M stock solution); bring to 100 mL total volume with MilliQ $H_2O$.
f. ATP: Sigma Cat. # A-7699, make up 10 mM stock solution (5.51 mg/mL).
g. TRIS-HCl: Fischer Cat. # BP 152-5, to 600 mL MilliQ $H_2O$ add 121.14 g material, adjust pH to 7.5 with HCl, bring to 1 L total volume with MilliQ $H_2O$.
h. NaCl: Fischer Cat. # S271-10, Make up 5 M stock solution with MilliQ $H_2O$.
i. $Na_3VO_4$: Fischer Cat. # S454-50; to 80 mL MilliQ $H_2O$, add 1.8 g material; adjust pH to 10.0 with HCl or NaOH; boil in a microwave; cool; check pH, repeat pH adjustment until pH remains stable after heating/cooling cycle; bring to 100 mL total volume with MilliQ $H_2O$; make 1 mL aliquots and store at −80° C.
j. $MgCl_2$: Fischer Cat. # M33-500, make up 1 M stock solution with MilliQ $H_2O$.
k. HEPES: Fischer Cat. # BP 310-500; too 200 mL MilliQ $H_2O$, add 59.6 g material, adjust pH to 7.5, bring to 250 mL total volume with MilliQ $H_2O$, sterile filter (1 M stock solution)
l. TBST Buffer: TBST Buffer: To 900 mL $dH_2O$ add 6.057 g TRIS and 8.766 g NaCl; adjust pH to 7.2 with HCl, add 1.0 mL Triton-X100; bring to 1 L total volume with $dH_2O$.
m. $MnCl_2$: Fischer Cat. # M87-100, make up 1 M stock solution with MilliQ $H_2O$.
n. DTT: Fischer Cat. # BP172-5.
o. TBS (TRIS Buffered Saline): to 900 mL MilliQ $H_2O$ add 6.057 g TRIS and 8.777 g NaCl; bring to 1 L total volume with MilliQ $H_2O$.
p. Kinase Reaction Mixture: Amount per assay plate (100 wells): 1.0 mL Kinase Buffer, 200 $\mu$g GST-ζ, bring to final volume of 8.0 mL with MilliQ $H_2O$.
q. Biotin labeled EEEYEEYEEEYEEEYEEEY: Make peptide stock solution (1 mM, 2.98 mg/mL) in water fresh just before use.
r. Vectastain ELITE ABC reagent: To prepare 14 mL of working reagent, add 1 drop of reagent A to 15 mL TBST and invert tube several times to mix. Then add 1 drop of reagent B. Put tube on orbital shaker at room temperature and mix for 30 minutes.
3. Procedures
a. Preparation of src coated ELISA plate
 1. Coat ELISA plate with 0.5 $\mu$g/well anti-src mab in 100 $\mu$L of pH 9.6 sodium carbonate buffer at 4° C. overnight.
 2. Wash wells once with PBS.
 3. Block plate with 0.15 mL 5% milk in PBS for 30 min. at room temperature.
 4. Wash plate 5× with PBS.
 5. Add 10 $\mu$g/well of src transformed yeast lysates diluted in Lysis Buffer (0.1 mL total volume per well). (Amount of lysate may vary between batches.) Shake plate for 20 minutes at room temperature.
b. Preparation of phosphotyrosine antibody-coated ELISA plate
 1. 4G10 plate: coat 0.5 $\mu$g/well 4G10 in 100 $\mu$l PBS overnight at 4° C. and block with 150 $\mu$L of 5% milk in PBS for 30 minutes at room temperature.
c. Kinase assay procedure
 1. Remove unbound proteins from step 1–7, above, and wash plates 5× with PBS.
 2. Add 0.08 mL Kinase Reaction Mixture per well (containing 10 $\mu$L of 10×Kinase Buffer and 10 $\mu$M (final concentration) biotin-EEEYEEYEEEYEEEYEEEY per well diluted in water.
 3. Add 10 $\mu$L of compound diluted in water containing 10% DMSO and pre-incubate for 15 minutes at room temperature.
 4. Start kinase reaction by adding 10 $\mu$L/well of 0.05 mM ATP in water (5 $\mu$M ATP final).
 5. Shake ELISA plate for 15 min. at room temperature.
 6. Stop kinase reaction by adding 10 $\mu$L of 0.5 M EDTA per well.
 7. Transfer 90 $\mu$L supernatant to a blocked 4G10 coated ELISA plate from section B, above.
 8. Incubate for 30 min. while shaking at room temperature.
 9. Wash plate 5× with TBST.
 10. Incubate with Vectastain ELITE ABC reagent (100 $\mu$L/well) for 30 min. at room temperature.
 11. Wash the wells 5× with TBST.
 12. Develop with Turbo TMB.
The $IC_{50}$ values were measured for several of the compounds of the invention. These values are shown in Table 6.

TABLE 6

| Compound | IC$_{50}$ ($\mu$M) |
| --- | --- |
| 5-acetyl-3-(4,5,6,7-tetrahydro-1H-indol-2-ylmethylene)-1,3-dihydro-indol-2-one | 17.76 |
| 6-hydroxy-3-(4,5,6,7-tetrahydro-1H-indol-2-ylmethylene)-1,3-dihydro-indol-2-one | 20.98 |

Example 10

BIOCHEMICAL LCK ASSAY—ELISA

This assay is used to determine lck protein kinase activities measuring phosphorylation of GST-ζ as the readout.

a. 1. Materials and Reagents b. Yeast transformed with lck. Schizosaccharomyces Pombe is used to express recombinant Lck (Superti-Furga, et al., *EMBO J*, 12:2625–2634; Superti-Furga, et al., *Nature Biotech.*, 14:600–605). S. Pombe strain SP200 (h-s leul.32 ura4 ade210) is grown as described and transformations with pRSP expression plasmids are done by the lithium acetate method (Superti-Furga, supra). Cells are grown in the presence of 1 $\mu$M thiamine to induce expression.

b. Cell lysates: Yeast cells expressing lck are pelleted, washed once in water, re-pelleted and stored frozen at −80° C. until use.

c. GST-ζ: DNA encoding for GST-ζ fusion protein for expression in bacteria obtained from Arthur Weiss of the Howard Hughes Medical Institute at the University of California, San Francisco. Transformed bacteria are grown overnight while shaking at 25° C. GST-ζ is purified by glutathione affinity chromatography, Pharmacia, Alameda, Calif.

d. DMSO: Sigma, St. Louis, Mo.

e. 96-Well ELISA plate: Corning 96 Well Easy Wash, Modified Flat Bottom Plate, Corning Cat. #25805-96.

f. NUNC 96-well V-bottom polypropylene plates for dilution of compounds: Applied Scientific Cat. # AS-72092.

g. Purified Rabbit anti-GST antiserum: Amrad Corporation (Australia) Cat. #90001605.

h. Goat anti-Rabbit-IgG-HRP: Amersham Cat. # V010301.

i. Sheep ant-mouse IgG (H+L): Jackson Labs Cat. # 5215-005-003.

j. Anti-Lck (3A5) mab: Santa Cruz Biotechnology Cat # sc-433.

k. Monoclonal anti-phosphotyrosine UBI 05-321 (UB40 may be used instead).

2. Buffer solutions a. PBS (Dulbecco's Phosphate-Buffered Saline) 1×solution: GIBCO PBS, GIBCO Cat. # 450-1300EB.

b. Blocking Buffer: 100 g. BSA, 12.1 g. TRIS-pH 7.5, 58.44 g NaCl, 10 mL Tween-20, bring up to 1 L total volume with MilliQ H$_2$O.

c. Carbonate Buffer: Na$_2$CO$_4$ from Fischer, Cat. # S495; make up 100 mM solution with MilliQ H$_2$O.

d. Kinase Buffer: 1.0 mL (from 1M stock solution) MgCl$_2$; 0.2 mL (from a 1M stock solution) MnCl$_2$; 0.2 mL (from a 1M stock solution) DTT; 5.0 mL (from a 1M stock solution) HEPES; 0.1 mL TX-100; bring to 10 mL total volume with MilliQ H$_2$O.

e. Lysis Buffer: 5.0 HEPES (from 1M stock solution.); 2.74 mL NaCl (from 5M stock solution); 10 mL glycerol; 1.0 mL TX-100; 0.4 mL EDTA (from a 100 mM stock solution); 1.0 mL PMSF (from a 100 mM stock solution); 0.1 mL Na$_3$VO$_4$ (from a 0.1 M stock solution); bring to 100 mL total volume with MilliQ H$_2$O.

f. ATP: Sigma Cat. # A-7699, make up 10 mM stock solution (5.51 mg/mL).

g. TRIS-HCl: Fischer Cat. # BP 152-5, to 600 mL MilliQ H$_2$O add 121.14 g material, adjust pH to 7.5 with HCl, bring to 1 L total volume with MilliQ H$_2$O.

h. NaCl: Fischer Cat. # S271-10, Make up 5M stock solution with MilliQ H$_2$O.

i. Na$_3$VO$_4$: Fischer Cat. # S454-50; to 80 mL MilliQ H$_2$O, add 1.8 g material; adjust pH to 10.0 with HCl or NaOH; boil in a microwave; cool; check pH, repeat pH adjustment until pH remains stable after heating/cooling cycle; bring to 100 mL total volume with MilliQ H$_2$O; make 1 mL aliquots and store at −80° C.

j. MgCl$_2$: Fischer Cat. # M33-500, make up 1 M stock solution with MilliQ H$_2$O.

k. HEPES: Fischer Cat. # BP 310-500; to 200 mL MilliQ H$_2$O, add 59.6 g material, adjust pH to 7.5, bring to 250 mL total volume with MilliQ H$_2$O, sterile filter (1M stock solution)

l. Albumin, Bovine (BSA), Sigma Cat. # A4503; to 150 mL MilliQ H$_2$O add 30 g material, bring 300 mL total volume with MilliQ H$_2$O, filter through 0.22 $\mu$m filter, store at 4° C.

m. TBST Buffer: To 900 mL dH$_2$O add 6.057 g TRIS and 8.766 g NaCl; adjust pH to 7.2 with HCl, add 1.0 mL Triton-X100; bring to 1 L total volume with dH$_2$O.

n. MnCl$_2$: Fischer Cat. # M87-100, make up 1 M stock solution with MilliQ H$_2$O.

o. DTT; Fischer Cat. # BP172-5.

p. TBS (TRIS Buffered Saline): to 900 mL MilliQ H$_2$O add 6.057 g TRIS and 8.777 g NaCl; bring to 1 L total volume with MilliQ H$_2$O.

q. Kinase Reaction Mixture: Amount per assay plate (100 wells): 1.0 mL Kinase Buffer, 200 $\mu$g GST-ζ, bring to final volume of 8.0 mL with MilliQ H$_2$O.

2. Procedures a. Preparation of Lck coated ELISA plate

1. Coat 2.0 $\mu$g/well Sheep anti-mouse IgG in 100 $\mu$l of pH 9.6 sodium carbonate buffer at 4° C. overnight.

2. Wash well once with PBS.

3. Block plate with 0.15 mL of blocking Buffer for 30 min. at room temp.

4. Wash plate 5× with PBS.

5. Add 0.5 $\mu$g/well of anti-lck (mab 3A5) in 0.1 mL PBS at room temperature for 1–2 hours.

6. Wash plate 5× with PBS.

7. Add 20 $\mu$g/well of lck transformed yeast lysates diluted in Lysis Buffer (0.1 mL total volume per well). (Amount of lysate may vary between batches) Shake plate at 4° C. overnight to prevent loss of activity.

b. Preparation of phosphotyrosine antibody-coated ELISA plate

1. UB40 plate: 1.0 $\mu$g/well UB40 in 100 $\mu$L of PBS overnight at 4° C. and block with 150 $\mu$L of Blocking Buffer for at least 1 hour.

c. Kinase assay procedure
1. Remove unbound proteins from step 1–7, above, and wash plates 5× with PBS.
2. Add 0.08 mL Kinase Reaction Mixture per well (containing 10 µl of 10×Kinase Buffer and 2 µg GST-ζ per well diluted with water).
3. Add 10 µL of compound diluted in water containing 10% DMSO and pre-incubate for 15 minutes at room temperature.
4. Start kinase reaction by adding 10 µL/well of 0.1 mM ATP in water (10 µM ATP final).
5. Shake ELISA plate for 60 min. at room temperature.
6. Stop kinase reaction by adding 10 µL of 0.5 M EDTA per well.
7. Transfer 90 µl supernatant to a blocked 4G10 coated ELISA plate from section B, above.
8. Incubate while shaking for 30 min. at room temperature.
9. Wash plate 5× with TBST.
10. Incubate with Rabbit anti-GST antibody at 1:5000 dilution in 100 µL TBST for 30 min. at room temperature.
11. Wash the wells 5× with TBST.
12. Incubate with Goat anti-Rabbit-IgG-HRP at 1:20,000 dilution in 100 µL of TBST for 30 min. at room temperature.
13. Wash the wells 5× with TBST.
14. Develop with Turbo TMB.

The $IC_{50}$ values were measured for one of the compounds of the invention. This value is shown in Table 7

TABLE 7

| Compound | $IC_{50}$ (µM) |
| --- | --- |
| 5-acetyl-3-(4,5,6,7-tetrahydro-1H-indol-2-ylmethylene)-1,3-dihydro-indol-2-one | >100 |

Example 11

ASSAY MEASURING PHOSPHORYLATING FUNCTION OF RAF

The following assay reports the amount of RAF-catalyzed phosphorylation of its target protein MEK as well as MEK's target MAPK. The RAF gene sequence is described in Bonner et al., 1985, *Molec. Cell. Biol.* 5: 1400–1407, and is readily accessible in multiple gene sequence data banks. Construction of the nucleic acid vector and cell lines utilized for this portion of the invention are fully described in Morrison et al., 1988, *Proc. Natl. Acad. Sci.* USA 85: 8855–8859.

Materials and Reagents
1. Sf9 (*Spodoptera frugiperda*) cells; GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5% Triton X-100;
3. Thioredoxin-MEK fusion protein (T-MEK): T-MEK expression and purification by affinity chromatography are performed according to the manufacturer's procedures. Catalog# K 350-01 and R 350-40, Invitrogen Corp., San Diego, Calif.
4. His-MAPK (ERK 2); His-tagged MAPK is expressed in XL1 Blue cells transformed with pUC18 vector encoding His-MAPK. His-MAPK is purified by Ni-affinity chromatography. Cat# 27-4949-01, Pharmacia, Alameda, Calif., as described herein.
5. Sheep anti mouse IgG: Jackson laboratories, West Grove, Pa. Catalog, # 515-006-008, Lot# 28563
6. RAF-1 protein kinase specific antibody: URP2653 from UBI.
7. Coating buffer: PBS; phosphate buffered saline, GIBCO-BRL, Gaithersburg, Md.
8. Wash buffer: TBST—50 mM Tris/HCL pH 7.2, 150 mM NaCl, 0.1% Triton X-100
9. Block buffer: TBST, 0.1% ethanolamine pH 7.4
10. DMSO, Sigma, St. Louis, Mo.
11. Kinase buffer (KB): 20 mM HEPES/HCl pH 7.2, 150 mM NaCl, 0.1% Triton X-100, 1 mM PMSF, 5 mg/L Aprotenin, 75 mM sodium ortho vanadate, 0.5 MM DTT and 10 mM $MgCl_2$.
12. ATP mix: 100 mM $MgCl_2$, 300 mM ATP, 10 mCi $^{33}P$ ATP (Dupont-NEN)/mL.
13. Stop solution: 1% phosphoric acid; Fisher, Pittsburgh, Pa.
14. Wallac Cellulose Phosphate Filter mats; Wallac, Turku, Finnland.
15. Filter wash solution: 1% phosphoric acid, Fisher, Pittsburgh, Pa.
16. Tomtec plate harvester, Wallac, Turku, Finnland.
17. Wallac beta plate reader # 1205, Wallac, Turku, Finnland.
18. NUNC 96-well V bottom polypropylene plates for compounds Applied Scientific Catalog # AS-72092.

Procedure

All of the following steps are conducted at room temperature unless specifically indicated.
1. ELISA plate coating: ELISA wells are coated with 100 mL of Sheep anti mouse affinity purified antiserum (1 mg/100 mL coating buffer) over night at 4° C. ELISA plates can be used for two weeks when stored at 4° C.
2. Invert the plate and remove liquid. Add 100 mL of blocking solution and incubate for 30 min.
3. Remove blocking solution and wash four times with wash buffer. Pat the plate on a paper towel to remove excess liquid.
4. Add 1 mg of antibody specific for RAF-1 to each well and incubate for 1 hour. Wash as described in step 3.
5. Thaw lysates from RAS/RAF infected Sf9 cells and dilute with TBST to 10 mg/100 mL. Add 10 mg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10 000×g). Aliquots of lysates are frozen in dry ice/ethanol and stored at −80° C. until use.
6. Remove non-bound material and wash as outlined above (step 3).
7. Add 2 mg of T-MEK and 2 mg of His-MAEPK per well and adjust the volume to 40 mL with kinase buffer. Methods for purifying T-MEK and MAPK from cell extracts are provided herein by example.
8. Pre-dilute compounds (stock solution 10 mg/mL DMSO) or extracts 20 fold in TBST plus 1% DMSO.

Add 5 mL of the pre-diluted compounds/extracts to the wells described in step 6. Incubate for 20 min. Controls receive no drug.

9. Start the kinase reaction by addition of 5 mL ATP mix; Shake the plates on an ELISA plate shaker during incubation.
10. Stop the kinase reaction after 60 min by addition of 30 mL stop solution to each well.
11. Place the phosphocellulose mat and the ELISA plate in the Tomtec plate harvester. Harvest and wash the filter with the filter wash solution according to the manufacturers recommendation. Dry the filter mats. Seal the filter mats and place them in the holder. Insert the holder into radioactive detection apparatus and quantify the radioactive phosphorous on the filter mats.

Alternatively, 40 mL aliquots from individual wells of the assay plate can be transferred to the corresponding positions on the phosphocellulose filter mat. After air drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

Example 12

CDK2/CYCLIN A—INHIBITION ASSAY

This assay analyzes the protein kinase activity of CDK2 in exogenous substrate.

Reagents

A. Buffer A (80 mM Tris ( pH 7.2), 40 mM $MgCl_2$): 4.84 G. Tris (F.W.=121.1 g/mol), 4.07 g. $MgCl_2$ (F.W.= 203.31 g/mol) dissolved in 500 mL $H_2O$. Adjust pH to 7.2 with HCl.
B. Histone H1 solution (0.45 mg/mL Histone H1 and 20 mM HEPES pH 7.2 (pH 7.4 is OK): 5 mg Histone H1 (Boehinger Mannheim) in 11.111 mL 20 mM HEPES pH 7.2 (477 mg HEPES (F.W.=238.3 g/mol) dissolved in 100 mL $ddH_2O$, stored in 1 mL aliquots at $-80°$ C.
C. ATP solution (60 µM ATP, 300 µg/mL BSA, 3 mM DTT): 120 µl 10 mM ATP, 600 µl 10 mg/mL BSA to 20 mL, stored in 1 mL aliquots at $-80°$ C.
D. CDK2 solution: cdk2/cyclin A in 10 mM HEPES pH 7.2, mM NaCl, o.5 mM DTT, 10% glycerol, stored in 9 µl aliquots at $-80°$ C.

Description of Assay

1. Prepare solutions of inhibitors at three times the desired final assay concentration in $ddH_2O$/15% DMSO by volume.
2. Dispense 20 µl of inhibitors to wells of polypropylene 96-well plates (or 20 µl 15% DMSO for positive and negative controls).
3. Thaw Histone H1 solution (1 mL/plate), ATP solution (1 mL/plate plus 1 aliquot for negative control), and CDK2 solution (9 µl/plate). Keep CDK2 on ice until use. Aliquot CDK2 solution appropriately to avoid repeated freeze-thaw cycles.
4. Dilute 9 µl CDK2 solution into 2.1 mL Buffer A (per plate). Mix. Dispense 20 µl into each well.
5. Mix 1 mL Histone H1 solution with 1 mL ATP solution (per plate) into a 10 mL screw cap tube. Add $\gamma^{33}$P ATP to a concentration of 0.15 µCi/20 µl (0.15 µCi/well in assay). Mix carefully to avoid BSA frothing. Add 20 µl to appropriate wells. Mix plates on plate shaker. For negative control, mix ATP solution with an equal amount of 20 mM HEPES pH 7.2 and add $\gamma^{33}$P ATP to a concentration of 0.15 µCi/20µl solution. Add 20 µl to appropriate wells.
6. Let reactions proceed for 60 minutes.
7. Add 35 µl 10% TCA to each well. Mix plates on plate shaker.
8. Spot 40 µl of each sample onto P30 filter mat squares. Allow mats to dry (approx. 10–20 minutes).
9. Wash filter mats 4×10 minutes with 250 mL 1% phosphoric acid (10 mL phosphoric acid per liter $ddH_2O$).
10. Count filter mats with beta plate reader.

Example 13

PDGF-, FGF-, AND EGF-INDUCED BRDU INCORPORATION ASSAY

Materials and Reagents (1) PDGF: human PDGF B/B; 1276-956, Boehringer Mannheim, Germany
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TME), ready to use, Cat. No. 1 647 229, Boehringer Mannheim, Germany.
(6) PBS Washing Solution: 1×PBS, pH 7.4, made in house.
(7) Albumin, Bovine (BSA): fraction V powder; A-8551, Sigma Chemical Co., USA.
(8) 3T3 cell line genetically engineered to express human PDGF-R.

Protocol

1. Cells were seeded at 8000 cells/well in DMEM, 10% CS, 2 mM Gln in a 96 well plate. Cells were incubated overnight at 37° C. in 5% $CO_2$.
2. After 24 hours, the cells were washed with PBS, and then were serum starved in serum free medium (0% CS DMEM with 0.1% BSA) for 24 hours.
3. On day 3, ligand (PDGF=3.8 nM, prepared in DMEM with 0.1% BSA) and test compounds were added to the cells simultaneously. The negative control wells received serum free DMEM with 0.1% BSA only; the positive control cells received the ligand (PDGF) but no test compound. Test compounds were prepared in serum free DMEM with ligand in a 96 well plate, and serially diluted for 7 test concentrations.
4. After 20 hours of ligand activation, diluted BrdU labeling reagent (1:100 in DMEM, 0.1% BSA) was added and the cells were incubated with BrdU (final concentration=10 µM) for 1.5 hours.
5. After incubation with labeling reagent, the medium was removed by decanting and tapping the inverted plate on a paper towel. FixDenat solution was added (50 µL/well) and the plates were incubated at room temperature for 45 minutes on a plate shaker.
6. The FixDenat solution was thoroughly removed by decanting and tapping the inverted plate on a paper towel. Milk was added (5% dehydrated milk in PBS, 200 µL/well) as a blocking solution and the plate was incubated for 30 minutes at room temperature on a plate shaker.

7. The blocking solution was removed by decanting and the wells were washed once with PBS. Anti-BrdU-POD solution (1:100 dilution in PBS, 1% BSA) was added (100 μL/well), and the plate was incubated for 90 minutes at room temperature on a plate shaker.
8. The antibody conjugate was thoroughly removed by decanting and rinsing the wells 5 times with PBS, and the space was dried by inverting and tapping on a paper towel.
9. TMB substrate solution was added (100 μL/well) and incubated for 20 minutes at room temperature on a plate shaker until color development was sufficient for photometric detection.
10. The absorbance of the samples were measured at 410 nm (in "dual wavelength" mode with a filter reading at 490 nm, as a reference wavelength) on a Dynatech ELISA plate reader.

The $IC_{50}$ values were measured for several of the compounds of the invention. These values are depicted in Table 8

TABLE 8

| Compound | EGFr $IC_{50}$ (μM) | PDGFr $IC_{50}$ (μM) | FGFr $IC_{50}$ (μM) |
| --- | --- | --- | --- |
| 6-methoxy-3-(4,5,6,7-tetrahydro-1H-indol-2-ylmethylene)-1,3-dihydro-indol-2-one | >50 | 1.08 | >50 |
| 5-acetyl-3-(4,5,6,7-tetrahydro-1H-indol-2-ylmethylene)-1,3-dihydro-indol-2-one | 36.51 | >0.07 | >50 |
| 6-hydroxy-3-(4,5,6,7-tetrahydro-1H-indol-2-ylmethylene)-1,3-dihydro-indol-2-one | 12.63 | 0.51 | 6.21 |
| 6-(3-methoxyphenyl)-3-(4,5,6,7-tetrahydro-1H-indol-2-ylmethylene)-1,3-dihydro-indol-2-one | 31.84 | >50 | >50 |
| 6-(3-ethoxyphenyl)-3-(4,5,6,7-tetrahydro-1H-indol-2-ylmethylene)-1,3-dihydro-indol-2-one | >50 | >50 | >50 |
| 6-phenyl-3-(4,5,6,7-tetrahydro-1H-indol-2-ylmethylene)-1,3-dihydro-indol-2-one | >50 | >50 | >50 |
| 6-(4-methoxyphenyl)-3-(4,5,6,7-tetrahydro-1H-indol-2-ylmethylene)-1,3-dihydro-indol-2-one | >50 | >50 | >50 |
| 6-(4-methoxyphenyl)-3-(3-methyl-4,5,6,7-tetrahydro-1H-indol-2-ylmethylene)-1,3-dihydro-indol-2-one | >50 | >50 | >50 |
| 6-(2-methoxyphenyl)-3-(4,5,6,7-tetrahydro-1H-indol-2-ylmethylene)-1,3-dihydro-indol-2-one | 34.08 | 1.06 | 43.59 |
| 6-(2-methoxyphenyl)-3-(3-methyl-4,5,6,7-tetrahydro-1H-indol-2-ylmethylene)-1,3-dihydro-indol-2-one | >50 | >50 | >50 |

Example 14

EGF-INDUCED HER2-DRIVEN BRDU INCORPORATION

Materials and Reagents
(1) EGF: mouse EGF, 201; Toyobo, Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1×PBS, pH 7.4, made in house.
(7) Albumin, Bovine (BSA): fraction V powder; A-8551, Sigma Chemical Co., USA.
(8) 3T3 cell line engineered to express a chimeric receptor having the extra-cellular domain of EGF-R and the intra-cellular domain of Her2.

Protocol
(1) Cells are seeded at 8000 cells/well in DMEM, 10% CS, 2 mM Gln in a 96-well plate. Cells are incubated overnight at 37° in 5% $CO_2$.
(2) After 24 hours, the cells are washed with PBS, and then are serum starved in serum free medium (0%CS DMEM with 0.1% BSA) for 24 hours.
(3) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration=10 μM) for 1.5 hours.
(5) After incubation with labeling reagent, the medium is removed by decanting and tapping the inverted plate on a paper towel. FixDenat solution is added (50 μl/well) and the plates are incubated at room temperature for 45 minutes on a plate shaker.
(6) The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.
(7) The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.
(8) The antibody conjugate is thoroughly removed by decanting and rinsing the wells 5 times with PBS, and the plate is dried by inverting and tapping on a paper towel.
(9) TMB substrate solution is added (100 μl/well) and incubated for 20 minutes at room temperature on a plate shaker until color development is sufficient for photometric detection.
(10) The absorbance of the samples are measured at 410 nm (in "dual wavelength" mode with a filter reading at 490 nm, as a reference wavelength) on a Dynatech ELISA plate reader.

Example 15

IGF1-INDUCED BRDU INCORPORATION ASSAY

Materials and Reagents
(1) IGF1 Ligand: human, recombinant; G511, Promega Corp, USA.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.

(6) PBS Washing Solution: 1×PBS, pH 7.4, made in house (Sugen, Inc., Redwood City, Calif.).

(7) Albumin, Bovine (BSA): fraction V powder; A-8551, Sigma Chemical Co., USA.

(8) 3T3 cell line genetically engineered to express human IGF-1 receptor.

Protocol (1) Cells are seeded at 8000 cells/well in DMEM, 10% CS, 2 mM Gln in a 96-well plate. Cells are incubated overnight at 37° C. in 5% $CO_2$.

(2) After 24 hours, the cells are washed with PBS, and then are serum starved in serum free medium (0%CS DMEM with 0.1% BSA) for 24 hours.

(3) On day 3, ligand (IGF1=3.3 nM, prepared in DMEM with 0.1% BSA) and test compounds are added to the cells simultaneously. The negative control wells receive serum free DMEM with 0.1% BSA only; the positive control cells receive the ligand (IGF1) but no test compound. Test compounds are prepared in serum free DMEM with ligand in a 96 well plate, and serially diluted for 7 test concentrations.

(4) After 16 hours of ligand activation, diluted BrdU labeling reagent (1:100 in DMEM, 0.1% BSA) is added and the cells are incubated with BrdU (final concentration=10 $\mu$M) for 1.5 hours.

(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 $\mu$L/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 $\mu$L/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 $\mu$l/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

Example 16

HUV-EC-C ASSAY

The following protocol may also be used to measure a compound's activity against PDGF-R, FGF-R, VEGF, aFGF or Flk-1/KDR, all of which are naturally expressed by HUV-EC cells.

DAY 0

1. Wash and trypsinize HUV-EC-C cells (human umbilical vein endothelial cells, (American Type Culture Collection; catalogue no. 1730 CRL). Wash with Dulbecco's phosphate-buffered saline (D-PBS; obtained from Gibco BRL; catalogue no. 14190-029) 2 times at about 1 mL/10 $cm^2$ of tissue culture flask. Trypsinize with 0.05% trypsin-EDTA in non-enzymatic cell dissociation solution (Sigma Chemical Company; catalogue no. C-1544). The 0.05% trypsin is made by diluting 0.25% trypsin/1 mM EDTA (Gibco; catalogue no. 25200-049) in the cell dissociation solution. Trypsinize with about 1 mL/25–30 $cm^2$ of tissue culture flask for about 5 minutes at 37° C. After cells have detached from the flask, add an equal volume of assay medium and transfer to a 50 mL sterile centrifuge tube (Fisher Scientific; catalogue no. 05-539-6).

2. Wash the cells with about 35 mL assay medium in the 50 mL sterile centrifuge tube by adding the assay medium, centrifuge for 10 minutes at approximately 200 g, aspirate the supernatant, and resuspend with 35 mL D-PBS. Repeat the wash two more times with D-PBS, resuspend the cells in about 1 mL assay medium/15 $cm^2$ of tissue culture flask. Assay medium consists of F12K medium (Gibco BRL; catalogue no. 21127-014)+0.5% heat-inactivated fetal bovine serum. Count the cells with a Coulter Counter, Coulter Electronics, Inc.) and add assay medium to the cells to obtain a concentration of $0.8–1.0×10^5$ cells/mL.

3. Add cells to 96-well flat-bottom plates at 100 $\mu$l/well or $0.8–1.0×10^4$ cells/well; incubate ~24 h at 37° C., 5% $CO_2$.

DAY 1

1. Make up two-fold drug titrations in separate 96-well plates, generally 50 $\mu$M on down to 0 $\mu$M. Use the same assay medium as mentioned in day 0, step 2 above. Titrations are made by adding 90 $\mu$l/well of drug at 200 $\mu$M (4×the final well concentration) to the top well of a particular plate column. Since the stock drug concentration is usually 20 mM in DMSO, the 200 $\mu$M drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 $\mu$l/well. Take 60 $\mu$l from the 120 $\mu$l of 200 $\mu$M drug dilution in the top well of the column and mix with the 60 $\mu$l in the second well of the column. Take 60 $\mu$l from this well and mix with the 60 $\mu$l in the third well of the column, and so on until two-fold titrations are completed. When the next-to-the-last well is mixed, take 60 $\mu$l of the 120 $\mu$l in this well and discard it. Leave the last well with 60 $\mu$l of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 $\mu$l/well of the drug dilutions to the 96-well assay plates containing the $0.8–1.0×10^4$ cells/100 $\mu$l/well of the HUV-EC-C cells from day 0 and incubate ~2 h at 37° C., 5% $CO_2$.

3. In triplicate, add 50 $\mu$l/well of 80 $\mu$g/mL VEGF, 20 ng/mL ECGF, or media control to each drug condition. As with the drugs, the growth factor concentrations are 4×the desired final concentration. Use the assay media from day 0 step 2 to make the concentrations of growth factors. Incubate approximately 24 hours at 37° C., 5% $CO_2$. Each well will have 50 $\mu$l drug dilution, 50 $\mu$l growth factor or media, and 100 ul cells, =200 ul/well total. Thus the 4×concentrations of drugs and growth factors become 1× once everything has been added to the wells.

DAY 2

1. Add $^3$H-thymidine (Amersham; catalogue no. TRK-686) at 1 μCi/well (10 μl/well of 100 μCi/mL solution made up in RPMI media+10% heat-inactivated fetal bovine serum) and incubate ~24 h at 37° C., 5% $CO_2$. RPMI is obtained from Gibco BRL, catalogue no. 11875-051.

DAY 3

1. Freeze plates overnight at −20° C.

DAY 4

1. Thaw plates and harvest with a 96-well plate harvester (Tomtec Harvester 96®) onto filter mats (Wallac; catalogue no. 1205-401); read counts on a Wallac Betaplate™ liquid scintillation counter.

The $IC_{50}$ values were measured for several of the compounds of the invention. These values are shown in Table 9

TABLE 9

| Compound | VEGF $IC_{50}$ (μM) | aFGF $IC_{50}$ (μM) |
| --- | --- | --- |
| 5-acetyl-3-(4,5,6,7-tetrahydro-1H-indol-2-ylmethylene)-1,3-dihydro-indol-2-one | >0.07 | 28.76 |
| 6-(3-methoxyphenyl)-3-(4,5,6,7-tetrahydro-1H-indol-2-ylmethylene)-1,3-dihydro-indol-2-one | >50 | >50 |
| 6-(3-ethoxyphenyl)-3-(4,5,6,7-tetrahydro-1H-indol-2-ylmethylene)-1,3-dihydro-indol-2-one | >25 | >25 |
| 6-phenyl-3-(4,5,6,7-tetrahydro-1H-indol-2-ylmethylene)-1,3-dihydro-indol-2-one | >12.5 | >12.5 |
| 6-(4-methoxyphenyl)-3-(4,5,6,7-tetrahydro-1H-indol-2-ylmethylene)-1,3-dihydro-indol-2-one | >12.5 | >12.5 |
| 6-(4-methoxyphenyl)-3-(3-methyl-4,5,6,7-tetrahydro-1H-indol-2-ylmethylene)-1,3-dihydro-indol-2-one | >50 | >50 |
| 6-(2-methoxyphenyl)-3-(4,5,6,7-tetrahydro-1H-indol-2-ylmethylene)-1,3-dihydro-indol-2-one | 13 | 14.64 |
| 6-(2-methoxyphenyl)-3-(3-methyl-4,5,6,7-tetrahydro-1H-indol-2-ylmethylene)-1,3-dihydro-indol-2-one | >12.5 | >12.5 |

EXAMPLE 17

IN VIVO ANIMAL MODELS

A. Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 μL excipient (DMSO, or VPD:D5W) can be delivered by IP injection at different concentrations generally starting at day one after implantation.

B. Tumor Invasion Model

The following tumor invasion model has been developed and maybe used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 μl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases, to various organs (lung, liver, brain, stomach, spleen, heart, muscle) are excised and analyzed (measurements of tumor size, grade of invasion, immunochemistry, and in situ hybridization).

D. Measurement Of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques (Mossman, 1983, *J. Immunol. Methods*, 65:55–63), by measuring the amount of LDH released (Korzeniewski and Callewaert, 1983, *J. Immunol. Methods*, 64:313; Decker and Lohmann-Matthes, 1988, *J. Immunol. Methods*, 115:61), or by measuring the lethal dose in animal models. Compounds with a large therapeutic index are preferred. The therapeutic index should be greater than 2, preferably at least 10, more preferably at least 50.

CONCLUSION

Thus, it will be appreciated that the compounds, methods and pharmacological compositions of the present invention are expected to modulate RTK and CTK activity and therefore to be effective as therapeutic agents against RTK- and CTK-related disorders.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed is:

1. A 3-(cyclohexanoheteroarylidene)-2-indolinone compound having the following chemical structure:

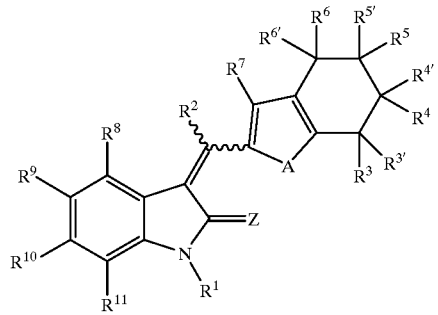

wherein,

A is selected from the group consisting of oxygen and sulfur;

Z is selected from the group consisting of oxygen, sulfur and $NR^{12}$ wherein,
$R^{12}$ is selected from the group consisting of hydrogen, alkyl, cycloalkyl, aryl, hydroxy, alkoxy, aryloxy, carbonyl, C-carboxy, O-carboxy, C-amido, guanyl, sulfonyl and trihalomethanesulfonyl;

$R^1$ is selected from the group consisting of hydrogen, alkyl, cycloalkyl, alkenyl, alkynyl, aryl, hydroxy, alkoxy, C-carboxy, C-amido, trihalomethanecarbonyl, trihalomethanesulfonyl and sulfonyl;

$R^2$ is selected from the group consisting of hydrogen, alkyl, cycloalkyl, aryl and halogen;

$R^3$, $R^{3'}$, $R^4$, $R^{4'}$, $R^5$, $R^{5'}$, $R^6$ and $R^{6'}$ are independently selected from the group consisting of hydrogen, alkyl, trihaloalkyl, cycloalkyl, alkenyl, alkynyl, aryl, heteroaryl, heteroalicyclic, alkoxy, aryloxy, thioalkoxy, thioaryloxy, heteroaryloxy, heteroalicycloxy, sulfinyl, sulfonyl, S-sulfonamido, N-Sulfonamido, trihalomethanesulfonyl, carbonyl, C-carboxy, O-carboxy, C-amido, N-amido, cyano, nitro, halo, O-carbamyl, N-carbamyl, O-thiocarbamyl, phosphonyl, N-thiocarbamyl, guanyl, guanidino, ureido, amino, trihalomethanesulfonamido, and —$NR^{13}R^{14}$; wherein
$R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;
when any of $R^3$, $R^4$, $R^5$ and $R^6$ are hydrogen, $R^{3'}$, $R^{4'}$, $R^{5'}$ and $R^{6'}$, respectively, in addition to being independently selected from the above group, may be independently selected from the group consisting of hydroxy and thiohydroxy;
combined, $R^3$ and $R^{3'}$, $R^4$ and $R^{4'}$, $R^5$ and $R^{5'}$, and $R^6$ and $R^{6'}$ may be independently selected from the group consisting of keto, five-member spirocycloalkyl, five-member spiroheteroalicyclyl, six-member spirocycloalkyl and six member spiroheteroalicyclyl;

$R^7$ is selected from the group consisting of hydrogen, alkyl, cycloalkyl, trihaloalkyl alkenyl, alkynyl, aryl, heteroaryl, C-carboxy, O-carboxy, halo, cyano, nitro, hydroxy, alkoxy, $R^8$, $R^9$, $R^{10}$ and $R^{11}$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicycloxy, halo, nitro, cyano, O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —$NR^{13}R^{14}$, wherein, $R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

or a physiologically acceptable salt thereof.

2. The compound or salt of claim 1, where Z is oxygen.
3. The compound or salt of claim 1, where $R^7$ is hydrogen.
4. The compound or salt of claim 1, where $R^2$ is hydrogen.
5. The compound or salt of claim 1, wherein $R^3$, $R^{3'}$, $R^4$, $R^{4'}$, $R^5$, $R^{5'}$, $R^6$ and $R^{6'}$ are hydrogen.
6. The compound or salt of claim 1, wherein $R^8$, $R^{10}$ and $R^{11}$ are hydrogen and $R^9$ is S-sulfonamido wherein $R^{13}$ and $R^{14}$ are independently selected from the group consisting of hydrogen and lower alkyl.
7. A pharmacological compositions comprising a compound or salt of claim 1; and,
a physiologically acceptable carrier or excipient.
8. A method for the modulation of the catalytic activity of a protein tyrosine kinase comprising administering said compound or salt of any one of claims 1–6 said protein tyrosine kinase.
9. A method for treating a protein tyrosine kinase related disorder in an organism comprising administering a therapeutically effective amount of a compound of any one of claims 1–6 to said organism.
10. The method of claim 9, wherein said protein tyrosine kinase related disorder comprises a cell proliferation, differentiation or growth disorder.
11. The method of claim 10, wherein protein tyrosine kinase related disorder comprises arthritis, diabetic retinopathy, restinosis, hepatic cirrhosis, atherosclerosis, angiogenesis, glomerulonephritis, diabetic nephropathy, thrombic microangiopathy syndromes, transplant rejection, autoimmune disease, diabetes or hyperimmune disease.
12. The method of claim 9, wherein said protein tyrosine kinase related disorder is a cellular tyrosine kinase related disorder.
13. The method of claim 12, wherein said cellular tyrosine kinase related disorder is a src kinase related disorder.
14. The method of claim 12, wherein said cellular tyrosine kinase related disorder is a lck kinase related disorder.
15. The method of claim 9, wherein said protein tyrosine kinase disorder is selected from the group consisting of cancer, arterial restenosis, osteoporosis, psoriasis, metastasis, rheumatoid arthritis, inflammatory disease, fibrosis, and sclerosis.
16. The method of claim 9, wherein said organism is a mammal.
17. The method of claim 16, wherein said mammal is a human being.
18. A combinatorial library of at least 10 3-(cyclohexanoheteroarylidene)-2-indolinone compounds according to claim 1 that are formed by reacting, at an elevated temperature in a solvent in the presence of a base, an oxindole with an acyl compound, wherein said oxindole has a structure set forth in formula 2:

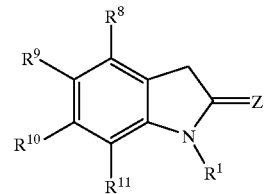

(2)

wherein

Z is selected from the group consisting of oxygen, sulfur and $NR^{12}$ wherein, $R^{12}$ is selected from the group consisting of hydrogen, alkyl, cycloalkyl, aryl, hydroxy, alkoxy, aryloxy, carbonyl, C-carboxy, O-carboxy, C-amido, guanyl, sulfonyl and trihalomethanesulfonyl;

$R^1$ is selected from the group consisting of hydrogen, alkyl, cycloalkyl, alkenyl, alkynyl, aryl, hydroxy, alkoxy, C-carboxy, C-amido, trihalomethanecarbonyl, trihalomethane-sulfonyl and sulfonyl; and $R^8$, $R^9$, $R^{10}$ and $R^{11}$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicycloxy, halo, nitro, cyano, O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —$NR^{13}R^{14}$, wherein, $R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

and wherein said acyl compound has the structure set forth in formula 3:

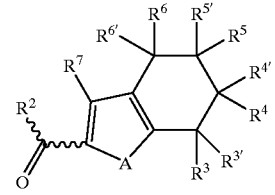

(3)

wherein:

A is selected from the group consisting of oxygen and sulfur;

$R^2$ is selected from the group consisting of hydrogen, alkyl, cycloalkyl, aryl and halogen;

$R^3$, $R^{3'}$, $R^4$, $R^{4'}$, $R^5$, $R^{5'}$, $R^6$ and $R^{6'}$ are independently selected from the group consisting of hydrogen, alkyl, trihaloalkyl, cycloalkyl, alkenyl, alkynyl, aryl, heteroaryl, heteroalicyclic, alkoxy, aryloxy, thioalkoxy, thioaryloxy, heteroaryloxy, heteroalicycloxy, sulfinyl, sulfonyl, S-sulfonamido, N-Sulfonamido, trihalomethanesulfonyl, carbonyl, C-carboxy, O-carboxy, C-amido, N-amido, cyano, nitro, halo, O-carbamyl, N-carbamyl, O-thiocarbamyl, phosphonyl, N-thiocarbamyl, guanyl, guanidino, ureido, amino, trihalomethanesulfonamido, and —NR$^{13}$R$^{14}$; wherein R$^{13}$ and R$^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

when any of R$^3$, R$^4$, R$^5$ and R$^6$ are hydrogen, R$^{3'}$, R$^{4'}$, R$^{5'}$ and R$^{6'}$, respectively, in addition to being independently selected from the above group, may be independently selected from the group consisting of hydroxy and thiohydroxy;

combined, R$^3$ and R$^{3'}$, R$^4$ and R$^{4'}$, R$^5$ and R$^{5'}$, and R$^6$ and R$^{6'}$ may be independently selected from the group consisting of keto, five-member spirocycloalkyl, five-member spiroheteroalicyclyl, six-member spirocycloalkyl and six member spiroheteroalicyclyl;

and,

R$^7$ is selected from the group consisting of hydrogen, alkyl, cycloalkyl, trihaloalkyl alkenyl, alkynyl, aryl, heteroaryl, C-carboxy, O-carboxy, halo, cyano, nitro, hydroxy, alkoxy.

19. The combinatorial library of claim 18, wherein said oxindole is selected from the group consisting of 2-indolinone, 5-acetyl-2-indolinone, 5-amino-2-indolinone, 5-aminosulfonyl-2-indolinone, 5-bromo-2-indolinone, 6-bromo-2-indolinone, 7-bromo-5-chloro-2-indolinone, 5-bromo-4-methyl-2-indolinone, 7-bromo-5-methyl-2-indolinone, 5-(2-bromoethyl)-2-indolinone, 5-n-butyl-2-indolinone, 5-carboxy-2-indolinone, 5-(4-carboxybenzamido)-2-indolinone, 5-(2-carboxyethyl)-2-indolinone, 5-(2-carboxyethyl)-4-methyl-2-indolinone, 5-chloro-2-indolinone, 6-chloro-2-indolinone, 5-chloro-7-methyl-2-indolinone, 5-(2-chloroethyl)-2-indolinone, 5,7-dibromo-2-indolinone, 5,7-dibromo-4-methyl-2-indolinone, 5,6-dimethoxy-2-indolinone, 4,6-dimethyl-2-indolinone, 6-(3-ethoxyphenyl)-2-indolinone, 5-ethyl-2-indolinone, 5-fluoro-2-indolinone, 6-fluoro-2-indolinone, 7-fluoro-2-indolinone, 6-hydroxy-2-indolinone, 5-iodo-2-indolinone, 5-iodo-4-methyl-2-indolinone, 5-methoxy-2-indolinone, 6-methoxy-2-indolinone, 5-methoxycarbonyl-2-indolinone, 5-(4-methoxycarbonylbenzamido)-2-indolinone, 6-(2-methoxyphenyl)-2-indolinone, 6-(3-methoxyphenyl)-2-indolinone, 6-(4-methoxyphenyl)-2-indolinone, 4-methyl-2-indolinone, 5-methyl-2-indolinone, 5-methylaminosulfonyl-2-indolinone, 5-(morpholin-4-sulfonyl)-2-indolinone, 5-(2-morpholin-4-ethyl)-2-indolinone, 5-nitro-2-indolinone, 6-phenyl-2-indolinone, 5-(piperidin-1-acetyl)-2-indolinone, 5-(2-piperidin-1-acetyl)-2-indolinone, 5-(2-piperidin-1-ethyl)-2-indolinone, 5-(2-pyrrolidin-1-ethyl)-2-indolinone, 5-trifluoromethyl-2-indolinone, 6-trifluoromethyl-2-indolinone, 5-[4-(trifluoromethyl)phenylaminosulfonyl]-2-indolinone, and 2-oxo-2,3-dihydro-1H-indole-4-carboxylic acid.

20. The combinatorial library of claim 18, wherein said acyl compound is selected from the group consisting of 2-formyl-4,5,6,7-tetrahydrobenzofuran, 3-cyano-2-formyl-4,5,6,7-tetrahydrobenzofuran, 3-ethoxycarbonyl-2-formyl-4,5,6,7-tetrahydrobenzofuran, 3-ethyl-2-formyl-4,5,6,7-tetrahydrobenzofuran, 2-formyl-3-methyl-4,5,6,7-tetrahydrobenzofuran, 2-formyl-3-(4-methylphenyl)-4,5,6,7-tetrahydrobenzofuran, 2-formyl-3-n-pentyl-4,5,6,7-tetrahydrobenzofuran, 2-formyl-3-phenyl-4,5,6,7-tetrahydrobenzofuran, 2-formyl-3-phenylaminomethyl-4,5,6,7-tetrahydrobenzofuran, 2-formyl-3-phenylsulfonylmethyl-4,5,6,7-tetrahydrobenzofuran, 2-formyl-4,5,6,7-tetrahydrobenzothiophene, 2-formyl-3-methoxycarbonyl-4,5,6,7-tetrahydrobenzothiophene, 2-formyl-3-vinyl-4,5,6,7-tetrahydrobenzothiophene, 3-carboxy-2-formyl-4,5,6,7-tetrahydrobenzothiophene, 3-ethoxycarbonyl-2-formyl-4,5,6,7-tetrahydrobenzothiophene, 3-(3-dimethylamino-n-propoxycarbonyl)-2-formyl-4,5,6,7-tetrahydrobenzothiophene, 3-(2-methylaminoethyl)-2-formyl-4,5,6,7-tetrahydrobenzothiophene, 3-(2-diethylaminoethoxycarbonyl)-2-formyl-4,5,6,7-tetrahydrobenzothiophene and 3-cyclopropylmethoxy-2-formyl-4,5,6,7-tetrahydrobenzothiophene.

21. A method for synthesizing a 3-(cyclohexanoarylidenyl)-2-indolinone compound of any one of claims 1–6 comprising the step of reacting a first reactant with a second reactant in a solvent and in the presence of a base at elevated temperatures, wherein said first reactant is an oxindole having the structure set forth in formula 2:

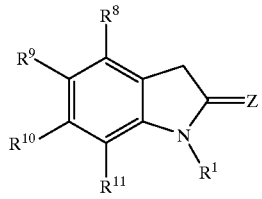

(2)

wherein

Z is selected from the group consisting of oxygen, sulfur and NR$^{12}$ wherein, R$^{12}$ is selected from the group consisting of hydrogen, alkyl, cycloalkyl, aryl, hydroxy, alkoxy, aryloxy, carbonyl, C-carboxy, O-carboxy, C-amido, guanyl, sulfonyl and trihalomethanesulfonyl;

R$^1$ is selected from the group consisting of hydrogen, alkyl, cycloalkyl, alkenyl, alkynyl, aryl, hydroxy, alkoxy, C-carboxy, C-amido, trihalomethanecarbonyl, trihalomethane-sulfonyl and sulfonyl; and R$^8$, R$^9$, R$^{10}$ and R$^{11}$ are independently selected from the group consisting of hydrogen, alkyl, trihaloalkyl, alkenyl, alkynyl, cycycloalkyl, aryl, heteroaryl, heteroalicyclic, hydroxy, alkoxy, cycloalkoxy, aryloxy, heteroaryloxy, heteroalicycloxy, thiohydroxy, thioalkyoxy, thiocycloalkoxy, thioheteraryloxy, thioheteralicycloxy, halo, nitro, cyano, O-carbamyl, N-carbamyl, O-thiocarbamyl, N-thiocarbamyl, silyl, phosphonyl, C-carboxy, O-carboxy, N-amido, C-amido, sulfinyl, sulfonyl, S-sulfonamido, N-sulfonamido, trihalomethanesulfonyl, guanyl, guanidino, trihalomethanesulfonamido, amino and —NR$^{13}$R$^{14}$, wherein, R$^{13}$ and R$^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

wherein said second reactant is an acyl compound, having a structure set forth in formula 3:

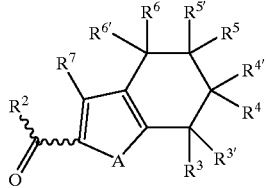

(3)

wherein:

A is selected from the group consisting of oxygen and sulfur;

$R^2$ is selected from the group consisting of hydrogen, alkyl, cycloalkyl, aryl and halogen;

$R^3$, $R^{3'}$, $R^4$, $R^{4'}$, $R^5$, $R^{5'}$, $R^6$ and $R^{6'}$ are independently selected from the group consisting of hydrogen, alkyl, trihaloalkyl, cycloalkyl, alkenyl, alkynyl, aryl, heteroaryl, heteroalicyclic, alkoxy, aryloxy, thioalkoxy, thioaryloxy, heteroaryloxy, heteroalicycloxy, sulfinyl, sulfonyl, S-sulfonamido, N-Sulfonamido, trihalomethanesulfonyl, carbonyl, C-carboxy, O-carboxy, C-amido, N-amido, cyano, nitro, halo, O-carbamyl, N-carbamyl, O-thiocarbamyl, phosphonyl, N-thiocarbamyl, guanyl, guanidino, ureido, amino, trihalomethanesulfonamido, and —$NR^{13}R^{14}$; wherein $R^{13}$ and $R^{14}$ are independently selected from the group consisting of hydrogen, alkyl, cycloalkyl, aryl, carbonyl, C-carboxy, sulfonyl, trihalomethanesulfonyl and, combined, a five- or six-member heteroalicyclic ring;

when any of $R^3$, $R^4$, $R^5$ and $R^6$ are hydrogen, $R^{3'}$, $R^{4'}$, $R^{5'}$ and $R^{6'}$, respectively, in addition to being independently selected from the above group, may be independently selected from the group consisting of hydroxy and thiohydroxy;

combined, $R^3$ and $R^{3'}$, $R^4$ and $R^{4'}$, $R^5$ and $R^{5'}$, and $R^6$ and $R^{6'}$ may be independently selected from the group consisting of keto, five-member spirocycloalkyl, five-member spiroheteroalicyclyl, six-member spirocycloalkyl and six member spiroheteroalicyclyl;

and $R^7$ is selected from the group consisting of hydrogen, alkyl, cycloalkyl, trihaloalkyl alkenyl, alkynyl, aryl, heteroaryl, C-carboxy, O-carboxy, halo, cyano, nitro, hydroxy, alkoxy.

22. The method of claim 21, wherein said first reactant is an oxindole selected from the group consisting 2-indolinone, 5-acetyl-2-indolinone, 5-amino-2-indolinone, 5-aminosulfonyl-2-indolinone, 5-bromo-2-indolinone, 6-bromo-2-indolinone, 7-bromo-5-chloro-2-indolinone, 5-bromo-4-methyl-2-indolinone, 7-bromo-5-methyl-2-indolinone, 5-(2-bromoethyl)-2-indolinone, 5-n-butyl-2-indolinone, 5-carboxy-2-indolinone, 5-(4-carboxybenzamido)-2-indolinone, 5-(2-carboxyethyl)-2-indolinone, 5-(2-carboxyethyl)-4-methyl-2-indolinone, 5-chloro-2-indolinone, 6-chloro-2-indolinone, 5-chloro-7-methyl-2-indolinone, 5-(2-chloroethyl)-2-indolinone, 5,7-dibromo-2-indolinone, 5,7-dibromo-4-methyl-2-indolinone, 5,6-dimethoxy-2-indolinone, 4,6-dimethyl-2-indolinone, 6-(3-ethoxyphenyl)-2-indolinone, 5-ethyl-2-indolinone, 5-fluoro-2-indolinone, 6-fluoro-2-indolinone, 7-fluoro-2-indolinone, 6-hydroxy-2-indolinone, 5-iodo-2-indolinone, 5-iodo-4-methyl-2-indolinone, 5-methoxy-2-indolinone, 6-methoxy-2-indolinone, 5-methoxycarbonyl-2-indolinone, 5-(4-methoxycarbonylbenzamido)-2-indolinone, 6-(2-methoxyphenyl)-2-indolinone, 6-(3-methoxyphenyl)-2-indolinone, 6-(4-methoxyphenyl)-2-indolinone, 4-methyl-2-indolinone, 5-methyl-2-indolinone, 5-methylaminosulfonyl-2-indolinone, 5-(morpholin-4-sulfonyl)-2-indolinone, 5-(2-morpholin-4-ethyl)-2-indolinone, 5-nitro-2-indolinone, 6-phenyl-2-indolinone, 5-(piperidin-1-acetyl)-2-indolinone, 5-(2-piperidin-1-acetyl)-2-indolinone, 5-(2-piperidin-1-ethyl)-2-indolinone, 5-(2-pyrrolidin-1-ethyl)-2-indolinone, 5-trifluoromethyl-2-indolinone, 6-trifluoromethyl-2-indolinone, 5-[4-(trifluoromethyl)phenylaminosulfonyl]-2-indolinone, and 2-oxo-2,3-dihydro-1H-indole-4-carboxylic acid.

23. The method of claim 21, wherein said second reactant is an acyl compound selected from the group consisting of 2-formyl-4,5,6,7-tetrahydrobenzofuran, 3-cyano-2-formyl-4,5,6,7-tetrahydrobenzofuran, 3-ethoxycarbonyl-2-formyl-4,5,6,7-tetrahydrobenzofuran, 3-ethyl-2-formyl-4,5,6,7-tetrahydrobenzofuran, 2-formyl-3-methyl-4,5,6,7-tetrahydrobenzofuran, 2-formyl-3-(4-methylphenyl)-4,5,6,7-tetrahydrobenzofuran, 2-formyl-3-n-pentyl-4,5,6,7-tetrahydrobenzofuran, 2-formyl-3-phenyl-4,5,6,7-tetrahydrobenzofuran, 2-formyl-3-phenylaminomethyl-4,5,6,7-tetrahydrobenzofuran, 2-formyl-3-phenylsulfonylmethyl-4,5,6,7-tetrahydrobenzofuran, 2-formyl-4,5,6,7-tetrahydrobenzothiophene, 2-formyl-3-methoxycarbonyl-4,5,6,7-tetrahydrobenzothiophene, 2-formyl-3-vinyl-4,5,6,7-tetrahydrobenzothiophene, 3-carboxy-2-formyl-4,5,6,7-tetrahydrobenzothiophene, 3-ethoxycarbonyl-2-formyl-4,5,6,7-tetrahydrobenzothiophene, 3-(3-dimethylamino-n-propoxycarbonyl)-2-formyl-4,5,6,7-tetrahydrobenzothiophene, 3-(2-methylaminoethyl)-2-formyl-4,5,6,7-tetrahydrobenzothiophene, 3-(2-diethylaminoethoxycarbonyl)-2-formyl-4,5,6,7-tetrahydrobenzothiophene and 3-cyclopropylmethoxy-2-formyl-4,5,6,7-tetrahydrobenzothiophene.

24. The method of claim 21, wherein said base is selected from the group consisting of a nitrogen base and an inorganic base.

25. The method of claim 21, wherein said solvent is selected from the group consisting of water, an alcohol, and dimethylformamide.

* * * * *